US010000483B2

(12) United States Patent
Gray et al.

(10) Patent No.: US 10,000,483 B2
(45) Date of Patent: Jun. 19, 2018

(54) BONE MARROW ON X CHROMOSOME KINASE (BMX) INHIBITORS AND USES THEREOF

(71) Applicants: Dana-Farber Cancer Institute, Inc., Boston, MA (US); Beth Israel Deaconess Medical Center, Inc., Boston, MA (US)

(72) Inventors: Nathanael Gray, Boston, MA (US); Steven Balk, Needham, MA (US); Qingsong Liu, Brookline, MA (US); Sen Chen, Brookline, MA (US)

(73) Assignees: Dana-Farber Cancer Institute, Inc., Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days. days.

(21) Appl. No.: 14/436,387

(22) PCT Filed: Oct. 18, 2013

(86) PCT No.: PCT/US2013/065689
§ 371 (c)(1),
(2) Date: Apr. 16, 2015

(87) PCT Pub. No.: WO2014/063054
PCT Pub. Date: Apr. 24, 2014

(65) Prior Publication Data
US 2015/0246913 A1    Sep. 3, 2015

Related U.S. Application Data

(60) Provisional application No. 61/717,345, filed on Oct. 23, 2012, provisional application No. 61/716,273, filed on Oct. 19, 2012.

(51) Int. Cl.
*C07D 471/04* (2006.01)
(52) U.S. Cl.
CPC ................... *C07D 471/04* (2013.01)
(58) Field of Classification Search
CPC ...... C07D 487/02; C07D 487/04; C07D 3/14; A61K 31/4162
USPC ............................................ 546/80; 514/290
See application file for complete search history.

(56) References Cited

U.S. PATENT DOCUMENTS

| | | |
|---|---|---|
| 4,231,938 A | 11/1980 | Monaghan et al. |
| 4,270,537 A | 6/1981 | Romaine et al. |
| 4,596,556 A | 6/1986 | Morrow et al. |
| 4,782,084 A | 11/1988 | Vyas et al. |
| 4,790,824 A | 12/1988 | Morrow et al. |
| 4,885,314 A | 12/1989 | Vyas et al. |
| 4,886,499 A | 12/1989 | Cirelli et al. |
| 4,940,460 A | 7/1990 | Casey et al. |
| 4,941,880 A | 7/1990 | Burns et al. |
| 5,015,235 A | 5/1991 | Crossman et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,420,245 A | 5/1995 | Brown et al. |
| 5,466,220 A | 11/1995 | Brenneman et al. |
| 5,480,381 A | 1/1996 | Weston et al. |
| 5,484,596 A | 1/1996 | Hanna et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hocolowski et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |

(Continued)

FOREIGN PATENT DOCUMENTS

| | | |
|---|---|---|
| CA | 2486101 A1 | 11/2003 |
| CA | 2503646 A1 | 5/2004 |

(Continued)

OTHER PUBLICATIONS

International Search Report and Written Opinion for PCT/US2012/065618, dated Mar. 19, 2013.

(Continued)

Primary Examiner — Rita J Desai
(74) Attorney, Agent, or Firm — Wolf, Greenfield & Sacks, P.C.

(57) ABSTRACT

The present invention provides novel compounds of Formula (I), and pharmaceutically acceptable salts, solvates, hydrates, polymorphs, co-crystals, tautomers, stereoisomers, isotopically labeled derivatives, prodrugs, and compositions thereof. Also provided are methods and kits involving the compounds of Formula (I) or (II), or compositions thereof, for treating or preventing a wide range of diseases (e.g., proliferative diseases (e.g., cancers, benign neoplasms, angiogenesis, inflammatory diseases, autoimmune diseases) and metabolic diseases (e.g., diabetes (e.g., type 2 diabetes, gestational diabetes)) in a subject. Treatment of a subject with a disease using a compound of Formula (I) or (II), or compositions thereof, may downregulate the expression and/or inhibit the activity of a kinase (e.g., a tyrosine kinase, such as a Tec kinase, in particular, bone marrow on X chromosome kinase (BMX)), and therefore, suppress tyrosine kinase singling in the subject.

37 Claims, 31 Drawing Sheets

(56) References Cited

U.S. PATENT DOCUMENTS

| | | |
|---|---|---|
| 5,750,567 A | 5/1998 | Baudoin et al. |
| 5,756,466 A | 5/1998 | Bemis et al. |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,921,763 B2 | 7/2005 | Hirst et al. |
| 6,939,874 B2 | 9/2005 | Harmange et al. |
| 6,992,089 B2 | 1/2006 | LaVoie et al. |
| 7,115,617 B2 | 10/2006 | Buchanan et al. |
| 7,312,225 B2 | 12/2007 | Luecking et al. |
| 7,319,105 B2 | 1/2008 | LaVoie et al. |
| 7,884,117 B2 | 2/2011 | Zhang et al. |
| 7,928,140 B2 | 4/2011 | Booker et al. |
| 8,088,781 B2 | 1/2012 | Honigberg et al. |
| 8,394,818 B2 * | 3/2013 | Gray ............... C07D 471/04 514/292 |
| 8,765,747 B2 | 7/2014 | Choi et al. |
| 8,889,706 B2 * | 11/2014 | Gray ............... C07D 471/04 514/292 |
| 8,987,275 B2 | 3/2015 | Gray et al. |
| 9,180,127 B2 | 11/2015 | Gray et al. |
| 9,358,231 B2 | 6/2016 | Gray et al. |
| 9,382,239 B2 | 7/2016 | Gray et al. |
| 9,505,784 B2 | 11/2016 | Choi et al. |
| 2003/0139416 A1 | 7/2003 | Buchanan et al. |
| 2004/0102443 A1 | 5/2004 | LaVoie et al. |
| 2004/0106634 A1 | 11/2004 | Yujia et al. |
| 2005/0250837 A1 | 11/2005 | D'Mello et al. |
| 2006/0106083 A1 | 5/2006 | Martina et al. |
| 2006/0189627 A1 | 8/2006 | Laird et al. |
| 2006/0199804 A1 | 9/2006 | Hummersone et al. |
| 2007/0093537 A1 | 4/2007 | Hynes et al. |
| 2007/0185171 A1 | 8/2007 | Germain et al. |
| 2007/0225286 A1 | 9/2007 | Ren et al. |
| 2007/0281907 A1 | 12/2007 | Watkins |
| 2008/0039629 A1 | 2/2008 | Ramesh et al. |
| 2008/0045538 A1 | 2/2008 | LaVoie et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0300267 A1 | 12/2008 | Okram et al. |
| 2009/0054392 A1 | 2/2009 | Pelletier et al. |
| 2009/0082346 A1 | 3/2009 | Brasca et al. |
| 2009/0105250 A1 | 4/2009 | Sim et al. |
| 2010/0197688 A1 | 8/2010 | Nantermet et al. |
| 2011/0086858 A1 | 4/2011 | Wang et al. |
| 2011/0098280 A1 | 4/2011 | Garcia-Echeverria et al. |
| 2011/0178070 A1 | 7/2011 | Gong et al. |
| 2011/0212053 A1 | 9/2011 | Qian et al. |
| 2011/0230476 A1 | 9/2011 | Niu et al. |
| 2011/0288091 A1 | 11/2011 | Gray et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0190676 A1 | 7/2012 | Moorman et al. |
| 2012/0202809 A1 | 8/2012 | Li et al. |
| 2012/0277248 A1 | 11/2012 | Caruso et al. |
| 2012/0329771 A1 | 12/2012 | Treu et al. |
| 2013/0040949 A1 | 2/2013 | Gray et al. |
| 2013/0184264 A1 | 7/2013 | Bradner et al. |
| 2014/0303112 A1 | 10/2014 | Chen et al. |
| 2014/0309249 A1 | 10/2014 | Gray et al. |
| 2015/0094315 A1 | 4/2015 | Choi et al. |
| 2015/0157629 A1 | 6/2015 | Gray et al. |
| 2015/0166532 A1 * | 6/2015 | Gray ............... C07D 519/00 514/267 |
| 2015/0274728 A1 | 10/2015 | Gray et al. |
| 2016/0046636 A1 | 2/2016 | Gray et al. |
| 2016/0122323 A1 | 5/2016 | Gray et al. |
| 2016/0368910 A1 | 12/2016 | Gray et al. |
| 2017/0044111 A1 | 2/2017 | Gray et al. |
| 2017/0044112 A1 | 2/2017 | Gray et al. |

FOREIGN PATENT DOCUMENTS

| | | |
|---|---|---|
| CA | 2526430 A1 | 12/2004 |
| CA | 2550128 A1 | 6/2005 |
| CA | 2563212 A1 | 10/2005 |
| CN | 101128440 A | 2/2008 |
| EP | 0604181 | 12/1993 |
| EP | 0618221 | 3/1994 |
| EP | 0675112 | 3/1995 |
| EP | 0696593 | 8/1995 |
| EP | 1 935 890 A1 | 6/2008 |
| EP | 2 311 842 A2 | 4/2011 |
| GB | 796524 A | 6/1958 |
| JP | 2003-503481 A | 1/2003 |
| JP | 2008-500320 A | 5/2004 |
| JP | 2004-529140 A | 9/2004 |
| JP | 2005-501860 A | 1/2005 |
| JP | 2005-505535 | 2/2005 |
| JP | 2005-530711 A | 10/2005 |
| JP | 2005-534635 A | 11/2005 |
| JP | 2005-538100 A | 12/2005 |
| JP | 2006-521394 | 9/2006 |
| JP | 2007-500226 A | 1/2007 |
| JP | 2007-500725 A | 1/2007 |
| JP | 2008-501669 A | 1/2008 |
| JP | 2008-502610 A | 1/2008 |
| JP | 2009-510110 A | 3/2009 |
| JP | 2010-511655 A | 4/2010 |
| JP | 2010-521487 A | 6/2010 |
| JP | 2011-516533 A | 5/2011 |
| JP | 2012-530071 A | 11/2012 |
| JP | 2016-533379 | 10/2016 |
| JP | 2016-533379 A | 10/2016 |
| JP | 2017-504651 | 2/2017 |
| JP | 2017-504651 A | 2/2017 |
| MX | 2016/009974 | 10/2016 |
| MX | 2016-009974 A | 10/2016 |
| MX | 2016/009975 | 10/2016 |
| MX | 2016-009975 A | 10/2016 |
| MX | 2016/009976 | 11/2016 |
| MX | 2016-009976 A | 11/2016 |
| WO | WO 1984/02131 A1 | 6/1984 |
| WO | WO 1994/19357 | 9/1994 |
| WO | WO 1995/08542 | 3/1995 |
| WO | WO 1995/10514 | 4/1995 |
| WO | WO 1995/10515 | 4/1995 |
| WO | WO 1995/10516 | 4/1995 |
| WO | WO 1995/11917 | 5/1995 |
| WO | WO 1995/12572 | 5/1995 |
| WO | WO 1995/12612 | 5/1995 |
| WO | WO 1995/25086 | 9/1995 |
| WO | WO 1995/26412 | 10/1995 |
| WO | WO 1995/32987 | 12/1995 |
| WO | WO 1995/34535 | 12/1995 |
| WO | WO 1996/00736 | 1/1996 |
| WO | WO 1996/05168 | 2/1996 |
| WO | WO 1996/05169 | 2/1996 |
| WO | WO 1996/17861 | 6/1996 |
| WO | WO 1996/21456 | 7/1996 |
| WO | WO 1996/22278 | 7/1996 |
| WO | WO 1996/24611 | 8/1996 |
| WO | WO 1996/30017 | 10/1996 |
| WO | WO 1996/30018 | 10/1996 |
| WO | WO 1996/30343 A1 | 10/1996 |
| WO | WO 1996/30362 | 10/1996 |
| WO | WO 1996/30363 | 10/1996 |
| WO | WO 1996/31111 | 10/1996 |
| WO | WO 1996/31477 | 10/1996 |
| WO | WO 1996/31478 | 10/1996 |
| WO | WO 1996/31501 | 10/1996 |
| WO | WO 1996/33159 | 10/1996 |
| WO | WO 1996/34850 | 11/1996 |
| WO | WO 1996/34851 | 11/1996 |
| WO | WO 1997/00252 | 1/1997 |
| WO | WO 1997/03047 | 1/1997 |

(56) References Cited

FOREIGN PATENT DOCUMENTS

| | | |
|---|---|---|
| WO | WO 1997/03050 | 1/1997 |
| WO | WO 1997/04785 | 2/1997 |
| WO | WO 1997/17070 | 5/1997 |
| WO | WO 1997/18813 | 5/1997 |
| WO | WO 1997/21701 | 6/1997 |
| WO | WO 1997/23478 | 7/1997 |
| WO | WO 1997/26246 | 7/1997 |
| WO | WO 1997/30053 | 8/1997 |
| WO | WO 1997/38665 A1 | 10/1997 |
| WO | WO 1997/44350 | 11/1997 |
| WO | WO 1998/02436 | 1/1998 |
| WO | WO 1998/28980 | 7/1998 |
| WO | WO 1998/29119 | 7/1998 |
| WO | WO 2000/44777 | 8/2000 |
| WO | WO 2000/50032 A1 | 8/2000 |
| WO | WO 2000/61186 | 10/2000 |
| WO | WO 2001/02369 A2 | 1/2001 |
| WO | WO 2001/019829 A2 | 3/2001 |
| WO | WO 02/076986 A1 | 10/2002 |
| WO | WO 02/079197 A1 | 10/2002 |
| WO | WO 02/080926 A1 | 10/2002 |
| WO | WO 02/096905 A1 | 12/2002 |
| WO | WO 02/102800 A1 | 12/2002 |
| WO | WO 2003/018021 A1 | 3/2003 |
| WO | WO 2003/018022 A1 | 3/2003 |
| WO | WO 03/026664 A1 | 4/2003 |
| WO | WO 2003/041660 A2 | 5/2003 |
| WO | WO 2003/051847 | 6/2003 |
| WO | WO 2003/078403 A2 | 9/2003 |
| WO | WO 2003/097610 A1 | 11/2003 |
| WO | WO 2004/005283 A1 | 1/2004 |
| WO | WO 2004/009601 A1 | 1/2004 |
| WO | WO 2004/010995 A1 | 2/2004 |
| WO | WO 2004/014906 A2 | 2/2004 |
| WO | WO 2004/014918 A1 | 2/2004 |
| WO | WO 2004/039796 A1 | 5/2004 |
| WO | WO 2004/078757 A2 | 9/2004 |
| WO | WO 2004/087699 A2 | 10/2004 |
| WO | WO 2004/100868 A2 | 11/2004 |
| WO | WO 2004/113303 A1 | 12/2004 |
| WO | WO 2004/113304 A1 | 12/2004 |
| WO | WO 2005/011597 A2 | 2/2005 |
| WO | WO 2005/058891 A1 | 6/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2006/065448 A2 | 6/2006 |
| WO | WO 2006/122806 A2 | 11/2006 |
| WO | WO 2007/002325 A1 | 1/2007 |
| WO | WO 2007/002433 A1 | 1/2007 |
| WO | WO 2007/002931 A2 | 1/2007 |
| WO | WO 2007/024680 A1 | 3/2007 |
| WO | WO 2007/035428 A1 | 3/2007 |
| WO | WO 2007/042786 A2 | 4/2007 |
| WO | WO 2007/048070 A2 | 4/2007 |
| WO | WO 2007/075869 A2 | 7/2007 |
| WO | WO 2007/087395 A2 | 8/2007 |
| WO | WO 2007/106503 A2 | 9/2007 |
| WO | WO 2007/129195 A2 | 11/2007 |
| WO | WO 2007/138277 A1 | 12/2007 |
| WO | WO 2008/063888 A2 | 5/2008 |
| WO | WO 2008/068171 A1 | 6/2008 |
| WO | WO 2008/074749 A1 | 6/2008 |
| WO | WO 2008/080015 A2 | 7/2008 |
| WO | WO 2008/112913 A1 | 9/2008 |
| WO | WO 2008/124393 A1 | 10/2008 |
| WO | WO 2008/144253 A1 | 11/2008 |
| WO | WO 2008/151183 A1 | 12/2008 |
| WO | WO 2009/017822 A2 | 2/2009 |
| WO | WO 2009/028655 A1 | 3/2009 |
| WO | WO 2009/032694 A1 | 3/2009 |
| WO | WO 2009/145360 A1 | 12/2009 |
| WO | WO 2009/155017 A2 | 12/2009 |
| WO | WO 2010/008847 A2 | 1/2010 |
| WO | WO 2010/044885 A2 | 4/2010 |
| WO | WO 2010/051781 A1 | 5/2010 |
| WO | WO 2010/125799 A1 | 11/2010 |
| WO | WO 2010/144909 A1 | 12/2010 |
| WO | WO 2011/115725 A2 | 9/2011 |
| WO | WO 2013/014162 A1 | 1/2013 |
| WO | WO 2013/040436 A2 | 3/2013 |
| WO | WO 2013/074986 A1 | 5/2013 |
| WO | WO 2013/136070 A1 | 9/2013 |
| WO | 2013154778 * 10/2013 | ........... C07D 471/04 |
| WO | WO 2013/154778 A1 | 10/2013 |
| WO | WO 2014/063054 A1 | 4/2014 |
| WO | WO 2014/063054 A8 | 4/2014 |
| WO | WO 2014/063061 A1 | 4/2014 |
| WO | WO 2014/063068 A1 | 4/2014 |
| WO | WO 2015/013635 | 1/2015 |
| WO | WO 2015/013635 A2 | 1/2015 |
| WO | WO 2015/058140 A1 | 4/2015 |
| WO | WO 2015/117087 A1 | 8/2015 |
| WO | WO 2015/154022 A1 | 10/2015 |
| WO | WO 2015/164604 A1 | 10/2015 |
| WO | WO 2015/164614 A1 | 10/2015 |
| WO | WO 2016/014542 A1 | 1/2016 |
| WO | WO 2016/014551 A1 | 1/2016 |
| WO | WO 2016/023014 A2 | 2/2016 |
| WO | WO 2015/058126 A1 | 4/2016 |
| WO | WO 2016/105528 A2 | 6/2016 |

OTHER PUBLICATIONS

International Preliminary Report on Patentability for PCT/US2012/065618, dated May 30, 2014.

International Search Report and Written Opinion for PCT/US2013/065708, dated Feb. 4, 2014.

International Preliminary Report on Patentability for PCT/US2013/065708, dated Apr. 30, 2015.

International Search Report and Written Opinion for PCT/US2013/065689, dated Mar. 4, 2014.

International Preliminary Report on Patentability for PCT/US2013/065689, dated Apr. 30, 2015.

International Search Report and Written Opinion for PCT/US2013/065698, dated Feb. 20, 2014.

International Preliminary Report on Patentability for PCT/US2013/065698, dated Apr. 30, 2015.

International Search Report and Written Opinion for PCT/US2014/061232, dated Dec. 23, 2014.

International Search Report and Written Opinion for PCT/US2015/027312, dated Jul. 10, 2015.

International Search Report and Written Opinion for PCT/US2015/027294, dated Jul. 10, 2015.

Invitation to Pay Additional Fees for PCT/US2015/041360, dated Sep. 24, 2015.

Extended European Search Report for EP 10786967.9, dated Oct. 23, 2012.

International Search Report and Written Opinion for PCT/US2010/038518, dated Aug. 6, 2010.

International Preliminary Report on Patentability for PCT/US2010/038518, dated Dec. 22, 2011.

Extended European Search Report for EP 10844280.7, dated Apr. 17, 2013.

Partial European Search Report for EP 15160591.2, dated Jul. 1, 2015.

International Search Report and Written Opinion for PCT/US2010/062310, dated Oct. 4, 2011.

International Preliminary Report on Patentability for PCT/US2010/062310, dated Jul. 12, 2012.

Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.

(56) References Cited

OTHER PUBLICATIONS

Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials. 16 pages.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Smith et al., The effect of the nature of the amine leaving group on the nature of the E2 transition state for the reaction of 1-phenylethylammonium ions sodium ethoxide in ethanol. Mar. 28, 1989;67:1457-67.
Stanovnik et al., The Tautomerism of Heterocycles: Substituent Tautomerism of Six-Membered Ring Heterocycles. Advances in Heterocyclic Chemistry. 2006;91:1-134.
Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.
Zhang et al., Discovery of potent and selective covalent inhibitors of JNK. Chem Biol. Jan. 27, 2012;19(1):140-54. doi: 10.1016/j.chembiol.2011.11.010.
International Search Report and Written Opinion for PCT/US2013/032488, dated Jun. 5, 2013.
International Preliminary Report on Patentability for PCT/US2013/032488, dated Oct. 23, 2014.
Invitation to Pay Additional Fees for PCT/US2015/041360 dated Sep. 24, 2015.
International Search Report and Written Opinion for PCT/US2015/041360 dated Dec. 15, 2015.
International Search Report and Written Opinion for PCT/US2015/41348 dated Oct. 28, 2015.
Extended European Search Report for EP 15160591.2, dated Nov. 2, 2015.
International Search Report and Written Opinion for PCT/US2015/000297, dated Mar. 4, 2016.
International Search Report and Written Opinion for PCT/US2016/037086, dated Sep. 2, 2016.
Invitation to Pay Additional Fees for PCT/US2016/024345, dated Aug. 9, 2016.
Invitation to Pay Additional Fees for PCT/US2015/044387, dated Jan. 28, 2016.
International Search Report and Written Opinion for PCT/US2015/044387, dated Mar. 25, 2016.
CAS Registry No. 916173-61-0, STN Entry Date Dec. 21, 2006.
CAS Registry No. 769961-42-4, STN Entry Date Oct. 27, 2004.
CAS Registry No. 769961-59-3, STN Entry Date Oct. 27, 2004.
PubChem-CID-68365059. Available at https://pubchem.ncbi.nlm.nih.gov/compound/68365059. Accessed Jun. 17, 2016.
Bain et al., The selectivity of protein kinase inhibitors: a further update. Biochem J. Dec. 15, 2007;408(3):297-315.
Berge et al., Pharmaceutical salts. J. Pharmaceutical Sciences 1977 66:1-19.
Carter et al., Inhibition of drug-resistant mutants of ABL, KIT, and EGF receptor kinases. Proc Natl Acad Sci U S A. Aug. 2, 2005;102(31):11011-6. Epub Jul. 26, 2005.
Chen et al., Tyrosine kinase BMX phosphorylates phosphotyrosine-primed motif mediating the activation of multiple receptor tyrosine kinases. Sci Signal. May 28, 2013;6(277):ra40.
Chong et al., Positive and negative regulation of Raf kinase activity and function by phosphorylation EMBO J. Jul. 16, 2001;20(14):3716-27.
Christensen et al., Targeting transcriptional addictions in small cell lung cancer with a covalent CDK7 inhibitor. Cancer Cell. Dec. 8, 2014;26(6):909-22.
Chu et al., c-Src protein kinase inhibitors block assembly and maturation of dengue virus. Proc Natl Acad Sci U S A. Feb. 27, 2007;104(9):3520-5. Epub Feb. 21, 2007.
Cohen et al., Structural bioinformatics-based design of selective, irreversible kinase inhibitors. Science. May 27, 2005;308(5726):1318-21.
Davies et al., Mutations of the BRAF gene in human cancer Nature. Jun. 27, 2002;417(6892):949-54. Epub Jun. 9, 2002.
Davis et al., Comprehensive analysis of kinase inhibitor selectivity. Nat Biotechnol. Oct. 30, 2011;29(11):1046-51. doi: 10.1038/nbt.1990.
Downward, Targeting RAS signalling pathways in cancer therapy Nat Rev Cancer. Jan. 2003;3(1):11-22.
Ercan et al., Reactivation of ERK signaling causes resistance to EGFR kinase inhibitors. Cancer Discov. Oct. 2012;2(10):934-47.
Fabian et al., A small molecule-kinase interaction map for clinical kinase inhibitors. Nat Biotechnol. Mar. 2005;23(3):329-36. Epub Feb. 13, 2005.
Feng et al., Synthesis of N-substituted 5-[2-(N alkylamino)ethyl]dibenzo[c,h][1,6]naphthyridines as novel topoisomerase I-targeting antitumor agents. Bioorg Med Chem. Oct. 15, 2008;16(20):9295-301. Epub Sep. 5, 2008.
Filippakopoulos et al., Selective inhibition of BET bromodomains. Nature. Dec. 23, 2010;468(7327):1067-73.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fry et al., Specific inhibition of cyclin-dependent kinase 4/6 by PD 0332991 and associated antitumor activity in human tumor xenografts. Mol Cancer Ther. Nov. 2004;3(11):1427-38.
Galkin et al., Identification of NVP-TAE684, a potent, selective, and efficacious inhibitor of NPM-ALK. Proc Natl Acad Sci U S A. Jan. 2, 2007;104(1):270-5. Epub Dec. 21, 2006. Erratum in: Proc Natl Acad Sci U S A. Feb. 6, 2007;104(6):2025.
Garnett et al., Guilty as charged: B-RAF is a human oncogene Cancer Cell. Oct. 2004;6(4):313-9.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Goldstein et al., High-throughput kinase profiling as a platform for drug discovery. Nat Rev Drug Discov. May 2008;7(5):391-7. doi:10.1038/nrd2541.

(56) References Cited

OTHER PUBLICATIONS

Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Henise et al., Irreversible Nek2 kinase inhibitors with cellular activity. J Med Chem. Jun. 23, 2011;54(12):4133-46. doi: 10.1021/jm200222m. Epub May 31, 2011.
Honigberg et al., The Bruton tyrosine kinase inhibitor PCI-32765 blocks B-cell activation and is efficacious in models of autoimmune disease and B-cell malignancy. Proc Natl Acad Sci U S A. Jul. 20, 2010;107(29):13075-80. doi: 10.1073/pnas.1004594107. Epub Jul. 6, 2010.
Huang et al., Finding new components of the target of rapamycin (TOR) signaling network through chemical genetics and proteome chips. Proc Natl Acad Sci U S A. Nov. 23, 2004;101(47):16594-9. Epub Nov. 11, 2004.
Johnson et al., Strategies for discovering and derisking covalent, irreversible enzyme inhibitors. Future Med Chem. Jun. 2010;2(6):949-64.
Kantarjian et al., Dasatinib versus imatinib in newly diagnosed chronic-phase chronic myeloid leukemia. N Engl J Med. Jun. 17, 2010;362(24):2260-70.
Karaman et al., A quantitative analysis of kinase inhibitor selectivity. Nat Biotechnol. Jan. 2008;26(1):127-32. doi: 10.1038/nbt1358.
King et al., Demonstration of a genetic therapeutic index for tumors expressing oncogenic BRAF by the kinase inhibitor SB-590885. Cancer Res. Dec. 1, 2006;66(23):11100-5.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Kontopidis et al., Differential binding of inhibitors to active and inactive CDK2 provides insights for drug design. Chem Biol. Feb. 2006;13(2):201-11.
Kwak et al., Irreversible inhibitors of the EGF receptor may circumvent acquired resistance to gefitinib. Proc Natl Acad Sci U S A. May 24, 2005;102(21):7665-70. Epub May 16, 2005.
Kwiatkowski et al., Small-molecule kinase inhibitors provide insight into Mps1 cell cycle function. Nat Chem Biol. May 2010;6(5):359-68. doi: 10.1038/nchembio.345. Epub Apr. 11, 2010.
Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 2014;33(1):1-9. doi: 10.1038/onc.2013.34. Epub Feb. 18, 2013.
Leproult et al., Cysteine mapping in conformationally distinct kinase nucleotide binding sites: application to the design of selective covalent inhibitors. J Med Chem. Mar. 10, 2011;54(5):1347-55. doi: 10.1021/jm101396q. Epub Feb. 15, 2011.
Lin et al., Phase II study of flavopiridol in relapsed chronic lymphocytic leukemia demonstrating high response rates in genetically high-risk disease. J Clin Oncol. Dec. 10, 2009;27(35):6012-8.
Liu et al., Discovery of 9-(6-aminopyridin-3-yl)-1-(3-(trifluoromethyl)phenyl)benzo[h][1,6]naphthyridin-2(1H)-one (Torin2) as a potent, selective, and orally available mammalian target of rapamycin (mTOR) inhibitor for treatment of cancer. J Med Chem. Mar. 10, 2011;54(5):1473-80. doi: 10.1021/jm101520v.
Liu et al., Rational design of inhibitors that bind to inactive kinase conformations. Nat Chem Biol. Jul. 2006;2(7):358-64.
Mallinson et al., Macrocycles in new drug discovery. Future Med Chem. Jul. 2012;4(11):1409-38. doi: 10.4155/fmc.12.93.
March, Advanced Organic Chemistry Reactions, Mechanisms and Structure. 4th ed. 1992:383-386.
Miduturu et al., High-throughput kinase profiling: a more efficient approach toward the discovery of new kinase inhibitors. Chem Biol. Jul. 29, 2011;18(7):868-79. doi: 10.1016/j.chembiol.2011.05.010.
Panchal et al., Identification of an antioxidant small-molecule with broad-spectrum antiviral activity. Antiviral Res. Jan. 2012;93(1):23-9.doi:10.1016/j.antiviral.2011.10.011.Epub Oct. 18, 2011.

Pelech, Hitting the right kinase targets: protein kinase selection for drug discovery. Bioforum Eur. Jun. 2008;12(6):36-8.
Ranson, ZD1839 (Iressa): for more than just non-small cell lung cancer. Oncologist. Aug. 2002;7 Suppl 4:16-24.
Reid et al., Dual inhibition of ErbB1 (EGFR/HER1) and ErbB2 (HER2/neu). Eur J Cancer. Feb. 2007;43(3):481-9. Epub Jan. 8, 2007.
Rewcastle et al., Tyrosine kinase inhibitors. 5. Synthesis and structure-activity relationships for 4-[(phenylmethyl)amino]- and 4-(phenylamino)quinazolines as potent adenosine 5'-triphosphate binding site inhibitors of the tyrosine kinase domain of the epidermal growth factor receptor. J Med Chem. Sep. 1, 1995;38(18):3482-7.
Savage et al., Imatinib mesylate—a new oral targeted therapy. N Engl J Med. Feb. 28, 2002;346(9):683-93.
Schirmer et al., Targeted covalent inactivation of protein kinases by resorcylic acid lactone polyketides. Proc Natl Acad Sci U S A. Mar. 14, 2006;103(11):4234-9. Epub Mar. 6, 2006.
Sharma et al., A chromatin-mediated reversible drug-tolerant state in cancer cell subpopulations. Cell. Apr. 2, 2010;141(1):69-80.
Singh et al., The resurgence of covalent drugs. Nat Rev Drug Discov. Apr. 2011;10(4):307-17. doi: 10.1038/nrd3410.
Smaill et al., Tyrosine kinase inhibitors. 17. Irreversible inhibitors of the epidermal growth factor receptor: 4-(phenylamino)quinazoline- and 4-(phenylamino)pyrido[3,2-d]pyrimidine-6-acrylamides bearing additional solubilizing functions. J Med Chem. Apr. 6, 2000;43(7):1380-97.
Smith et al., Recent advances in the research and development of RAF kinase inhibitors. Curr. Top Med. Chem. 2006; 6(11):1071-89.
Stauffer et al., Blocking the PI3K/PKB pathway in tumor cells. Curr Med Chem Anticancer Agents. Sep. 2005;5(5):449-62.
Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.
Terai et al., Activation of the FGF2-FGFR1 autocrine pathway: a novel mechanism of acquired resistance to gefitinib in NSCLC. Mol Cancer Res. Jul. 2013;11(7):759-67.
Thoreen et al., An ATP-competitive mammalian target of rapamycin inhibitor reveals rapamycin-resistant functions of mTORC1. J Biol Chem. Mar. 20, 2009;284(12):8023-32. doi: 10.1074/jbc.M900301200. Epub Jan. 15, 2009.
Tsou et al., Optimization of 6,7-disubstituted-4-(arylamino)quinoline-3-carbonitriles as orally active, irreversible inhibitors of human epidermal growth factor receptor-2 kinase activity. J Med Chem. Feb. 24, 2005;48(4):1107-31.
Verheijen et al., Phosphatidylinositol 3-kinase (PI3K) inhibitors as anticancer drugs. Drugs Fut. Jun. 2007;32(6):537-47.
Wang et al., 2-Anilino-4-(thiazol-5-yl)pyrimidine CDK inhibitors: synthesis, SAR analysis, X-ray crystallography, and biological activity. J Med Chem. Mar. 25, 2004;47(7):1662-75.
Weerapana et al., Disparate proteome reactivity profiles of carbon electrophiles. Nat Chem Biol. Jul. 2008;4(7):405-7. doi:10.1038/nchembio.91. Epub May 18. 2008. Erratum in: Nat Chem Biol. Jul. 2008;4(7):following 407.
Weerapana et al., Quantitative reactivity profiling predicts functional cysteines in proteomes. Nature. Dec. 9, 2010;468(7325):790-5. doi: 10.1038/nature09472. Epub Nov. 17, 2010.
Wellbrock et al., The RAF proteins take centre stage Nat Rev Mol Cell Biol. Nov. 2004;5(11):875-85.
Wu et al., Discovery of a potent, covalent BTK inhibitor for B-cell lymphoma. ACS Chem Biol. May 16, 2014;9(5):1086-91. doi: 10.1021/cb4008524. Epub Mar. 17, 2014.
Yang et al., Pharmacological inhibition of BMK1 suppresses tumor growth through promyelocytic leukemia protein. Cancer Cell. Sep. 14, 2010;18(3):258-67. doi:10.1016/j.ccr.2010.08.008. Erratum in: Cancer Cell. Oct. 19, 2010;18(4):396.
Zebisch et al., Back to the roots: the remarkable RAF oncogene story Cell Mol Life Sci. Jun. 2006;63(11):1314-30.
Zhou et al., A structure-guided approach to creating covalent FGFR inhibitors. Chem Biol. Mar. 26, 2010;17(3):285-95. doi: 10.1016/j.chembiol.2010.02.007.
Zhou et al., Novel mutant-selective EGFR kinase inhibitors against EGFR T790M. Nature. Dec. 24, 2009;462(7276):1070-4.

(56) References Cited

OTHER PUBLICATIONS

Kauraniemi et al., New amplified and highly expressed genes discovered in the ERBB2 amplicon in breast cancer by cDNA microarrays. Cancer Res. Nov. 15, 2001;61(22):8235-40.
Kwiatkowski et al., Targeting transcription regulation in cancer with a covalent CDK7 inhibitor. Nature. Jul. 2014; 511:616-20.
Lee et al., BRAF mutations in non-Hodgkin's lymphoma. Br J Cancer. Nov. 17, 2003;89(10):1958-60.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.
Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.
U.S. Appl. No. 15/538,763, filed Jun. 22, 2017, Gray et al.
PCT/US2015/000297, Jul. 6, 2017, International Preliminary Report on Patentability.
International Preliminary Report on Patentability PCT/US2015/000297, dated Jul. 6, 2017.
Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.
U.S. Appl. No. 15/188,545, filed Jun. 21, 2016, Gray et al.
U.S. Appl. No. 14/391,638, filed Oct. 9, 2014, Gray et al.
U.S. Appl. No. 14/552,229, filed Nov. 24, 2014, Gray et al.
U.S. Appl. No. 14/921,894, filed Oct. 23, 2015, Gray et al.
U.S. Appl. No. 15/305,801, filed Oct. 21, 2016, Gray et al.
U.S. Appl. No. 15/305,845, filed Oct. 21, 2016, Gray et al.
U.S. Appl. No. 13/583,974, filed Dec. 5, 2012, Gray et al.
PCT/US2015/027312, dated Nov. 3, 2016, International Preliminary Report on Patentability.
PCT/US2016/024345, dated Oct. 6, 2016, International Search Report and Written Opinion.
PCT/US2016/051118, dated Dec. 1, 2016, Invitation to Pay Additional Fees.
PCT/US2016/051118, dated Mar. 13, 2017, International Search Report and Written Opinion.
PCT/US2011/025423, dated May 31, 2011, Invitation to Pay Additional Fees.
International Preliminary Report on Patentability for PCT/US2015/027312, dated Nov. 3, 2016.
International Search Report and Written Opinion for PCT/US2016/024345, dated Oct. 6, 2016.
Invitation to Pay Additional Fees for PCT/US2016/051118, dated Dec. 1, 2016.
International Search Report and Written Opinion for PCT/US2016/051118, dated Mar. 13, 2017.
Invitation to Pay Additional Fees for PCT/US2011/025423, dated May 31, 2011.
International Search Report and Written Opinion from PCT/US2011/025423, dated Nov. 5, 2012.
International Preliminary Report on Patentability PCT/US2011/025423, dated Nov. 29, 2012.
CAS Registry No. 1334419-59-8, STN Entry Date Dec. 30, 2013.
GenBank Accession No. M80629. Lapidot-Lifson et al., Dec. 31, 1994. 2 pages.
GenBank Accession No. NP_001790. Yang et al., Oct. 6, 2016. 4 pages.
Uniprot No. Q9NYV4. Last modified Mar. 15, 2017. 14 pages.
Akhtar et al., TFIIH kinase places bivalent marks on the carboxy-terminal domain of RNA polymerase II. Mol Cell. May 15, 2009;34(3):387-93. doi: 10.1016/j.molcel.2009.04.016.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13/2541. Epub Nov. 15, 2013.

Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Bell et al., Integrated genomic analyses of ovarian carcinoma. Nature. Jun. 29, 2011;474(7353):609-15. doi: 10.1038/nature10166.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.
Benezra et al., In vivo angiogenic activity of interleukins. Archives of Opthamology 1990;108:573.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bosken et al., The structure and substrate specificity of human Cdk12/Cyclin K. Nat Commun. Mar. 24, 2014;5:3505. doi: 10.1038/ncomms4505.
Brower et al., Tumor Angiogenesis: New drugs on the block. Nature Biotechnology 1999;17:963-8.
Brunton et al., eds., Chemotherapy of Neoplastic Diseases. In Goodman & Gilman's The Pharmacological Basis of Therapeutics. 2008; 11th edition:853-908.
Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Chakraborty et al., Developmental expression of the cyclo-oxygenase-1 and cyclo-oxygenase-2 genes in the peri-implantation mouse uterus and their differential regulation by the blastocyst and ovarian steroids. Journal of Molecular Endocrinology 1996;16:107-122.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Chiarugi et al., Cox-2, iNOS and p53 as play-makers of tumor angiogenesis. International Journal of Molecular Medicine 1998;2:715-9.
Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.
Christian et al., Flavopiridol in chronic lymphocytic leukemia: a concise review. Clin Lymphoma Myeloma. 2009;9 Suppl 3:S179-85. doi: 10.3816/CLM.2009.s.009.
Desai et al., Effects of phosphorylation by CAK on cyclin binding by CDC2 and CDK2. Mol Cell Biol. Jan. 1995;15(1):345-50.
Diaz-Flores et al., Intense vascular sprouting from rat femoral vein induced by prostaglandins E1 and E2. Anatomical Record 1994;238:68-76.
Drapkin et al., Human cyclin-dependent kinase-activating kinase exists in three distinct complexes. Proc Natl Acad Sci U S A. Jun. 25, 1996;93(13):6488-93.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Fernandez et al., Neovascularization produced by angiotensin I. Journal of Laboratory and Clinical Medicine 1985;105(2):141-5.
Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.
Fizazi, The role of Src in prostate cancer. Ann Oncol. Nov. 2007;18(11):1765-73. Epub Apr. 10, 2007.
Fleisher et al., Improved oral drug delivery: solubility limitations overcome by the use of prodrugs. Advanced Drug Delivery Reviews 1996;19:115-30.

(56) References Cited

OTHER PUBLICATIONS

Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hla et al., Human cyclooxygenase-2 cDNA. Proceedings of the National Academy of Sciences 1992;89(16):7384-8.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Kaldis et al., Analysis of CAK activities from human cells. Eur J Biochem. Jul. 2000;267(13):4213-21.
Kauraniemi et al., New amplified and highly expressed genes discovered in the ERBB2 amplicon in breast cancer by cDNA microarrays. Cancer Res. Nov. 15, 2011;61(22):8235-40.
Kim et al., Inhibition of vascular endothelial growth factor-induced angiogenesis suppresses tumour growth in vivo. Nature 1993;362:841.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Larochelle et al., Requirements for Cdk7 in the assembly of Cdk1/cyclin B and activation of Cdk2 revealed by chemical genetics in human cells. Mol Cell. Mar. 23, 2007;25(6):839-50.
Lavis et al., Bright ideas for chemical biology. ACS Chem Biol. Mar. 20, 2008;3(3):142-55. doi: 10.1021/cb700248m.
Liu et al., Two cyclin-dependent kinases promote RNA polymerase II transcription and formation of the scaffold complex. Mol Cell Biol. Feb. 2004;24(4):1721-35.
Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.
Majima et al., Significant Roles of Inducible Cyclooxygenase (COX)-2 in Angiogenesis in Rat Sponge Implants. Japanese Journal of Pharmacology 1997;75;105-14.
Marques et al., A new subfamily of high molecular mass CDC2-related kinases with PITAI/VRE motifs. Biochem Biophys Res Commun. Dec. 29, 2000;279(3):832-7.
Mukaiyama et al., The unexpected and the unpredictable in organic synthesis. Tetrahedron Jul. 1999;55(29):8609-70.
Neklesa et al., Small-molecule hydrophobic tagging-induced degradation of HaloTag fusion proteins. Nat Chem Biol. Jul. 3, 2011;7(8):538-43. doi: 10.1038/nchembio.597.
Obenauf et al., Therapy-induced tumour secretomes promote resistance and tumour progression. Nature. Apr. 16, 2015;520(7547):368-72. doi: 10.1038/nature14336. Epub Mar. 25, 2015.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.
Seed et al., The Inhibition of colon-26 Adenocarcinoma Development and Angiogenesis by Topical Diclofenac in 2.5% Hyaluronan. Cancer Research 1997;57:1625-9.
Serizawa et al., Association of Cdk-activating kinase subunits with transcription factor TFIIH. Nature. Mar. 16, 1995;374(6519):280-2.
Shiekhattar et al., Cdk-activating kinase complex is a component of human transcription factor TFIIH. Nature. Mar. 16, 1995;374(6519):283-7.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Tsujii et al., Cyclooxygenase regulates angiogenesis induced by colon cancer cells. Cell. May 29, 1998;93(5):705-16.
Wang et al., Ligand-associated ERBB2/3 activation confers acquired resistance to FGFR inhibition in FGER3-dependent cancer cells. Oncogene. Apr. 23, 2015;34(17):2167-77. doi: 10.1038/onc.2014.161. Epub Jun. 9, 2014.
Wilen et al., Strategies in optical resolutions. Tetrahedron 33:2725 (1977).
Xin et al., Peroxisome proliferator-activated receptor gamma ligands are potent inhibitors of angiogenesis in vitro and in vivo. Journal of Biological Chemistry 1996;274(13):9116-21.
Yalpani, Cholesterol Lowering Drugs. Chemistry and Industry Feb. 1996;3:85-89.
Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.
Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.
Ziche et al., Role of prostaglandin E1 and copper in angiogenesis. Journal of the National Cancer Institute 1982;69(2):475.
PCT/US2011/ 025423, dated Nov. 5, 2012, International Search Report and Written Opinion.
PCT/US2011/025423, dated Nov. 29, 2012, International Preliminary Report on Patentability.
PCT/US2013/032488, dated Jun. 5, 2013, International Search Report and Written Opinion.
PCT/US2013/032488, dated Oct. 23, 2014, International Preliminary Report on Patentability.
PCT/US2015/041360, dated Sep. 24, 2015, Invitation to Pay Additional Fees.
PCT/US2015/041360, dated Dec. 15, 2015, International Search Report and Written Opinion.
PCT/US2015/041348, dated Oct. 28, 2015, International Search Report and Written Opinion.
EP 15160591.2, dated Nov. 2, 2015, Partial European Search Report.
PCT/US2015/000297, dated Mar. 4, 2016, International Search Report and Written Opinion.
PCT/US2016/037086, dated Sep. 2, 2016, International Search Report and Written Opinion.
PCT/US2016/024345, dated Aug. 9, 2016, Invitation to Pay Additional Fees.
PCTfUS2015/044387, dated Jan. 28, 2016, Invitation to Pay Additional Fees.
PCT/US2015/044387, dated Mar. 25, 2016, International Search Report and Written Opinion.

\* cited by examiner

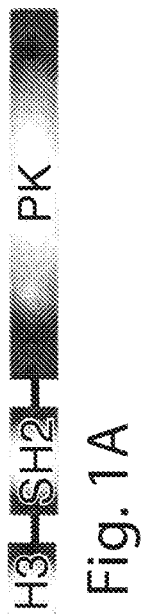

Fig. 1A

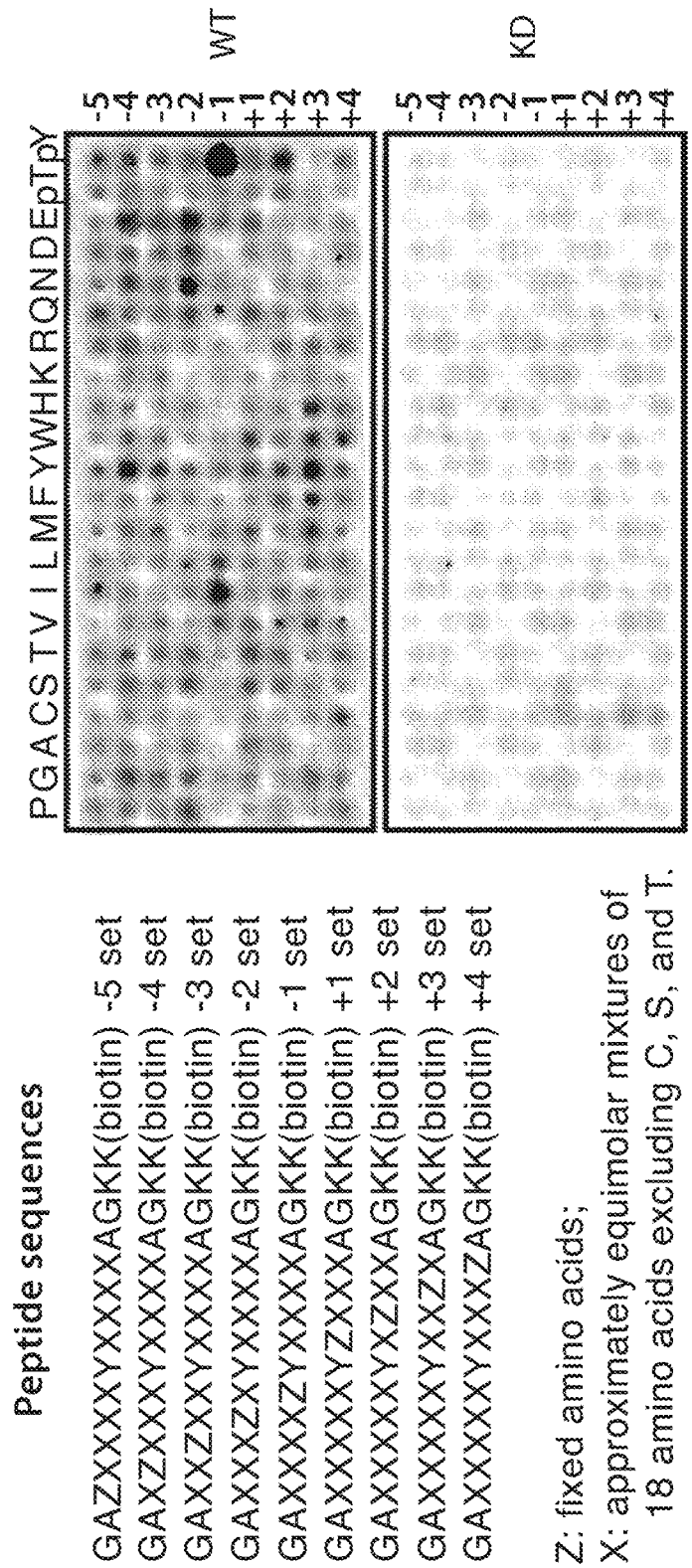

Peptide sequences

GAZXXXYXXXXAGKK(biotin) -5 set
GAXZXXYXXXXAGKK(biotin) -4 set
GAXXZXYXXXXAGKK(biotin) -3 set
GAXXXZYXXXXAGKK(biotin) -2 set
GAXXXXZYXXXXAGKK(biotin) -1 set
GAXXXXYZXXXAGKK(biotin) +1 set
GAXXXXYXZXXAGKK(biotin) +2 set
GAXXXXYXXZXAGKK(biotin) +3 set
GAXXXXYXXXZAGKK(biotin) +4 set Z: fixed amino acids;
X: approximately equimolar mixtures of
18 amino acids excluding C, S, and T.

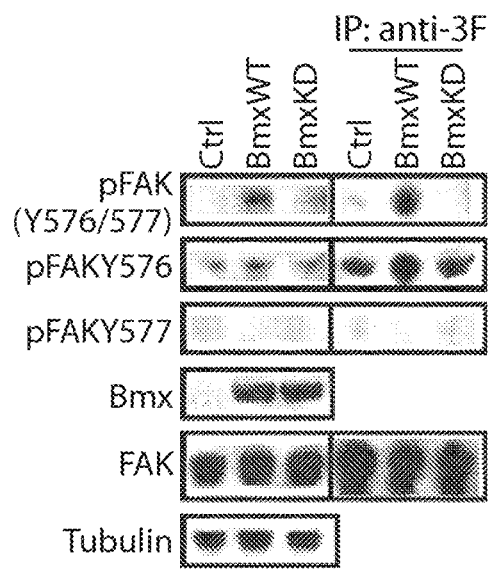
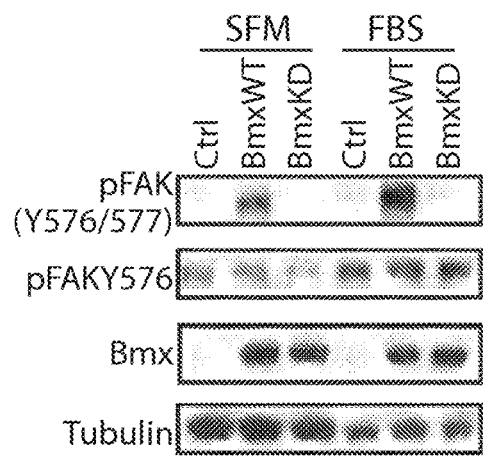
Fig. 1E
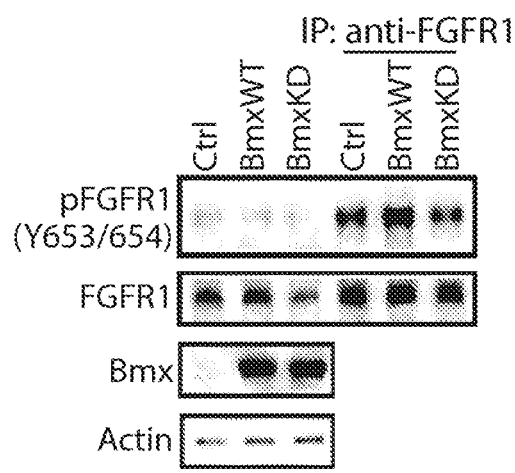
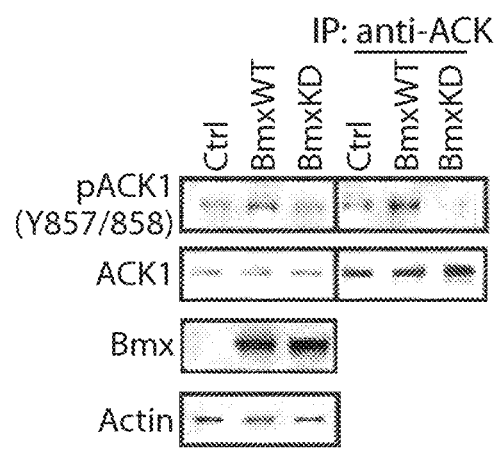
Fig. 1F      Fig. 1G

| | |
|---|---|
| Y194 | EKKSNYEVLE |
| Y441 | VHQGIYMSPE |
| Y576 | MEDSTYYKASY |
| Y576/577 | MEDSTYYKASY |
| Y742 | VQINHYDVSG |
| Y861 | GNQHIYIPVG |
| Y898 | SPADSYNEGV |
| Y925 | SNDKVYENVI |
| Y1007 | KLAQQYVMTSY |

Fig. 2A

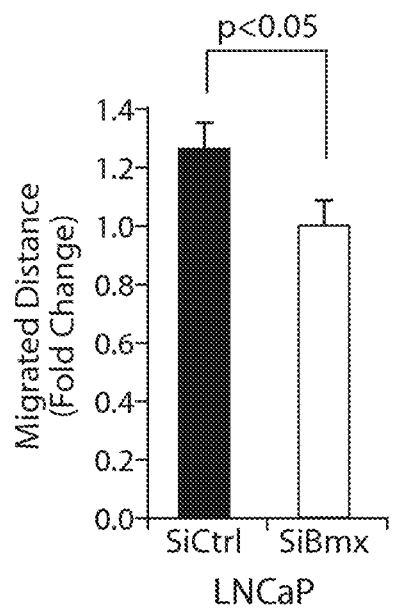
Fig. 12
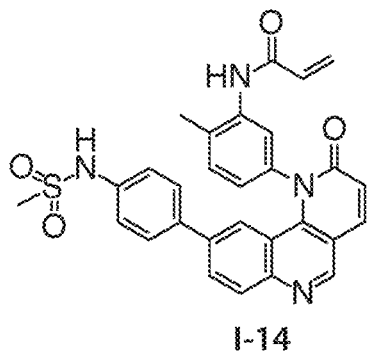
I-14
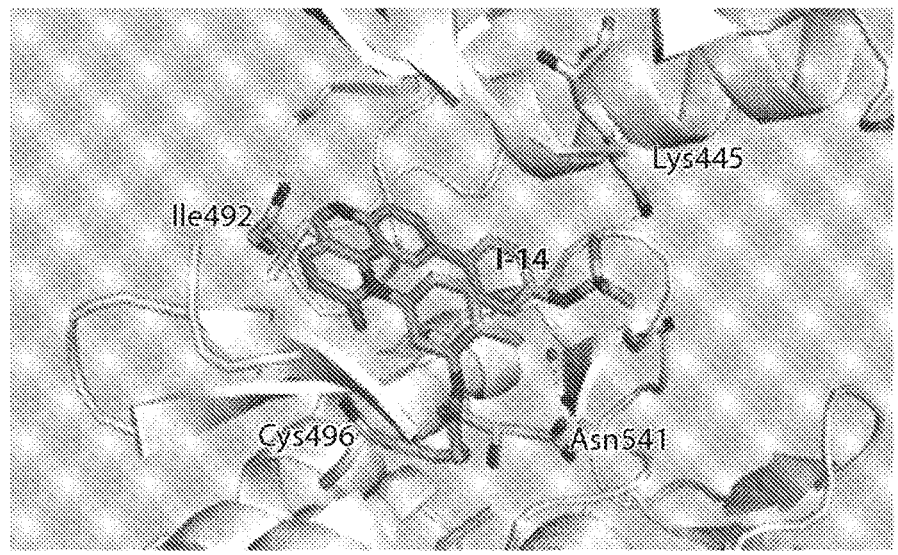
Fig. 13

Cysteine residues to which the compounds
of Formula (I) or (II) may attach

| | |
|---|---|
| EGFR_EGFR | V Q L I T Q L M P F G C L L D Y V R |
| EGFR_HER2/ErbB2 | V Q L V T Q L M P Y G C L L D H V R |
| EGFR_HER4/ErbB4 | I Q L V T Q L M P H G C L L E Y V H |
| JakA_JAK3 | L R L V M E Y L P S G C L R D F L Q |
| Src_BLK | I Y I V T E Y M A R G C L L D F L K |
| CAMKL_LKB1 | Q K M Y M V M E Y C V C G M Q E M L |
| Tec_BMX | I Y I V T E Y I S N G C L L N Y L R |
| Tec_BTK | I F I I T E Y M A N G C L L N Y L R |
| Tec_TEC | I Y I V T E F M E R G C L L N F L R |
| Tec_TXK | L Y I V T E F M E N G C L L N Y L R |
| Tec_ITK | I C L V F E F M E H G C L S D Y L R |

Fig. 14

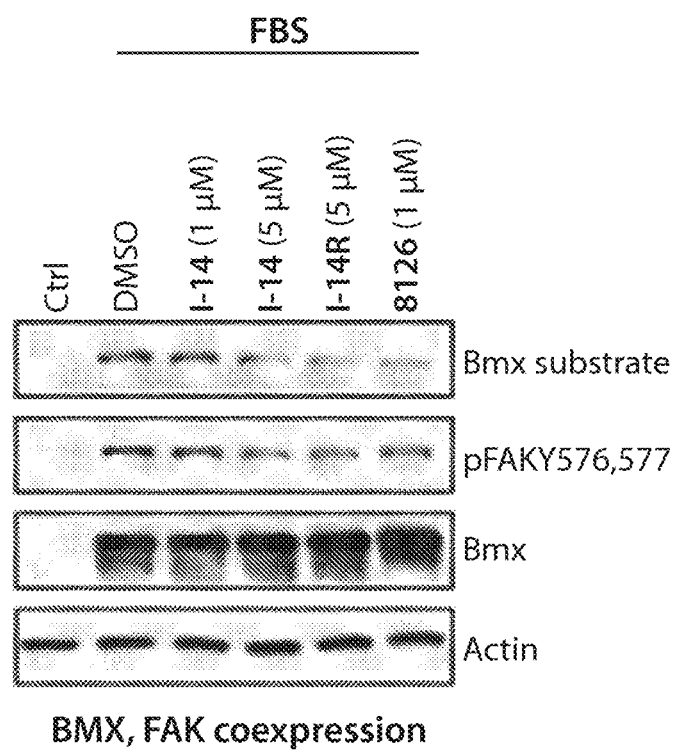
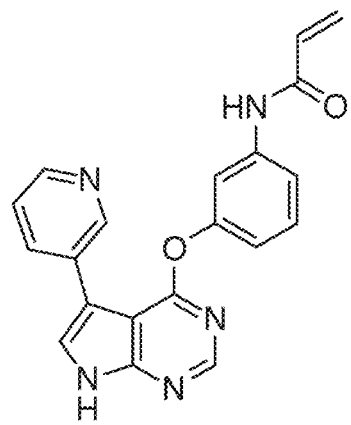
8126 (WZ8126)
Fig. 17A

BONE MARROW ON X CHROMOSOME KINASE (BMX) INHIBITORS AND USES THEREOF

RELATED APPLICATIONS

This application is a national stage filing under 35 U.S.C § 371 of international PCT application, PCT/US2013/065689, filed Oct. 18, 2013, which claims priority under 35 U.S.C. § 119(e) to U.S. Provisional Patent Applications, U.S. Ser. No. 61/716,273, filed Oct. 19, 2012, and U.S. Ser. No. 61/717,345, filed Oct. 23, 2012, each of which are incorporated herein by reference.

GOVERNMENT SUPPORT

This invention was made with government support under grant number W81XWH-09-1-0435 awarded by the U.S. Department of the Army. The government has certain rights in the invention.

BACKGROUND OF THE INVENTION

"Bone Marrow on X chromosome" kinase (BMX, also termed ETK) is a non-receptor tyrosine kinase and is activated downstream of phosphatidylinositol-3 kinase (PI-3K) and v-src sarcoma (Schmidt-Ruppin A-2) viral oncogene homolog (SRC), but its substrates are unknown. Positional scanning peptide library screening revealed a marked preference for a priming phosphotyrosine (pY) in the −1 position. Potential substrates include multiple tyrosine kinases with kinase domain pYpY sites required for full activity. BMX has been found to phosphorylate residue Y577 of focal adhesion kinase (FAK) subsequent to Y576 phosphorylation by SRC. In addition, BMX loss by RNA interference and mouse embryonic fibroblasts (MEFs) from Bmx negative (Bmx⁻) mice displayed impaired FAK signaling. Insulin receptor (IR) phosphorylation similarly was decreased by BMX loss, as was hepatic IR phosphorylation in Bmx⁻ mice. However, glucose tolerance was increased, reflecting a marked compensatory decrease in the activity of the AKT phosphatase PHLPP. These findings reveal a mechanism through which BMX functions as a central regulator of multiple kinase pathways.

Tec kinases, which include TEC, BTK, ITK, RLK/TXK, and BMX, are non-receptor tyrosine kinases expressed primarily in lymphoid and myeloid lineages. They are related in structure to SRC in that they have an SH3 domain followed by an SH2 domain and tyrosine kinase domain but lack the C-terminal tyrosine that negatively regulates SRC kinases (Afar et al., *Mol. Cell. Biol.* 16, 3465 (1996); Andreotti et al., *Nature* 385, 93 (1997); Nore et al., *Biochim. Biophys. Acta* 1645, 123 (2003); Park et al., *Immunity* 4, 515 (1996)). (FIG. 1A). The Tec kinases are unique in having a pleckstrin homology (PH) domain that mediates membrane targeting in response to PI-3K activation by binding to phosphatidylinositol 3,4,5-triphosphate ($PIP_3$) (Qiu et al., *Oncogene* 19, 5651 (2000)), which results in SRC-mediated phosphorylation of a kinase domain tyrosine that activates the enzyme. Mutations in BTK, which is restricted to B cells, cause X-linked agammaglobulinemia (de Weers et al., *Hum. Mol. Genet.* 3, 161 (1994)), while loss of ITK expressed in T cells results in a variety of T cell defects (Andreotti et al., *Cold Spring Harb. Perspect. Biol.* 2, a002287 (2010)). BMX is broadly expressed by cell types outside the lymphoid/myeloid lineage including arterial endothelium and epithelial cells (Chott et al., *Am. J. Pathol.* 155, 1271 (1999); Rajantie et al., *Mol. Cell Biol.* 21, 4647 (2001); Robinson et al., *Proc. Natl. Acad. Sci. U.S.A.* 93, 5958 (1996); Tamagnone et al., *Oncogene* 9, 3683 (1994)). While Bmx⁻ mice have only a modest defect in ischemia-induced angiogenesis (Rajantie et al., *Mol. Cell Biol.* 21, 4647 (2001); He et al., *J. Clin. Invest.* 116, 2344 (2006); Zhang et al., *J. Biol. Chem.* 278, 51267 (2003); Pan et al., *Mol. Cell Biol.* 22, 7512 (2002)), increasing evidence indicates that BMX has diverse modulatory roles in multiple cellular processes (Tu et al., *Cancer Res.* 68, 2861 (2008); Jiang et al., *J. Biol. Chem.* 279, 50181 (2004); Kim et al., *J. Biol. Chem.* 277, 30066 (2002); Bagheri-Yarmand et al., *J. Biol. Chem.* 276, 29403 (2001); Chau et al., *Oncogene* 21, 8817 (2002); Semaan et al., *J. Immunol.* 180, 3485 (2008)). However, the direct downstream targets of BMX remain elusive, and substrate motifs for BMX and other Tec kinases have not been identified.

SUMMARY OF THE INVENTION

The present invention is based, at least in part, on the discovery that BMX functions to amplify tyrosine kinase signaling by phosphorylation of kinase domain pYY sites. The initial priming tyrosine phosphorylation may be mediated by autophosphorylation in response to hormone binding or by other kinases (such as SRC for FAK). BMX may be recruited through its SH2 domain and mediate transphosphorylation to achieve full activation. While acute down-regulation of BMX may suppress multiple signal transduction pathways, downstream signaling may be enhanced in response to some stimuli. Therefore, BMX inhibitors may be useful in treating and/or preventing a range of proliferative diseases (e.g., cancers, benign neoplasms, angiogenesis, inflammatory diseases, and autoimmune diseases) that are associated with increased tyrosine kinase signaling. Conversely, chronic exposure to BMX inhibitors may also enhance signaling downstream of some receptor tyrosine kinases and may be efficacious in treating and/or preventing diseases associated with insulin resistance (e.g., diabetes (e.g., type 2 diabetes and gestational diabetes)). The present invention provides BMX inhibitors, and pharmaceutical compositions thereof, as well as methods of using and preparing the inventive BMX inhibitors.

In one aspect, the present invention provides inhibitors of BMX or other kinases (e.g., Tec kinases, tyrosine kinases, non-receptor tyrosine kinases). In certain embodiments, the present invention provides compounds of Formula (I):

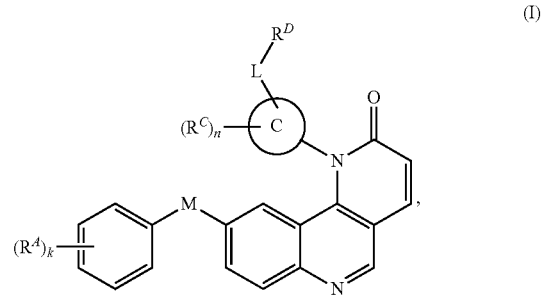

and pharmaceutically acceptable salts, solvates, hydrates, polymorphs, co-crystals, tautomers, stereoisomers, isotopically labeled derivatives, and prodrugs thereof.

Exemplary compounds of Formula (I) include, but are not limited to:

(I-7)
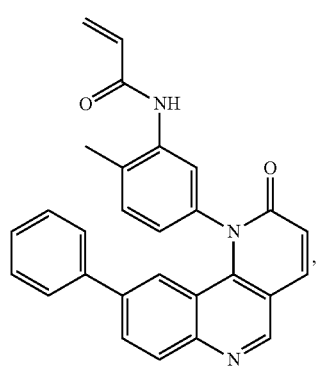
(I-8)
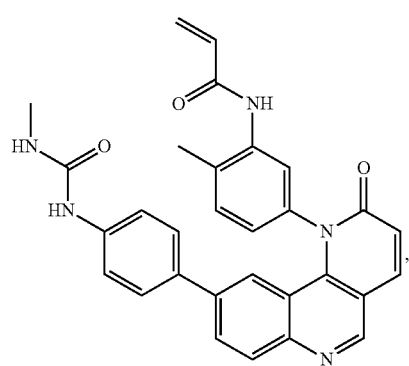
(I-9)
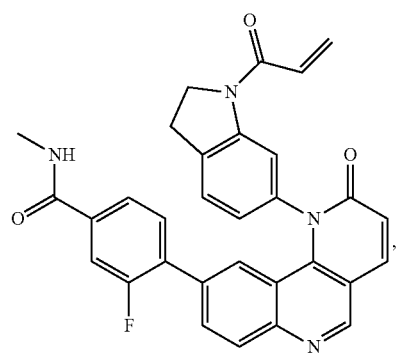
(I-10)
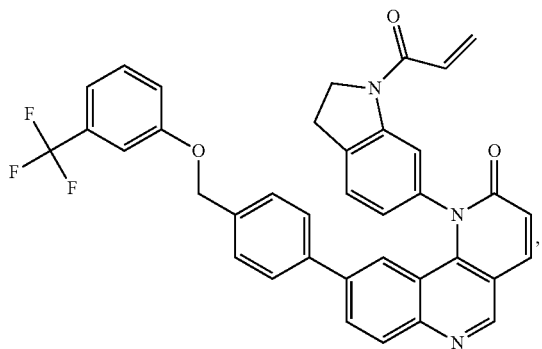
(I-11)
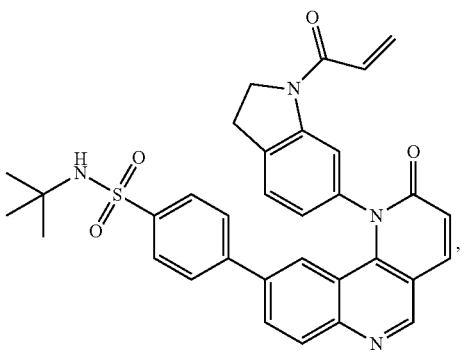
(I-12)
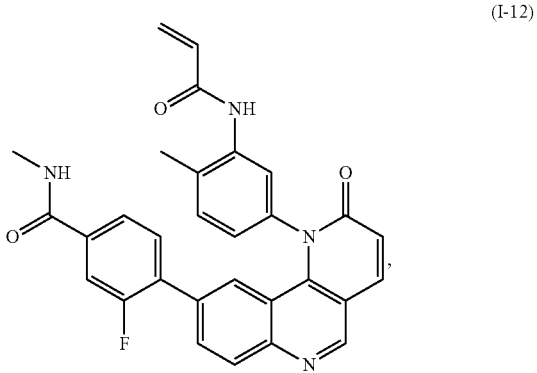
(I-13)
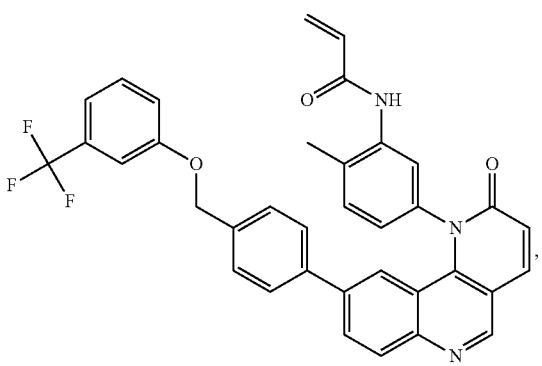
(I-14)
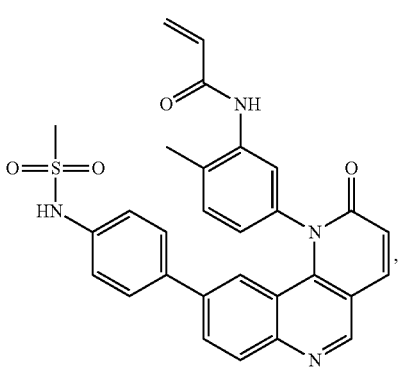

(I-15)
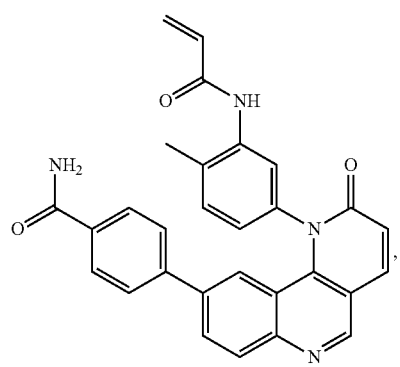
(I-16)
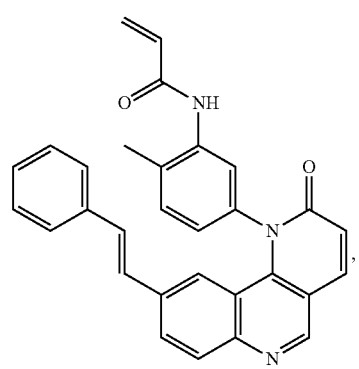
(I-17)
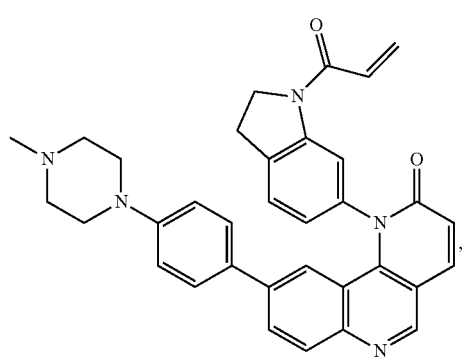
(I-18)
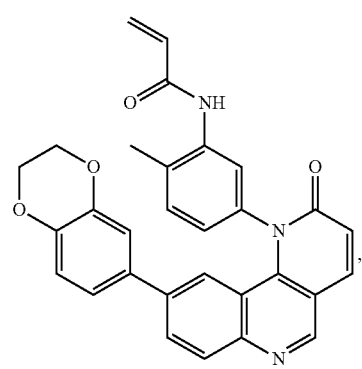
(I-19)
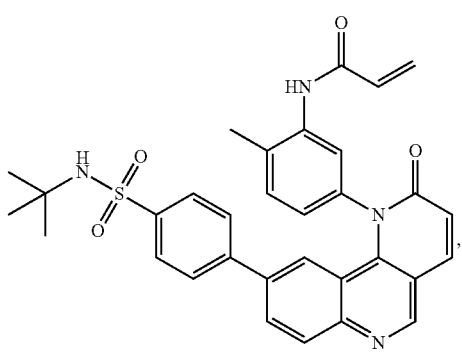
(I-20)
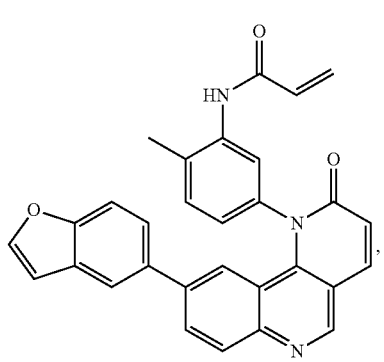
(I-21)
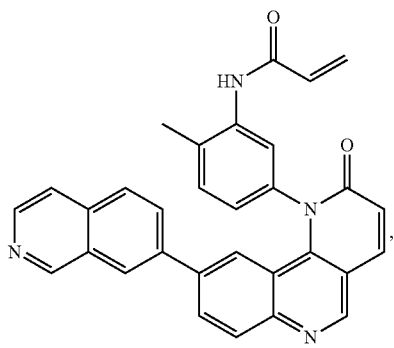
(I-22)
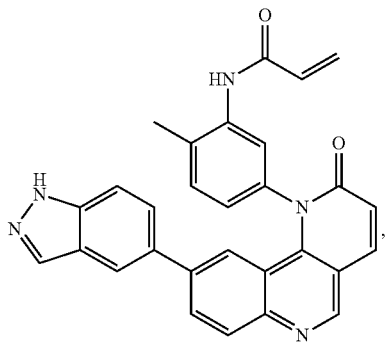

(I-23)
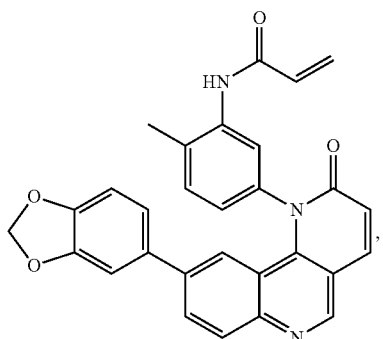

(I-24)
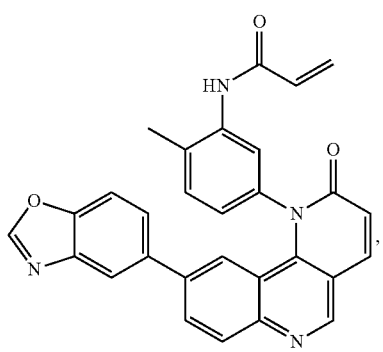

(I-25)
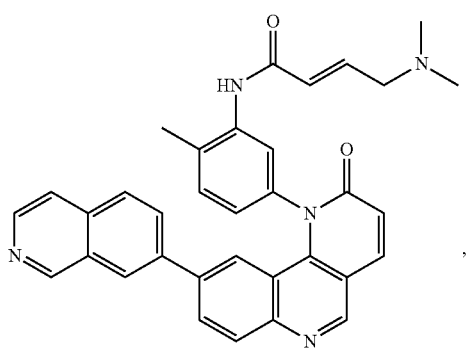

(I-26)
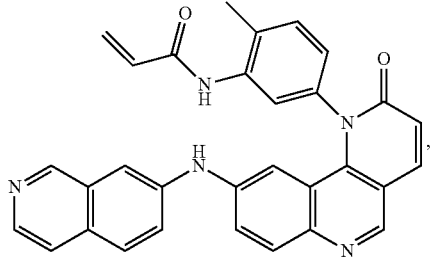

(I-27)
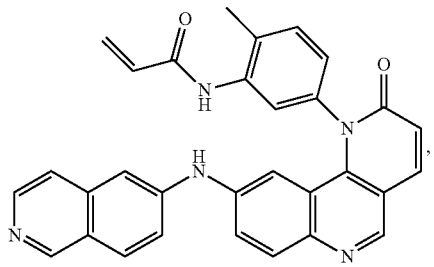

(I-28)
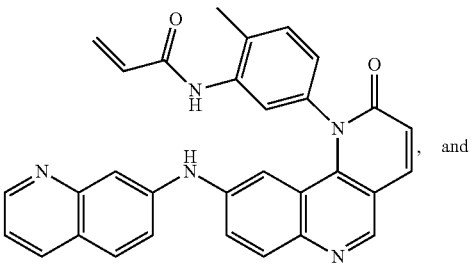

, and (I-28)
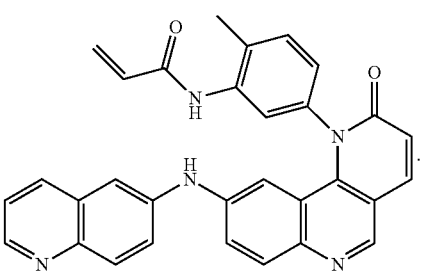

.

In another aspect, the present invention provides pharmaceutical compositions comprising a compound of Formula (I), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of Formula (I), or a pharmaceutically acceptable salt, solvate, hydrate, polymorph, co-crystal, tautomer, stereoisomer, isotopically labeled derivative, or prodrug thereof.

Compounds of Formula (I) or (II):

(II)
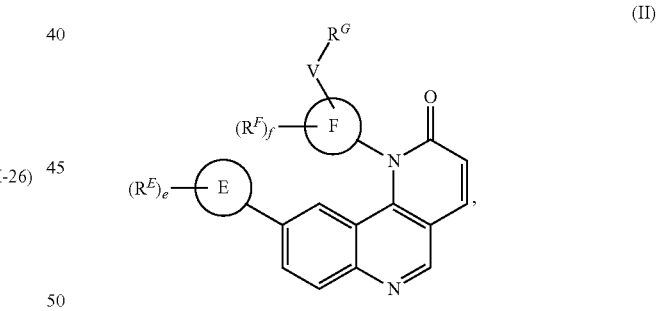

, and compositions thereof, have been found to inhibit the activity of a kinase. Compounds of Formula (II) are described in U.S. Provisional Patent Application, U.S. Ser. No. 61/622,828, filed Apr. 11, 2012, which is incorporated in its entirety by reference. In certain embodiments, the compounds of Formula (I) or (II) are inhibitors of one or more kinases. In certain embodiments, the kinase is a tyrosine kinase. In certain embodiments, the kinase is a non-receptor tyrosine kinase. In certain embodiments, the kinase is a Tec kinase. In certain embodiments, the Tec kinase is Tec, BTK, Itk, Rlk/TXK and/or Bmx. In certain embodiments, the kinase is BMX. The present invention further provides methods of using compounds of Formula (I) or (II), and compositions thereof, to study the inhibition of BMX and as therapeutics for the prevention and/or treatment of diseases associated with the overexpression, increased activity, and/or aberrant activity of BMX, or insulin resistance. In certain embodiments, compounds of Formula (I) or (II) are used for the prevention and/or treatment of a variety of diseases (e.g. proliferative diseases (e.g., cancers, benign neoplasms, angiogenesis, inflammatory diseases, autoimmune diseases) and metabolic diseases (e.g., diabetes (e.g., type 2 diabetes and gestational diabetes))) in a subject.
Exemplary compounds of Formula (II) include, but are not limited to:
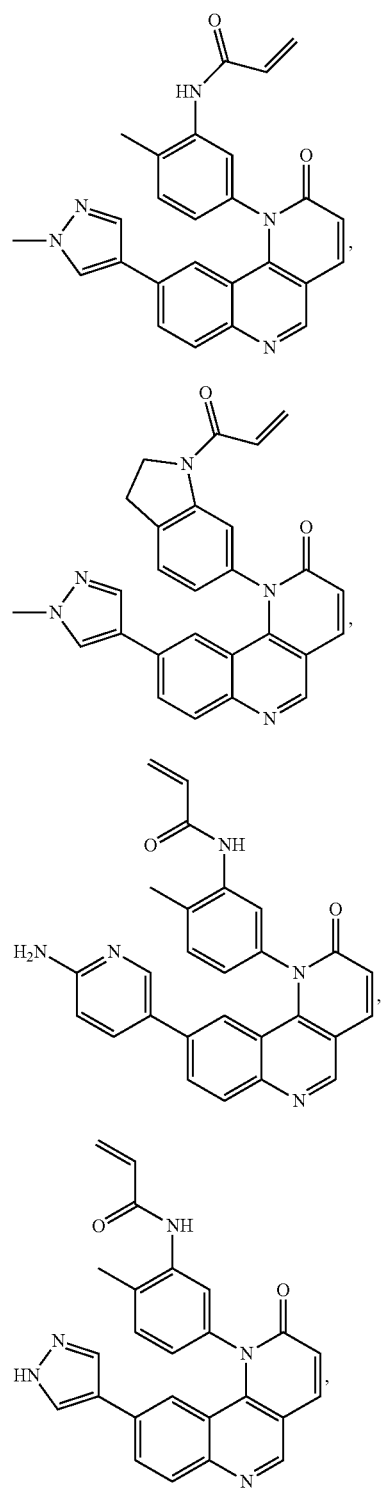
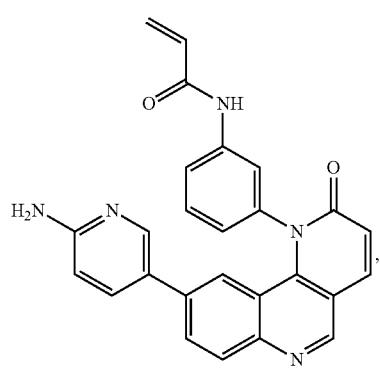
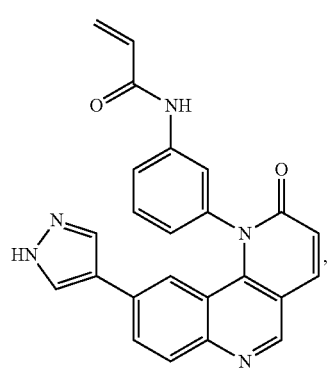
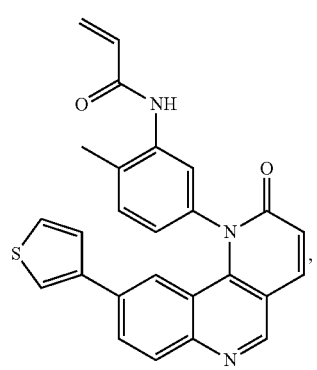

(II-11)
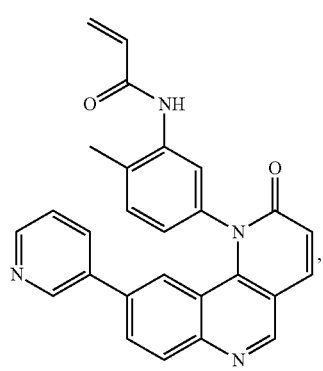
(II-12)
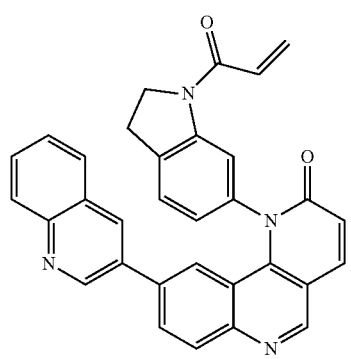
(II-13)
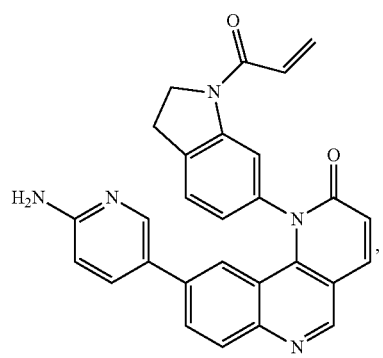
(II-14)
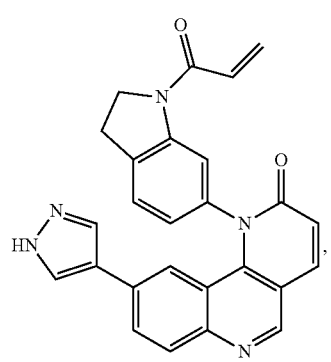
(II-15)
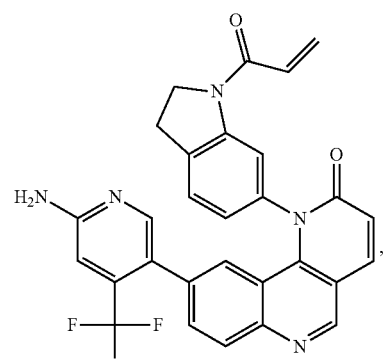
(II-16)
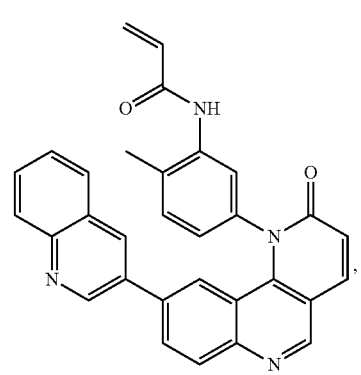
(II-17)
(II-18)
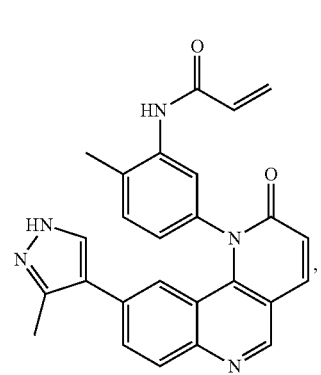

(II-19)

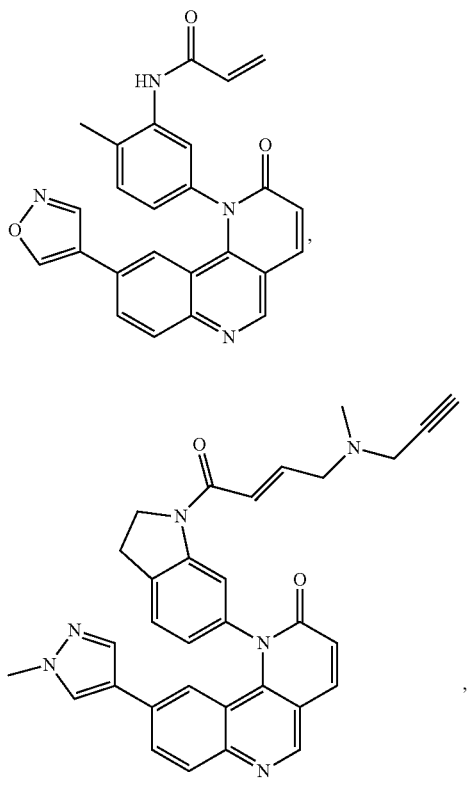

(II-20)

(II-21)

(II-22)

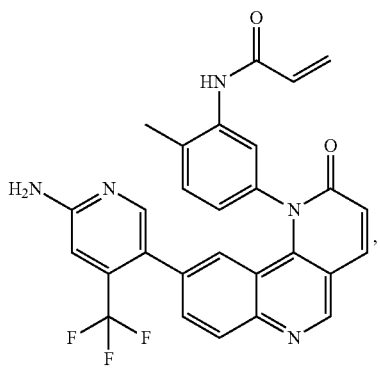

(II-23)

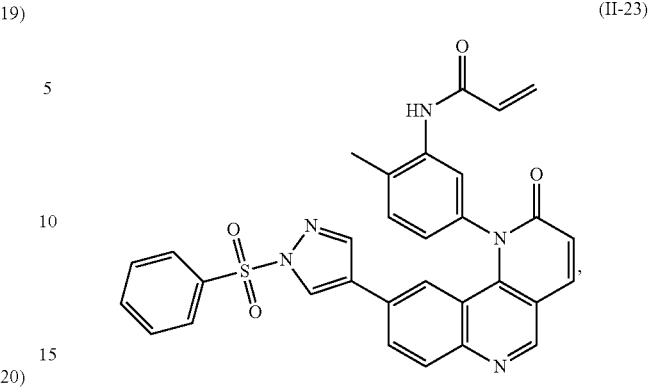

and pharmaceutically acceptable salts, solvates, hydrates, polymorphs, co-crystals, tautomers, stereoisomers, isotopically labeled derivatives, and prodrugs compositions thereof.

In still another aspect, the present invention provides methods of downregulating the expression of a kinase (e.g., a tyrosine kinase (e.g., a non-receptor tyrosine kinase, such as a Tec kinase, e.g., TEC, BTK, ITK, RLK/TXK, BMX) in a biological sample or subject.

Another aspect of the invention relates to methods of inhibiting the activity of a kinase (e.g., a tyrosine kinase (e.g., BMX)) in a biological sample or subject.

Also provided in the present invention are methods of suppressing kinase signaling in a biological sample or subject. In certain embodiments, the kinase signaling is tyrosine kinase signaling.

In another aspect, the present invention provides methods of enhancing downstream kinase singling in a biological sample or subject. In certain embodiments, the downstream kinase singling is downstream tyrosine kinase singling.

In certain embodiments, the methods of the present invention comprise administering to a biological sample or subject a compound of Formula (I) or (II), or a pharmaceutically acceptable salt, solvate, hydrate, polymorph, co-crystal, tautomer, stereoisomer, isotopically labeled derivative, or prodrug thereof, or a pharmaceutical composition thereof.

Another aspect of the invention relates to methods of screening a library of compounds of Formula (I) or (II) to identify one or more compounds that are useful in the treatment and/or prevention of a disease (e.g., proliferative disease (e.g., cancer, benign neoplasm, angiogenesis, inflammatory diseases, and autoimmune diseases) or diabetes (e.g., type 2 diabetes and gestational diabetes)) in a subject.

In yet another aspect, the present invention provides compounds of Formula (I) or (II), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., proliferative disease (e.g., cancer, benign neoplasm, angiogenesis, inflammatory diseases, and autoimmune diseases) or diabetes (e.g., type 2 diabetes and gestational diabetes)) in a subject.

Another aspect of the present invention relates to kits comprising a container with a compound of Formula (I) or (II), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of Formula (I) or (II), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for the treatment and/or prevention of a proliferative disease (e.g., cancer (e.g., leukemia, melanoma, multiple myeloma), benign neoplasm, angiogenesis, inflammatory diseases, and autoimmune diseases) in a subject. In certain embodiments, the kits described herein further include instructions for administering the compound of Formula (I) or (II), or the pharmaceutically acceptable salt, solvate, hydrate, polymorph, co-crystal, tautomer, stereoisomer, isotopically labeled derivative, or prodrug thereof, or the pharmaceutical composition thereof.

The details of particular embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds of Formula (I) or (II) can comprise one or more asymmetric centers, and thus can exist in various isomeric forms, e.g., enantiomers and/or diastereomers. For example, the compounds of Formula (I) or (II) can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, a "hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —C$^A$H(C$^B$H$_2$C$^C$H$_3$)— includes only one carbon unit C$^A$. The term "$C_x$ hydrocarbon chain," wherein x is a positive integer, refers to a hydrocarbon chain that includes x number of carbon unit(s) between the two radicals of the hydrocarbon chain. If there are more than one possibility of x, the smallest possibility of x is used for the definition of the hydrocarbon chain. For example, —CH(C$_2$H$_5$)— is a $C_1$ hydrocarbon chain, and

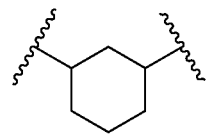 [SMILES: *C1CCCC(*)C1]

is a $C_3$ hydrocarbon chain. When a range of values is used, e.g., a $C_{1-6}$ hydrocarbon chain, the meaning of the range is as described herein. A hydrocarbon chain may be saturated (e.g., —(CH$_2$)$_4$—). A hydrocarbon chain may also be unsaturated and include one or more C═C and/or C≡C bonds anywhere in the hydrocarbon chain. For instance, —CH═CH(CH$_2$)$_2$—, —CH$_2$—, —C≡C—CH$_2$—, —C≡C—CH═CH— are all examples of a unsubstituted and unsaturated hydrocarbon chain. In certain embodiments, the hydrocarbon chain is unsubstituted (e.g., —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

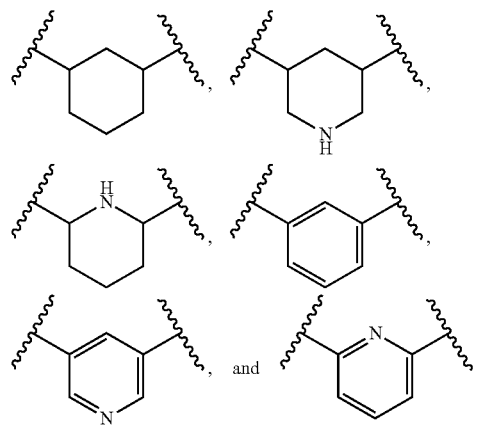

are all examples of hydrocarbon chains. In contrast,

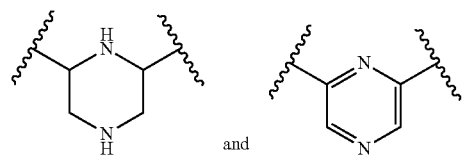 [SMILES: *C1CNCC(*)N1 ; *c1cncc(*)n1]

are not within the scope of the hydrocarbon chains described herein. "Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2\text{-}6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix-ene, e.g., alkylene, alkenylene, alkynylene, carbocyclylene, heterocyclylene, arylene, and heteroarylene.

As used herein, the term "optionally substituted" refers to substituted or unsubstituted.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-5}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_6$14 aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxido, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxyl)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, alkoxy, N,O-dimethylhydroxylamino, pixyl, and haloformates. In certain embodiments, the leaving group is —OS(=O)$_r$R$^{z1}$; wherein R$^{z1}$ is selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl; and r is 1 or 2. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{14}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) or (II) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2 H$_2$O) and hexahydrates (R·6 H$_2$O)).

The term "tautomers" refer to compounds that are interchangeable forms of a particular compound structure, and that vary in the displacement of hydrogen atoms and electrons. Thus, two structures may be in equilibrium through the movement of πi electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I) or (II), which have cleavable groups and become by solvolysis or under physiological conditions the compounds of Formula (I) or (II), which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I).

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," as used herein refers to implanting, absorbing, ingesting, injecting, or inhaling an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formula (I) or (II) refers to an amount sufficient to elicit the desired biological response, i.e., treating the condition. As will be appreciated by those of ordinary skill in this art, the effective amount of a compound of Formula (I) or (II) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I) or (II) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I) or (II) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein, the term "cancer" refers to a malignant neoplasm (Stedman's Medical Dictionary, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyosifis, pemphigus, pemphigoid, diabetes (e.g., Type I), myasthenia gravis, Hashimoto's thyroditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomylitis, optic neuritis, temporal arteritis, transverse myelitis, necrotizing fascilitis, and necrotizing enterocolitis.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications that decrease the immune response. Exemplary autoimmune diseases include, but are not limited to, glomerulonephritis, Goodspature's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis, Sjogren's syndrome, Crohn's disease, Reiter's syndrome, ankylosing spondylitis, Lyme arthritis, Guillain-Barre syndrome, Hashimoto's thyroiditis, and cardiomyopathy.

As used herein, "diabetes," or "diabetes mellitus," is a group of metabolic diseases in which a subject has high blood sugar levels, either because the body of the subject does not produce enough insulin, or because cells in the body do not respond to the insulin that is produced by the body. These high blood sugar levels produce the classical symptoms of polyuria (frequent urination), polydipsia (increased thirst), and polyphagia (increased hunger). There are three main types of diabetes. Type 1 diabetes results from the body's failure to produce insulin and presently requires the subject to be administered insulin. Insulin resistance also plays a role in the type 1 diabetes disease process. For example, the onset of type 1 diabetes is often heralded by an antecedent illness and/or the onset of puberty, both conditions associated with insulin resistance. Type 2 diabetes results from insulin resistance, a condition in which cells fail to use insulin properly, sometimes combined with an absolute insulin deficiency. Some women develop gestational diabetes, a third type of diabetes, in the middle to late stages of pregnancy. Gestational diabetes is typically caused by the hormones of pregnancy or a shortage of insulin. Decreased maternal pregravid insulin sensitivity (insulin resistance) coupled with an inadequate insulin response are the chief pathophysiological mechanisms underlying the development of gestational diabetes.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those non-human biological samples that are transgenic, such as transgenic non-human oocyte, sperm cell, blastocyst, embryo, fetus, donor cell, or cell nucleus.

A "protein" or "peptide" comprises a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be just a fragment of a naturally occurring protein or peptide. A protein may be naturally occurring, recombinant, or synthetic, or any combination of these.

As used herein "kinase" refers to a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation and proliferation. There are estimated to be about 2,000 distinct protein kinases in the human body and although each of these phosphorylate particular protein/peptide substrates, they all bind the same second substrate ATP in a highly conserved pocket. About 50% of the known oncogene products are protein tyrosine kinases PTKs and their kinase activity has been shown to lead to cell transformation.

Preferably the kinase is a tyrosine kinase. As used herein "tyrosine kinase" refers to an enzyme that phosphorylates a tyrosine residue on a protein using ATP as a substrate. In some embodiments, the tyrosine kinase is a non-receptor tyrosine kinase. The mammalian nonreceptor tyrosine kinases (NRTKs) are divided into ten families: Src, Abl, Jak, Ack, Csk, Fak, Fes, Frk, Tec, and Syk. In addition to their tyrosine kinase catalytic domains, they all contain noncatalytic domains that are important in enzyme regulation and substrate recognition. Like all eukaryotic protein kinases, NRTK catalytic domains have an N-terminal lobe (N-lobe) that contacts ATP, and a larger C-terminal lobe (C-lobe). The activation state of the tyrosine kinases depends on the orientation of an alpha helix (αC) located in the N-lobe. In the active conformation, the αC helix projects inward toward the ATP-binding site. The conformation of a flexible segment in the C-lobe (the activation loop) also has a key role in the regulation of the enzyme activity. The regulatory importance of the phosphorylation of the activation loop varies in the different families of NRTKs.

The Tec kinases represent the second largest family of mammalian non-receptor tyrosine kinases and are distinguished by the presence of distinct proline-rich regions and pleckstrin homology domains that are required for proper regualtion and activation. TEC kinases include five family members: TEC, BTK, ITK (also known as TSK), RLK (also known as TXK) and BMX.

Tec kinase participates as a signal transducer in multiple downstream pathways, including regulation of the actin cytoskekleton. It plays a redundant role to ITK in regulation of the adaptive immune response. It also regulates the development, function and differentiation of conventional T-cells and nonconventional NKT-cells, and is involved in both growth and differentiation mechanisms of myeloid cells through activation by the granulocyte colony-stimulating factor (GCSF)3. Tec is involved in G protein-coupled receptor- and integrin-mediated signalings in blood platelets, and also plays a role in hepatocyte proliferation and liver regeneration.

Bruton's tyrosine kinase (BTK) is a key signaling enzyme expressed in all hematopoietic cells types except T lymphocytes and natural killer cells. BTK plays an essential role in the B cell signaling pathway linking cell surface B cell receptor BCR stimulation to downstream intracellular responses. BTK is a key regulator of B cell development activation signaling and survival (Kurosaki, Curr Op Imm, 2000, 276-281; Schaeffer and Schwartzberg, Curr Op Imm, 2000, 282-288). In addition BTK plays a role in a number of other hematopoietic cell signaling pathways, e.g., Toll like receptor (TLR) and cytokine receptor-mediated TNF-α production in macrophages, IgE receptor (FcepsilonRI) signaling in mast cells, inhibition of Fas/APO-1 apoptotic signaling in B-lineage lymphoid cells, and collagen stimulated platelet aggregation. See e.g., C. A. Jeffries, et al. (2003) Journal of Biological Chemistry, 278:26258-26264; N. J. Horwood, et al. (2003) The Journal of Experimental Medicine 197:1603-1611; Iwaki et al. (2005) Journal of Biological Chemistry 280(48): 40261-40270; Vassilev et al. (1999) Journal of Biological Chemistry 274(3):1646-1656; and Quek et al. (1998) Current Biology, 8 (20):1137-1140.

Interleukin-2 tyrosine kinase (ITK) is expressed in T mast cells and natural killer cells. It is activated in T cells upon stimulation of the T cell receptor (TCR) and in mast cells upon activation of the high affinity IgE receptor. Following receptor stimulation in T cells, Lck, a src tyrosine family member phosphorylates Y511 in the kinase domain activation loop of Itk (S.D. Heyeck et al. (1997) J. Biol. Chem. 272, 25401-25408). Activated Itk together with Zap-70 is required for phosphorylation and activation of PLC-gamma (S. C. Bunnell et al. (2000) J. Biol. Chem. 275: 2219-2230). PLC-gamma catalyzes the formation of inositol 1,4,5-triphosphate and diacylglycerol, leading to calcium mobilization and PKC activation, respectively. These events activate numerous downstream pathways and lead ultimately degranulation (mast cells) and cytokine gene expression (T cells) (Y. Kawakami et al. (1999) J. Leukocyte Biol., 65:286-290).

Resting lymphocyte kinase (Rlk) displays highly cell type-specific expression largely restricted to T cells and some mast cell and myeloid cell lines. Rlk has src homology (SH)2 and SH3 domains and a nuclear localization signal sequence but lacks a pleckstrin homology domain. The NH2 terminus of Rlk in humans possesses an unusual cysteine-rich string, suggesting that Txk/Rlk functions in a manner that differs from the other pleckstrin homology domain-containing Tec family kinases. Rlk is capable of phosphorylating CTL-associated antigen (CTLA)-4, suggesting that Rlk may participate in CTLA-4 function.

Bone Marrow X kinase (BMX) contains an $NH_2$-terminal pleckstrin homology domain, a Src homology 3 domain, a Src homology 2 domain, and a COOH-terminal tyrosine kinase domain. BMX can be activated by several extracellular stimuli, including growth factors, cytokines, extracellular matrix and hormones. BMX protein is present in cytoplasm with strong perinuclear staining in cells when examined using immunofluorescence microscopy. BMX has been shown to play a role in various cellular processes including cell proliferation, transformation, differentiation, and metastasis.

BRIEF DESCRIPTION OF THE DRAWINGS

FIG. 1 illustrates the identification of BMX substrate motif and target candidates. FIG. 1A is a schematic showing the structure of BMX. FIG. 1B shows biotinylated peptide libraries that were phosphorylated using wild-type Bmx (BmxWT, WT) or mutant kinase-dead Bmx (BmxKD, KD), captured on membranes, and analyzed. Representative images from one of three independent experiments are shown. FIG. 1D, right panel, depicts the immunoblotting results where 293 cells were transfected with BmxWT, BmxKD, or empty vector control plasmids (Ctrl), serum starved for 48 h (SFM) or then HGF stimulated for 10 min, and whole cell lysates were then immunoblotted with antibodies against FAK that has been phosphorylated at tyrosines 576 and 577 (pFAK Y576/577), or antibodies against FAK that has just been phosphorylated at tyrosine 576 (pFAK Y576) or tyrosine 577 (pFAK Y577). FIG. 1E, left panel, depicts the immunoblotting results where 293 cells were cotransfected with 3xFlag-FAK and BmxWT, BmxKD, or empty vector control plasmids (Ctrl). Whole cell lysates or Flag-immunoprecipitated FAK were then immunoblotted with antibodies against FAK that has been phosphorylated at tyrosines 576 and 577 (pFAK Y576/577), or antibodies against FAK that has just been phosphorylated at tyrosine 576 (pFAK Y576) or tyrosine 577 (pFAK Y577). FIG. 1E, right panel, depicts the immunoblotting results where 293 cells were transfected with BmxWT, BmxKD, or empty vector control plasmids (Ctrl), serum starved for 48 h (SFM) or then serum stimulated for 10 min (FBS), and whole cell lysates were then immunoblotted. FIG. 1F depicts the immunoblotting results where 293 cells were cotransfected with FGFR1 and BmxWT, BmxKD, or empty vector control plasmids (Ctrl). Whole cell lysates or immunoprecipitated FGFR1 then were immunoblotted. FIG. 1G depicts the immunoblotting results where 293 cells were cotransfected with Myc tagged ACK1 and BmxWT, BmxKD, or empty vector control plasmids (Ctrl). Whole cell lysates or Myc-immunoprecipitated ACK1 were then immunoblotted.

FIG. 3 demonstrates that BMX regulates FAK through phosphorylation of Y576/577 site.

FIG. 4 illustrates that BMX regulates insulin receptor (IR) phosphorylation and signaling.

FIG. 12 shows that BMX knockdown impairs wound healing in LNCaP cells. Scratch wounds were introduced in LNCaP cells expressing BMX (SiBmx) or control siRNA (SiCtrl), and pictures were taken at 0 and 24 h. The migrated distance was measured and normalized to the BMX knockdown group. Error bars depict the standard error (SE) of three independent experiments.

FIG. 13 depicts an energy-minimized structure of a complex of the BMX (published X-ray structure (Protein Database: 3SXR)) with compound I-14, obtained by molecular modeling.

FIG. 14 shows the sequences of fragments of exemplary kinases that include cysteine residues to which the compounds of Formula (I) or (II) may attach.

FIG. 15 confirms that the potency of the BMX inhibitors is due to covalent binding to cysteine 496.

FIG. 16 shows that compound I-14 more potently inhibits growth of cells expressing the wild-type BMX than the C496S mutant.

FIG. 17 shows that compound I-14 inhibits BMX mediated phosphorylation of pYpY site on FAK. FIG. 17A shows that the BMX inhibitors decrease levels of FAK that is dually phosphorylated at Y576 and Y577, based on blotting with a Bmx substrate antibody (recognizing pYpY) or an antibody recognizing the pYpY site specfically in FAK (pFAK576/577), in RV1 cells cotransfected with BMX and FAK.

FIG. 18 shows that compound I-14 can inhibit the growth of RV1 cells and cause apoptosis.

DETAILED DESCRIPTION OF CERTAIN EMBODIMENTS OF THE INVENTION

Figures 1C, 1D:
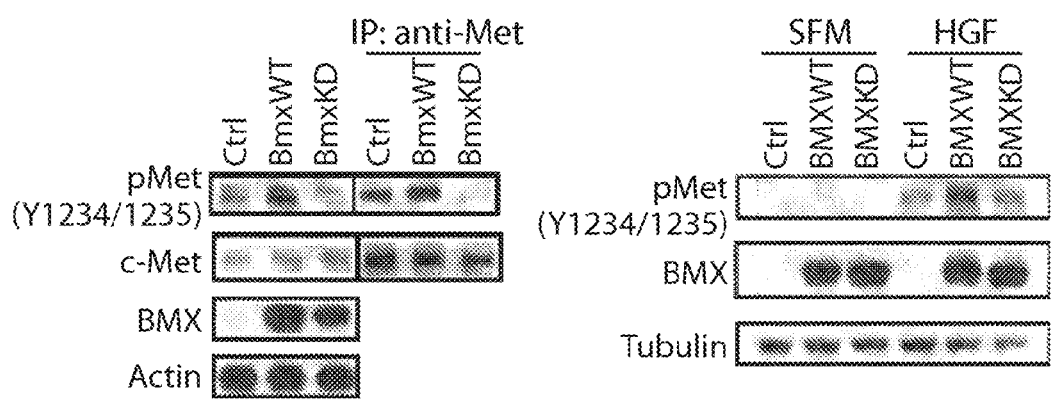
FIG. 1C shows the optimal BMX substrate motifs based on either pY or I at −1 position.
FIG. 1D, left panel, depicts the immunoblotting results where 293 cells were cotransfected with MET and BmxWT, BmxKD, or empty vector control plasmids (Ctrl). Whole cell lysates or immunoprecipitated MET were then immunoblotted as indicated with an antibody recognizing MET that has been phosphorylated at tyrosines 1234 and 1235 (pMET Y1234/1235).

The present invention provides compounds of Formula (I). These compounds have been found to be kinase inhibitors. Also provided are methods of using kinase inhibitors, such as compounds of Formula (I) or (II), to downregulate the expression and/or inhibit the activity of a kinase in a subject or biological sample. In certain embodiments, the kinase is a tyrosine kinase. In certain embodiments, the kinase is a non-receptor tyrosine kinase. In certain embodiments, the kinase is a Tec kinase. In certain embodiments, the Tec kinase is TEC, BTK, ITK, RLK and/or BMX. In certain embodiments, the kinase is "Bone Marrow on X chromosome" kinase (BMX). The present invention further provides methods of using compounds of Formula (I) or (II), e.g., as biological probes to study the downrelegation of the expression and/or inhibition of the activity of a kinase (e.g., a tyrosine kinase (e.g., BMX)), and as therapeutics, e.g., in the treatment and/or prevention of diseases associated with the overexpression and/or aberrant activity of the kinase (e.g., a tyrosine kinase (e.g., BMX)). In certain embodiments, the disease is a proliferative diseases. Exemplary proliferative diseases include, but are not limited to, cancer, benign neoplasm, angiogenesis, inflammatory diseases, and autoimmune diseases. In certain embodiments, the disease is diabetes (e.g., type 2 diabetes and gestational diabetes). The disease being treated or prevented by a compound of Formula (I) or (II) may be associated with the overexpression, increase activity, and/or aberrant activity of a kinase (e.g., a tyrosine kinase (e.g., BMX)).

Compounds

In one aspect of the present invention, provided are compounds of Formula (I):

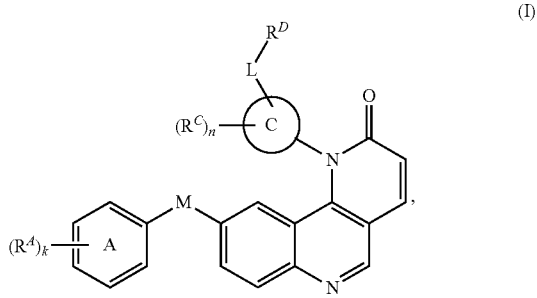

(I)

and pharmaceutically acceptable salts, solvates, hydrates, polymorphs, co-crystals, tautomers, stereoisomers, isotopically labeled derivatives, and prodrugs thereof;

wherein:

each instance of $R^A$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A1})_2$, —$SR^{A1}$, —CN, —C(=O)$R^{A1}$, —C(=O)$SR^{A1}$, —C(=O)N($R^{A1}$)$_2$, —C(=S)$R^{A1}$, —C(=S)$OR^{A1}$, —C(=S)$SR^{A1}$, —C(=S)N($R^{A1}$)$_2$, —C(=N$R^{A1}$)$R^{A1}$, —C(=N$R^{A1}$)$OR^{A1}$, —C(=N$R^{A1}$)$SR^{A1}$, —C(=N$R^{A1}$)N($R^{A1}$)$_2$, —NO$_2$, —N$_3$, —N($R^{A1}$)$_3^+$X$^-$, wherein X$^-$ is a counterion, —N(O$R^{A1}$)$R^{A1}$, —NR$^{A1}$C(=O)$R^{A1}$, —NR$^{A1}$C(=O)$OR^{A1}$, —NR$^{A1}$C(=O)$SR^{A1}$, —NR$^{A1}$C(=O)N($R^{A1}$)$_2$, —NR$^{A1}$C(=S)$R^{A1}$, —NR$^{A1}$C(=S)$OR^{A1}$, —NR$^{A1}$C(=S)$SR^{A1}$, —NR$^{A1}$C(=S)N($R^{A1}$)$_2$, —NR$^{A1}$C(=N$R^{A1}$)$R^{A1}$, —NR$^{A1}$C(=N$R^{A1}$)$OR^{A1}$, —NR$^{A1}$C(=N$R^{A1}$)$SR^{A1}$, —NR$^{A1}$C(=N$R^{A1}$)N($R^{A1}$)$_2$, —NR$^{A1}$S(=O)$_2$$R^{A1}$, —NR$^{A1}$S(=O)$_2$$OR^{A1}$, —NR$^{A1}$S(=O)$_2$$SR^{A1}$, —NR$^{A1}$S(=O)$_2$N($R^{A1}$)$_2$, —NR$^{A1}$S(=O)$R^{A1}$, —NR$^{A1}$S(=O)$OR^{A1}$, —NR$^{A1}$S(=O)$SR^{A1}$, —NR$^{A1}$S(=O)N($R^{A1}$)$_2$, —NR$^{A1}$P(=O), —NR$^{A1}$P(=O)$_2$, —NR$^{A1}$P(=O)($R^{A1}$)$_2$, —NR$^{A1}$P(=O)$R^{A1}$(O$R^{A1}$), —NR$^{A1}$P(=O)(O$R^{A1}$)$_2$, —OC(=O)$R^{A1}$, —OC(=O)O$R^{A1}$, —OC(=O)SR$^{A1}$, —OC(=O)N($R^{A1}$)$_2$, —OC(=N$R^{A1}$)$R^{A1}$, —OC(=N$R^{A1}$)O$R^{A1}$, —OC(=N$R^{A1}$)N($R^{A1}$)$_2$, —OC(=S)$R^{A1}$, —OC(=S)O$R^{A1}$, —OC(=S)SR$^{A1}$, —OC(=S)N($R^{A1}$)$_2$, —ON($R^{A1}$)$_2$, —OS(=O)$R^{A1}$, —OS(=O)O$R^{A1}$, —OS(=O)SR$^{A1}$, —OS(=O)N($R^{A1}$)$_2$, —OS(=O)$_2$$R^{A1}$, —OS(=O)$_2$O$R^{A1}$, —OS(=O)$_2$SR$^{A1}$, —OS(=O)$_2$N($R^{A1}$)$_2$, —OP(=O)$_2$, —OP(=O)($R^{A1}$)$_2$, —OP(=O)$R^{A1}$(O$R^{A1}$), —OP(=O)(O$R^{A1}$)$_2$, —OP(=O), —OP($R^{A1}$)$_2$, —OPR$^{A1}$(O$R^{A1}$), —OP(O$R^{A1}$)$_2$, —OSi($R^{A1}$)$_3$, —OSi($R^{A1}$)$_2$O$R^{A1}$, —OSi($R^{A1}$)(O$R^{A1}$)$_2$, —OSi(O$R^{A1}$)$_3$, —SSR$^{A1}$, —S(=O)$R^{A1}$, —S(=O)O$R^{A1}$, —S(=O)N($R^{A1}$)$_2$, —S(=O)$_2$$R^{A1}$, —S(=O)$_2$O$R^{A1}$, —S(=O)$_2$N($R^{A1}$)$_2$, —SC(=O)$R^{A1}$, —SC(=O)O$R^{A1}$, —SC(=O)SR$^{A1}$, —SC(=O)N($R^{A1}$)$_2$, —SC(=S)$R^{A1}$, —SC(=S)O$R^{A1}$, —SC(=S)SR$^{A1}$, —SC(=S)N($R^{A1}$)$_2$, —P($R^{A1}$)$_2$, —PR$^{A1}$(O$R^{A1}$), —P(O$R^{A1}$)$_2$, —P(=O), —P(=O)($R^{A1}$)$_2$, —P(=O)(O$R^{A1}$)$_2$, —P(=O)$R^{A1}$(O$R^{A1}$), —P(=O)$_2$, —B($R^{A1}$)$_2$, —B(O$R^{A1}$)$_2$, —BRA(O$R^{A1}$), —Si($R^{A1}$)$_3$, —Si($R^{A1}$)$_2$O$R^{A1}$, —SiR$^{A1}$(O$R^{A1}$)$_2$, and —Si(O$R^{A1}$)$_3$, or two $R^A$ groups are joined to form an optionally substituted carbocyclic, optionally substituted heterocyclic, optionally substituted aryl, or optionally substituted heteroaryl ring; wherein each occurrence of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1}$ groups are joined to form an optionally substituted heterocyclic ring;

k is 0, 1, 2, 3, 4, or 5;

M is a bond, —O—, —S—, —NR$^M$—, —NR$^M$C(=O)—, —C(=O)NR$^M$—, —SC(=O)—, —C(=O)S—, —OC(=O)—, —C(=O)O—, —NR$^M$C(=S)—, —C(=S)NR$^M$—, trans-CR$^M$=CR$^M$—, cis-CR$^M$=CR$^M$—, —C≡C—, —S(=O)$_2$O—, —OS(=O)$_2$—, —S(=O)$_2$NR$^M$—, or —NR$^M$S(=O)$_2$—, or an optionally substituted $C_{1-6}$ hydrocarbon chain, optionally wherein one or more carbon units of the hydrocarbon chain is replaced with —O—, —S—, —NR$^M$—, —NR$^M$C(=O)—, —C(=O)NR$^M$—, —SC(=O)—, —C(=O)S—, —OC(=O)—, —C(=O)O—, —NR$^M$C(=S)—, —C(=S)NR$^M$—, trans-CR$^M$=CR$^M$—, cis-CR$^M$=CR$^M$—, —C≡C—, —S(=O)$_2$O—, —OS(=O)$_2$—, —S(=O)$_2$NR$^M$—, or —NR$^M$S(=O)$_2$—, wherein R$^M$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl or a nitrogen protecting group, or two R$^M$ groups are joined to form an optionally substituted carbocyclic ring, an optionally substituted heterocyclic ring, optionally substituted aryl ring, optionally substituted heteroaryl ring;

Ring C is an optionally substituted carbocyclic, optionally substituted heterocyclic, optionally substituted aryl, or optionally substituted heteroaryl ring;

each instance of $R^C$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{C1}$, —$N(R^{C1})_2$, —$SR^{C1}$, —CN, —C(=O)$R^{C1}$, —C(=O)$SR^{C1}$, —C(=O)N($R^{C1}$)$_2$, —C(=S)$R^{C1}$, —C(=S)$OR^{C1}$, —C(=S)$SR^{C1}$, —C(=S)N($R^{C1}$)$_2$, —C(=N$R^{C1}$)$R^{C1}$, —C(=N$R^{C1}$)$OR^{C1}$, —C(=N$R^{C1}$)$SR^{C1}$, —C(=N$R^{C1}$)N($R^{C1}$)$_2$, —N$_3$, —N($R^{C1}$)$_3^+$X$^-$, wherein X$^-$ is a counterion, —N(O$R^{C1}$)$R^{C1}$, —NR$^{C1}$C(=O)$R^{C1}$, —NR$^{C1}$C(=O)O$R^{C1}$, —NR$^{C1}$C(=O)SR$^{C1}$, —NR$^{C1}$C(=O)N($R^{C1}$)$_2$, —NR$^{C1}$C(=S)$R^{C1}$, —NR$^{C1}$C(=S)O$R^{C1}$, —NR$^{C1}$C(=S)SR$^{C1}$, —NR$^{C1}$C(=S)N($R^{C1}$)$_2$, —NR$^{C1}$C(=N$R^{C1}$)$R^{C1}$, —NR$^{C1}$C(=N$R^{C1}$)O$R^{C1}$, —NR$^{C1}$C(=N$R^{C1}$)SR$^{C1}$, —NR$^{C1}$C(=N$R^{C1}$)N($R^{C1}$)$_2$, —NR$^{C1}$S(=O)$_2$$R^{C1}$, —NR$^{C1}$S(=O)$_2$O$R^{C1}$, —NR$^{C1}$S(=O)$_2$SR$^{C1}$, —NR$^{C1}$S(=O)$_2$N($R^{C1}$)$_2$, —NR$^{C1}$S(=O)$R^{C1}$, —NR$^{C1}$S(=O)O$R^{C1}$, —NR$^{C1}$S(=O)SR$^{C1}$, —NR$^{C1}$S(=O)N($R^{C1}$)$_2$, —NR$^{C1}$P(=O), —NR$^{C1}$P(=O)$_2$, —NR$^{C1}$P(=O)($R^{C1}$)$_2$, —NR$^{C1}$P(=O)$R^{C1}$(O$R^{C1}$), —NR$^{C1}$P(=O)(O$R^{C1}$)$_2$, —OC(=O)$R^{C1}$, —OC(=O)O$R^{C1}$, —OC(=O)SR$^{C1}$, —OC(=O)N($R^{C1}$)$_2$, —OC(=N$R^{C1}$)$R^{C1}$, —OC(=N$R^{C1}$)O$R^{C1}$, —OC(=N$R^{C1}$)N($R^{C1}$)$_2$, —OC(=S)$R^{C1}$, —OC(=S)O$R^{C1}$, —OC(=S)SR$^{C1}$, —OC(=S)N($R^{C1}$)$_2$, —ON($R^{C1}$)$_2$, —OS(=O)$R^{C1}$, —OS(=O)O$R^{C1}$, —OS(=O)SR$^{C1}$, —OS(=O)N($R^{C1}$)$_2$, —OS(=O)$_2$$R^{C1}$, —OS(=O)$_2$O$R^{C1}$, —OS(=O)$_2$SR$^{C1}$, —OS(=O)$_2$N($R^{C1}$)$_2$, —OP(=O)$_2$, —OP(=O)($R^{C1}$)$_2$, —OP(=O)$R^{C1}$(O$R^{C1}$), —OP(=O)(O$R^{C1}$)$_2$, —OP(=O), —OP($R^{C1}$)$_2$, —OPR$^{C1}$(O$R^{C1}$), —OP(O$R^{C1}$)$_2$, —OSi($R^{C1}$)$_3$, —OSi($R^{C1}$)$_2$O$R^{C1}$, —OSi($R^{C1}$)(O$R^{C1}$)$_2$, —OSi(O$R^{C1}$)$_3$, —SSR$^{C1}$, —S(=O)$R^{C1}$, —S(=O)O$R^{C1}$, —S(=O)N($R^{C1}$)$_2$, —S(=O)$_2$$R^{C1}$, —S(=O)$_2$O$R^{C1}$, —S(=O)$_2$N($R^{C1}$)$_2$, —SC(=O)$R^{C1}$, —SC(=O)O$R^{C1}$, —SC(=O)SR$^{C1}$, —SC(=O)N($R^{C1}$)$_2$, —SC(=S)$R^{C1}$, —SC(=S)OR$^{C1}$, —SC(=S)SR$^{C1}$, —SC(=S)N(R$^{C1}$)$_2$, —P(R$^{C1}$)$_2$, —PR$^{C1}$(OR$^{C1}$), —P(OR$^{C1}$)$_2$, —P(=O), —P(=O)(R$^{C1}$)$_2$, —P(=O)(OR$^{C1}$)$_2$, —P(=O)R$^{C1}$(OR$^{C1}$), —P(=O)$_2$, —B(R$^{C1}$)$_2$, —B(OR$^{C1}$)$_2$, —BR$^{C1}$(OR$^{C1}$), —Si(R$^{C1}$)$_3$, —Si(R$^{C1}$)$_2$OR$^{C1}$, —SiR$^{C1}$(OR$^{C1}$)$_2$, and —Si(OR$^{C1}$)$_3$, wherein each occurrence of R$^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{C1}$ groups are joined to form an optionally substituted heterocyclic ring or optionally substituted heteroaryl ring;

n is 0, 1, 2, 3, or 4;

L is a bond or an optionally substituted C$_{1-6}$ hydrocarbon chain;

R$^D$ is any one of Formulae (i-1)-(i-17):

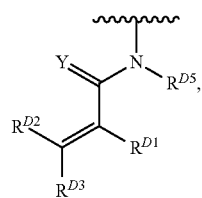 (i-1)

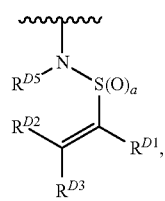 (i-2)

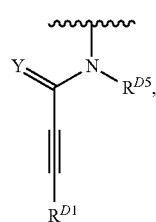 (i-3)

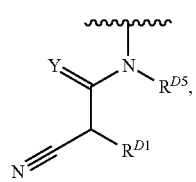 (i-4)

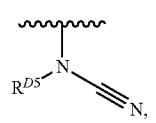 (i-5)

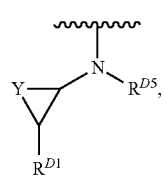 (i-6)

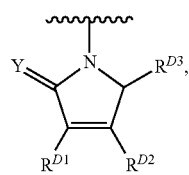 (i-7)

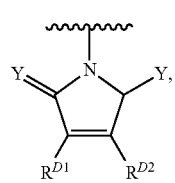 (i-8)

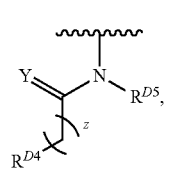 (i-9)

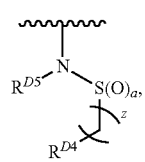 (i-10)

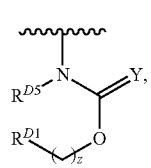 (i-11)

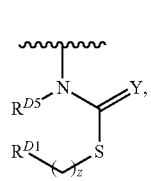 (i-12)

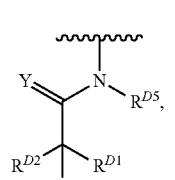 (i-13)

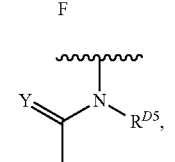 (i-14)

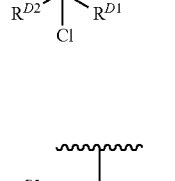 (i-15)

(i-16)

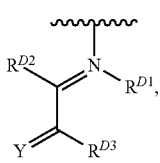

(i-17)

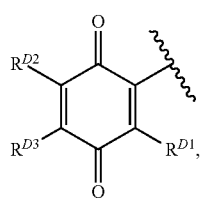

$R^{D1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, C(=O)N(R$^{D1a}$)$_2$, —C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, and —C(=NR$^{D1a}$)N(R$^{D1a}$)$_2$, wherein each occurrence of R$^{D1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D1a}$ groups are joined to form an optionally substituted heterocyclic ring;

$R^{D2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, C(=O)N(R$^{D2a}$)$_2$, —C(=S)R$^{D2a}$, —C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, —C(=NR$^{D2a}$)SR$^{D2a}$, and —C(=NR$^{D2a}$)N(R$^{D2a}$)$_2$, wherein each occurrence of R$^{D2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D2a}$ groups are joined to form an optionally substituted heterocyclic ring;

$R^{D3}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, —C(=O)SR$^{D3a}$, —C(=O)N(R$^{D3a}$)$_2$, —C(=S)R$^{D3a}$, —C(=S)OR$^{D3a}$, —C(=S)SR$^{D3a}$, —C(=S)N(R$^{D3a}$)$_2$, —C(=NR$^{D3a}$)R$^{D3a}$, —C(=NR$^{D3a}$)OR$^{D3a}$, —C(=NR$^{D3a}$)SR$^{D3a}$, and —C(=NR$^{D3a}$)N(R$^{D3a}$)$_2$, wherein each occurrence of R$^{D3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D3a}$ groups are joined to form an optionally substituted heterocyclic ring;

optionally R$^{D1}$ and R$^{D3}$, or R$^{D2}$ and R$^{D3}$, or R$^{D1}$ and R$^{D2}$ are joined to form an optionally substituted carbocyclic or optionally substituted heterocyclic ring;

R$^{D4}$ is a leaving group;

R$^{D5}$ is hydrogen, C$_{1-6}$ alkyl, or a nitrogen protecting group;

Y is O, S, or NR$^{D6}$, wherein R$^{D6}$ is hydrogen, C$_{1-6}$ alkyl, or a nitrogen protecting group;

a is 1 or 2;

z is 0, 1, 2, 3, 4, 5, or 6; and optionally R$^{D5}$ and one R$^{D6}$ are joined to form an optionally substituted heterocyclic ring.

In certain embodiments, provided by the present invention are compounds of Formula (I), and pharmaceutically acceptable salts thereof.

Compounds of Formula (I) include a phenyl ring A optionally substituted with one or more R$^A$ groups. In certain embodiments, the phenyl ring A is unsubstituted, and thus k is 0. In certain embodiments, k is 1. In certain embodiments, the phenyl ring A is of the formula:

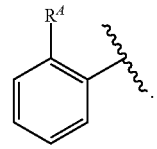

In certain embodiments, the phenyl ring A is of the formula:

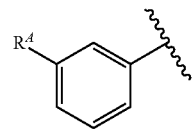

. In certain embodiments, the phenyl ring A is of the formula:

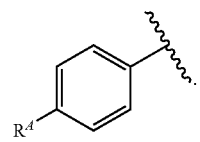

In certain embodiments, k is 2. In certain embodiments, the phenyl ring A is of the formula:

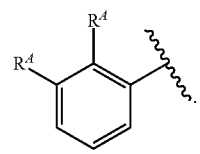

In certain embodiments, the phenyl ring A is of the formula:

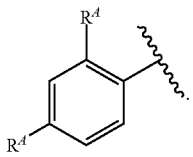

In certain embodiments, the phenyl ring A is of the formula:

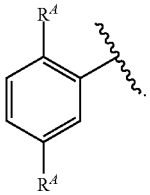

In certain embodiments, the phenyl ring A is of the formula:

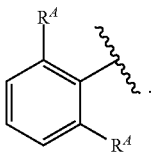

In certain embodiments, the phenyl ring A is of the formula:

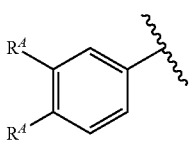

In certain embodiments, the phenyl ring A is of the formula:

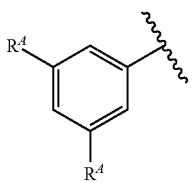

In certain embodiments, k is 3. In certain embodiments, k is 4. In certain embodiments, k is 5.

In compounds of Formula (I), phenyl ring A may be substituted with one or more $R^A$ groups. In certain embodiments, at least one $R^A$ is H. In certain embodiments, at least one $R^A$ is halogen. In certain embodiments, at least one $R^A$ is F. In certain embodiments, at least one $R^A$ is Cl. In certain embodiments, at least one $R^A$ is Br. In certain embodiments, at least one $R^A$ is I (iodine). In certain embodiments, at least one $R^A$ is substituted acyl. In certain embodiments, at least one $R^A$ is —C(=O)N($R^{A1}$)$_2$. In certain embodiments, at least one $R^A$ is —C(=O)NH$R^{A1}$. In certain embodiments, at least one $R^A$ is —C(=O)NH(C$_{1-6}$ alkyl). In certain embodiments, at least one $R^A$ is —C(=O)NHMe. In certain embodiments, at least one $R^A$ is —C(=O)NH$_2$. In certain embodiments, at least one $R^A$ is unsubstituted acyl. In certain embodiments, at least one $R^A$ is acetyl. In certain embodiments, at least one $R^A$ is substituted alkyl. In certain embodiments, at least one $R^A$ is substituted methyl. In certain embodiments, at least one $R^A$ is

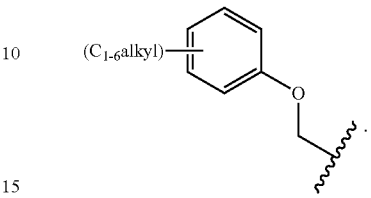

In certain embodiments, at least one $R^A$ is

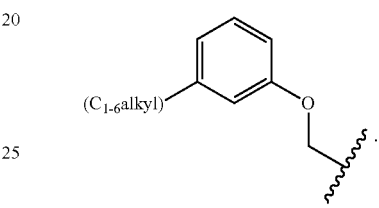

In certain embodiments, at least one $R^A$ is

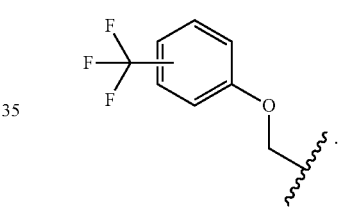

In certain embodiments, at least one $R^A$ is

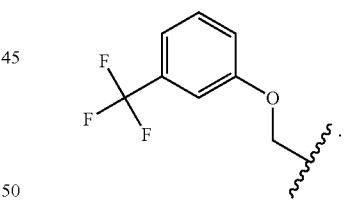

In certain embodiments, at least one $R^A$ is unsubstituted alkyl. In certain embodiments, at least one $R^A$ is C$_{1-6}$ alkyl. In certain embodiments, at least one $R^A$ is methyl. In certain embodiments, at least one $R^A$ is ethyl. In certain embodiments, at least one $R^A$ is propyl. In certain embodiments, at least one $R^A$ is butyl. In certain embodiments, at least one $R^A$ is substituted alkenyl. In certain embodiments, at least one $R^A$ is unsubstituted alkenyl. In certain embodiments, at least one $R^A$ is substituted alkynyl. In certain embodiments, at least one $R^A$ is unsubstituted alkynyl. In certain embodiments, at least one $R^A$ is substituted carbocyclyl. In certain embodiments, at least one $R^A$ is unsubstituted carbocyclyl. In certain embodiments, at least one $R^A$ is substituted heterocyclyl. In certain embodiments, at least one $R^A$ is unsubstituted heterocyclyl. In certain embodiments, at least one $R^A$ is substituted aryl. In certain embodiments, at least one $R^A$ is unsubstituted aryl. In certain embodiments, at least one $R^A$ is substituted phenyl. In certain embodiments, at least one $R^A$ is unsubstituted phenyl. In certain embodiments, at least one $R^A$ is substituted heteroaryl. In certain embodiments, at least one $R^A$ is unsubstituted heteroaryl. In certain embodiments, at least one $R^A$ is substituted pyridyl. In certain embodiments, at least one $R^A$ is unsubstituted pyridyl. In certain embodiments, at least one $R^A$ is —$OR^{A1}$. In certain embodiments, at least one $R^A$ is —$O(C_{1-6}$ alkyl). In certain embodiments, at least one $R^A$ is —OMe. In certain embodiments, at least one $R^A$ is —OH. In certain embodiments, at least one $R^A$ is —$N(R^{A1})_2$. In certain embodiments, at least one $R^A$ is —$N(C_{1-6}$ alkyl$)_2$. In certain embodiments, at least one $R^A$ is

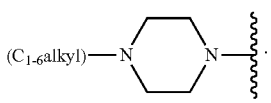

In certain embodiments, at least one $R^A$ is

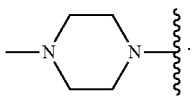

In certain embodiments, at least one $R^A$ is

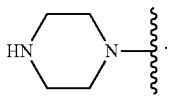

In certain embodiments, at least one $R^A$ is —$NMe_2$. In certain embodiments, at least one $R^A$ is —$NH_2$. In certain embodiments, at least one $R^A$ is —$SR^{A1}$. In certain embodiments, at least one $R^A$ is —SH. In certain embodiments, at least one $R^A$ is —$NR^{A1}C(=O)N(R^{A1})_2$. In certain embodiments, at least one $R^A$ is —$NHC(=O)N(R^{A1})_2$. In certain embodiments, at least one $R^A$ is —$NHC(=O)NHR^{A1}$. In certain embodiments, at least one $R^A$ is —$NHC(=O)NH(C_{1-6}$ alkyl). In certain embodiments, at least one $R^A$ is —$NHC(=O)NHMe$. In certain embodiments, at least one $R^A$ is —$NHC(=O)NH_2$. In certain embodiments, at least one $R^A$ is —$NR^{A1}C(=O)NHR^{A1}$ certain embodiments, at least one $R^A$ is —$NR^{A1}C(=O)NH_2$. In certain embodiments, at least one $R^A$ is —$NR^{A1}S(=O)_2R^{A1}$. In certain embodiments, at least one $R^A$ is —$NHS(=O)_2R^{A1}$. In certain embodiments, at least one $R^A$ is —$NHS(=O)_2(C_{1-6}$ alkyl). In certain embodiments, at least one $R^A$ is —$NHS(=O)_2Me$. In certain embodiments, at least one $R^A$ is —$S(=O)_2N(R^{A1})_2$. In certain embodiments, at least one $R^A$ is —$S(=O)_2N(R^{A1})_2$. In certain embodiments, at least one $R^A$ is —$S(=O)_2N(C_{1-6}$ alkyl$)_2$. In certain embodiments, at least one $R^A$ is —$S(=O)_2NH(C_{1-6}$ alkyl). In certain embodiments, at least one $R^A$ is —$S(=O)_2NH(t-Bu)$. In certain embodiments, at least one $R^A$ is —$S(=O)_2NH_2$.

In certain embodiments, at least one $R^{A1}$ is H. In certain embodiments, at least one $R^{A1}$ is substituted acyl. In certain embodiments, at least one $R^{A1}$ is unsubstituted acyl. In certain embodiments, at least one $R^{A1}$ is acetyl. In certain embodiments, at least one $R^{A1}$ is substituted alkyl. In certain embodiments, at least one $R^{A1}$ is unsubstituted alkyl. In certain embodiments, at least one $R^{A1}$ is $C_{1-6}$ alkyl. In certain embodiments, at least one $R^{A1}$ is methyl. In certain embodiments, at least one $R^{A1}$ is ethyl. In certain embodiments, at least one $R^{A1}$ is propyl. In certain embodiments, at least one $R^{A1}$ is butyl. In certain embodiments, at least one $R^{A1}$ is substituted alkenyl. In certain embodiments, at least one $R^{A1}$ is unsubstituted alkenyl. In certain embodiments, at least one $R^{A1}$ is substituted alkynyl. In certain embodiments, at least one $R^{A1}$ is unsubstituted alkynyl. In certain embodiments, at least one $R^{A1}$ is substituted carbocyclyl. In certain embodiments, at least one $R^{A1}$ is unsubstituted carbocyclyl. In certain embodiments, at least one $R^{A1}$ is substituted heterocyclyl. In certain embodiments, at least one $R^{A1}$ is unsubstituted heterocyclyl. In certain embodiments, at least one $R^{A1}$ is substituted aryl. In certain embodiments, at least one $R^{A1}$ is unsubstituted aryl. In certain embodiments, at least one $R^{A1}$ is substituted phenyl. In certain embodiments, at least one $R^{A1}$ is unsubstituted phenyl. In certain embodiments, at least one $R^{A1}$ is substituted heteroaryl. In certain embodiments, at least one $R^{A1}$ is unsubstituted heteroaryl. In certain embodiments, at least one $R^{A1}$ is substituted pyridyl. In certain embodiments, at least one $R^{A1}$ is unsubstituted pyridyl. In certain embodiments, at least one $R^{A1}$ is a nitrogen protecting group when attached to a nitrogen atom. In certain embodiments, at least one $R^{A1}$ is Bn, BOC, Cbz, Fmoc, trifluoroacetyl, triphenylmethyl, or Ts when attached to a nitrogen atom. In certain embodiments, $R^{A1}$ is an oxygen protecting group when attached to an oxygen atom. In certain embodiments, $R^{A1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1}$ is a sulfur protecting group when attached to a sulfur atom. In certain embodiments, $R^{A1}$ is acetamidomethyl, t-Bu, 3-nitro-2-pyridine sulfenyl, 2-pyridine-sulfenyl, or triphenylmethyl when attached to a sulfur atom.

In compounds of Formula (I), two $R^{A1}$ groups may be joined to form an optionally substituted carbocyclic, optionally substituted heterocyclic, optionally substituted aryl, or optionally substituted heteroaryl ring. In certain embodiments, two $R^{A1}$ groups are joined to form a substituted carbocyclic ring. In certain embodiments, two $R^{A1}$ groups are joined to form an unsubstituted carbocyclic ring. In certain embodiments, two $R^{A1}$ groups are joined to form

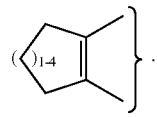

In certain embodiments, two $R^{A1}$ groups are joined to form

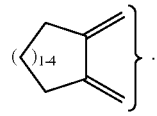

In certain embodiments, two $R^{A1}$ groups are joined to form a substituted heterocyclic ring. In certain embodiments, two $R^{A1}$ groups are joined to form an unsubstituted heterocyclic ring. In certain embodiments, two $R^{A1}$ groups are joined to form In certain embodiments, two $R^{A1}$ groups are joined to form

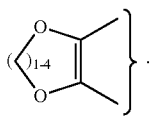

In certain embodiments, two $R^{A1}$ groups are joined to form

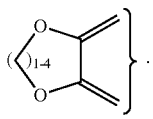

In certain embodiments, two $R^{A1}$ groups are joined to form

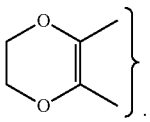

In certain embodiments, two $R^{A1}$ groups are joined to form

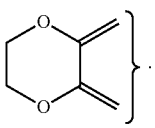

In certain embodiments, two $R^{A1}$ groups are joined to form

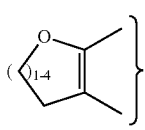

In certain embodiments, two $R^{A1}$ groups are joined to form

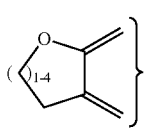

In certain embodiments, two $R^{A1}$ groups are joined to form a substituted aryl ring. In certain embodiments, two $R^{A1}$ groups are joined to form an unsubstituted aryl ring. In certain embodiments, two $R^{A1}$ groups are joined to form a substituted phenyl ring. In certain embodiments, two $R^{A1}$ groups are joined to form an unsubstituted phenyl ring. In certain embodiments, two $R^{A1}$ groups are joined to form a substituted heteroaryl ring. In certain embodiments, two $R^{A1}$ groups are joined to form an unsubstituted heteroaryl ring. In certain embodiments, two $R^{A1}$ groups are joined to form a substituted pyridyl ring. In certain embodiments, two $R^{A1}$ groups are joined to form an unsubstituted pyridyl ring.

In certain embodiments, $R^A$ is substituted $C_{1-6}$ alkyl; and k is 1. In certain embodiments, $R^A$ is unsubstituted $C_{1-6}$ alkyl; and k is 1. In certain embodiments, $R^A$ is methyl; and k is 1. In certain embodiments, $R^A$ is ethyl; and k is 1. In certain embodiments, $R^A$ is propyl; and k is 1. In certain embodiments, $R^A$ is butyl; and k is 1.

In certain embodiments, $R^A$ is halogen; and k is 1. In certain embodiments, $R^A$ is F; and k is 1. In certain embodiments, $R^A$ is Cl; and k is 1. In certain embodiments, $R^A$ is Br; and k is 1. In certain embodiments, $R^A$ is I (iodine); and k is 1.

In certain embodiments, $R^A$ is —C(=O)N($R^{A1}$)$_2$; and k is 1. In certain embodiments, $R^A$ is —C(=O)NH($C_{1-6}$ alkyl); and k is 1. In certain embodiments, $R^A$ is —C(=O)NHMe; and k is 1. In certain embodiments, $R^A$ is

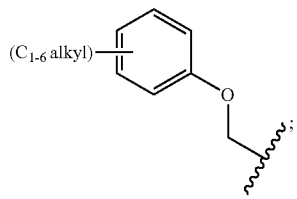

and k is 1. In certain embodiments, $R^A$ is

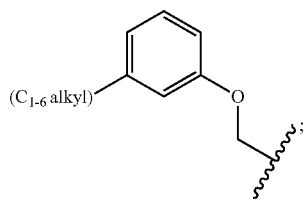

and k is 1. In certain embodiments, $R^A$ is

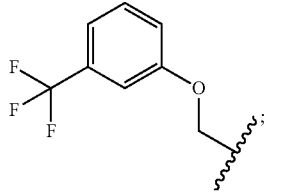 [SMILES: *COc1cccc(C(F)(F)F)c1]

and k is 1. In certain embodiments, $R^A$ is —N($R^{A1}$)$_2$; and k is 1. In certain embodiments, $R^A$ is

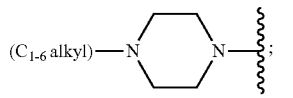

and k is 1. In certain embodiments, $R^A$ is

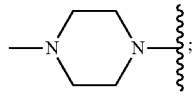

and k is 1. In certain embodiments, $R^A$ is

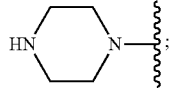

and k is 1. In certain embodiments, $R^A$ is —$NR^{A1}$C(=O)N($R^{A1}$)$_2$; and k is 1. In certain embodiments, $R^A$ is —NHC(=O)NH($C_{1-6}$ alkyl); and k is 1. In certain embodiments, $R^A$ is —NHC(=O)NHMe; and k is 1. In certain embodiments, $R^A$ is —$NR^{A1}$S(=O)$_2$$R^{A1}$; and k is 1. In certain embodiments, $R^A$ is —NHS(=O)$_2$($C_{1-6}$ alkyl); and k is 1. In certain embodiments, $R^A$ is —NHS(=O)$_2$Me; and k is 1. In certain embodiments, $R^A$ is —S(=O)$_2$N($R^{A1}$)$_2$; and k is 1. In certain embodiments, $R^A$ is —S(=O)$_2$NH($C_{1-6}$ alkyl); and k is 1. In certain embodiments, $R^A$ is —S(=O)$_2$NH(t-Bu); and k is 1.

In certain embodiments, one instance of $R^A$ is —C(=O)N($R^{A1}$)$_2$; the other instance of $R^A$ is halogen; and k is 2. In certain embodiments, one instance of $R^A$ is —C(=O)NH($C_{1-6}$ alkyl), the other instance of $R^A$ is F; and k is 2. In certain embodiments, two $R^{A1}$ groups are joined to form

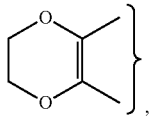, and k is 2. In certain embodiments, two $R^{A1}$ groups are joined to form

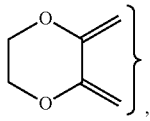, and k is 2. In certain embodiments, two $R^{A1}$ groups are joined to form

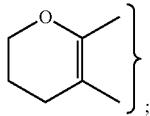;

and k is 2. In certain embodiments, two $R^{A1}$ groups are joined to form

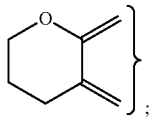;

and k is 2. In certain embodiments, two $R^{A1}$ groups are joined to form

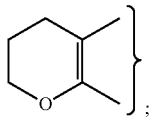;

and k is 2. In certain embodiments, two $R^{A1}$ groups are joined to form

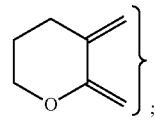;

and k is 2. In certain embodiments, two $R^{A1}$ groups are joined to form

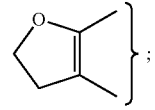;

and k is 2. In certain embodiments, two $R^{A1}$ groups are joined to form

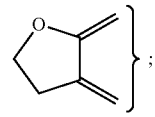;

and k is 2. In certain embodiments, two $R^{A1}$ groups are joined to form

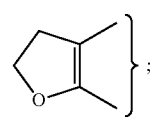;

and k is 2. In certain embodiments, two $R^A$ groups are joined to form

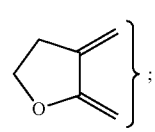;

and k is 2.

In compounds of Formula (I), linker M is a divalent linker moiety. In certain embodiments, M is a bond. In certain embodiments, M is a single bond. In certain embodiments, M is a substituted or unsubstituted, branched or unbranched, saturated or unsaturated $C_{1-6}$ hydrocarbon chain. In certain embodiments, M is a $C_1$ hydrocarbon chain substituted with one or more $R^M$ groups. In certain embodiments, M is —C($R^M$)$_2$—. In certain embodiments, M is —CH$_2$—. In certain embodiments, M is a $C_2$ hydrocarbon chain substituted with one or more $R^M$ groups. In certain embodiments, M is —C($R^M$)$_2$—C($R^M$)$_2$—. In certain embodiments, M is —CH$R^M$—CH$R^M$—. In certain embodiments, M is —(CH$_2$)$_2$—. In certain embodiments, M is trans-C$R^M$=C$R^M$—. In certain embodiments, M is trans-CH=CH—. In certain embodiments, M is cis-C$R^M$=C$R^M$—. In certain embodiments, M is cis-CH=CH—. In certain embodiments, M is —C≡C—. In certain embodiments, M is a $C_3$ hydrocarbon chain substituted with one or more $R^M$ groups. In certain embodiments, M is —C($R^M$)$_2$—C($R^M$)$_2$—C($R^M$)$_2$—. In certain embodiments, M is —(CH$_2$)$_3$—. In certain embodiments, M is —C(R$^M$)=C(R$^M$)—C(R$^M$)$_2$—, wherein C=C is cis or trans. In certain embodiments, M is —C(R$^M$)=C(R$^M$)=C(R$^M$)—, wherein C=C is cis or trans. In certain embodiments, M is —C≡C—C(R$^M$)$_2$—. In certain embodiments, M is —C(R$^M$)$_2$—C≡C—. In certain embodiments, M is a C$_4$ hydrocarbon chain substituted with one or more R$^M$ groups. In certain embodiments, M is —C(R$^M$)$_2$—C(R$^M$)$_2$—C(R$^M$)$_2$R$^M$)$_2$—C(R$^M$)$_2$—. In certain embodiments, M is —(CH$_2$)$_4$—. In certain embodiments, M is —C(R$^M$)=C(R$^M$)—C(R$^M$)$_2$—C(R$^M$)$_2$—, wherein C=C is cis or trans. In certain embodiments, M is —C(R$^M$)$_2$—C(R$^M$)=C(R$^M$)—C(R$^M$)$_2$—, wherein C=C is cis or trans. In certain embodiments, M is —C(R$^M$)$_2$—C(R$^M$)$_2$—C(R$^M$)=C(R$^M$)—, wherein C=C is cis or trans. In certain embodiments, M is —C≡C—C(R$^M$)$_2$—C(R$^M$)$_2$—. In certain embodiments, M is —C(R$^M$)$_2$—C≡C(R$^M$)$_2$—. In certain embodiments, M is —C(R$^M$)$_2$—C(R$^M$)$_2$—C≡C—. In certain embodiments, M is —C(R$^M$)=C(R$^M$)—C(R$^M$)=C(R$^M$)—, wherein each occurrence of C=C is independently cis or trans. In certain embodiments, M is —C(R$^M$)=C(R$^M$)—C≡C—, wherein C=C is cis or trans. In certain embodiments, M is —C≡C—C(R$^M$)=C(R$^M$)—, wherein the C=C is cis or trans. In certain embodiments, M is —C≡C—C≡C—. In certain embodiments, M is a C$_5$ hydrocarbon chain substituted with one or more R$^M$ groups. In certain embodiments, M is —C(R$^M$)$_2$—C(R$^M$)$_2$—C(R$^M$)$_2$—C(R$^M$)$_2$—C(R$^M$)$_2$—. In certain embodiments, M is —(CH$_2$)$_5$—. In certain embodiments, M is a C$_6$ hydrocarbon chain substituted with one or more R$^M$ groups. In certain embodiments, M is —C(R$^M$)$_2$—C(R$^M$)$_2$—C(R$^M$)$_2$—C(R$^M$)$_2$—C(R$^M$)$_2$—C(R$^M$)$_2$—. In certain embodiments, M is —(CH$_2$)$_6$—. In certain embodiments, one or more carbon units of the hydrocarbon chain is replaced with —O—, —S—, —NR$^M$—, —NR$^M$C(=O)—, —C(=O)NR$^M$—, —SC(=O)—, —C(=O)S—, —OC(=O)—, —C(=O)O—, —NR$^M$C(=S)—, —C(=S)NR$^M$—, trans-CR$^M$=CR$^M$—, cis-CR$^M$=CR$^M$—, —C≡C—, —S(=O)$_2$O—, —OS(=O)$_2$—, —S(=O)$_2$NR$^M$—, or —NR$^M$S(=O)$_2$—. In certain embodiments, M is —NH—.

In certain embodiments, at least one R$^M$ is H. In certain embodiments, at least one R$^M$ is halogen. In certain embodiments, at least one R$^M$ is F. In certain embodiments, at least one R$^M$ is Cl. In certain embodiments, at least one R$^M$ is Br. In certain embodiments, at least one R$^M$ is I (iodine). In certain embodiments, at least one R$^M$ is substituted alkyl. In certain embodiments, at least one R$^M$ is unsubstituted alkyl. In certain embodiments, at least one R$^M$ is C$_{1-6}$ alkyl. In certain embodiments, at least one R$^M$ is methyl. In certain embodiments, at least one R$^M$ is ethyl. In certain embodiments, at least one R$^M$ is propyl. In certain embodiments, at least one R$^M$ is butyl. In certain embodiments, at least one R$^M$ is substituted alkenyl. In certain embodiments, at least one R$^M$ is unsubstituted alkenyl. In certain embodiments, at least one R$^M$ is vinyl. In certain embodiments, at least one R$^M$ is substituted alkynyl. In certain embodiments, at least one R$^M$ is unsubstituted alkynyl. In certain embodiments, at least one R$^M$ is ethynyl. In certain embodiments, at least one R$^M$ is substituted carbocyclyl. In certain embodiments, at least one R$^M$ is unsubstituted carbocyclyl. In certain embodiments, at least one R$^M$ is substituted heterocyclyl. In certain embodiments, at least one R$^M$ is unsubstituted heterocyclyl. In certain embodiments, at least one R$^M$ is substituted aryl. In certain embodiments, at least one R$^M$ is unsubstituted aryl. In certain embodiments, at least one R$^M$ is substituted phenyl. In certain embodiments, at least one R$^M$ is unsubstituted phenyl. In certain embodiments, at least one R$^M$ is substituted heteroaryl. In certain embodiments, at least one R$^M$ is unsubstituted heteroaryl. In certain embodiments, at least one R$^M$ is substituted pyridyl. In certain embodiments, at least one R$^M$ is unsubstituted pyridyl. In certain embodiments, two R$^M$ groups are joined to form a substituted carbocyclic ring. In certain embodiments, two R$^M$ groups are joined to form an unsubstituted carbocyclic ring. In certain embodiments, two R$^M$ groups are joined to form a substituted heterocyclic ring. In certain embodiments, two R$^M$ groups are joined to form an unsubstituted heterocyclic ring. In certain embodiments, two R$^M$ groups are joined to form a substituted aryl ring. In certain embodiments, two R$^M$ groups are joined to form an unsubstituted aryl ring. In certain embodiments, two R$^M$ groups are joined to form a substituted phenyl ring. In certain embodiments, two R$^M$ groups are joined to form an unsubstituted phenyl ring. In certain embodiments, two R$^M$ groups are joined to form a substituted heteroaryl ring. In certain embodiments, two R$^M$ groups are joined to form an unsubstituted heteroaryl ring.

Compounds of Formula (I) include an optionally substituted carbocyclic, optionally substituted heterocyclic, optionally substituted aryl, or optionally substituted heteroaryl ring as Ring C. Ring C may be substituted with one or more R$^C$ groups. R$^C$ may be a substituent on a carbon atom or heteroatom, as valency permits. In certain embodiments, Ring C is a substituted carbocyclic ring. In certain embodiments, Ring C is an unsubstituted carbocyclic ring. In certain embodiments, Ring C is a saturated carbocyclic ring. In certain embodiments, Ring C is an unsaturated carbocyclic ring. In certain embodiments, Ring C is a monocyclic carbocyclic ring. In certain embodiments, Ring C is a bicyclic carbocyclic ring. In certain embodiments, Ring C is an optionally substituted carbocyclic ring fused with one or more optionally substituted carbocyclic, optionally substituted heterocyclic, optionally substituted aryl, or optionally substituted heteroaryl groups wherein the point of attachment is on the carbocyclic ring.

Ring C of Formula (I) may be an optionally substituted heterocyclic ring. In certain embodiments, Ring C is a substituted heterocyclic ring. In certain embodiments, Ring C is an unsubstituted heterocyclic ring. In certain embodiments, Ring C is a saturated heterocyclic ring. In certain embodiments, Ring C is an unsaturated heterocyclic ring. In certain embodiments, Ring C is a monocyclic heterocyclic ring. In certain embodiments, Ring C is a bicyclic heterocyclic ring. In certain embodiments, Ring C is an optionally substituted heterocyclic ring fused with one or more optionally substituted carbocyclic, optionally substituted heterocyclic, optionally substituted aryl, or optionally substituted heteroaryl groups wherein the point of attachment is on the heterocyclic ring.

Ring C of Formula (I) may be an optionally substituted aryl ring. In certain embodiments, Ring C is a substituted aryl ring. In certain embodiments, Ring C is an unsubstituted aryl ring. In certain embodiments, Ring C is a monocyclic aryl ring. In certain embodiments, Ring C is substituted phenyl. In certain embodiments, Ring C is unsubstituted phenyl. In certain embodiments, Ring C is a bicyclic aryl ring. In certain embodiments, Ring C is substituted naphthyl. In certain embodiments, Ring C is unsubstituted naphthyl. In certain embodiments, Ring C is a tricyclic aryl ring. In certain embodiments, Ring C is substituted anthracenyl. In certain embodiments, Ring C is unsubstituted anthracenyl. In certain embodiments, Ring C is an optionally substituted aryl ring fused with one or more optionally substituted carbocyclic, optionally substituted heterocyclic, optionally substituted aryl, or optionally substituted heteroaryl groups wherein the point of attachment is on the aryl ring.

In certain embodiments, the compound of Formula (I) is of the formula:

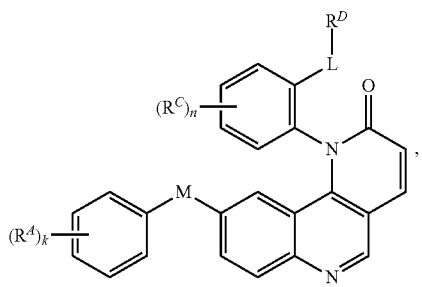

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

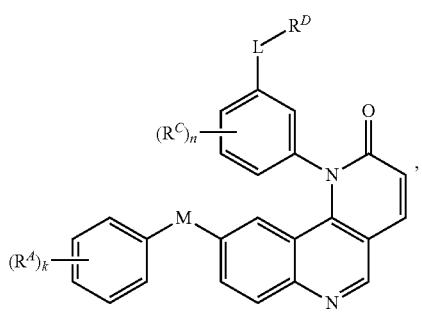

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

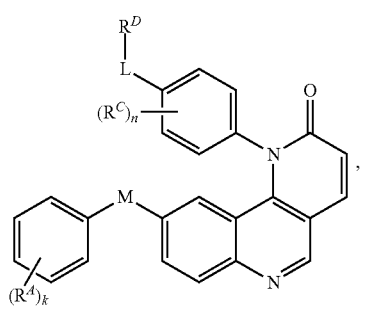

or a pharmaceutically acceptable salt, solvate, hydrate, polymorph, co-crystal, tautomer, stereoisomer, isotopically labeled derivative, or prodrug thereof.

Ring C of Formula (I) may also be an optionally substituted heteroaryl ring. In certain embodiments, Ring C is a substituted heteroaryl ring. In certain embodiments, Ring C is an unsubstituted heteroaryl ring. In certain embodiments, Ring C is a monocyclic heteroaryl ring. In certain embodiments, Ring C is a 5-membered monocyclic heteroaryl ring. In certain embodiments, Ring C is a 5-membered monocyclic heteroaryl ring with one heteroatom selected from the group consisting of S, N, and O. In certain embodiments, Ring C is a 5-membered monocyclic heteroaryl ring with two heteroatoms selected from the group consisting of S, N, and O. In certain embodiments, Ring C is a 5-membered monocyclic heteroaryl ring with three heteroatoms selected from the group consisting of S, N, and O. In certain embodiments, Ring C is substituted pyrrolyl. In certain embodiments, Ring C is unsubstituted pyrrolyl. In certain embodiments, Ring C is substituted furanyl. In certain embodiments, Ring C is unsubstituted furanyl. In certain embodiments, Ring C is substituted thienyl. In certain embodiments, Ring C is unsubstituted thienyl. In certain embodiments, Ring C is substituted pyrazolyl. In certain embodiments, Ring C is unsubstituted pyrazolyl. In certain embodiments, Ring C is substituted imidazolyl. In certain embodiments, Ring C is unsubstituted imidazolyl. In certain embodiments, Ring C is substituted oxazolyl. In certain embodiments, Ring C is unsubstituted oxazolyl. In certain embodiments, Ring C is substituted isoxazolyl. In certain embodiments, Ring C is unsubstituted isoxazolyl. In certain embodiments, Ring C is substituted thiazolyl. In certain embodiments, Ring C is unsubstituted thiazolyl. In certain embodiments, Ring C is substituted isothiazolyl. In certain embodiments, Ring C is unsubstituted isothiazolyl. In certain embodiments, Ring C is substituted triazolyl. In certain embodiments, Ring C is unsubstituted triazolyl. In certain embodiments, Ring C is substituted oxadiazolyl. In certain embodiments, Ring C is unsubstituted oxadiazolyl. In certain embodiments, Ring C is substituted thiadiazolyl. In certain embodiments, Ring C is unsubstituted thiadiazolyl. In certain embodiments, Ring C is a 6-membered monocyclic heteroaryl ring. In certain embodiments, Ring C is a 6-membered monocyclic heteroaryl ring with one heteroatom selected from the group consisting of S, N, and O. In certain embodiments, Ring C is a 6-membered monocyclic heteroaryl ring with two heteroatoms selected from the group consisting of S, N, and O. In certain embodiments, Ring C is a 6-membered monocyclic heteroaryl ring with three heteroatoms selected from the group consisting of S, N, and O. In certain embodiments, Ring C is substituted pyridyl. In certain embodiments, Ring C is unsubstituted pyridyl. In certain embodiments, Ring C is substituted pyridazinyl. In certain embodiments, Ring C is unsubstituted pyridazinyl. In certain embodiments, Ring C is substituted pyrimidinyl. In certain embodiments, Ring C is unsubstituted pyrimidinyl. In certain embodiments, Ring C is substituted pyrazinyl. In certain embodiments, Ring C is unsubstituted pyrazinyl. In certain embodiments, Ring C is substituted triazinyl. In certain embodiments, Ring C is unsubstituted triazinyl. In certain embodiments, Ring C is an optionally substituted heteroaryl ring fused with one or more optionally substituted carbocyclic, optionally substituted heterocyclic, optionally substituted aryl, or optionally substituted heteroaryl groups wherein the point of attachment is on any one of the heteroaryl ring, or carbocyclic, heterocyclic, aryl, or heteroaryl groups, as valency permits. In certain embodiments, Ring C is a bicyclic heteroaryl ring. In certain embodiments, Ring C is an optionally substituted heteroaryl ring fused with an optionally substituted phenyl ring. In certain embodiments, Ring C is substituted indolyl. In certain embodiments, Ring C is unsubstituted indolyl. In certain embodiments, Ring C is substituted isoindolyl. In certain embodiments, Ring C is unsubstituted isoindolyl. In certain embodiments, Ring C is substituted indazolyl. In certain embodiments, Ring C is unsubstituted indazolyl. In certain embodiments, Ring C is substituted benzothienyl. In certain embodiments, Ring C is unsubstituted benzothienyl. In certain embodiments, Ring C is substituted isobenzothienyl. In certain embodiments, Ring C is unsubstituted isobenzothienyl. In certain embodiments, Ring C is substituted benzofuranyl. In certain embodiments, Ring C is unsubstituted benzofuranyl. In certain embodiments, Ring C is substituted benzoisofuranyl. In certain embodiments, Ring C is unsubstituted benzoisofuranyl. In certain embodiments, Ring C is substituted benzimidazolyl. In certain embodiments, Ring C is unsubstituted benzimidazolyl. In certain embodiments, Ring C is substituted benzoxazolyl. In certain embodiments, Ring C is unsubstituted benzoxazolyl. In certain embodiments, Ring C is substituted benzisoxazolyl. In certain embodiments, Ring C is unsubstituted benzisoxazolyl. In certain embodiments, Ring C is substituted benzothiazolyl. In certain embodiments, Ring C is unsubstituted benzothiazolyl. In certain embodiments, Ring C is substituted benzisothiazolyl. In certain embodiments, Ring C is unsubstituted benzisothiazolyl. In certain embodiments, Ring C is substituted benzotriazolyl. In certain embodiments, Ring C is unsubstituted benzotriazolyl. In certain embodiments, Ring C is substituted benzoxadiazolyl. In certain embodiments, Ring C is unsubstituted benzoxadiazolyl. In certain embodiments, Ring C is substituted quinolinyl. In certain embodiments, Ring C is unsubstituted quinolinyl. In certain embodiments, Ring C is substituted isoquinolinyl. In certain embodiments, Ring C is unsubstituted isoquinolinyl. In certain embodiments, Ring C is substituted cinnolinyl. In certain embodiments, Ring C is unsubstituted cinnolinyl. In certain embodiments, Ring C is substituted quinoxalinyl. In certain embodiments, Ring C is unsubstituted quinoxalinyl. In certain embodiments, Ring C is substituted phthalazinyl. In certain embodiments, Ring C is unsubstituted phthalazinyl. In certain embodiments, Ring C is substituted quinazolinyl. In certain embodiments, Ring C is unsubstituted quinazolinyl. In certain embodiments, Ring C is a tricyclic heteroaryl ring.

In certain embodiments, the compound of Formula (I) is of the formula:

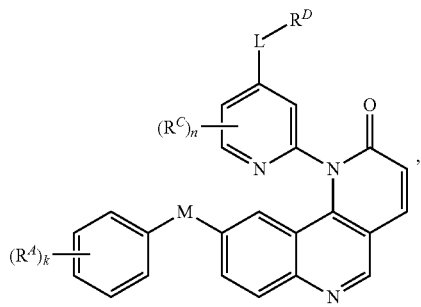

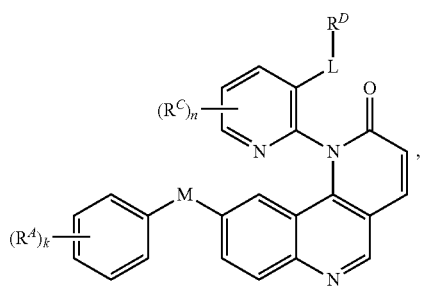

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

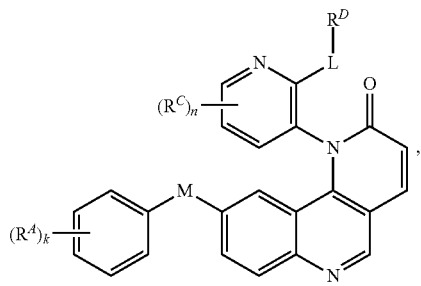

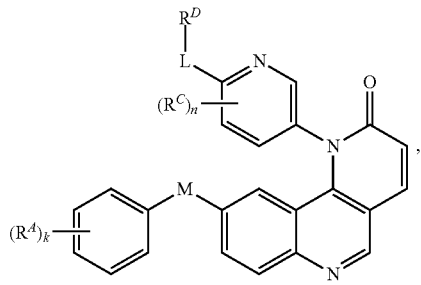

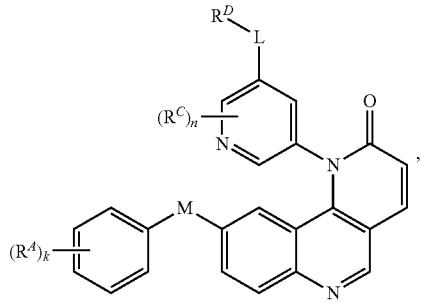

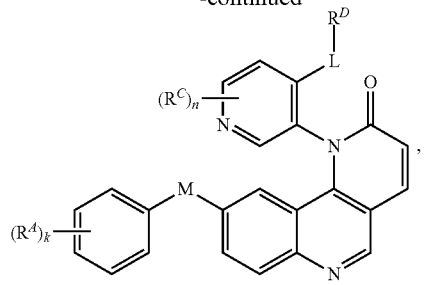

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

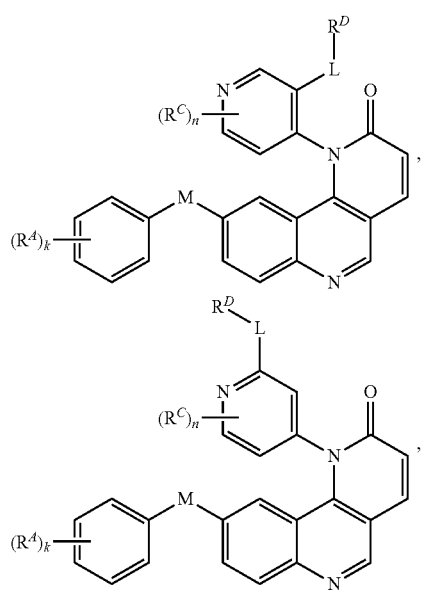

or a pharmaceutically acceptable salt, solvate, hydrate, polymorph, co-crystal, tautomer, stereoisomer, isotopically labeled derivative, or prodrug thereof.

Ring C of Formula (I) may be unsubstituted or substituted with one or more $R^C$ groups. $R^C$ may be attached to a carbon atom or heteroatom, as valency permits. In certain embodiments, Ring C is unsubstituted, and thus n is 0. In certain embodiments, n is 1. In certain embodiments, the compound of Formula (I) is of the formula:

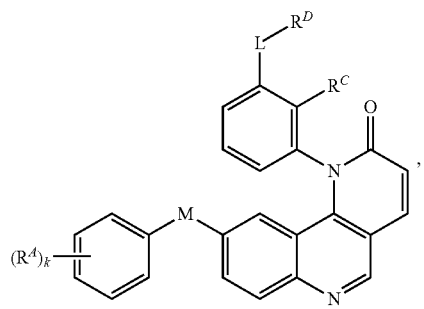

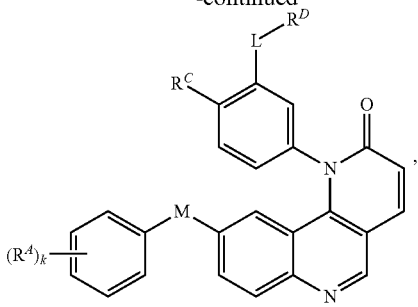

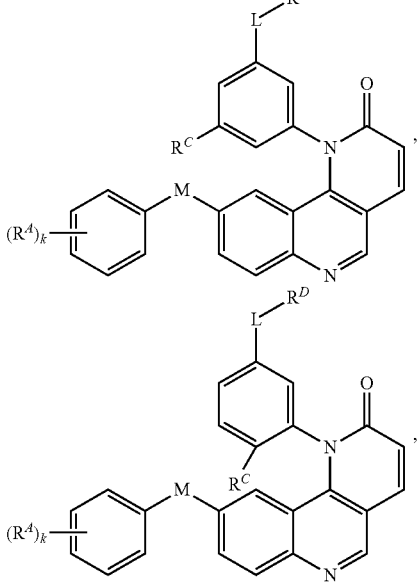

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

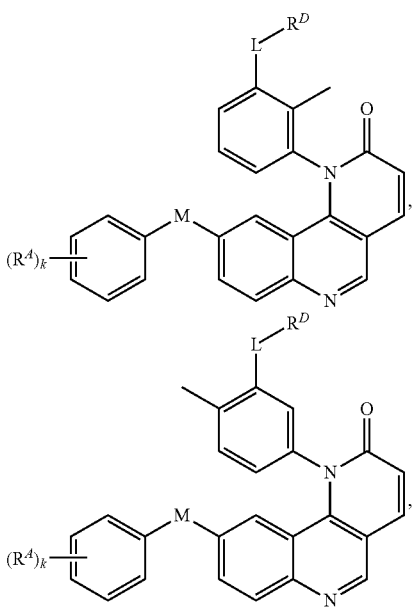

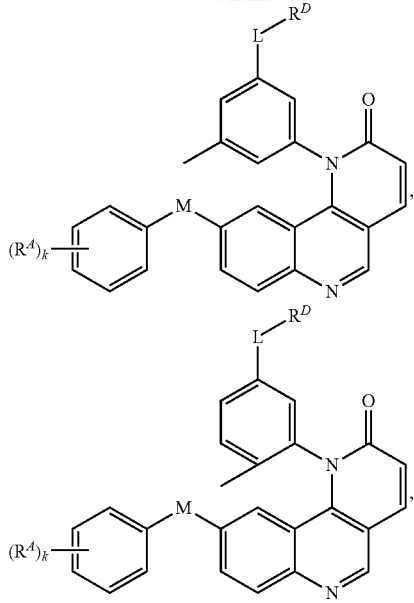

or a pharmaceutically acceptable salt, solvate, hydrate, polymorph, co-crystal, tautomer, stereoisomer, isotopically labeled derivative, or prodrug thereof.

In certain embodiments, n is 2. In certain embodiments, the compound of Formula (I) is of the formula:

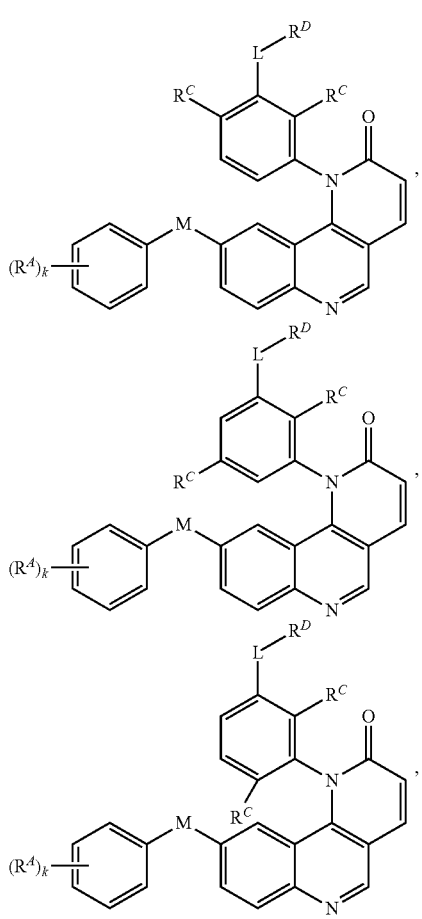

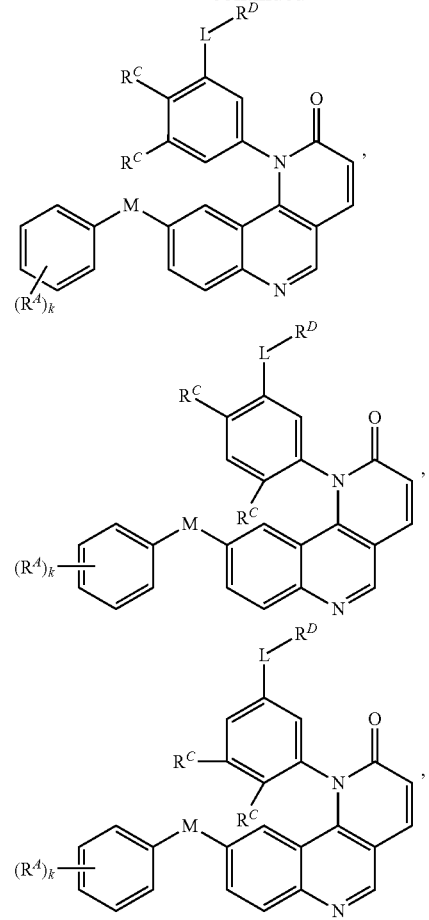

or a pharmaceutically acceptable salt, solvate, hydrate, polymorph, co-crystal, tautomer, stereoisomer, isotopically labeled derivative, or prodrug thereof.

In certain embodiments, n is 3. In certain embodiments, n is 4.

In certain embodiments, at least one $R^C$ is H. In certain embodiments, at least one $R^C$ is halogen. In certain embodiments, at least one $R^C$ is F. In certain embodiments, at least one $R^C$ is Cl. In certain embodiments, at least one $R^C$ is Br. In certain embodiments, at least one $R^C$ is I (iodine). In certain embodiments, at least one $R^C$ is substituted acyl. In certain embodiments, at least one $R^C$ is unsubstituted acyl. In certain embodiments, at least one $R^C$ is acetyl. In certain embodiments, at least one $R^C$ is substituted alkyl. In certain embodiments, at least one $R^C$ is unsubstituted alkyl. In certain embodiments, at least one $R^C$ is $C_{1-6}$ alkyl. In certain embodiments, at least one $R^C$ is methyl. In certain embodiments, at least one $R^C$ is ethyl. In certain embodiments, at least one $R^C$ is propyl. In certain embodiments, at least one $R^C$ is butyl. In certain embodiments, at least one $R^C$ is substituted alkenyl. In certain embodiments, at least one $R^C$ is unsubstituted alkenyl. In certain embodiments, at least one $R^C$ is substituted alkynyl. In certain embodiments, at least one $R^C$ is unsubstituted alkynyl. In certain embodiments, at least one $R^C$ is substituted carbocyclyl. In certain embodiments, at least one $R^C$ is unsubstituted carbocyclyl. In certain embodiments, at least one $R^C$ is substituted heterocyclyl. In certain embodiments, at least one $R^C$ is unsubstituted heterocyclyl. In certain embodiments, at least one $R^C$ is substituted aryl. In certain embodiments, at least one $R^C$ is unsubstituted aryl. In certain embodiments, at least one $R^C$ is substituted phenyl. In certain embodiments, at least one $R^C$ is unsubstituted phenyl. In certain embodiments, at least one $R^C$ is substituted heteroaryl. In certain embodiments, at least one $R^C$ is unsubstituted heteroaryl. In certain embodiments, at least one $R^C$ is substituted pyridyl. In certain embodiments, at least one $R^C$ is unsubstituted pyridyl. In certain embodiments, at least one $R^C$ is —$OR^{C1}$. In certain embodiments, at least one $R^C$ is —OH. In certain embodiments, at least one $R^C$ is —$N(R^{C1})_2$. In certain embodiments, at least one $R^C$ is —$NH_2$. In certain embodiments, at least one $R^C$ is —$SR^{C1}$. In certain embodiments, at least one $R^C$ is —SH.

In certain embodiments, when $R^C$ is —$OR^{C1}$, —$N(R^{C1})_2$, or —$SR^{C1}$, at least one $R^{C1}$ is H. In certain embodiments, at least one $R^{C1}$ is substituted acyl. In certain embodiments, at least one $R^{C1}$ is unsubstituted acyl. In certain embodiments, at least one $R^{C1}$ is acetyl. In certain embodiments, at least one $R^{C1}$ is substituted alkyl. In certain embodiments, at least one $R^{C1}$ is unsubstituted alkyl. In certain embodiments, at least one $R^{C1}$ is $C_{1-6}$ alkyl. In certain embodiments, at least one $R^{C1}$ is methyl. In certain embodiments, at least one $R^{C1}$ is ethyl. In certain embodiments, at least one $R^{C1}$ is propyl. In certain embodiments, at least one $R^{C1}$ is butyl. In certain embodiments, at least one $R^{C1}$ is substituted alkenyl. In certain embodiments, at least one $R^{C1}$ is unsubstituted alkenyl. In certain embodiments, at least one $R^{C1}$ is substituted alkynyl. In certain embodiments, at least one $R^{C1}$ is unsubstituted alkynyl. In certain embodiments, at least one $R^{C1}$ is substituted carbocyclyl. In certain embodiments, at least one $R^{C1}$ is unsubstituted carbocyclyl. In certain embodiments, at least one $R^{C1}$ is substituted heterocyclyl. In certain embodiments, at least one $R^{C1}$ is unsubstituted heterocyclyl. In certain embodiments, at least one $R^{C1}$ is substituted aryl. In certain embodiments, at least one $R^{C1}$ is unsubstituted aryl. In certain embodiments, at least one $R^{C1}$ is substituted phenyl. In certain embodiments, at least one $R^{C1}$ is unsubstituted phenyl. In certain embodiments, at least one $R^{C1}$ is substituted heteroaryl. In certain embodiments, at least one $R^{C1}$ is unsubstituted heteroaryl. In certain embodiments, at least one $R^{C1}$ is substituted pyridyl. In certain embodiments, at least one $R^{C1}$ is unsubstituted pyridyl. In certain embodiments, at least one $R^{C1}$ is a nitrogen protecting group when attached to a nitrogen atom. In certain embodiments, at least one $R^{C1}$ is Bn, BOC, Cbz, Fmoc, trifluoroacetyl, triphenylmethyl, or Ts when attached to a nitrogen atom. In certain embodiments, $R^{C1}$ is an oxygen protecting group when attached to an oxygen atom. In certain embodiments, $R^{C1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{C1}$ is a sulfur protecting group when attached to a sulfur atom. In certain embodiments, $R^{C1}$ is acetamidomethyl, t-Bu, 3-nitro-2-pyridine sulfenyl, 2-pyridine-sulfenyl, or triphenylmethyl when attached to a sulfur atom. In certain embodiments, two $R^{C1}$ groups are joined to form a substituted heterocyclic ring. In certain embodiments, two $R^{C1}$ groups are joined to form an unsubstituted heterocyclic ring.

In certain embodiments, $R^C$ is substituted $C_{1-6}$ alkyl; and n is 1. In certain embodiments, $R^C$ is unsubstituted $C_{1-6}$ alkyl; and n is 1. In certain embodiments, $R^C$ is methyl; and n is 1. In certain embodiments, $R^C$ is ethyl; and n is 1. In certain embodiments, $R^C$ is propyl; and n is 1. In certain embodiments, $R^C$ is butyl; and n is 1. In certain embodiments, $R^C$ is halogen; and n is 1. In certain embodiments, $R^C$ is F; and n is 1. In certain embodiments, $R^C$ is Cl; and n is 1. In certain embodiments, $R^C$ is Br; and n is 1. In certain embodiments, $R^C$ is I (iodine); and n is 1.

In compounds of Formula (I), linker L is a divalent linker moiety. L may be a bond. In certain embodiments, L is a single bond. L may also be a $C_{1-6}$ hydrocarbon chain. L may be saturated or unsaturated. L may be substituted or unsubstituted. L may also be branched or unbranched. In certain embodiments, L is a $C_1$ hydrocarbon chain substituted with one or more $R^L$ groups. In certain embodiments, L is —$C(R^L)_2$—. In certain embodiments, L is —$CH_2$—. In certain embodiments, L is a $C_2$ hydrocarbon chain substituted with one or more $R^L$ groups. In certain embodiments, L is —$C(R^L)_2$—$C(R^L)_2$—. In certain embodiments, L is —$CHR^L$—$CHR^L$—. In certain embodiments, L is —$(CH_2)_2$—. In certain embodiments, L is trans-$CR^L$=$CR^L$—. In certain embodiments, L is trans-CH=CH—. In certain embodiments, L is cis-$CR^L$=$CR^L$—. In certain embodiments, L is cis-CH=CH—. In certain embodiments, L is —C≡C—. In certain embodiments, L is a $C_3$ hydrocarbon chain substituted with one or more $R^L$ groups. In certain embodiments, L is —$C(R^L)_2$—$C(R^L)_2$—$C(R^L)_2$—. In certain embodiments, L is —$(CH_2)_3$—. In certain embodiments, L is —$C(R^L)$=$C(R^L)$—$C(R^L)_2$—, wherein C=C is cis or trans. In certain embodiments, L is —$C(R^L)_2$—$C(R^L)$=$C(R^L)$—, wherein C=C is cis or trans. In certain embodiments, L is —C—C≡$C(R^L)_2$—. In certain embodiments, L is —$C(R^L)_2$—C≡C—. In certain embodiments, L is a $C_4$ hydrocarbon chain substituted with one or more $R^L$ groups. In certain embodiments, L is —$C(R^L)_2$—$C(R^L)_2$—$C(R^L)_2$—$C(R^L)_2$—. In certain embodiments, L is —$(CH_2)_4$—. In certain embodiments, L is —$C(R^L)$=$C(R^L)$—$C(R^L)_2$—$C(R^L)_2$—, wherein C=C is cis or trans. In certain embodiments, L is —$C(R^L)_2$—$C(R^L)$=$C(R^L)$—$C(R^L)_2$—, wherein C=C is cis or trans. In certain embodiments, L is —$C(R^L)_2$—$C(R^L)_2$—$C(R^L)$=$C(R^L)$—, wherein C=C is cis or trans. In certain embodiments, L is —C≡C—$C(R^L)_2$—$C(R^L)_2$—. In certain embodiments, L is —$C(R^L)_2$—C≡C—$C(R^L)_2$—. In certain embodiments, L is —$C(R^L)_2$—$C(R^L)_2$—C≡C—. In certain embodiments, L is —$C(R^L)$=$C(R^L)$—$C(R^L)$=$C(R^L)$—, wherein each occurrence of C=C is independently cis or trans. In certain embodiments, L is —$C(R^L)$=$C(R^L)$—C≡C—, wherein C=C is cis or trans. In certain embodiments, L is —C≡C—$C(R^L)$=$C(R^L)$—, wherein the C=C is cis or trans. In certain embodiments, L is —C≡C—C≡C—. In certain embodiments, L is a $C_5$ hydrocarbon chain substituted with one or more $R^L$ groups. In certain embodiments, L is —$C(R^L)_2$—$C(R^L)_2$—$C(R^L)_2$—$C(R^L)_2$—$C(R^L)_2$—. In certain embodiments, L is —$(CH_2)_5$—. In certain embodiments, L is a $C_6$ hydrocarbon chain substituted with one or more $R^L$ groups. In certain embodiments, L is —$C(R^L)_2$—$C(R^L)_2$—$C(R^L)_2$—$C(R^L)_2$—$C(R^L)_2$—$C(R^L)_2$—. In certain embodiments, L is —$(CH_2)_6$—. In certain embodiments, one or more carbon units of the hydrocarbon chain is replaced with —O—, —S—, —$NR^L$—, —$NR^LC(=O)$—, —$C(=O)NR^L$—, —$SC(=O)$—, —$C(=O)S$—, —$OC(=O)$—, —$C(=O)O$—, —$NR^LC(=S)$—, —$C(=S)NR^L$—, trans-$CR^L$=$CR^L$—, cis-$CR^L$=$CR^L$—, —C≡C—, —$S(=O)_2O$—, —$OS(=O)_2$—, —$S(=O)_2NR^L$—, or —$NR^LS(=O)_2$—.

In certain embodiments, at least one $R^L$ is H. In certain embodiments, at least one $R^L$ is halogen. In certain embodiments, at least one $R^L$ is F. In certain embodiments, at least one $R^L$ is Cl. In certain embodiments, at least one $R^L$ is Br. In certain embodiments, at least one $R^L$ is I (iodine). In certain embodiments, at least one $R^L$ is substituted alkyl. In certain embodiments, at least one $R^L$ is unsubstituted alkyl. In certain embodiments, at least one $R^L$ is $C_{1-6}$ alkyl. In certain embodiments, at least one $R^L$ is methyl. In certain embodiments, at least one $R^L$ is ethyl. In certain embodiments, at least one $R^L$ is propyl. In certain embodiments, at least one $R^L$ is butyl. In certain embodiments, at least one $R^L$ is substituted alkenyl. In certain embodiments, at least one $R^L$ is unsubstituted alkenyl. In certain embodiments, at least one $R^L$ is vinyl. In certain embodiments, at least one $R^L$ is substituted alkynyl. In certain embodiments, at least one $R^L$ is unsubstituted alkynyl. In certain embodiments, at least one $R^L$ is ethynyl. In certain embodiments, at least one $R^L$ is substituted carbocyclyl. In certain embodiments, at least one $R^L$ is unsubstituted carbocyclyl.

In certain embodiments, at least one $R^L$ is substituted heterocyclyl. In certain embodiments, at least one $R^L$ is unsubstituted heterocyclyl. In certain embodiments, at least one $R^L$ is substituted aryl. In certain embodiments, at least one $R^L$ is unsubstituted aryl. In certain embodiments, at least one $R^L$ is substituted phenyl. In certain embodiments, at least one $R^L$ is unsubstituted phenyl. In certain embodiments, at least one $R^L$ is substituted heteroaryl. In certain embodiments, at least one $R^L$ is unsubstituted heteroaryl. In certain embodiments, at least one $R^L$ is substituted pyridyl. In certain embodiments, at least one $R^L$ is unsubstituted pyridyl. In certain embodiments, two $R^L$ groups are joined to form a substituted carbocyclic ring. In certain embodiments, two $R^L$ groups are joined to form an unsubstituted carbocyclic ring. In certain embodiments, two $R^L$ groups are joined to form a substituted heterocyclic ring. In certain embodiments, two $R^L$ groups are joined to form an unsubstituted heterocyclic ring. In certain embodiments, two $R^L$ groups are joined to form a substituted aryl ring. In certain embodiments, two $R^L$ groups are joined to form an unsubstituted aryl ring. In certain embodiments, two $R^L$ groups are joined to form a substituted phenyl ring. In certain embodiments, two $R^L$ groups are joined to form an unsubstituted phenyl ring. In certain embodiments, two $R^L$ groups are joined to form a substituted heteroaryl ring. In certain embodiments, two $R^L$ groups are joined to form an unsubstituted heteroaryl ring.

In compounds of Formula (I), $R^D$ is a substituent on Ring C through linker L. In certain embodiments, $R^D$ comprises a Michael acceptor moiety. This Michael acceptor moiety may react with a cysteine or other nucleophilic residue of a kinase (e.g., bone marrow kinase on X chromosome (BMX) or other Tec kinase) to allow covalent attachment of the compound to the kinase. In certain embodiments, the covalent attachment is irreversible. In other embodiments, the covalent attachment is reversible. In certain embodiments, $R^D$ is of Formula (i-1). In certain embodiments, $R^D$ is of Formula (i-2). In certain embodiments, $R^D$ is of Formula (i-3). In certain embodiments, $R^D$ is of Formula (i-4). In certain embodiments, $R^D$ is of Formula (i-5). In certain embodiments, $R^D$ is of Formula (i-6). In certain embodiments, $R^D$ is of Formula (i-7). In certain embodiments, $R^D$ is of Formula (i-8). In certain embodiments, $R^D$ is of Formula (i-9). In certain embodiments, $R^D$ is of Formula (i-10). In certain embodiments, $R^D$ is of Formula (i-11). In certain embodiments, $R^D$ is of Formula (i-12). In certain embodiments, $R^D$ is of Formula (i-13). In certain embodiments, $R^D$ is of Formula (i-14). In certain embodiments, $R^D$ is of Formula (i-15). In certain embodiments, $R^D$ is of Formula (i-16). In certain embodiments, $R^D$ is of Formula (i-17).

In compounds of Formula (I), $R^D$ may include a substituent $R^{D1}$. In certain embodiments, $R^{D1}$ is H. In certain embodiments, $R^{D1}$ is halogen. In certain embodiments, $R^{D1}$ is F. In certain embodiments, $R^{D1}$ is Cl. In certain embodiments, $R^{D1}$ is Br. In certain embodiments, $R^{D1}$ is I (iodine). In certain embodiments, $R^{D1}$ is substituted acyl. In certain embodiments, $R^{D1}$ is unsubstituted acyl. In certain embodiments, $R^{D1}$ is acetyl. In certain embodiments, $R^{D1}$ is substituted alkyl. In certain embodiments, $R^{D1}$ is unsubstituted alkyl. In certain embodiments, $R^{D1}$ is $C_{1-6}$ alkyl. In certain embodiments, $R^{D1}$ is methyl. In certain embodiments, $R^{D1}$ is ethyl. In certain embodiments, $R^{D1}$ is propyl. In certain embodiments, RD is butyl. In certain embodiments, $R^{D1}$ is substituted alkenyl. In certain embodiments, $R^{D1}$ is unsubstituted alkenyl. In certain embodiments, $R^{D1}$ is substituted alkynyl. In certain embodiments, $R^{D1}$ is unsubstituted alkynyl. In certain embodiments, $R^{D1}$ is substituted carbocyclyl. In certain embodiments, $R^{D1}$ is unsubstituted carbocyclyl. In certain embodiments, $R^{D1}$ is substituted heterocyclyl. In certain embodiments, $R^{D1}$ is unsubstituted heterocyclyl. In certain embodiments, $R^{D1}$ is substituted aryl. In certain embodiments, $R^{D1}$ is unsubstituted aryl. In certain embodiments, $R^{D1}$ is substituted phenyl. In certain embodiments, $R^{D1}$ is unsubstituted phenyl. In certain embodiments, $R^{D1}$ is substituted heteroaryl. In certain embodiments, $R^{D1}$ is unsubstituted heteroaryl. In certain embodiments, $R^{D1}$ is substituted pyridyl. In certain embodiments, $R^{D1}$ is unsubstituted pyridyl. In certain embodiments, $R^{D1}$ is —CN. In certain embodiments, $R^{D1}$ is —$NO_2$. In certain embodiments, $R^{D1}$ is —$OR^{D1a}$. In certain embodiments, $R^{D1}$ is —$N(R^{D1a})_2$. In certain embodiments, $R^{D1}$ is —$SR^{D1a}$. In certain embodiments, $R^{D1}$ is —$CH_2OR^{D1a}$. In certain embodiments, $R^{D1}$ is —$CH_2N(R^{D1a})_2$. In certain embodiments, $R^{D1}$ is —$CH_2SR^{D1a}$.

In certain embodiments, at least one $R^{D1a}$ is H. In certain embodiments, at least one $R^{D1a}$ is substituted acyl. In certain embodiments, at least one $R^{D1a}$ is unsubstituted acyl. In certain embodiments, at least one $R^{D1a}$ is acetyl. In certain embodiments, at least one $R^{D1a}$ is substituted alkyl. In certain embodiments, at least one $R^{D1a}$ is unsubstituted alkyl. In certain embodiments, at least one $R^{D1a}$ is $C_{1-6}$ alkyl. In certain embodiments, at least one $R^{D1a}$ is methyl. In certain embodiments, at least one $R^{D1a}$ is ethyl. In certain embodiments, at least one $R^{D1a}$ is propyl. In certain embodiments, at least one $R^{D1a}$ is butyl. In certain embodiments, at least one $R^{D1a}$ is substituted alkenyl. In certain embodiments, at least one $R^{D1a}$ is unsubstituted alkenyl. In certain embodiments, at least one $R^{D1a}$ is substituted alkynyl. In certain embodiments, at least one $R^{D1a}$ is unsubstituted alkynyl. In certain embodiments, at least one $R^{D1a}$ is substituted carbocyclyl. In certain embodiments, at least one $R^{D1a}$ is unsubstituted carbocyclyl. In certain embodiments, at least one $R^{D1a}$ is substituted heterocyclyl. In certain embodiments, at least one $R^{D1a}$ is unsubstituted heterocyclyl. In certain embodiments, at least one $R^{D1a}$ is substituted aryl. In certain embodiments, at least one $R^{D1a}$ is unsubstituted aryl. In certain embodiments, at least one $R^{D1a}$ is substituted phenyl. In certain embodiments, at least one $R^{D1a}$ is unsubstituted phenyl. In certain embodiments, at least one $R^{D1a}$ is substituted heteroaryl. In certain embodiments, at least one $R^{D1a}$ is unsubstituted heteroaryl. In certain embodiments, at least one $R^{D1a}$ is substituted pyridyl. In certain embodiments, at least one $R^{D1a}$ is unsubstituted pyridyl. In certain embodiments, at least one $R^{D1a}$ is a nitrogen protecting group when attached to a nitrogen atom. In certain embodiments, at least one $R^{D1a}$ is Bn, BOC, Cbz, Fmoc, trifluoroacetyl, triphenylmethyl, or Ts when attached to a nitrogen atom. In certain embodiments, $R^{D1a}$ is an oxygen protecting group when attached to an oxygen atom. In certain embodiments, $R^{D1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1a}$ is a sulfur protecting group when attached to a sulfur atom. In certain embodiments, $R^{D1a}$ is acetamidomethyl, t-Bu, 3-nitro-2-pyridine sulfenyl, 2-pyridine-sulfenyl, or triphenylmethyl when attached to a sulfur atom. In certain embodiments, two $R^{D1a}$ groups are joined to form a substituted heterocyclic ring. In certain embodiments, two $R^{D1a}$ groups are joined to form an unsubstituted heterocyclic ring.

In compounds of Formula (I), $R^D$ may include a substituent $R^{D2}$. In certain embodiments, $R^{D2}$ is H. In certain embodiments, $R^{D2}$ is halogen. In certain embodiments, $R^{D2}$ is F. In certain embodiments, $R^{D2}$ is Cl. In certain embodiments, $R^{D2}$ is Br. In certain embodiments, $R^{D2}$ is I (iodine). In certain embodiments, $R^{D2}$ is substituted acyl. In certain embodiments, $R^{D2}$ is unsubstituted acyl. In certain embodiments, $R^{D2}$ is acetyl. In certain embodiments, $R^{D2}$ is substituted alkyl. In certain embodiments, $R^{D2}$ is unsubstituted alkyl. In certain embodiments, $R^{D2}$ is $C_{1-6}$ alkyl. In certain embodiments, $R^{D2}$ is methyl. In certain embodiments, $R^{D2}$ is ethyl. In certain embodiments, $R^{D2}$ is propyl. In certain embodiments, $R^{D2}$ is butyl. In certain embodiments, $R^{D2}$ is substituted alkenyl. In certain embodiments, $R^{D2}$ is unsubstituted alkenyl. In certain embodiments, $R^{D2}$ is substituted alkynyl. In certain embodiments, $R^{D2}$ is unsubstituted alkynyl. In certain embodiments, $R^{D2}$ is substituted carbocyclyl. In certain embodiments, $R^{D2}$ is unsubstituted carbocyclyl. In certain embodiments, $R^{D2}$ is substituted heterocyclyl. In certain embodiments, $R^{D2}$ is unsubstituted heterocyclyl. In certain embodiments, $R^{D2}$ is substituted aryl. In certain embodiments, $R^{D2}$ is unsubstituted aryl. In certain embodiments, $R^{D2}$ is substituted phenyl. In certain embodiments, $R^{D2}$ is unsubstituted phenyl. In certain embodiments, $R^{D2}$ is substituted heteroaryl. In certain embodiments, $R^{D2}$ is unsubstituted heteroaryl. In certain embodiments, $R^{D2}$ is substituted pyridyl. In certain embodiments, $R^{D2}$ is unsubstituted pyridyl. In certain embodiments, $R^{D2}$ is —CN. In certain embodiments, $R^{D2}$ is —NO$_2$. In certain embodiments, $R^{D2}$ is —OR$^{D2a}$. In certain embodiments, $R^{D2}$ is —N(R$^{D2a}$)$_2$. In certain embodiments, $R^{D2}$ is —SR$^{D2a}$. In certain embodiments, $R^{D2}$ is —CH$_2$OR$^{D2a}$. In certain embodiments, $R^{D2}$ is —CH$_2$N(R$^{D2a}$)$_2$. In certain embodiments, $R^{D2}$ is —CH$_2$SR$^{D2a}$.

In certain embodiments, at least one $R^{D2a}$ is H. In certain embodiments, at least one $R^{D2a}$ is substituted acyl. In certain embodiments, at least one $R^{D2a}$ is unsubstituted acyl. In certain embodiments, at least one $R^{D2a}$ is acetyl. In certain embodiments, at least one $R^{D2a}$ is substituted alkyl. In certain embodiments, at least one $R^{D2a}$ is unsubstituted alkyl. In certain embodiments, at least one $R^{D2a}$ is $C_{1-6}$ alkyl. In certain embodiments, at least one $R^{D2a}$ is methyl. In certain embodiments, at least one $R^{D2a}$ is ethyl. In certain embodiments, at least one $R^{D2a}$ is propyl. In certain embodiments, at least one $R^{D2a}$ is butyl. In certain embodiments, at least one $R^{D2a}$ is substituted alkenyl. In certain embodiments, at least one $R^{D2a}$ is unsubstituted alkenyl. In certain embodiments, at least one $R^{D2a}$ is substituted alkynyl. In certain embodiments, at least one $R^{D2a}$ is unsubstituted alkynyl. In certain embodiments, at least one $R^{D2a}$ is substituted carbocyclyl. In certain embodiments, at least one $R^{D2a}$ is unsubstituted carbocyclyl. In certain embodiments, at least one $R^{D2a}$ is substituted heterocyclyl. In certain embodiments, at least one $R^{D2a}$ is unsubstituted heterocyclyl. In certain embodiments, at least one $R^{D2a}$ is substituted aryl. In certain embodiments, at least one $R^{D2a}$ is unsubstituted aryl. In certain embodiments, at least one $R^{D2a}$ is substituted phenyl. In certain embodiments, at least one $R^{D2a}$ is unsubstituted phenyl. In certain embodiments, at least one $R^{D2a}$ is substituted heteroaryl. In certain embodiments, at least one $R^{D2a}$ is unsubstituted heteroaryl. In certain embodiments, at least one $R^{D2a}$ is substituted pyridyl. In certain embodiments, at least one $R^{D2a}$ is unsubstituted pyridyl. In certain embodiments, at least one $R^{D2a}$ is a nitrogen protecting group when attached to a nitrogen atom. In certain embodiments, at least one $R^{D2a}$ is Bn, BOC, Cbz, Fmoc, trifluoroacetyl, triphenylmethyl, or Ts when attached to a nitrogen atom. In certain embodiments, $R^{D2a}$ is an oxygen protecting group when attached to an oxygen atom. In certain embodiments, $R^{D2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D2a}$ is a sulfur protecting group when attached to a sulfur atom. In certain embodiments, $R^{D2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{D2a}$ groups are joined to form a substituted heterocyclic ring. In certain embodiments, two $R^{D2a}$ groups are joined to form an unsubstituted heterocyclic ring.

In compounds of Formula (I), $R^D$ may include a substituent $R^{D3}$. In certain embodiments, $R^{D3}$ is H. In certain embodiments, $R^{D3}$ is halogen. In certain embodiments, $R^{D3}$ is F. In certain embodiments, $R^{D3}$ is Cl. In certain embodiments, $R^{D3}$ is Br. In certain embodiments, $R^{D3}$ is I (iodine). In certain embodiments, $R^{D3}$ is substituted acyl. In certain embodiments, $R^{D3}$ is unsubstituted acyl. In certain embodiments, $R^{D3}$ is acetyl. In certain embodiments, $R^{D3}$ is substituted alkyl. In certain embodiments, $R^{D3}$ is unsubstituted alkyl. In certain embodiments, $R^{D3}$ is $C_{1-6}$ alkyl. In certain embodiments, $R^{D3}$ is methyl. In certain embodiments, $R^{D3}$ is ethyl. In certain embodiments, $R^{D3}$ is propyl. In certain embodiments, $R^{D3}$ is butyl. In certain embodiments, $R^{D3}$ is substituted alkenyl. In certain embodiments, $R^{D3}$ is unsubstituted alkenyl. In certain embodiments, $R^{D3}$ is substituted alkynyl. In certain embodiments, $R^{D3}$ is unsubstituted alkynyl. In certain embodiments, $R^{D3}$ is substituted carbocyclyl. In certain embodiments, $R^{D3}$ is unsubstituted carbocyclyl. In certain embodiments, $R^{D3}$ is substituted heterocyclyl. In certain embodiments, $R^{D3}$ is unsubstituted heterocyclyl. In certain embodiments, $R^{D3}$ is substituted aryl. In certain embodiments, $R^{D3}$ is unsubstituted aryl. In certain embodiments, $R^{D3}$ is substituted phenyl. In certain embodiments, $R^{D3}$ is unsubstituted phenyl. In certain embodiments, $R^{D3}$ is substituted heteroaryl. In certain embodiments, $R^{D3}$ is unsubstituted heteroaryl. In certain embodiments, $R^{D3}$ is substituted pyridyl. In certain embodiments, $R^{D3}$ is unsubstituted pyridyl. In certain embodiments, $R^{D3}$ is —CN. In certain embodiments, $R^{D3}$ is —NO$_2$. In certain embodiments, $R^{D3}$ is —OR$^{D3a}$. In certain embodiments, $R^{D3}$ is —N(R$^{D3a}$)$_2$. In certain embodiments, $R^{D3}$ is —SR$^{D3a}$. In certain embodiments, $R^{D3}$ is —CH$_2$OR$^{D3a}$. In certain embodiments, $R^{D3}$ is —CH$_2$N(R$^{D3a}$)$_2$. In certain embodiments, $R^{D3}$ is —CH$_2$SR$^{D3a}$ In certain embodiments, at least one $R^{D3a}$ is H. In certain embodiments, at least one $R^{D3a}$ is substituted acyl. In certain embodiments, at least one $R^{D3a}$ is unsubstituted acyl. In certain embodiments, at least one $R^{D3a}$ is acetyl. In certain embodiments, at least one $R^{D3a}$ is substituted alkyl. In certain embodiments, at least one $R^{D3a}$ is unsubstituted alkyl. In certain embodiments, at least one $R^{D3a}$ is $C_{1-6}$ alkyl. In certain embodiments, at least one $R^{D3a}$ is methyl. In certain embodiments, at least one $R^{D3a}$ is ethyl. In certain embodiments, at least one $R^{D3a}$ is propyl. In certain embodiments, at least one $R^{D3a}$ is butyl. In certain embodiments, at least one $R^{D3a}$ is substituted alkenyl. In certain embodiments, at least one $R^{D3a}$ is unsubstituted alkenyl. In certain embodiments, at least one $R^{D3a}$ is substituted alkynyl. In certain embodiments, at least one $R^{D3a}$ is unsubstituted alkynyl. In certain embodiments, at least one $R^{D3a}$ is substituted carbocyclyl. In certain embodiments, at least one $R^{D3a}$ is unsubstituted carbocyclyl. In certain embodiments, at least one $R^{D3a}$ is substituted heterocyclyl. In certain embodiments, at least one $R^{D3a}$ is unsubstituted heterocyclyl. In certain embodiments, at least one $R^{D3a}$ is substituted aryl. In certain embodiments, at least one $R^{D3a}$ is unsubstituted aryl. In certain embodiments, at least one $R^{D3a}$ is substituted phenyl. In certain embodiments, at least one $R^{D3a}$ is unsubstituted phenyl. In certain embodiments, at least one $R^{D3a}$ is substituted heteroaryl. In certain embodiments, at least one $R^{D3a}$ is unsubstituted heteroaryl. In certain embodiments, at least one $R^{D3a}$ is substituted pyridyl. In certain embodiments, at least one $R^{D3a}$ is unsubstituted pyridyl. In certain embodiments, at least one $R^{D3a}$ is a nitrogen protecting group when attached to a nitrogen atom. In certain embodiments, at least one $R^{D3a}$ is Bn, BOC, Cbz, Fmoc, trifluoroacetyl, triphenylmethyl, or Ts when attached to a nitrogen atom. In certain embodiments, $R^{D3a}$ is an oxygen protecting group when attached to an oxygen atom. In certain embodiments, $R^{D3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D3a}$ is a sulfur protecting group when attached to a sulfur atom. In certain embodiments, $R^{D3a}$ is acetamidomethyl, t-Bu, 3-nitro-2-pyridine sulfenyl, 2-pyridine-sulfenyl, or triphenylmethyl when attached to a sulfur atom. In certain embodiments, two $R^{D3a}$ groups are joined to form a substituted heterocyclic ring. In certain embodiments, two $R^{D3a}$ groups are joined to form an unsubstituted heterocyclic ring.

In compounds of Formula (I), $R^D$ may include a substituent $R^{D4}$. In certain embodiments, $R^{D4}$ is a leaving group. In certain embodiments, $R^{D4}$ is halogen. In certain embodiments, $R^{D4}$ is F. In certain embodiments, $R^{D4}$ is Cl. In certain embodiments, $R^{D4}$ is Br. In certain embodiments, $R^{D4}$ is I (iodine). In certain embodiments, $R^{D4}$ is —OS($=$O)$_w R^{D4a}$. In certain embodiments, w is 1. In certain embodiments, w is 2. In certain embodiments, $R^{D4}$ is —OMs. In certain embodiments, $R^{D4}$ is —OTf. In certain embodiments, $R^{D4}$ is —OTs. In certain embodiments, $R^{D4}$ is —OBs. In certain embodiments, $R^{D4}$ is 2-nitrobenzenesulfonyloxy. In certain embodiments, $R^{D4}$ is —OR$^{D4a}$. In certain embodiments, $R^{D4}$ is —OMe. In certain embodiments, $R^{D4}$ is —OCF$_3$. In certain embodiments, $R^{D4}$ is —OPh. In certain embodiments, $R^{D4}$ is —OC($=$O)$R^{D4a}$. In certain embodiments, $R^{D4}$ is —OC($=$O)Me. In certain embodiments, $R^{D4}$ is —OC($=$O)CF$_3$. In certain embodiments, $R^{D4}$ is —OC($=$O)Ph. In certain embodiments, $R^{D4}$ is —OC($=$O)Cl. In certain embodiments, $R^{D4}$ is —OC($=$O)OR$^{D4a}$. In certain embodiments, $R^{D4}$ is —OC($=$O)OMe. In certain embodiments, $R^{D4}$ is —OC($=$O)O(t-Bu).

In certain embodiments, $R^{D4a}$ is substituted alkyl. In certain embodiments, $R^{D4a}$ is unsubstituted alkyl. In certain embodiments, $R^{D4a}$ is $C_{1-6}$ alkyl. In certain embodiments, $R^{D4a}$ is methyl. In certain embodiments, $R^{D4a}$ is ethyl. In certain embodiments, $R^{D4a}$ is propyl. In certain embodiments, $R^{D4a}$ is butyl. In certain embodiments, $R^{D4a}$ is substituted alkenyl. In certain embodiments, $R^{D4a}$ is unsubstituted alkenyl. In certain embodiments, $R^{D4a}$ is vinyl. In certain embodiments, $R^{D4a}$ is substituted alkynyl. In certain embodiments, $R^{D4a}$ is unsubstituted alkynyl. In certain embodiments, $R^{D4a}$ is ethynyl. In certain embodiments, $R^{D4a}$ is substituted carbocyclyl. In certain embodiments, $R^{D4a}$ is unsubstituted carbocyclyl. In certain embodiments, $R^{D4a}$ is substituted heterocyclyl. In certain embodiments, $R^{D4a}$ is unsubstituted heterocyclyl. In certain embodiments, $R^{D4a}$ is substituted aryl. In certain embodiments, $R^{D4a}$ is unsubstituted aryl. In certain embodiments, $R^{D4a}$ is substituted phenyl. In certain embodiments, $R^{D4a}$ is unsubstituted phenyl. In certain embodiments, $R^{D4a}$ is substituted heteroaryl. In certain embodiments, $R^{D4a}$ is unsubstituted heteroaryl. In certain embodiments, $R^{D4a}$ is substituted pyridyl. In certain embodiments, $R^{D4a}$ is unsubstituted pyridyl.

In compounds of Formula (I), $R^D$ may include a substituent $R^{D5}$. In certain embodiments, $R^{D5}$ is H. In certain embodiments, $R^{D5}$ is substituted alkyl. In certain embodiments, $R^{D5}$ is unsubstituted alkyl. In certain embodiments, $R^{D5}$ is $C_{1-6}$ alkyl. In certain embodiments, $R^{D5}$ is methyl. In certain embodiments, $R^{D5}$ is ethyl. In certain embodiments, $R^{D5}$ is propyl. In certain embodiments, $R^{D5}$ is butyl. In certain embodiments, $R^{D5}$ is a nitrogen protecting group. In certain embodiments, $R^{D5}$ is Bn, BOC, Cbz, Fmoc, trifluoroacetyl, triphenylmethyl, or Ts.

In certain embodiments, $R^{D1}$ and $R^{D2}$ are each hydrogen. In certain embodiments, $R^{D1}$ and $R^{D3}$ are each hydrogen. In certain embodiments, $R^{D2}$ and $R^{D3}$ are each hydrogen. In certain embodiments, $R^{D1}$, $R^{D2}$, and $R^{D3}$ are each hydrogen. In certain embodiments, $R^{D1}$, $R^{D2}$, and $R^{D3}$, and $R^{D5}$ are each hydrogen.

In certain embodiments, a is 1. In certain embodiments, a is 2.

In certain embodiments, z is 0. In certain embodiments, z is 1. In certain embodiments, z is 2. In certain embodiments, z is 3. In certain embodiments, z is 4. In certain embodiments, z is 5. In certain embodiments, z is 6.

In certain embodiments, Y is —O—. In certain embodiments, Y is $=$O. In certain embodiments, Y is —S—. In certain embodiments, Y is $=$S. In certain embodiments, Y is —NR$^{D6}$—, wherein $R^{D6}$ is hydrogen, $C_{1-6}$ alkyl, or a nitrogen protecting group. In certain embodiments, Y is —NH—. In certain embodiments, Y is —NCH$_3$—. In certain embodiments, Y is —N(BOC)—. In certain embodiments, Y is —N(Fmoc)-. In certain embodiments, Y is —N(Cbz)-. In certain embodiments, Y is —N(Bn)-. In certain embodiments, Y is $=$NR$^{D6}$ wherein $R^{D6}$ is hydrogen, $C_{1-6}$ alkyl, or a nitrogen protecting group. In certain embodiments, Y is $=$NH. In certain embodiments, Y is $=$NCH$_3$. In certain embodiments, Y is $=$NTs. In certain embodiments, Y is $=$NBn. In certain embodiments, Y is $=$NCH(Ph)$_2$.

In certain embodiments, $R^D$ is of the formula:

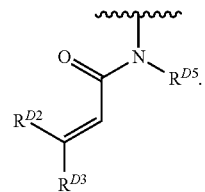

In certain embodiments, $R^D$ is of the formula:

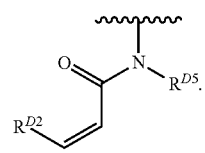

In certain embodiments, $R^D$ is of the formula

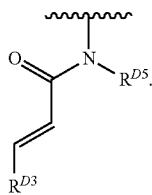

In certain embodiments, $R^D$ is of the formula:

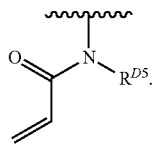

In certain embodiments, $R^D$ is of the formula:

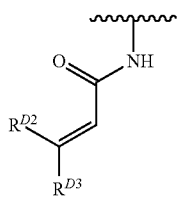

In certain embodiments, $R^D$ is of the formula:

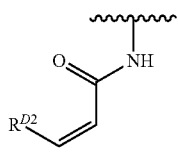

In certain embodiments, $R^D$ is of the formula:

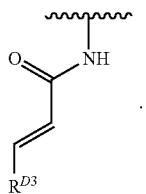

In certain embodiments, $R^D$ is of the formula:

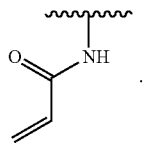

In certain embodiments, $R^D$ is of the formula:

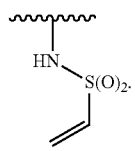

In certain embodiments, $R^D$ is of the formula:

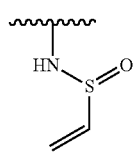

In certain embodiments, $R^D$ is of the formula:

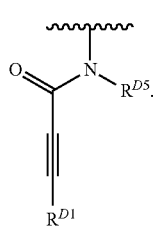

In certain embodiments, $R^D$ is of the formula:

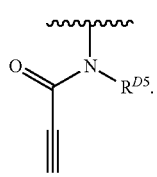

In certain embodiments, $R^D$ is of the formula:

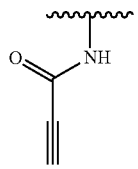

In certain embodiments, $R^D$ is of the formula:

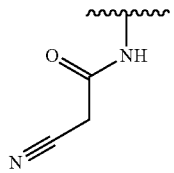

In certain embodiments, $R^D$ is of the formula:

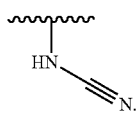 [SMILES: *NC#N]

In certain embodiments, $R^D$ is of the formula:

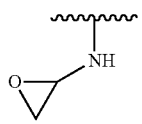

In certain embodiments, $R^D$ is of the formula:

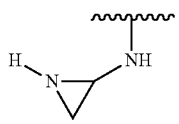

In certain embodiments, $R^D$ is of the formula:

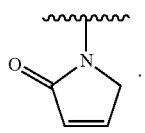

In certain embodiments, $R^D$ is of the formula:

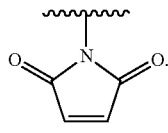

In certain embodiments, $R^D$ is of the formula:

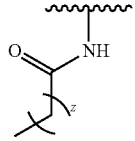

In certain embodiments, $R^D$ is of the formula:

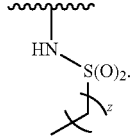

In certain embodiments, $R^D$ is of the formula:

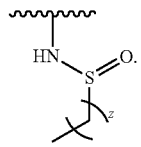

In certain embodiments, $R^D$ is of the formula:

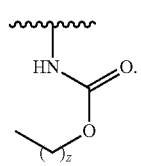

In certain embodiments, $R^D$ is of the formula:

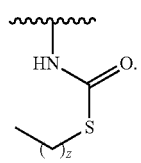

In certain embodiments $R^D$ is of the formula:

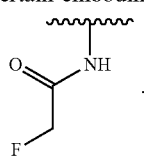

In certain embodiments, $R^D$ is of the formula:

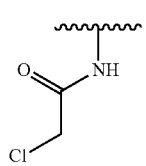

In certain embodiments, the compound of Formula (I) is of Formula (I-1):

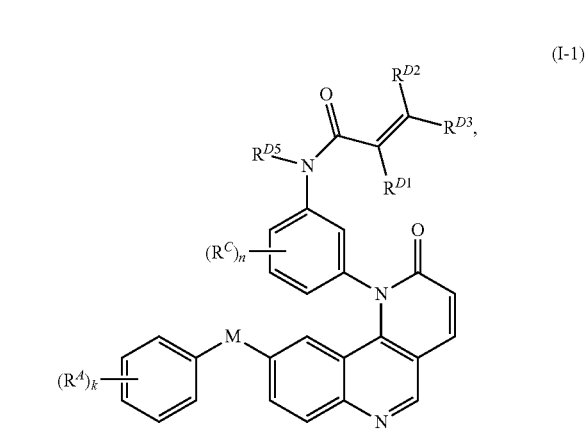

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of the formula:

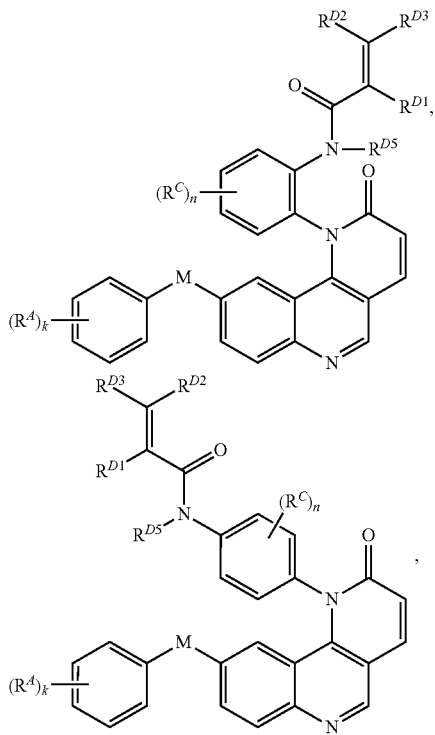

or a pharmaceutically acceptable salt, solvate, hydrate, polymorph, co-crystal, tautomer, stereoisomer, isotopically labeled derivative, and prodrug thereof.

In compounds of Formula (I), $R^{D5}$ and one $R^C$ may be joined to form a substituted heterocyclic ring. $R^{D5}$ and one $R^C$ may also be joined to form an unsubstituted heterocyclic ring. In certain embodiments, $R^{D5}$ and one $R^C$ are joined to form an unsubstituted 5-membered heterocyclic ring. In certain embodiments, the compound of Formula (I) is of Formula (I-2):

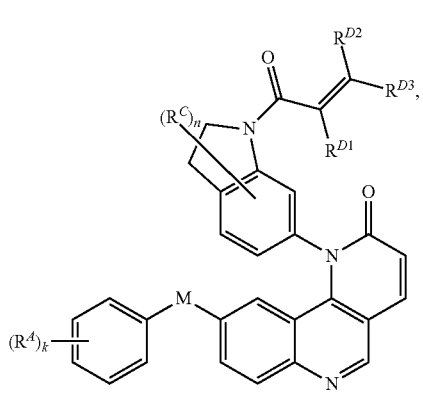

(I-2)

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of the formula:

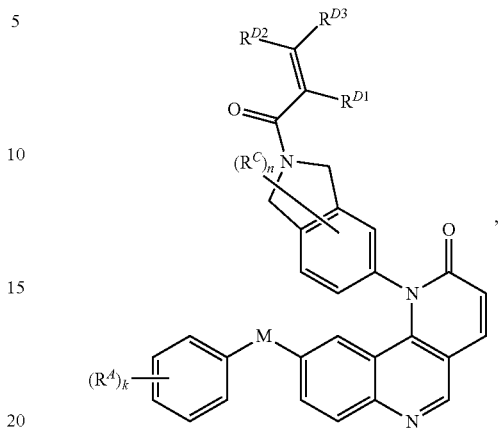

or a pharmaceutically acceptable salt, solvate, hydrate, polymorph, co-crystal, tautomer, stereoisomer, isotopically labeled derivative, and prodrug thereof.

In certain embodiments, $R^{D5}$ and one $R^C$ are joined to form a substituted 6-membered heterocyclic ring. In certain embodiments, $R^{D5}$ and one $R^C$ are joined to form an unsubstituted 6-membered heterocyclic ring. In certain embodiments, the compound of Formula (I) is of the formula:

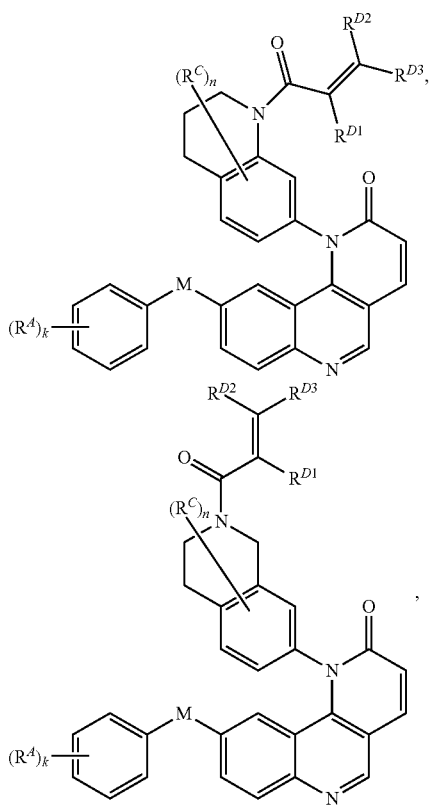

or a pharmaceutically acceptable salt, solvate, hydrate, polymorph, co-crystal, tautomer, stereoisomer, isotopically labeled derivative, and prodrug thereof.

In compounds of Formula (I), $R^{D5}$ and one $R^C$ may be joined to form a substituted heteroaryl ring. $R^{D5}$ and one $R^C$ may also be joined to form an unsubstituted heteroaryl ring. In certain embodiments, $R^{D5}$ and one $R^C$ are joined to form a substituted 7-membered heteroaryl ring. In certain embodiments, $R^{D5}$ and one $R^C$ are joined to form an unsubstituted 7-membered heteroaryl ring. In certain embodiments, $R^{D5}$ and one $R^C$ are joined to form a substituted 5-membered heteroaryl ring. In certain embodiments, $R^{D5}$ and one $R^C$ are joined to form an unsubstituted 5-membered heteroaryl ring. In certain embodiments, the compound of Formula (I) is of the formula:

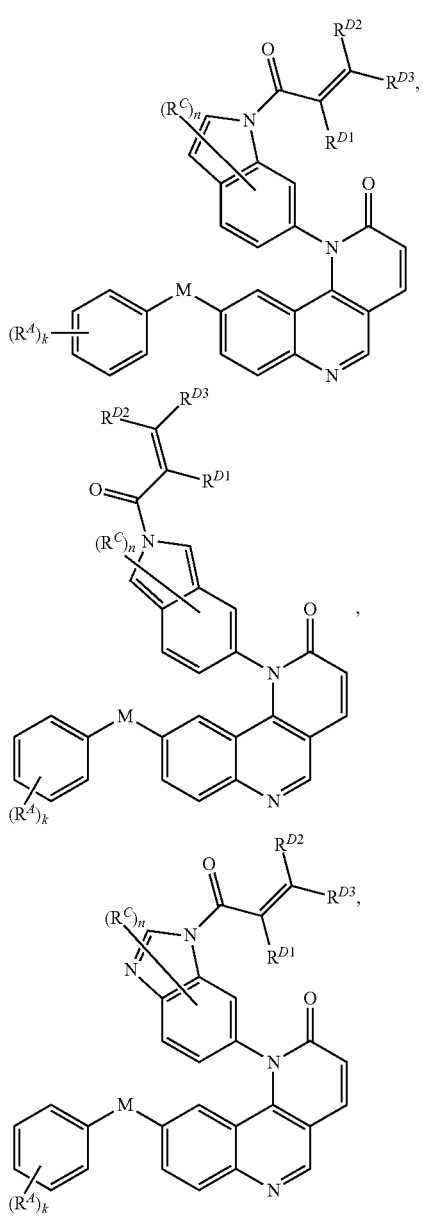

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of Formula (I-3):

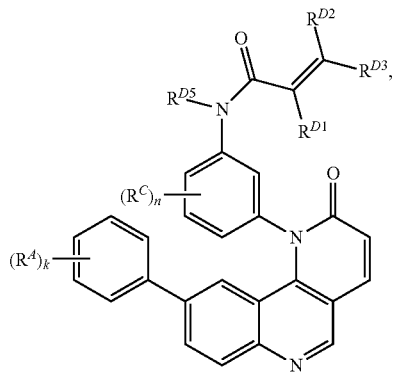
(I-3)

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of the formula:

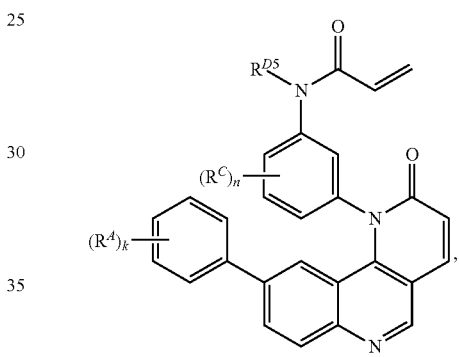

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of Formula (I-4):

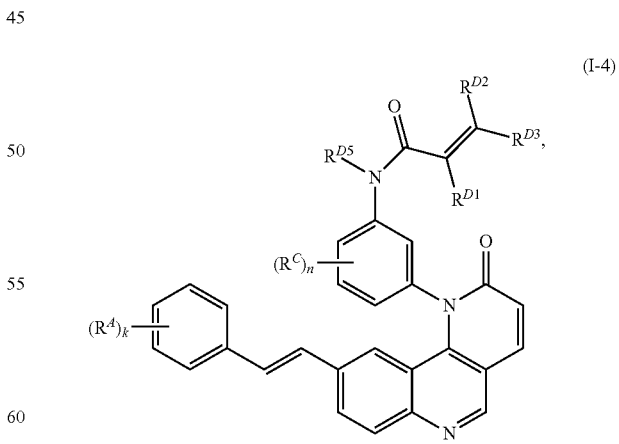
(I-4)

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of the formula:

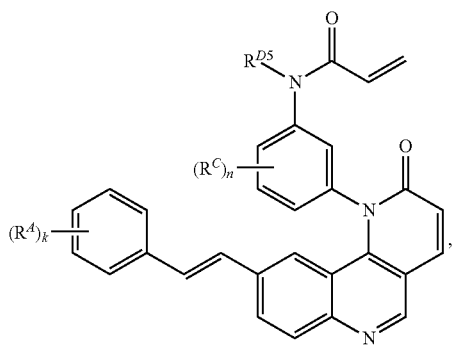

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of Formula (I-5):

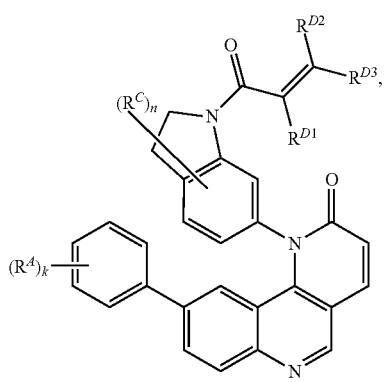

(I-5)

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of the formula:

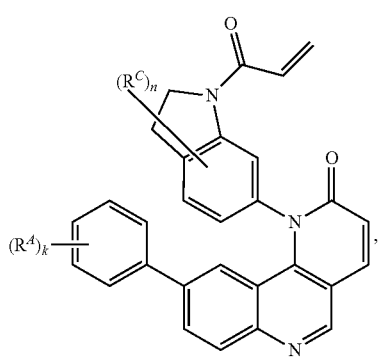

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of Formula (I-6):

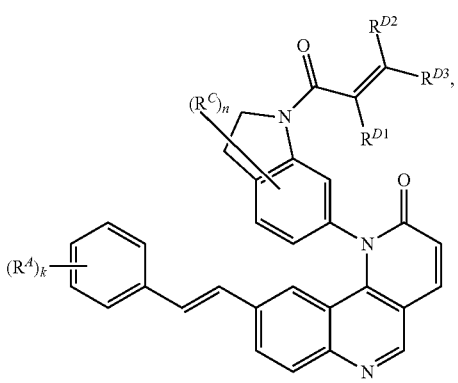

(I-6)

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of the formula:

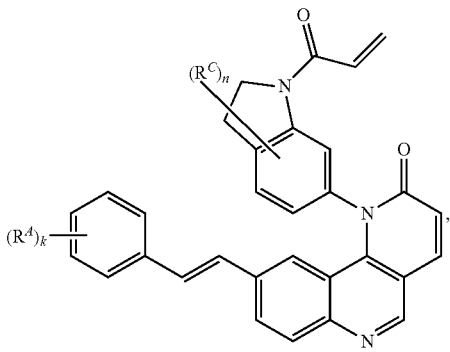

or a pharmaceutically acceptable salt, solvate, hydrate, polymorph, co-crystal, tautomer, stereoisomer, isotopically labeled derivative, and prodrug thereof.

In certain embodiments, the compound of Formula (I) is selected from the group consisting of:

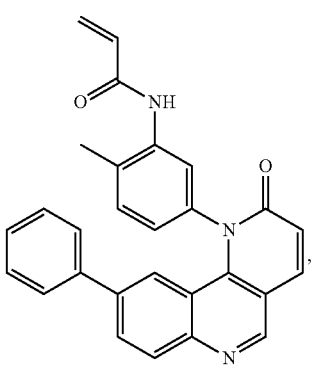

(I-7)

(I-8), (I-9), (I-10), (I-11), (I-12), (I-13), (I-14), (I-15)

-continued
(I-16)
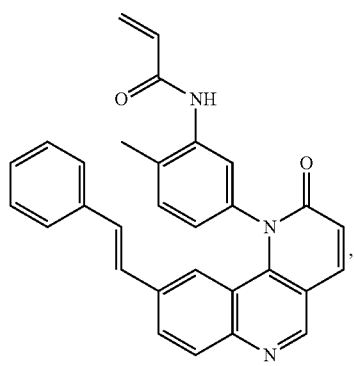
(I-17)
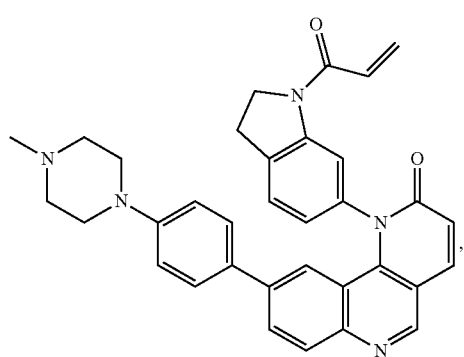
(I-18)
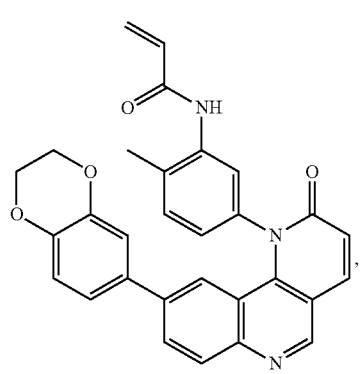
(I-19)
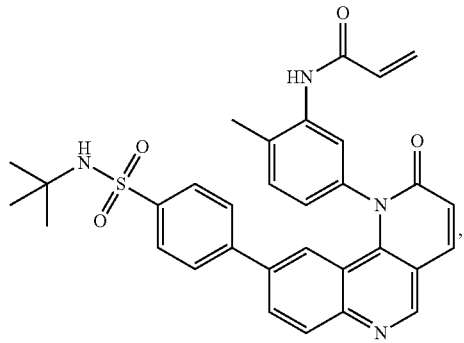
-continued
(I-20)
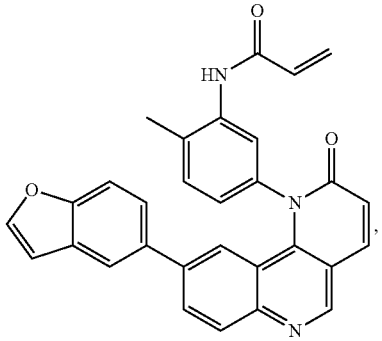
(I-21)
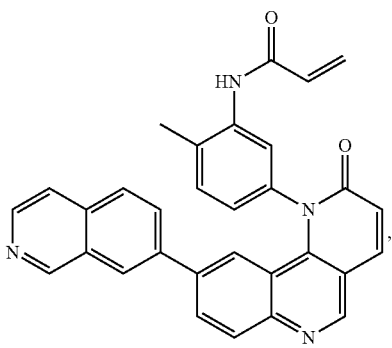
(I-22)
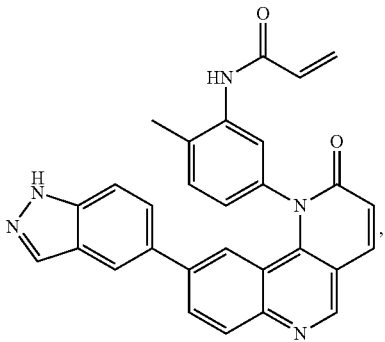
(I-23)
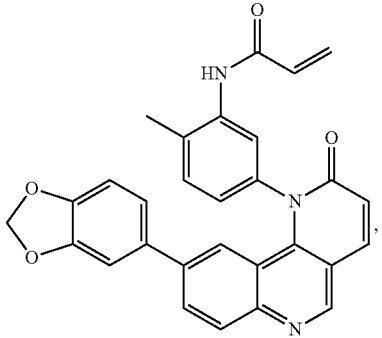

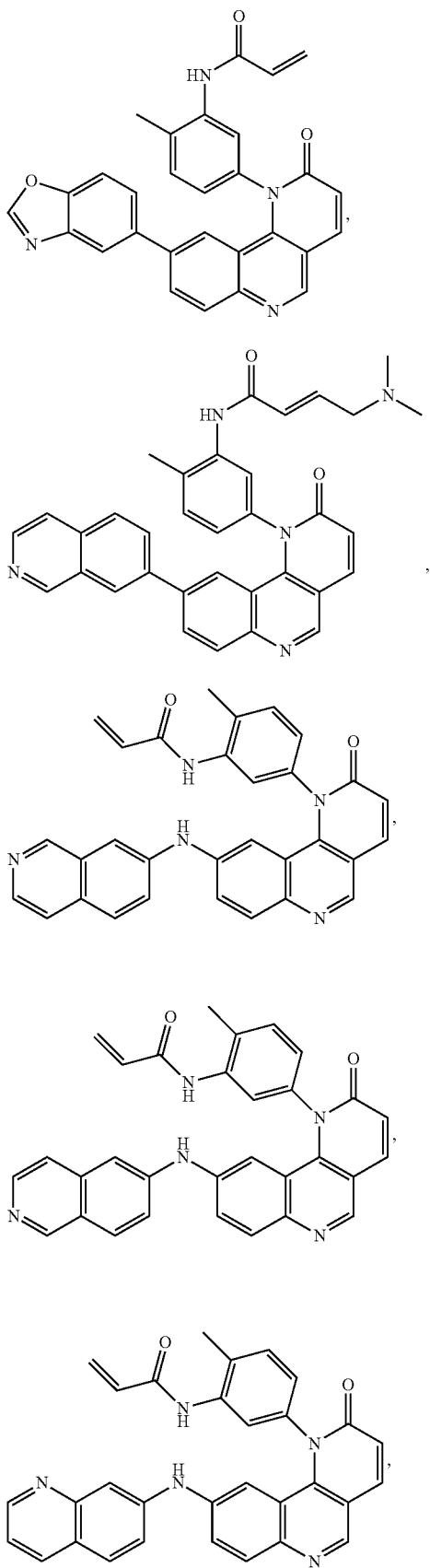

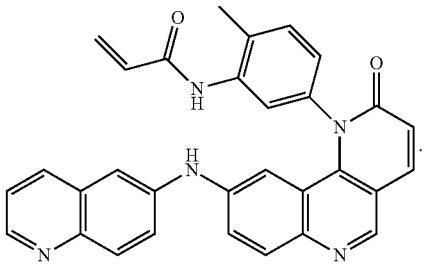

or a pharmaceutically acceptable salt, solvate, hydrate, polymorph, co-crystal, tautomer, stereoisomer, isotopically labeled derivative, and prodrug thereof.

The compounds of Formula (I) may bear multiple binding motifs for binding to BMX or other kinases. Ring A of the inventive compounds may be accommodated by a hydrophobic pocket in the ATP-binding site of BMX. Functionalities on Ring A and/or RD may bind to residues of BMX, such as hinge residues Tyr491, Ile492, Leu543, and Val403. Functional groups of $R^D$ may form one or more hydrogen bonds with BMX. Moreover, the Michael acceptor moiety of $R^D$ may react with a cysteine residue (e.g., Cys496) of BMX to allow covalent attachment of the compound to BMX.

In certain embodiments, compounds of the present invention include those which:
exhibit the ability to inhibit protein phosphorylation of specific targets exemplified, but not limited to those shown in Table 2,
exhibit kinase inhibitory activity,
exhibit tyrosine kinase inhibitory activity,
exhibit non-receptor tyrosine kinase inhibitory activity,
exhibit the ability to inhibit Tec kinases,
exhibit the ability to inhibit Tec, Btk, Itk, Rlk, and/or Bmx,
exhibit the ability to inhibit Bmx,
exhibit cytotoxic or growth inhibitory effect on cancer cell lines maintained in vitro or in animal studies using a scientifically acceptable cancer cell xenograft model; and/or
exhibit a therapeutic profile (e.g., optimum safety and curative effect) that is superior to existing chemotherapeutic agents.

In certain embodiments, the compounds of Formula (I) and (II) are specific inhibitors of BMX. Thus, it is desired that the compounds not be general inhibitors of transcription, enzyme activity or translation but that they have high specificity for the gene/enzyme target. The term "high specificity" as used herein is understood to mean that in contrast to many kinase inhibitors of the prior art, the compounds do not act on a great number or on two or more kinases having similar potency but act specifically i.e., only on tyrosine kinases, more preferably act specifically i.e., only on non-receptor tyrosine kinases, even more preferably act specifically i.e., only on Tec kinases, even more preferably act specifically i.e., only on Tec, Btk, Itk, Rlk, and Bmx, and even more preferably act specifically i.e., only on Bmx.

In certain embodiments of the invention, the specificity of the inhibitors is given by the $IC_{50}$ value. The $IC_{50}$ value is defined as the concentration of inhibitor required to inhibit 50% of the kinase activity. In certain embodiments, the compounds of Formula (I) or (II) may exhibit $IC_{50}$ values<100 µM. In certain other embodiments, the compounds exhibit $IC_{50}$ values<50 µM. In certain other embodiments, the compounds exhibit IC$_{50}$ values<40 µM. In certain other embodiments, the compounds exhibit IC$_{50}$ values<30 µM. In certain other embodiments, the compounds exhibit IC$_{50}$ values<20 µM. In certain other embodiments, the compounds exhibit IC$_{50}$ values<10 µM. In certain other embodiments, the compounds exhibit IC$_{50}$ values<7.5 µM. In certain embodiments, the compounds exhibit IC$_{50}$ values<5 µM. In certain other embodiments, the compounds exhibit IC$_{50}$ values<2.5 µM. In certain embodiments, the compounds exhibit IC$_{50}$ values<1 µM. In certain embodiments, the compounds exhibit IC$_{50}$ values<0.75 µM. In certain embodiments, the compounds exhibit IC$_{50}$ values<0.5 µM. In certain embodiments, the compounds exhibit IC$_{50}$ values<0.25 µM. In certain embodiments, the compounds exhibit IC$_{50}$ values<0.1 µM. In certain other embodiments, the compounds exhibit IC$_{50}$ values<75 nM. In certain other embodiments, the compounds exhibit IC$_{50}$ values<50 nM. In certain other embodiments, the compounds exhibit IC$_{50}$ values<25 nM. In certain other embodiments, the compounds exhibit IC$_{50}$ values<10 nM. In other embodiments, the compounds exhibit IC$_{50}$ values<7.5 nM. In other embodiments, the compounds exhibit IC$_{50}$ values<5 nM.

Pharmaceutical Compositions, Kits, and Administration

The present invention provides pharmaceutical compositions comprising a compound Formula (I) or (II), and pharmaceutically acceptable salts, solvates, hydrates, polymorphs, co-crystals, tautomers, stereoisomers, isotopically labeled derivatives, and prodrugs thereof, and optionally a pharmaceutically acceptable excipient.

Compounds of Formula (II) are of the formula:

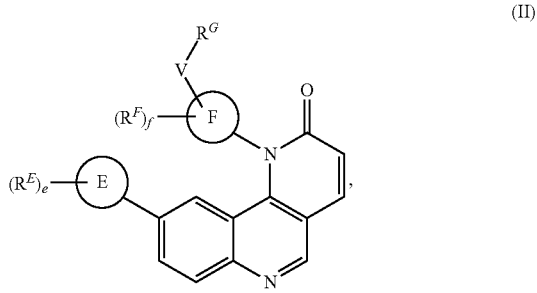

(II)

and pharmaceutically acceptable salts, solvates, hydrates, polymorphs, co-crystals, tautomers, stereoisomers, isotopically labeled derivatives, and prodrugs thereof;
wherein:

Ring E is an optionally substituted heteroaryl ring;

each instance of $R^E$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{E1}$, —N(R$^{E1}$)$_2$, —SR$^{E1}$, —CN, —C(=O)R$^{E1}$, —C(=O)OR$^{E1}$, —C(=O)SR$^{E1}$, —C(=O)N(R$^{E1}$)$_2$, —C(=S)R$^{E1}$, —C(=S)OR$^{E1}$, —C(=S)SR$^{E1}$, —C(=S)N(R$^{E1}$)$_2$, —C(=NR$^{E1}$)R$^{E1}$, —C(=NR$^{E1}$)OR$^{E1}$, —C(=NR$^{E1}$)SR$^{E1}$, —C(=NR$^{E1}$)N(R$^{E1}$)$_2$, —NO$_2$, —N$_3$, —N(R$^{E1}$)$_3$$^+$X$^-$, wherein X$^-$ is a counterion, —N(OR$^{E1}$)R$^{E1}$, —NR$^{E1}$C(=O)R$^{E1}$, —NR$^{E1}$C(=O)OR$^{E1}$, —NR$^{E1}$C(=O)SR$^{E1}$, —NR$^{E1}$C(=O)N(R$^{E1}$)$_2$, —NR$^{E1}$C(=S)R$^{E1}$, —NR$^{E1}$C(=S)OR$^{E1}$, —NR$^{E1}$C(=S)SR$^{E1}$, —NR$^{E1}$C(=S)N(R$^{E1}$)$_2$, —NR$^{E1}$C(=NR$^{E1}$)R$^{E1}$, —NR$^{E1}$C(=NR$^{E1}$)OR$^{E1}$, —NR$^{E1}$C(=NR$^{E1}$)SR$^{E1}$, —NR$^{E1}$C(=NR$^{E1}$)N(R$^{E1}$)$_2$, —NR$^{E1}$S(=O)$_2$R$^{E1}$, —NR$^{E1}$S(=O)$_2$OR$^{E1}$, —NR$^{E1}$S(=O)$_2$SR$^{E1}$, —NR$^{E1}$S(=O)$_2$N(R$^{E1}$)$_2$, —NR$^{E1}$S(=O)R$^{E1}$, —NR$^{E1}$S(=O)OR$^{E1}$, —NR$^{E1}$S(=O)SR$^{E1}$, —NR$^{E1}$S(=O)N(R$^{E1}$)$_2$, —NR$^{E1}$P(=O), NR$^{E1}$P(=O)$_2$, —NR$^{E1}$P(=O)(R$^{E1}$)$_2$, —NR$^{E1}$P(=O)R$^{E1}$(OR$^{E1}$), —NR$^{E1}$P(=O)(OR$^{E1}$)$_2$, —OC(=O)R, —OC(=O)OR$^{E1}$, —OC(=O)SR$^{E1}$, —OC(=O)N(R$^{E1}$)$_2$, —OC(=NR$^{E1}$)R$^{E1}$, —OC(=NR$^{E1}$)OR$^{E1}$, —OC(=NR$^{E1}$)N(R$^{E1}$)$_2$, —OC(=S)R$^{E1}$, —OC(=S)OR$^{E1}$, —OC(=S)SR$^{E1}$, —OC(=S)N(R$^{E1}$)$_2$, —ON(R$^{E1}$)$_2$, —OS(=O)R$^{E1}$, —OS(=O)OR$^{E1}$, —OS(=O)SR$^{E1}$, —OS(=O)N(R$^{E1}$)$_2$, —OS(=O)$_2$R$^{E1}$, —OS(=O)$_2$OR$^{E1}$, —OS(=O)$_2$SR$^{E1}$, —OS(=O)$_2$N(R$^{E1}$)$_2$, —OP(=O)$_2$, —OP(=O)(R$^{E1}$)$_2$, —OP(=O)R$^{E1}$(OR$^{E1}$), —OP(=O)(OR$^{E1}$)$_2$, —OP(=O), —OP(R$^{E1}$)$_2$, —OPR$^{E1}$(OR$^{E1}$), —OP(OR$^{E1}$)$_2$, —OSi(R$^{E1}$)$_3$, —OSi(R$^{E1}$)$_2$OR$^{E1}$, —OSi(R$^{E1}$)(OR$^{E1}$)$_2$, —OSi(OR$^{E1}$)$_3$, —SSR$^{E1}$, —S(=O)R$^{E1}$, —S(=O)OR$^{E1}$, —S(=O)N(R$^{E1}$)$_2$, —S(=O)$_2$R$^{E1}$, —S(=O)$_2$R$^{E1}$, —S(=)$_2$N(R$^{E1}$)$_2$, —SC(=O)R$^{E1}$ SC(=O)OR$^{E1}$, —SC(=O)SR$^{E1}$, —SC(=O)N(R$^{E1}$)$_2$, —SC(=S)R$^{E1}$, —SC(=S)OR$^{E1}$, —SC(=S)SR$^{E1}$, —SC(=S)N(R$^{E1}$)$_2$, —P(R$^{E1}$)$_2$, —PR$^{E1}$(OR$^{E1}$), —P(OR$^{E1}$)$_2$, —P(=O), —P(=O)(R$^{E1}$)$_2$, —P(=O)(OR$^{E1}$)$_2$, —P(=O)R$^{E1}$(OR$^{E1}$), —P(=O)$_2$, —B(R$^{E1}$)$_2$, —B(OR$^{E1}$)$_2$, —BR$^{E1}$(OR$^{E1}$), —Si(R$^{E1}$)$_3$, —Si(R$^{E1}$)$_2$OR$^{E1}$, —SiR$^{E1}$(OR$^{E1}$)$_2$, and —Si(OR$^{E1}$)$_3$, or two R$^E$ groups are joined to form an optionally substituted carbocyclic, optionally substituted heterocyclic, optionally substituted aryl, or optionally substituted heteroaryl ring; wherein each occurrence of R$^{E1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{E1}$ groups are joined to form an optionally substituted heterocyclic ring;

e is 0, 1, 2, 3, 4, or 5;

Ring F is an optionally substituted carbocyclic, optionally substituted heterocyclic, optionally substituted aryl, or optionally substituted heteroaryl ring;

each instance of RF is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{F1}$, —N(R$^{F1}$)$_2$, —SR$^{F1}$, —CN, —C(=O)R$^{F1}$ —C(=O)OR$^{F1}$, —C(=O)SR$^{F1}$, —C(=O)N(R$^{F1}$)$_2$, —C(=S)R$^{F1}$, —C(=S)OR$^{F1}$, —C(=S)SR$^{F1}$, —C(=S)N(R$^{F1}$)$_2$, —C(=NR$^{F1}$)R$^{F1}$, —C(=NR$^{F1}$)OR$^{F1}$, —C(=NR$^{F1}$)SR$^{F1}$, —C(=NR$^{F1}$)N(R$^{F1}$)$_2$, —NO$_2$, —N$_3$, —N(R$^{F1}$)$_3$$^+$X$^-$, wherein X$^-$ is a counterion, —N(OR$^{F1}$)R$^{F1}$, —NR$^{F1}$ C(=O)R$^{F1}$, —NR$^{F1}$C(=O)OR$^{F1}$, —NR$^{F1}$C(=O)SR$^{F1}$, —NR$^{F1}$C(=O)N(R$^{F1}$)$_2$, —NR$^{F1}$C(=S)R$^{F1}$, —NR$^{F1}$C(=S)OR$^{F1}$, —NR$^{F1}$C(=S)SR$^{F1}$, —NR$^{F1}$C(=S)N(R$^{F1}$)$_2$, —NR$^{F1}$C(=NR$^{F1}$)R$^{F1}$, —NR$^{F1}$C(=NR$^{F1}$)OR$^{F1}$, —NR$^{F1}$C(=NR$^{F1}$)SR$^{F1}$, —NR$^{F1}$C(=NR$^{F1}$)N(R$^{F1}$)$_2$, —NR$^{F1}$S(=O)$_2$R$^{F1}$, —NR$^{F1}$S(=O)$_2$OR$^{F1}$, —NR$^{F1}$S(=O)$_2$SR$^{F1}$, —NR$^{F1}$S(=O)$_2$N(R$^{F1}$)$_2$, —NR$^{F1}$S(=O)R$^{F1}$, —NR$^{F1}$S(=O)OR$^{F1}$, —NR$^{F1}$S(=O)SR$^{F1}$, —NR$^{F1}$S(=O)N(R$^{F1}$)$_2$, —NR$^{F1}$P(=O), —NR$^{F1}$P(=O)$_2$, —NR$^{F1}$P(=O)(R$^{F1}$)$_2$, —NR$^{F1}$P(=O)R$^{F1}$(OR$^{F1}$), —NR$^{F1}$P(=O)(OR$^{F1}$)$_2$, —OC(=O)R, —OC(=O)SR$^{F1}$, —OC(=O)N(R$^{F1}$)$_2$, —OC(=NR$^{F1}$)R$^{F1}$, —OC(=NR$^{F1}$)OR$^{F1}$, —OC(=NR$^{F1}$)N(R$^{F1}$)$_2$, —OC(=S) R$^{F1}$, —OC(=S)OR$^{F1}$, —OC(=S)SR$^{F1}$, —OC(=S)

$N(R^{F1})_2$, $-ON(R^{F1})_2$, $-OS(=O)R^{F1}$, $-OS(=O)OR^{F1}$, $-OS(=O)SR^{F1}$, $-OS(=O)N(R^{F1})_2$, $-OS(=O)_2R^{F1}$, $-OS(=O)_2OR^{F1}$, $-OS(=O)_2SR^{F1}$, $-OS(=O)_2N(R^{F1})_2$, $-OP(=O)_2$, $-OP(=O)(R^{F1})_2$, $-OP(=O)R^{F1}(OR^{F1})$, $-OP(=O)(OR^{F1})_2$, $-OP(=O)$, $-OP(R^{F1})_2$, $-OPR^{F1}(OR^{F1})$, $-OP(OR^{F1})_2$, $-OSi(R^{F1})_3$, $-OSi(R^{F1})_2OR^{F1}$, $-OSi(R^{F1})(OR^{F1})_2$, $-OSi(OR^{F1})_3$, $-SSR^{F1}$, $-S(=O)R^{F1}$, $-S(=O)OR^{F1}$, $-S(=O)N(R^{F1})_2$, $-S(=O)_2R^{F1}$, $-S(=O)_2OR^{F1}$, $-S(=O)_2N(R^{F1})_2$, $-SC(=O)R^{F1}$, $-SC(=O)OR^{F1}$, $-SC(=O)SR^{F1}$, $-SC(=O)N(R^{F1})_2$, $-SC(=S)R^{F1}$, $-SC(=S)OR^{F1}$, $-SC(=S)SR^{F1}$, $-SC(=S)N(R^{F1})_2$, $-P(R^{F1})_2$, $-PR^{F1}(OR^{F1})$, $-P(OR^{F1})_2$, $-P(=O)$, $-P(=O)(R^{F1})_2$, $-P(=O)(OR^{F1})_2$, $-P(=O)_2$, $-B(R^{F1})_2$, $-B(OR^{F1})_2$, $-BR^{F1}(OR^{F1})$, $-Si(R^{F1})_3$, $-Si(R^{F1})_2OR^{F1}$, $-SiR^{F1}(OR^{F1})_2$, and $-Si(OR^{F1})_3$, wherein each occurrence of $R^{F1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{F1}$ groups are joined to form an optionally substituted heterocyclic ring or optionally substituted heteroaryl ring;

f is 0, 1, 2, 3, or 4;

V is a bond or an optionally substituted $C_{1-6}$ hydrocarbon chain;

$R^G$ is of any one of Formulae (ii-1)-(ii-17):

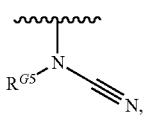
(ii-1)

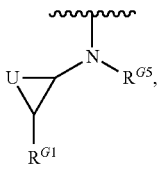
(ii-2)

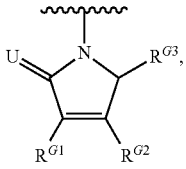
(ii-3)

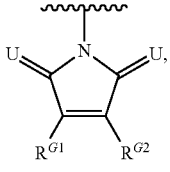
(ii-4)

-continued

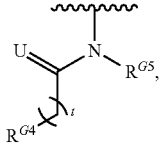
(ii-5)

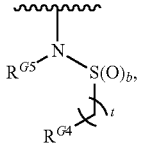
(ii-6)

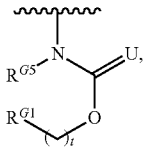
(ii-7)

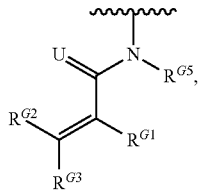
(ii-8)

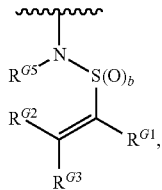
(ii-9)

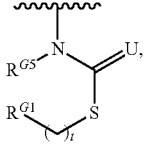
(ii-10)

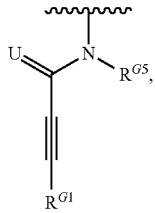
(ii-11)

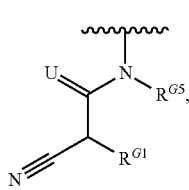
(ii-12)

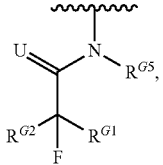
(ii-13)

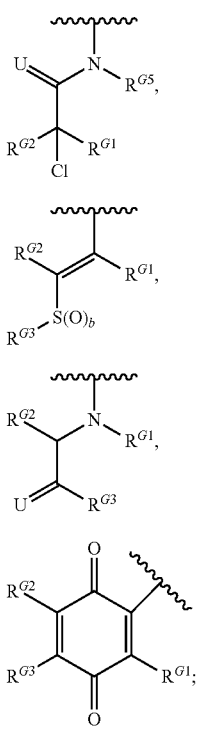

(ii-14)

(ii-15)

(ii-16)

(ii-17)

$R^{G1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{G1a}$, —N(R$^{G1a}$)$_2$, —SR$^{G1a}$, —CH$_2$OR$^{G1a}$, —CH$_2$N(R$^{G1a}$)$_2$, or —CH$_2$SR$^{G1a}$, —C(=O)R$^{G1a}$, —C(=O)OR$^{G1a}$, —C(=O)SR$^{G1a}$, —C(=O)N(R$^{G1a}$)$_2$, —C(=S)R$^{G1a}$, —C(=S)OR$^{G1a}$, —C(=S)SR$^{G1a}$, —C(=S)N(R$^{G1a}$)$_2$, —C(=NR$^{G1a}$)R$^{G1a}$, —C(=NR$^{G1a}$)OR$^{G1a}$, —C(=NR$^{G1a}$)SR$^{G1a}$, and —C(=NR$^{G1a}$)N(R$^{G1a}$)$_2$, wherein each occurrence of R$^{G1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{G1a}$ groups are joined to form an optionally substituted heterocyclic ring;

$R^{G2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{G2a}$, —N(R$^{G2a}$)$_2$, —SR$^{G2a}$, —CH$_2$OR$^{G2a}$, —CH$_2$N(R$^{G2a}$)$_2$, or —CH$_2$SR$^{G2a}$, —C(=O)R$^{G2a}$, —C(=O)OR$^{G2a}$, —C(=O)SR$^{G2a}$, —C(=O)N(R$^{G2a}$)$_2$, —C(=S)R$^{G2a}$, —C(=S)OR$^{G2a}$, —C(=S)SR$^{G2a}$, —C(=S)N(R$^{G2a}$)$_2$, —C(=NR$^{G2a}$)R$^{G2a}$, —C(=NR$^{G2a}$)OR$^{G2a}$, —C(=NR$^{G2a}$)SR$^{G2a}$, and —C(=NR$^{G2a}$)N(R$^{G2a}$)$_2$, wherein each occurrence of R$^{G2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{G2a}$ groups are joined to form an optionally substituted heterocyclic ring;

R$^{G3}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{G3a}$, —N(R$^{G3a}$)$_2$, —SR$^{G3a}$, —CH$_2$OR$^{G3a}$, —CH$_2$N(R$^{G3a}$)$_2$, or —CH$_2$SR$^{G3a}$, —C(=O)R$^{G3a}$, —C(=O)OR$^{G3a}$, —C(=O)SR$^{G3a}$, —C(=O)N(R$^{G3a}$)$_2$, —C(=S)R$^{G3a}$, —C(=S)OR$^{G3a}$, —C(=S)SR$^{G3a}$, —C(=S)N(R$^{G3a}$)$_2$, —C(=NR$^{G3a}$)R$^{G3a}$, —C(=NR$^{G3a}$)OR$^{G3a}$, —C(=NR$^{G3a}$)SR$^{G3a}$, and —C(=NR$^{G3a}$)N(R$^{G3a}$)$_2$, wherein each occurrence of R$^{G3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{G3a}$ groups are joined to form an optionally substituted heterocyclic ring;

optionally R$^{G1}$ and R$^{G3}$, or R$^{G2}$ and R$^{G3}$, or R$^{G1}$ and R$^{G2}$ are joined to form an optionally substituted carbocyclic or optionally substituted heterocyclic ring;

R$^{G4}$ is a leaving group;

R$^{G5}$ is hydrogen, C$_{1-6}$ alkyl, or a nitrogen protecting group;

U is O, S, or NR$^{G6}$, wherein R$^{G6}$ is hydrogen, C$_{1-6}$ alkyl, or a nitrogen protecting group;

b is 1 or 2;

t is 0, 1, 2, 3, 4, 5, or 6; and optionally R$^{G5}$ and one R$^F$ are joined to form an optionally substituted heterocyclic ring.

In certain embodiments, the BMX inhibitor is a compound of Formula (II), or a pharmaceutically acceptable salt thereof.

Compounds of Formula (II) include a heteroaryl ring as Ring E. Ring E may be substituted with one or more substituents R$^E$. The substituent R$^E$ may be attached to a carbon atom or heteroatom of Ring E, as valency permits. In certain embodiments, Ring E is a substituted heteroaryl ring. In other embodiments, Ring E is an unsubstituted heteroaryl ring.

In certain embodiments, Ring E is a monocyclic heteroaryl ring. In certain embodiments, Ring E is a 6-membered monocyclic heteroaryl ring. In certain embodiments, Ring E is substituted pyridyl. In certain embodiments, Ring E is unsubstituted pyridyl. In certain embodiments, Ring E is of the formula:

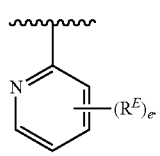

In certain embodiments, Ring E is of the formula:

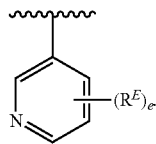

In certain embodiments, Ring E is of the formula:

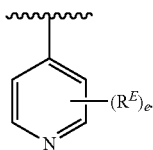

In certain embodiments, Ring E is of the formula:

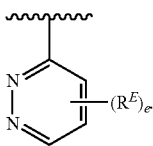

In certain embodiments, Ring E is of the formula:

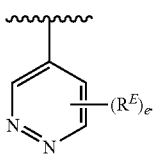

In certain embodiments, Ring E is of the formula:

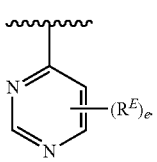

In certain embodiments, Ring E is of the formula:

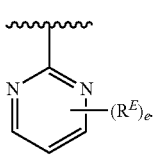

In certain embodiments, Ring E is of the formula:

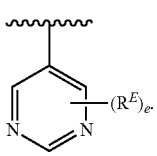

In certain embodiments, Ring E is of the formula:

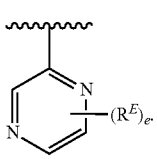

In certain embodiments, Ring E is of the formula:

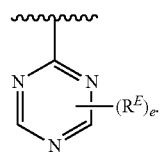

Ring E of Formula (II) may also be a 5-membered monocyclic heteroaryl ring. In certain embodiments, Ring E is a 5-membered monocyclic heteroaryl ring wherein one of the five ring carbon atoms is replaced by nitrogen oxygen, or sulfur. In certain embodiments, Ring E is of the formula:

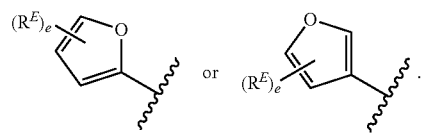

In certain embodiments, Ring E is of the formula:

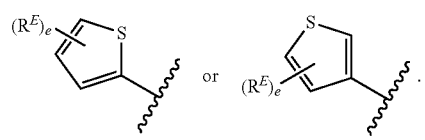

In certain embodiments, Ring E is of the formula:

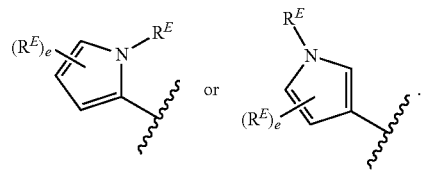

In certain embodiments, Ring E is a 5-membered monocyclic heteroaryl ring wherein two of the five ring carbon atoms are independently replaced by nitrogen, oxygen, or sulfur. In certain embodiments, Ring E is of the formula:

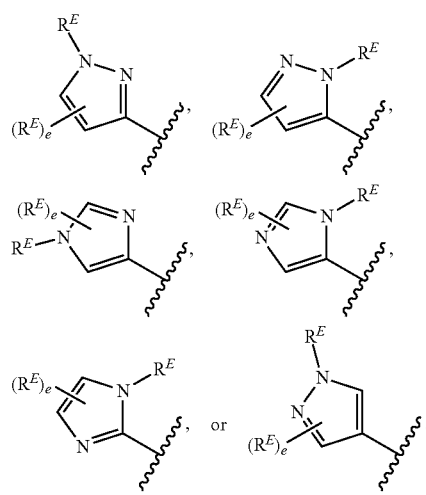

In certain embodiments, Ring E is of the formula:

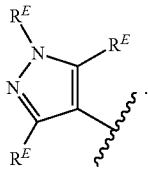

In certain embodiments, Ring E is of the formula:

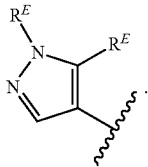

In certain embodiments, Ring E is of the formula:

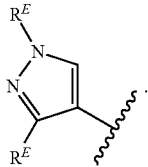

In certain embodiments, Ring E is of the formula:

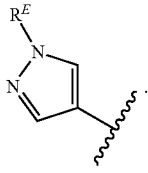

In certain embodiments, Ring E is of the formula:

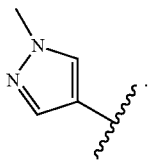

In certain embodiments, Ring E is of the formula:

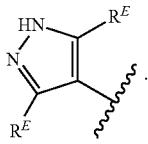

In certain embodiments, Ring E is of the formula:

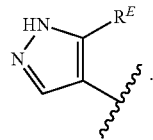

In certain embodiments, Ring E is of the formula

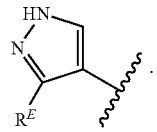

In certain embodiments, Ring E is of the formula:

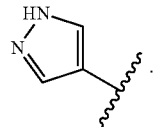

In certain embodiments, Ring E is of the formula:

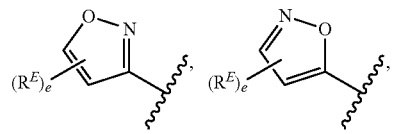

certain embodiments, Ring E is of the formula:

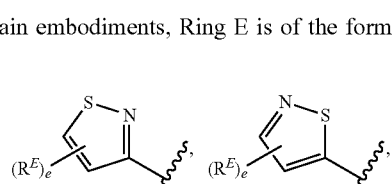

In certain embodiments, Ring E is a 5-membered monocyclic heteroaryl ring wherein three of the five ring carbon atoms are independently replaced by nitrogen, oxygen, or sulfur. In certain embodiments, Ring E is of the formula:

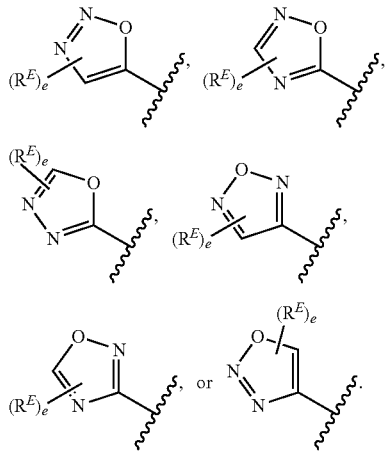

In certain embodiments, Ring E is of the formula:

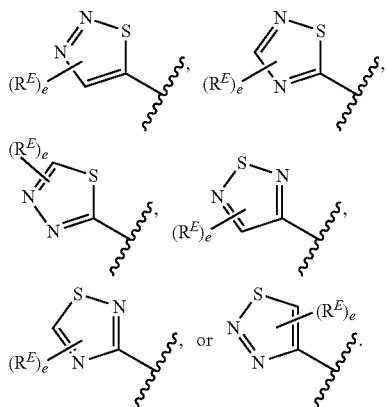

In certain embodiments, Ring E is of the formula:

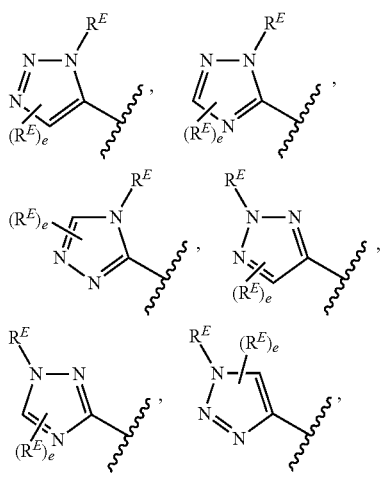

-continued

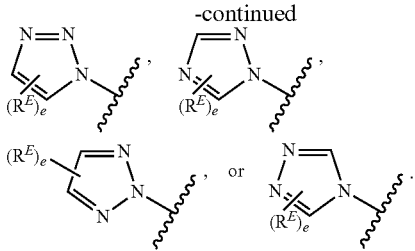

In certain embodiments, Ring E is a 5-membered monocyclic heteroaryl ring wherein four of the five ring carbon atoms are independently replaced by nitrogen, oxygen, or sulfur.

In certain embodiments, Ring E is a heteroaryl ring fused with one or more carbocyclic, heterocyclic, aryl, or heteroaryl groups wherein the point of attachment is on the heteroaryl ring. In certain embodiments, Ring E is a bicyclic heteroaryl ring. In certain embodiments, Ring E is a monocyclic heteroaryl ring fused with an aryl ring. In certain embodiments, Ring E is a 6-membered monocyclic heteroaryl ring fused with an aryl ring. In certain embodiments, Ring E is a 6-membered monocyclic heteroaryl ring fused with a phenyl ring. In certain embodiments, Ring E is a pyridyl ring fused with a phenyl ring. In certain embodiments, Ring E is of the formula:

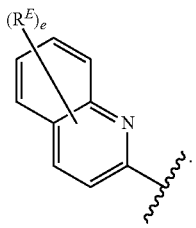

In certain embodiments, Ring E is of the formula:

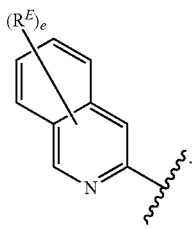

In certain embodiments, Ring E is of the formula:

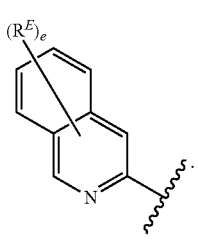

In certain embodiments, Ring E is of the formula:

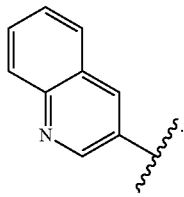 [SMILES: *c1cnc2ccccc2c1]

In certain embodiments, Ring E is of the formula:

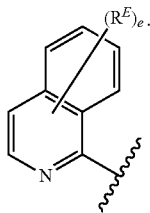

In certain embodiments, Ring E is of the formula:

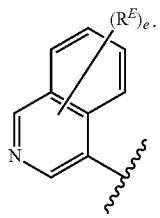

In certain embodiments, Ring E is of the formula:

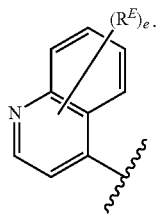

In certain embodiments, Ring E is a 5-membered monocyclic heteroaryl ring fused with an aryl ring. In certain embodiments, Ring E is a 5-membered monocyclic heteroaryl ring fused with a phenyl ring.

In certain embodiments, Ring E is a monocyclic heteroaryl ring fused with another monocyclic heteroaryl ring, and the point of attachment may be on any atom of the two heteroaryl rings, as valency permits. In certain embodiments, Ring E is a 6-membered monocyclic heteroaryl ring fused with another 6-membered monocyclic heteroaryl ring. In certain embodiments, Ring E is a 6-membered monocyclic heteroaryl ring fused with a 5-membered monocyclic heteroaryl ring. In certain embodiments, Ring E is a 5-membered monocyclic heteroaryl ring fused with another 5-membered monocyclic heteroaryl ring.

In certain embodiments, Ring E is a tricyclic heteroaryl ring.

In compounds of Formula (II), Ring E may be substituted with one or more $R^E$ groups. In certain embodiments, at least one $R^E$ is H. In certain embodiments, at least one $R^E$ is halogen. In certain embodiments, at least one $R^E$ is F. In certain embodiments, at least one $R^E$ is Cl. In certain embodiments, at least one $R^E$ is Br. In certain embodiments, at least one $R^E$ is I (iodine). In certain embodiments, at least one $R^E$ is substituted acyl. In certain embodiments, at least one $R^E$ is unsubstituted acyl. In certain embodiments, at least one $R^E$ is acetyl. In certain embodiments, at least one $R^E$ is substituted alkyl. In certain embodiments, at least one $R^E$ is unsubstituted alkyl. In certain embodiments, at least one $R^E$ is $C_{1-6}$ alkyl. In certain embodiments, at least one $R^E$ is methyl. In certain embodiments, at least one $R^E$ is ethyl. In certain embodiments, at least one $R^E$ is propyl. In certain embodiments, at least one $R^E$ is butyl. In certain embodiments, at least one $R^E$ is substituted alkenyl. In certain embodiments, at least one $R^E$ is unsubstituted alkenyl. In certain embodiments, at least one $R^E$ is substituted alkynyl. In certain embodiments, at least one $R^E$ is unsubstituted alkynyl. In certain embodiments, at least one $R^E$ is substituted carbocyclyl. In certain embodiments, at least one $R^E$ is unsubstituted carbocyclyl. In certain embodiments, at least one $R^E$ is substituted heterocyclyl. In certain embodiments, at least one $R^E$ is unsubstituted heterocyclyl. In certain embodiments, at least one $R^E$ is substituted aryl. In certain embodiments, at least one $R^E$ is unsubstituted aryl. In certain embodiments, at least one $R^E$ is substituted phenyl. In certain embodiments, at least one $R^E$ is unsubstituted phenyl. In certain embodiments, at least one $R^E$ is substituted heteroaryl. In certain embodiments, at least one $R^E$ is unsubstituted heteroaryl. In certain embodiments, at least one $R^E$ is substituted pyridyl. In certain embodiments, at least one $R^E$ is unsubstituted pyridyl. In certain embodiments, at least one $R^E$ is $-OR^{E1}$. In certain embodiments, at least one $R^E$ is $-O(C_{1-6}$ alkyl). In certain embodiments, at least one $R^E$ is $-OH$. In certain embodiments, at least one $R^E$ is $-N(R^{E1})_2$. In certain embodiments, at least one $R^E$ is sub-$N(C_{1-6}$ alkyl)$_2$. In certain embodiments, at least one $R^E$ is $-NH_2$. In certain embodiments, at least one $R^E$ is $-SR^{E1}$. In certain embodiments, at least one $R^E$ is $-SH$.

In compounds of Formula (II), two $R^E$ groups may be joined to form an optionally substituted carbocyclic, optionally substituted heterocyclic, optionally substituted aryl, or optionally substituted heteroaryl ring. In certain embodiments, two $R^E$ groups are joined to form a substituted carbocyclic ring. In certain embodiments, two $R^E$ groups are joined to form an unsubstituted carbocyclic ring. In certain embodiments, two $R^E$ groups are joined to form a substituted heterocyclic ring. In certain embodiments, two $R^E$ groups are joined to form an unsubstituted heterocyclic ring. In certain embodiments, two $R^E$ groups are joined to form a substituted aryl ring. In certain embodiments, two $R^E$ groups are joined to form an unsubstituted aryl ring. In certain embodiments, two $R^E$ groups are joined to form a substituted phenyl ring. In certain embodiments, two $R^E$ groups are joined to form an unsubstituted phenyl ring. In certain embodiments, two $R^E$ groups are joined to form a substituted heteroaryl ring. In certain embodiments, two $R^E$ groups are joined to form an unsubstituted heteroaryl ring. In certain embodiments, two $R^E$ groups are joined to form a substituted pyridyl ring. In certain embodiments, two $R^E$ groups are joined to form an unsubstituted pyridyl ring.

In certain embodiments, at least one $R^{E1}$ is H. In certain embodiments, at least one $R^{E1}$ is substituted acyl. In certain embodiments, at least one $R^{E1}$ is unsubstituted acyl. In certain embodiments, at least one $R^{E1}$ is acetyl. In certain embodiments, at least one $R^{E1}$ is substituted alkyl. In certain embodiments, at least one $R^{E1}$ is perfluoronated alkyl. In certain embodiments, at least one $R^{E1}$ is $-CF_3$. In certain embodiments, at least one $R^{E1}$ is —$C_2F_5$. In certain embodiments, at least one $R^{E1}$ is unsubstituted alkyl. In certain embodiments, at least one $R^{E1}$ is $C_{1-6}$ alkyl. In certain embodiments, at least one $R^{E1}$ is methyl. In certain embodiments, at least one $R^{E1}$ is ethyl. In certain embodiments, at least one $R^{E1}$ is propyl. In certain embodiments, at least one $R^{E1}$ is butyl. In certain embodiments, at least one $R^{E1}$ is substituted alkenyl. In certain embodiments, at least one $R^{E1}$ is unsubstituted alkenyl. In certain embodiments, at least one $R^{E1}$ is substituted alkynyl. In certain embodiments, at least one $R^{E1}$ is unsubstituted alkynyl. In certain embodiments, at least one $R^{E1}$ is substituted carbocyclyl. In certain embodiments, at least one $R^{E1}$ is unsubstituted carbocyclyl. In certain embodiments, at least one $R^{E1}$ is substituted heterocyclyl. In certain embodiments, at least one $R^{E1}$ is unsubstituted heterocyclyl. In certain embodiments, at least one $R^{E1}$ is substituted aryl. In certain embodiments, at least one $R^{E1}$ is unsubstituted aryl. In certain embodiments, at least one $R^{E1}$ is substituted phenyl. In certain embodiments, at least one $R^{E1}$ is unsubstituted phenyl. In certain embodiments, at least one $R^{E1}$ is substituted heteroaryl. In certain embodiments, at least one $R^{E1}$ is unsubstituted heteroaryl. In certain embodiments, at least one $R^{E1}$ is substituted pyridyl. In certain embodiments, at least one $R^{E1}$ is unsubstituted pyridyl. In certain embodiments, at least one $R^{E1}$ is a nitrogen protecting group when attached to a nitrogen atom. In certain embodiments, at least one $R^{E1}$ is Bn, BOC, Cbz, Fmoc, trifluoroacetyl, triphenylmethyl, or Ts when attached to a nitrogen atom. In certain embodiments, $R^{E1}$ is an oxygen protecting group when attached to an oxygen atom. In certain embodiments, $R^{E1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E1}$ is a sulfur protecting group when attached to a sulfur atom. In certain embodiments, $R^{E1}$ is acetamidomethyl, t-Bu, 3-nitro-2-pyridine sulfenyl, 2-pyridine-sulfenyl, or triphenylmethyl when attached to a sulfur atom.

In compounds of Formula (II), two $R^{E1}$ groups may be joined to form an optionally substituted carbocyclic, optionally substituted heterocyclic, optionally substituted aryl, or optionally substituted heteroaryl ring. In certain embodiments, two $R^{E1}$ groups are joined to form a substituted carbocyclic ring. In certain embodiments, two $R^{E1}$ groups are joined to form an unsubstituted carbocyclic ring. In certain embodiments, two $R^{E1}$ groups are joined to form a substituted heterocyclic ring. In certain embodiments, two $R^{E1}$ groups are joined to form an unsubstituted heterocyclic ring. In certain embodiments, two $R^{E1}$ groups are joined to form a substituted aryl ring. In certain embodiments, two $R^{E1}$ groups are joined to form an unsubstituted aryl ring. In certain embodiments, two $R^{E1}$ groups are joined to form a substituted phenyl ring. In certain embodiments, two $R^{E1}$ groups are joined to form an unsubstituted phenyl ring. In certain embodiments, two $R^{E1}$ groups are joined to form a substituted heteroaryl ring. In certain embodiments, two $R^{E1}$ groups are joined to form an unsubstituted heteroaryl ring. In certain embodiments, two $R^{E1}$ groups are joined to form a substituted pyridyl ring. In certain embodiments, two $R^{E1}$ groups are joined to form an unsubstituted pyridyl ring.

In certain embodiments, $R^E$ is substituted $C_{1-6}$ alkyl; and e is 1. In certain embodiments, $R^E$ is —$CF_3$; and e is 1. In certain embodiments, $R^E$ is unsubstituted $C_{1-6}$ alkyl; and e is 1. In certain embodiments, $R^E$ is methyl; and e is 1. In certain embodiments, $R^E$ is ethyl; and e is 1. In certain embodiments, $R^E$ is propyl; and e is 1. In certain embodiments, $R^E$ is butyl; and e is 1. In certain embodiments, $R^E$ is halogen; and e is 1. In certain embodiments, $R^E$ is F; and e is 1. In certain embodiments, $R^E$ is Cl; and e is 1. In certain embodiments, $R^E$ is Br; and e is 1. In certain embodiments, $R^E$ is I (iodine); and e is 1. In certain embodiments, $R^E$ is —$OR^{E1}$; and e is 1. In certain embodiments, $R^E$ is —$O(C_{1-6}$ alkyl); and e is 1. In certain embodiments, $R^E$ is —OH; and e is 1. In certain embodiments, $R^E$ is —$N(R^{E1})_2$; and e is 1. In certain embodiments, $R^E$ is —$N(C_{1-6}$ alkyl$)_2$; and e is 1. In certain embodiments, $R^E$ is —$NH_2$; and e is 1. In certain embodiments, $R^E$ is —$SR^{E1}$; and e is 1. In certain embodiments, $R^E$ is —$S(C_{1-6}$ alkyl); and e is 1. In certain embodiments, $R^E$ is —SH; and e is 1.

Compounds of Formula (II) include an optionally substituted carbocyclic, optionally substituted heterocyclic, optionally substituted aryl, or optionally substituted heteroaryl ring as Ring F. Ring F may be substituted with one or more substituents $R^F$. $R^F$ may be a substituent on a carbon atom or heteroatom as valency permits. In certain embodiments, Ring F is a carbocyclic ring. In certain embodiments, Ring F is a monocyclic carbocyclic ring. In certain embodiments, Ring F is a bicyclic carbocyclic ring. In certain embodiments, Ring F is a substituted carbocyclic ring. In certain embodiments, Ring F is an unsubstituted carbocyclic ring. In certain embodiments, Ring F is a saturated carbocyclic ring. In certain embodiments, Ring F is an unsaturated carbocyclic ring. In certain embodiments, Ring F is a carbocyclic ring fused with one or more carbocyclic, heterocyclic, aryl, or heteroaryl groups wherein the point of attachment is on the carbocyclic ring.

Ring F of Formula (II) may be a heterocyclic ring. In certain embodiments, Ring F is a monocyclic heterocyclic ring. In certain embodiments, Ring F is a bicyclic heterocyclic ring. In certain embodiments, Ring F is a substituted heterocyclic ring. In certain embodiments, Ring F is an unsubstituted heterocyclic ring. In certain embodiments, Ring F is a saturated heterocyclic ring. In certain embodiments, Ring F is an unsaturated heterocyclic ring. In certain embodiments, Ring F is a heterocyclic ring fused with one or more carbocyclic, heterocyclic, aryl, or heteroaryl groups wherein the point of attachment is on the heterocyclic ring.

Ring F of Formula (II) may be an aryl ring. In certain embodiments, Ring F is a monocyclic aryl ring. In certain embodiments, Ring F is a bicyclic aryl ring. In certain embodiments, Ring F is a tricyclic aryl ring. In certain embodiments, Ring F is a substituted aryl ring. In certain embodiments, Ring F is an unsubstituted aryl ring. In certain embodiments, Ring F is substituted phenyl. In certain embodiments, Ring F is unsubstituted phenyl. In certain embodiments, Ring F is an aryl ring fused with one or more carbocyclic, heterocyclic, aryl, or heteroaryl groups wherein the point of attachment is on the aryl ring. In certain embodiments, Ring F is substituted naphthyl. In certain embodiments, Ring F is unsubstituted naphthyl.

In certain embodiments, the compound of Formula (II) is of the formula:

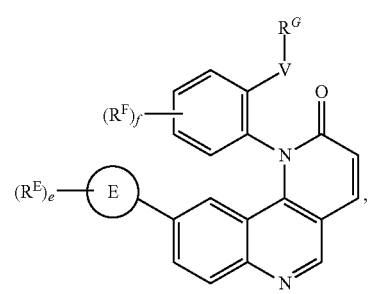

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

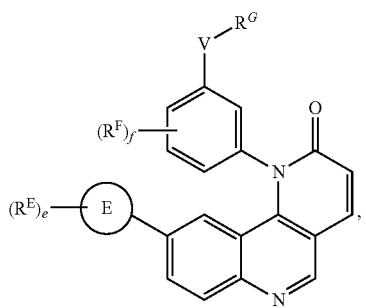

or a pharmaceutically acceptable salt, solvate, hydrate, polymorph, co-crystal, tautomer, stereoisomer, isotopically labeled derivative, and prodrug thereof.

In certain embodiments, the compound of Formula (II) is of the formula:

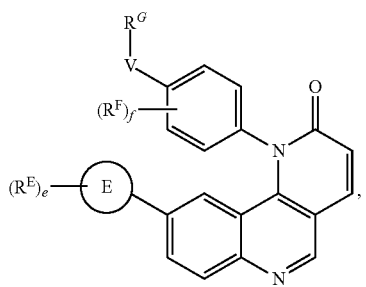

or a pharmaceutically acceptable salt, solvate, hydrate, polymorph, co-crystal, tautomer, stereoisomer, isotopically labeled derivative, and prodrug thereof.

Ring F of Formula (II) may also be an optionally substituted heteroaryl ring. In certain embodiments, Ring F is a substituted heteroaryl ring. In certain embodiments, Ring F is an unsubstituted heteroaryl ring. In certain embodiments, Ring F is a monocyclic heteroaryl ring. In certain embodiments, Ring F is a 5-membered monocyclic heteroaryl ring. In certain embodiments, Ring F is substituted pyrrolyl. In certain embodiments, Ring F is unsubstituted pyrrolyl. In certain embodiments, Ring F is substituted furanyl. In certain embodiments, Ring F is unsubstituted furanyl. In certain embodiments, Ring F is substituted thienyl. In certain embodiments, Ring F is unsubstituted thienyl. In certain embodiments, Ring F is substituted pyrazolyl. In certain embodiments, Ring F is unsubstituted pyrazolyl. In certain embodiments, Ring F is substituted imidazolyl. In certain embodiments, Ring F is unsubstituted imidazolyl. In certain embodiments, Ring F is substituted oxazolyl. In certain embodiments, Ring F is unsubstituted oxazolyl. In certain embodiments, Ring F is substituted isoxazolyl. In certain embodiments, Ring F is unsubstituted isoxazolyl. In certain embodiments, Ring F is substituted thiazolyl. In certain embodiments, Ring F is unsubstituted thiazolyl. In certain embodiments, Ring F is substituted isothiazolyl. In certain embodiments, Ring F is unsubstituted isothiazolyl. In certain embodiments, Ring F is substituted triazolyl. In certain embodiments, Ring F is unsubstituted triazolyl. In certain embodiments, Ring F is substituted oxadiazolyl. In certain embodiments, Ring F is unsubstituted oxadiazolyl. In certain embodiments, Ring F is substituted thiadiazolyl. In certain embodiments, Ring F is unsubstituted thiadiazolyl. In certain embodiments, Ring F is a 6-membered monocyclic heteroaryl ring. In certain embodiments, Ring F is substituted pyridyl. In certain embodiments, Ring F is unsubstituted pyridyl. In certain embodiments, Ring F is substituted pyridazinyl. In certain embodiments, Ring F is unsubstituted pyridazinyl. In certain embodiments, Ring F is substituted pyrimidinyl. In certain embodiments, Ring F is unsubstituted pyrimidinyl. In certain embodiments, Ring F is substituted pyrazinyl. In certain embodiments, Ring F is unsubstituted pyrazinyl. In certain embodiments, Ring F is substituted triazinyl. In certain embodiments, Ring F is unsubstituted triazinyl. In certain embodiments, Ring F is an optionally substituted heteroaryl ring fused with one or more optionally substituted carbocyclic, optionally substituted heterocyclic, optionally substituted aryl, or optionally substituted heteroaryl groups wherein the point of attachment is on any one of the heteroaryl ring, or carbocyclic, heterocyclic, aryl, or heteroaryl groups, as valency permits. In certain embodiments, Ring F is a bicyclic heteroaryl ring. In certain embodiments, Ring F is an optionally substituted heteroaryl ring fused with an optionally substituted phenyl ring. In certain embodiments, Ring F is substituted indolyl. In certain embodiments, Ring F is unsubstituted indolyl. In certain embodiments, Ring F is substituted isoindolyl. In certain embodiments, Ring F is unsubstituted isoindolyl. In certain embodiments, Ring F is substituted indazolyl. In certain embodiments, Ring F is unsubstituted indazolyl. In certain embodiments, Ring F is substituted benzothienyl. In certain embodiments, Ring F is unsubstituted benzothienyl. In certain embodiments, Ring F is substituted isobenzothienyl. In certain embodiments, Ring F is unsubstituted isobenzothienyl. In certain embodiments, Ring F is substituted benzofuranly. In certain embodiments, Ring F is unsubstituted benzofuranly. In certain embodiments, Ring F is substituted benzoisofuranly. In certain embodiments, Ring F is unsubstituted benzoisofuranly. In certain embodiments, Ring F is substituted benzimidazolyl. In certain embodiments, Ring F is unsubstituted benzimidazolyl. In certain embodiments, Ring F is substituted benzoxazolyl. In certain embodiments, Ring F is unsubstituted benzoxazolyl. In certain embodiments, Ring F is substituted benzisoxazolyl. In certain embodiments, Ring F is unsubstituted benzisoxazolyl. In certain embodiments, Ring F is substituted benzothiazolyl. In certain embodiments, Ring F is unsubstituted benzothiazolyl. In certain embodiments, Ring F is substituted benzisothiazolyl. In certain embodiments, Ring F is unsubstituted benzisothiazolyl. In certain embodiments, Ring F is substituted benzotriazolyl. In certain embodiments, Ring F is unsubstituted benzotriazolyl. In certain embodiments, Ring F is substituted benzoxadiazolyl. In certain embodiments, Ring F is unsubstituted benzoxadiazolyl. In certain embodiments, Ring F is substituted quinolinyl. In certain embodiments, Ring F is unsubstituted quinolinyl. In certain embodiments, Ring F is substituted isoquinolinyl. In certain embodiments, Ring F is unsubstituted isoquinolinyl. In certain embodiments, Ring F is substituted cinnolinyl. In certain embodiments, Ring F is unsubstituted cinnolinyl. In certain embodiments, Ring F is substituted quinoxalinyl. In certain embodiments, Ring F is unsubstituted quinoxalinyl. In certain embodiments, Ring F is substituted phthalazinyl. In certain embodiments, Ring F is unsubstituted phthalazinyl. In certain embodiments, Ring F is substituted quinazolinyl. In certain embodiments, Ring F is unsubstituted quinazolinyl. In certain embodiments, Ring F is a tricyclic heteroaryl ring.

Ring F of Formula (II) may be unsubstituted or substituted with one or more $R^F$ groups. $R^F$ may be attached to a carbon atom or heteroatom, as valency permits. In certain embodiments, Ring F is unsubstituted, and thus n is 0. In certain embodiments, n is 1. In certain embodiments, the compound of Formula (II) is of the formula:

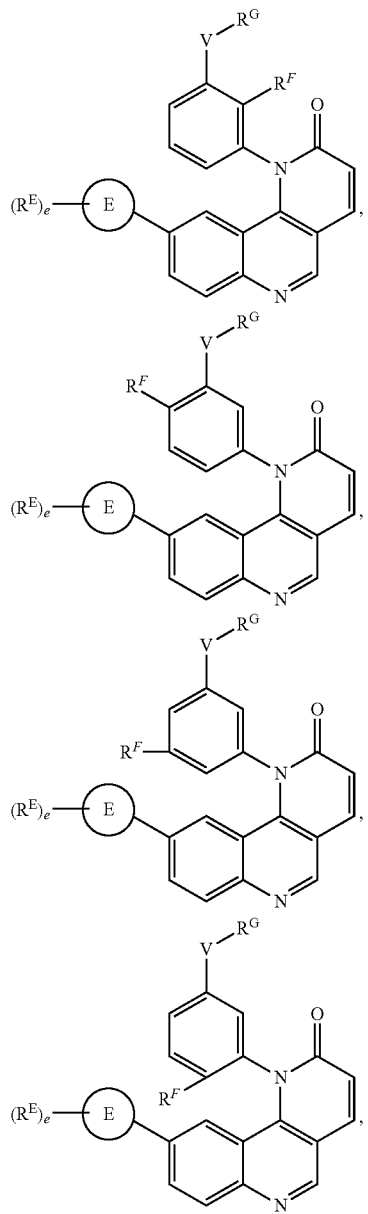

or a pharmaceutically acceptable salt, solvate, hydrate, polymorph, co-crystal, tautomer, stereoisomer, isotopically labeled derivative, and prodrug thereof.

In certain embodiments, f is 2. In certain embodiments, the compound of Formula (II) is of the formula:

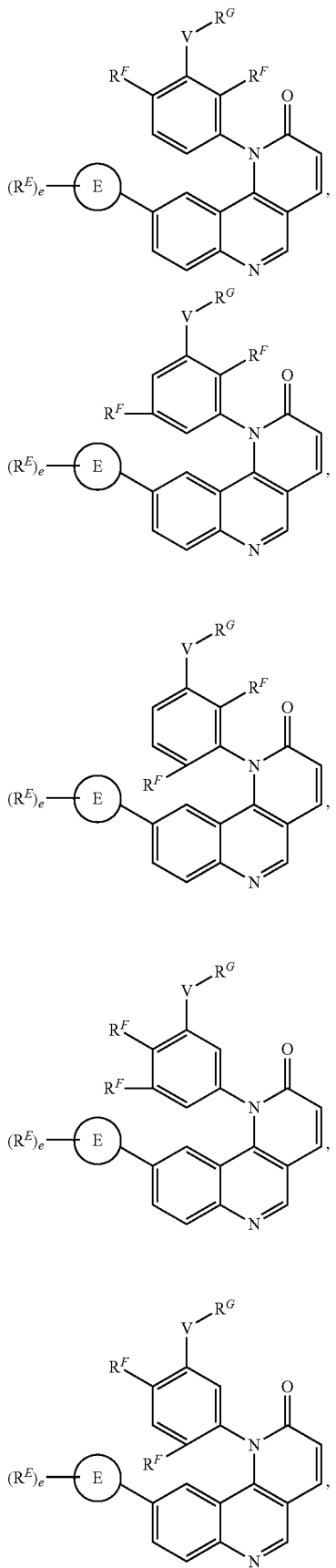

-continued

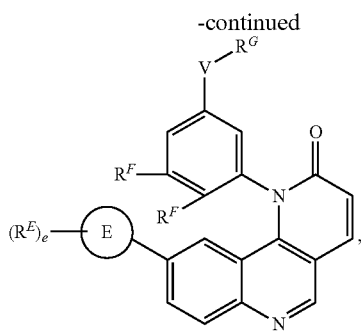

or a pharmaceutically acceptable salt, solvate, hydrate, polymorph, co-crystal, tautomer, stereoisomer, isotopically labeled derivative, and prodrug thereof.

In certain embodiments, f is 3. In certain embodiments, f is 4.

In certain embodiments, at least one $R^F$ is H. In certain embodiments, at least one $R^F$ is halogen. In certain embodiments, at least one $R^F$ is F. In certain embodiments, at least one $R^F$ is Cl. In certain embodiments, at least one $R^F$ is Br. In certain embodiments, at least one $R^F$ is I (iodine). In certain embodiments, at least one $R^F$ is substituted acyl. In certain embodiments, at least one $R^F$ is unsubstituted acyl. In certain embodiments, at least one $R^F$ is acetyl. In certain embodiments, at least one $R^F$ is substituted alkyl. In certain embodiments, at least one $R^F$ is unsubstituted alkyl. In certain embodiments, at least one $R^F$ is $C_{1-6}$ alkyl. In certain embodiments, at least one $R^F$ is methyl. In certain embodiments, at least one $R^F$ is ethyl. In certain embodiments, at least one $R^F$ is propyl. In certain embodiments, at least one $R^F$ is butyl. In certain embodiments, at least one $R^F$ is substituted alkenyl. In certain embodiments, at least one $R^F$ is unsubstituted alkenyl. In certain embodiments, at least one $R^F$ is substituted alkynyl. In certain embodiments, at least one $R^F$ is unsubstituted alkynyl. In certain embodiments, at least one $R^F$ is substituted carbocyclyl. In certain embodiments, at least one $R^F$ is unsubstituted carbocyclyl. In certain embodiments, at least one $R^F$ is substituted heterocyclyl. In certain embodiments, at least one $R^F$ is unsubstituted heterocyclyl. In certain embodiments, at least one $R^F$ is substituted aryl. In certain embodiments, at least one $R^F$ is unsubstituted aryl. In certain embodiments, at least one $R^F$ is substituted phenyl. In certain embodiments, at least one $R^F$ is unsubstituted phenyl. In certain embodiments, at least one $R^F$ is substituted heteroaryl. In certain embodiments, at least one $R^F$ is unsubstituted heteroaryl. In certain embodiments, at least one $R^F$ is substituted pyridyl. In certain embodiments, at least one $R^F$ is unsubstituted pyridyl. In certain embodiments, at least one $R^F$ is —$OR^{F1}$. In certain embodiments, at least one $R^F$ is —OH. In certain embodiments, at least one $R^F$ is —$N(R^{F1})_2$. In certain embodiments, at least one $R^F$ is —$NH_2$. In certain embodiments, at least one $R^F$ is —$SR^{F1}$. In certain embodiments, at least one $R^F$ is —SH.

In certain embodiments, when $R^F$ is —$OR^{F1}$, —$N(R^{F1})_2$, or —$SR^{F1}$, at least one $R^{F1}$ is H. In certain embodiments, at least one $R^{F1}$ is substituted acyl. In certain embodiments, at least one $R^{F1}$ is unsubstituted acyl. In certain embodiments, at least one $R^{F1}$ is acetyl. In certain embodiments, at least one $R^{F1}$ is substituted alkyl. In certain embodiments, at least one $R^{F1}$ is unsubstituted alkyl. In certain embodiments, at least one $R^{F1}$ is $C_{1-6}$ alkyl. In certain embodiments, at least one $R^{F1}$ is methyl. In certain embodiments, at least one $R^{F1}$ is ethyl. In certain embodiments, at least one $R^{F1}$ is propyl. In certain embodiments, at least one $R^{F1}$ is butyl. In certain embodiments, at least one $R^{F1}$ is substituted alkenyl. In certain embodiments, at least one $R^{F1}$ is unsubstituted alkenyl. In certain embodiments, at least one $R^{F1}$ is substituted alkynyl. In certain embodiments, at least one $R^{F1}$ is unsubstituted alkynyl. In certain embodiments, at least one $R^{F1}$ is substituted carbocyclyl. In certain embodiments, at least one $R^{F1}$ is unsubstituted carbocyclyl. In certain embodiments, at least one $R^{F1}$ is substituted heterocyclyl. In certain embodiments, at least one $R^{F1}$ is unsubstituted heterocyclyl. In certain embodiments, at least one $R^{F1}$ is substituted aryl. In certain embodiments, at least one $R^{F1}$ is unsubstituted aryl. In certain embodiments, at least one $R^{F1}$ is substituted phenyl. In certain embodiments, at least one $R^{F1}$ is unsubstituted phenyl. In certain embodiments, at least one $R^{F1}$ is substituted heteroaryl. In certain embodiments, at least one $R^{F1}$ is unsubstituted heteroaryl. In certain embodiments, at least one $R^{F1}$ is substituted pyridyl. In certain embodiments, at least one $R^{F1}$ is unsubstituted pyridyl. In certain embodiments, at least one $R^{F1}$ is a nitrogen protecting group when attached to a nitrogen atom. In certain embodiments, at least one $R^{F1}$ is Bn, BOC, Cbz, Fmoc, trifluoroacetyl, triphenylmethyl, or Ts when attached to a nitrogen atom. In certain embodiments, $R^{F1}$ is an oxygen protecting group when attached to an oxygen atom. In certain embodiments, $R^{F1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{F1}$ is a sulfur protecting group when attached to a sulfur atom. In certain embodiments, $R^{F1}$ is acetamidomethyl, t-Bu, 3-nitro-2-pyridine sulfenyl, 2-pyridine-sulfenyl, or triphenylmethyl when attached to a sulfur atom. In certain embodiments, two $R^{F1}$ groups are joined to form a substituted heterocyclic ring. In certain embodiments, two $R^{F1}$ groups are joined to form an unsubstituted heterocyclic ring.

In certain embodiments, $R^F$ is substituted $C_{1-6}$ alkyl; and f is 1. In certain embodiments, $R^F$ is unsubstituted $C_{1-6}$ alkyl; and f is 1. In certain embodiments, $R^F$ is methyl; and f is 1. In certain embodiments, $R^F$ is ethyl; and f is 1. In certain embodiments, $R^F$ is propyl; and f is 1. In certain embodiments, $R^F$ is butyl; and f is 1. In certain embodiments, $R^F$ is halogen; and f is 1. In certain embodiments, $R^F$ is F; and f is 1. In certain embodiments, $R^F$ is Cl; and f is 1. In certain embodiments, $R^F$ is Br; and f is 1. In certain embodiments, $R^F$ is I (iodine); and f is 1.

In compounds of Formula (II), linker V is a divalent linker moiety. V may be a bond. In certain embodiments, V is a single bond. V may also be a $C_{1-6}$ hydrocarbon chain. V may be saturated or unsaturated. V may be substituted or unsubstituted. V may also be branched or unbranched. In certain embodiments, V is a $C_1$ hydrocarbon chain substituted with one or more $R^V$ groups. In certain embodiments, V is —$C(R^V)_2$—. In certain embodiments, V is —$CH_2$—. In certain embodiments, V is a $C_2$ hydrocarbon chain substituted with one or more $R^V$ groups. In certain embodiments, V is —$C(R^V)_2$—$C(R^V)_2$—. In certain embodiments, V is —$CHR^V$—$CHR^V$—. In certain embodiments, V is —$(CH_2)_2$—. In certain embodiments, V is trans-$CR^V$=$CR^V$—. In certain embodiments, V is trans-CH=CH—. In certain embodiments, V is cis-$CR^V$=$CR^V$—. In certain embodiments, V is cis-CH=CH—. In certain embodiments, V is —C≡C—. In certain embodiments, V is a $C_3$ hydrocarbon chain substituted with one or more $R^V$ groups. In certain embodiments, V is —$C(R^V)_2$—$C(R^V)_2$—$(RV)_2$—. In certain embodiments, V is —$(CH_2)_3$—. In certain embodiments, V is —$C(R^V)$=C$(R^V)_2$—$C(R^V)_2$—, wherein C=C is cis or trans. In certain embodiments, V is —C(R$^V$)$_2$—C(R$^V$)=C(R$^V$)—, wherein C=C is cis or trans. In certain embodiments, V is —C≡C—C(R$^V$)$_2$—. In certain embodiments, V is —C(R$^V$)$_2$—C≡C—. In certain embodiments, V is a C$_4$ hydrocarbon chain substituted with one or more R$^V$ groups. In certain embodiments, V is —C(R$^V$)$_2$—C(R$^V$)$_2$—C(R$^V$)$_2$—C(R$^V$)$_2$—. In certain embodiments, V is —(CH$_2$)$_4$—. In certain embodiments, V is —C(R$^V$)=C(R$^V$)—C(R—C(R$^V$)$_2$—, wherein C=C is cis or trans. In certain embodiments, V is —C(R$^V$)$_2$—C(R$^V$)=(R$^V$)—C(R$^V$)$_2$—, wherein C=C is cis or trans. In certain embodiments, V is —C(R$^V$)$_2$—C(R$^V$)$_2$—C(R$^V$)=C(R$^V$)—, wherein C=C is cis or trans. In certain embodiments, V is —C≡C—C(R$^V$)$_2$—C(R$^V$)$_2$—. In certain embodiments, V is —C(R$^V$)$_2$—C≡C—C(R$^V$)$_2$—. In certain embodiments, V is —C(R$^V$)$_2$—C(R$^V$)$_2$—C≡C—. In certain embodiments, V is —C(R$^V$)=C(R$^V$)—C(R$^V$)=C(R$^V$)—, wherein each occurrence of C=C is independently cis or trans. In certain embodiments, V is —C(R$^V$)=C(R$^V$)—C≡C—, wherein C=C is cis or trans. In certain embodiments, V is —C≡C—C(R$^V$)=C(R$^V$)—, wherein the C=C is cis or trans. In certain embodiments, V is —C≡C—C≡C—. In certain embodiments, V is a C$_5$ hydrocarbon chain substituted with one or more R$^V$ groups. In certain embodiments, V is —C(R$^V$)$_2$—C(R$^V$)$_2$—C(R$^V$)$_2$—C(R$^V$)$_2$—C(R$^V$)$_2$—. In certain embodiments, V is —(CH$_2$)$_5$—. In certain embodiments, V is a C$_6$ hydrocarbon chain substituted with one or more R$^V$V groups. In certain embodiments, V is —C(R$^V$)$_2$—C(R$^V$)$_2$—C(R$^V$—C(R$^V$)$_2$—C(R$^V$)$_2$—C(R$^V$)$_2$—. In certain embodiments, V is —(CH$_2$)$_6$—. In certain embodiments, one or more carbon units of the hydrocarbon chain is replaced with —O—, —S—, —NR$^V$—, —NR$^V$C(=O)—, —C(=O)NR$^V$—, —SC(=O)—, —C(=O)S—, —OC(=O)—, —C(=O)O—, —NR$^V$C(=S)—, —C(=S)NR$^V$—, trans-CR$^V$=CR$^V$—, cis-CR$^V$=CR$^V$—, —C≡C—, —S(=O)$_2$O—, —OS(=O)$_2$—, —S(=O)$_2$NR$^V$—, or —NR$^V$S(=O)$_2$-.

In certain embodiments, at least one R$^V$ is H. In certain embodiments, at least one R$^V$ is halogen. In certain embodiments, at least one R$^V$ is F. In certain embodiments, at least one R$^V$ is Cl. In certain embodiments, at least one R$^V$ is Br. In certain embodiments, at least one R$^V$ is I (iodine). In certain embodiments, at least one R$^V$ is substituted alkyl. In certain embodiments, at least one R$^V$ is unsubstituted alkyl. In certain embodiments, at least one RV is C$_{1-6}$ alkyl. In certain embodiments, at least one R$^V$ is methyl. In certain embodiments, at least one R$^V$ is ethyl. In certain embodiments, at least one R$^V$ is propyl. In certain embodiments, at least one R$^V$ is butyl. In certain embodiments, at least one R$^V$ is substituted alkenyl. In certain embodiments, at least one R$^V$ is unsubstituted alkenyl. In certain embodiments, at least one R$^V$ is vinyl. In certain embodiments, at least one R$^V$ is substituted alkynyl. In certain embodiments, at least one R$^V$ is unsubstituted alkynyl. In certain embodiments, at least one R$^V$ is ethynyl. In certain embodiments, at least one R$^V$ is substituted carbocyclyl. In certain embodiments, at least one R$^V$ is unsubstituted carbocyclyl. In certain embodiments, at least one R$^V$ is substituted heterocyclyl. In certain embodiments, at least one R$^V$ is unsubstituted heterocyclyl. In certain embodiments, at least one R$^V$ is substituted aryl. In certain embodiments, at least one R$^V$ is unsubstituted aryl. In certain embodiments, at least one R$^V$ is substituted phenyl. In certain embodiments, at least one R$^V$ is unsubstituted phenyl. In certain embodiments, at least one R$^V$ is substituted heteroaryl. In certain embodiments, at least one R$^V$ is unsubstituted heteroaryl. In certain embodiments, at least one R$^V$ is substituted pyridyl. In certain embodiments, at least one R$^V$ is unsubstituted pyridyl. In certain embodiments, two R$^V$ groups are joined to form a substituted carbocyclic ring. In certain embodiments, two R$^V$ groups are joined to form an unsubstituted carbocyclic ring. In certain embodiments, two R$^V$ groups are joined to form a substituted heterocyclic ring. In certain embodiments, two R$^V$ groups are joined to form an unsubstituted heterocyclic ring. In certain embodiments, two R$^V$ groups are joined to form a substituted aryl ring. In certain embodiments, two R$^V$ groups are joined to form an unsubstituted aryl ring. In certain embodiments, two R$^V$ groups are joined to form a substituted phenyl ring. In certain embodiments, two R$^V$ groups are joined to form an unsubstituted phenyl ring. In certain embodiments, two R$^V$ groups are joined to form a substituted heteroaryl ring. In certain embodiments, two R$^V$ groups are joined to form an unsubstituted heteroaryl ring.

In compounds of Formula (II), R$^G$ is a substituent on Ring F through linker V. In certain embodiments, R$^G$ comprises a Michael acceptor moiety. This Michael acceptor moiety may react with a cysteine residue of a kinase (e.g., bone marrow kinase on X chromosome (BMX)) to allow covalent attachment of the compound to the kinase. In certain embodiments, the covalent attachment is irreversible. In other embodiments, the covalent attachment is reversible. In certain embodiments, R$^G$ is of Formula (ii-1). In certain embodiments, R$^G$ is Of Formula (ii-2). In certain embodiments, R$^G$ is Of Formula (ii-3). In certain embodiments, R$^G$ is Of Formula (ii-4). In certain embodiments, R$^G$ is Of Formula (ii-5). In certain embodiments, R$^G$ is of Formula (ii-6). In certain embodiments, R$^G$ is of Formula (ii-7). In certain embodiments, R$^G$ is Of Formula (ii-8). In certain embodiments, R$^G$ is of Formula (ii-9). In certain embodiments, R$^G$ is Of Formula (ii-10). In certain embodiments, R$^G$ is of Formula (ii-11). In certain embodiments, R$^G$ is of Formula (ii-12). In certain embodiments, R$^G$ is Of Formula (ii-13). In certain embodiments, R$^G$ is Of Formula (ii-14). In certain embodiments, R$^G$ is Of Formula (ii-15). In certain embodiments, R$^G$ is Of Formula (ii-16). In certain embodiments, R$^G$ is of Formula (ii-17).

In compounds of Formula (II), R$^G$ may include a substituent R$^{G1}$. In certain embodiments, R$^{G1}$ is H. In certain embodiments, R$^{G1}$ is halogen. In certain embodiments, R$^{G1}$ is F. In certain embodiments, R$^{G1}$ is Cl. In certain embodiments, R$^{G1}$ is Br. In certain embodiments, R$^{G1}$ is I (iodine). In certain embodiments, R$^{G1}$ is substituted acyl. In certain embodiments, R$^{G1}$ is unsubstituted acyl. In certain embodiments, R$^{G1}$ is acetyl. In certain embodiments, R$^{G1}$ is substituted alkyl. In certain embodiments, R$^{G1}$ is unsubstituted alkyl. In certain embodiments, R$^{G1}$ is C$_{1-6}$ alkyl. In certain embodiments, R$^{G1}$ is methyl. In certain embodiments, R$^{G1}$ is ethyl. In certain embodiments, R$^{G1}$ is propyl. In certain embodiments, R$^{G1}$ is butyl. In certain embodiments, R$^{G1}$ is substituted alkenyl. In certain embodiments, R$^{G1}$ is unsubstituted alkenyl. In certain embodiments, R$^{G1}$ is substituted alkynyl. In certain embodiments, R$^{G1}$ is unsubstituted alkynyl. In certain embodiments, R$^{G1}$ is substituted carbocyclyl. In certain embodiments, R$^{G1}$ is unsubstituted carbocyclyl. In certain embodiments, R$^{G1}$ is substituted heterocyclyl. In certain embodiments, R$^{G1}$ is unsubstituted heterocyclyl. In certain embodiments, R$^{G1}$ is substituted aryl. In certain embodiments, R$^{G1}$ is unsubstituted aryl. In certain embodiments, R$^{G1}$ is substituted phenyl. In certain embodiments, R$^{G1}$ is unsubstituted phenyl. In certain embodiments, R$^{G1}$ is substituted heteroaryl. In certain embodiments, R$^{G1}$ is unsubstituted heteroaryl. In certain embodiments, R$^{G1}$ is substituted pyridyl. In certain embodiments, R$^{G1}$ is unsubstituted pyridyl. In certain embodiments, R$^{G1}$ is —CN. In certain embodiments, R$^{G1}$ is —NO$_2$. In certain embodiments, $R^{G1}$ is —$OR^{G1a}$. In certain embodiments, $R^{G1}$ is —$N(R^{G1a})_2$. In certain embodiments, $R^{G1}$ is —$SR^{G1a}$. In certain embodiments, $R^{G1}$ is —$CH_2OR^{G1a}$. In certain embodiments, $R^{G1}$ is —$CH_2N(R^{G1a})_2$. In certain embodiments, $R^{G1}$ is —$CH_2SR^{G1a}$.

In certain embodiments, at least one $R^{G1a}$ is H. In certain embodiments, at least one $R^{G1a}$ is substituted acyl. In certain embodiments, at least one $R^{G1a}$ is unsubstituted acyl. In certain embodiments, at least one $R^{G1a}$ is acetyl. In certain embodiments, at least one $R^{G1a}$ is substituted alkyl. In certain embodiments, at least one $R^{G1a}$ is unsubstituted alkyl. In certain embodiments, at least one $R^{G1a}$ is $C_{1-6}$ alkyl. In certain embodiments, at least one $R^{G1a}$ is methyl. In certain embodiments, at least one $R^{G1a}$ is ethyl. In certain embodiments, at least one $R^{G1a}$ is propyl. In certain embodiments, at least one $R^{G1a}$ is butyl. In certain embodiments, at least one $R^{G1a}$ is substituted alkenyl. In certain embodiments, at least one $R^{G1a}$ is unsubstituted alkenyl. In certain embodiments, at least one $R^{G1a}$ is substituted alkynyl. In certain embodiments, at least one $R^{G1a}$ is unsubstituted alkynyl. In certain embodiments, at least one $R^{G1a}$ is substituted carbocyclyl. In certain embodiments, at least one $R^{G1a}$ is unsubstituted carbocyclyl. In certain embodiments, at least one $R^{G1a}$ is substituted heterocyclyl. In certain embodiments, at least one $R^{G1a}$ is unsubstituted heterocyclyl. In certain embodiments, at least one $R^{G1a}$ is substituted aryl. In certain embodiments, at least one $R^{G1a}$ is unsubstituted aryl. In certain embodiments, at least one $R^{G1a}$ is substituted phenyl. In certain embodiments, at least one $R^{G1a}$ is unsubstituted phenyl. In certain embodiments, at least one $R^{G1a}$ is substituted heteroaryl. In certain embodiments, at least one $R^{G1a}$ is unsubstituted heteroaryl. In certain embodiments, at least one $R^{G1a}$ is substituted pyridyl. In certain embodiments, at least one $R^{G1a}$ is unsubstituted pyridyl. In certain embodiments, at least one $R^{G1a}$ is a nitrogen protecting group when attached to a nitrogen atom. In certain embodiments, at least one $R^{G1a}$ is Bn, BOC, Cbz, Fmoc, trifluoroacetyl, triphenylmethyl, or Ts when attached to a nitrogen atom. In certain embodiments, $R^{G1a}$ is an oxygen protecting group when attached to an oxygen atom. In certain embodiments, $R^{G1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{G1a}$ is a sulfur protecting group when attached to a sulfur atom. In certain embodiments, $R^{G1a}$ is acetamidomethyl, t-Bu, 3-nitro-2-pyridine sulfenyl, 2-pyridine-sulfenyl, or triphenylmethyl when attached to a sulfur atom. In certain embodiments, two $R^{G1a}$ groups are joined to form a substituted heterocyclic ring. In certain embodiments, two $R^{G1a}$ groups are joined to form an unsubstituted heterocyclic ring.

In compounds of Formula (II), $R^G$ may include a substituent $R^{G2}$. In certain embodiments, $R^{G2}$ is H. In certain embodiments, $R^{G2}$ is halogen. In certain embodiments, $R^{G2}$ is F. In certain embodiments, $R^{G2}$ is Cl. In certain embodiments, $R^{G2}$ is Br. In certain embodiments, $R^{G2}$ is I (iodine). In certain embodiments, $R^{G2}$ is substituted acyl. In certain embodiments, $R^{G2}$ is unsubstituted acyl. In certain embodiments, $R^{G2}$ is acetyl. In certain embodiments, $R^{G2}$ is substituted alkyl. In certain embodiments, $R^{G2}$ is unsubstituted alkyl. In certain embodiments, $R^{G2}$ is $C_{1-6}$ alkyl. In certain embodiments, $R^{G2}$ is methyl. In certain embodiments, $R^{G2}$ is ethyl. In certain embodiments, $R^{G2}$ is propyl. In certain embodiments, $R^{G2}$ is butyl. In certain embodiments, $R^{G2}$ is substituted alkenyl. In certain embodiments, $R^{G2}$ is unsubstituted alkenyl. In certain embodiments, $R^{G2}$ is substituted alkynyl. In certain embodiments, $R^{G2}$ is unsubstituted alkynyl. In certain embodiments, $R^{G2}$ is substituted carbocyclyl. In certain embodiments, $R^{G2}$ is unsubstituted carbocyclyl. In certain embodiments, $R^{G2}$ is substituted heterocyclyl. In certain embodiments, $R^{G2}$ is unsubstituted heterocyclyl. In certain embodiments, $R^{G2}$ is substituted aryl. In certain embodiments, $R^{G2}$ is unsubstituted aryl. In certain embodiments, $R^{G2}$ is substituted phenyl. In certain embodiments, $R^{G2}$ is unsubstituted phenyl. In certain embodiments, $R^{G2}$ is substituted heteroaryl. In certain embodiments, $R^{G2}$ is unsubstituted heteroaryl. In certain embodiments, $R^{G2}$ is substituted pyridyl. In certain embodiments, $R^{G2}$ is unsubstituted pyridyl. In certain embodiments, $R^{G2}$ is —CN. In certain embodiments, $R^{G2}$ is —$NO_2$. In certain embodiments, $R^{G2}$ is —$OR^{G2a}$. In certain embodiments, $R^{G2}$ is —$N(R^{G2a})_2$. In certain embodiments, $R^{G2}$ is —$SR^{G2a}$. In certain embodiments, $R^{G2}$ is —$CH_2OR^{G2a}$. In certain embodiments, $R^{G2}$ is —$CH_2N(R^{G2a})_2$. In certain embodiments, $R^{G2}$ is —$CH_2SR^{G2a}$.

In certain embodiments, at least one $R^{G2a}$ is H. In certain embodiments, at least one $R^{G2a}$ is substituted acyl. In certain embodiments, at least one $R^{G2a}$ is unsubstituted acyl. In certain embodiments, at least one $R^{G2a}$ is acetyl. In certain embodiments, at least one $R^{G2a}$ is substituted alkyl. In certain embodiments, at least one $R^{G2a}$ is unsubstituted alkyl. In certain embodiments, at least one $R^{G2a}$ is $C_{1-6}$ alkyl. In certain embodiments, at least one $R^{G2a}$ is methyl. In certain embodiments, at least one $R^{G2a}$ is ethyl. In certain embodiments, at least one $R^{G2a}$ is propyl. In certain embodiments, at least one $R^{G2a}$ is butyl. In certain embodiments, at least one $R^{G2a}$ is substituted alkenyl. In certain embodiments, at least one $R^{G2a}$ is unsubstituted alkenyl. In certain embodiments, at least one $R^{G2a}$ is substituted alkynyl. In certain embodiments, at least one $R^{G2a}$ is unsubstituted alkynyl. In certain embodiments, at least one $R^{G2a}$ is substituted carbocyclyl. In certain embodiments, at least one $R^{G2a}$ is unsubstituted carbocyclyl. In certain embodiments, at least one $R^{G2a}$ is substituted heterocyclyl. In certain embodiments, at least one $R^{G2a}$ is unsubstituted heterocyclyl. In certain embodiments, at least one $R^{G2a}$ is substituted aryl. In certain embodiments, at least one $R^{G2a}$ is unsubstituted aryl. In certain embodiments, at least one $R^{G2a}$ is substituted phenyl. In certain embodiments, at least one $R^{G2a}$ is unsubstituted phenyl. In certain embodiments, at least one $R^{G2a}$ is substituted heteroaryl. In certain embodiments, at least one $R^{G2a}$ is unsubstituted heteroaryl. In certain embodiments, at least one $R^{G2a}$ is substituted pyridyl. In certain embodiments, at least one $R^{G2a}$ is unsubstituted pyridyl. In certain embodiments, at least one $R^{G2a}$ is a nitrogen protecting group when attached to a nitrogen atom. In certain embodiments, at least one $R^{G2a}$ is Bn, BOC, Cbz, Fmoc, trifluoroacetyl, triphenylmethyl, or Ts when attached to a nitrogen atom. In certain embodiments, $R^{G2a}$ is an oxygen protecting group when attached to an oxygen atom. In certain embodiments, $R^{G2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{G2a}$ is a sulfur protecting group when attached to a sulfur atom. In certain embodiments, $R^{G2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{G2a}$ groups are joined to form a substituted heterocyclic ring. In certain embodiments, two $R^{G2a}$ groups are joined to form an unsubstituted heterocyclic ring.

In compounds of Formula (II), $R^G$ may include a substituent $R^{G3}$. In certain embodiments, $R^{G3}$ is H. In certain embodiments, $R^{G3}$ is halogen. In certain embodiments, $R^{G3}$ is F. In certain embodiments, $R^{G3}$ is Cl. In certain embodiments, $R^{G3}$ is Br. In certain embodiments, $R^{G3}$ is I (iodine). In certain embodiments, $R^{G3}$ is substituted acyl. In certain embodiments, $R^{G3}$ is unsubstituted acyl. In certain embodiments, $R^{G3}$ is acetyl. In certain embodiments, $R^{G3}$ is substituted alkyl. In certain embodiments, $R^{G3}$ is unsubstituted alkyl. In certain embodiments, $R^{G3}$ is $C_{1-6}$ alkyl. In certain embodiments, $R^{G3}$ is methyl. In certain embodiments, $R^{G3}$ is ethyl. In certain embodiments, $R^{G3}$ is propyl. In certain embodiments, $R^{G3}$ is butyl. In certain embodiments, $R^{G3}$ is substituted alkenyl. In certain embodiments, $R^{G3}$ is unsubstituted alkenyl. In certain embodiments, $R^{G3}$ is substituted alkynyl. In certain embodiments, $R^{G3}$ is unsubstituted alkynyl. In certain embodiments, $R^{G3}$ is substituted carbocyclyl. In certain embodiments, $R^{G3}$ is unsubstituted carbocyclyl. In certain embodiments, $R^{G3}$ is substituted heterocyclyl. In certain embodiments, $R^{G3}$ is unsubstituted heterocyclyl. In certain embodiments, $R^{G3}$ is substituted aryl. In certain embodiments, $R^{G3}$ is unsubstituted aryl. In certain embodiments, $R^{G3}$ is substituted phenyl. In certain embodiments, $R^{G3}$ is unsubstituted phenyl. In certain embodiments, $R^{G3}$ is substituted heteroaryl. In certain embodiments, $R^{G3}$ is unsubstituted heteroaryl. In certain embodiments, $R^{G3}$ is substituted pyridyl. In certain embodiments, $R^{G3}$ is unsubstituted pyridyl. In certain embodiments, $R^{G3}$ is —CN. In certain embodiments, $R^{G3}$ is —$NO_2$. In certain embodiments, $R^{G3}$ is —$OR^{G3a}$. In certain embodiments, $R^{G3}$ is —$N(R^{G3a})_2$. In certain embodiments, $R^{G3}$ is —$SR^{G3a}$. In certain embodiments, $R^{G3}$ is —$CH_2OR^{G3a}$. In certain embodiments, $R^{G3}$ is —$CH_2N(R^{G3a})_2$. In certain embodiments, $R^{G3}$ is —$CH_2SR^{G3a}$.

In certain embodiments, at least one $R^{G3a}$ is H. In certain embodiments, at least one $R^{G3a}$ is substituted, at least one $R^{G3a}$ is acetyl. In certain embodiments, at least one $R^{G3a}$ is certain embodiments, at least one $R^{G3a}$ is acetyl. In certain embodiments, at least one $R^{G3a}$ is substituted alkyl. In certain embodiments, at least one $R^{G3a}$ is unsubstituted alkyl. In certain embodiments, at least one $R^{G3a}$ is $C_{1-6}$ alkyl. In certain embodiments, at least one $R^{G3a}$ is methyl. In certain embodiments, at least one $R^{G3a}$ is ethyl. In certain embodiments, at least one $R^{G3a}$ is propyl. In certain embodiments, at least one $R^{G3a}$ is butyl. In certain embodiments, at least one $R^{G3a}$ is substituted alkenyl. In certain embodiments, at least one $R^{G3a}$ is unsubstituted alkenyl. In certain embodiments, at least one $R^{G3a}$ is substituted alkynyl. In certain embodiments, at least one $R^{G3a}$ is unsubstituted alkynyl. In certain embodiments, at least one $R^{G3a}$ is substituted carbocyclyl. In certain embodiments, at least one $R^{G3a}$ is unsubstituted carbocyclyl. In certain embodiments, at least one $R^{G3a}$ is substituted heterocyclyl. In certain embodiments, at least one $R^{G3a}$ is unsubstituted heterocyclyl. In certain embodiments, at least one $R^{G3a}$ is substituted aryl. In certain embodiments, at least one $R^{G3a}$ is unsubstituted aryl. In certain embodiments, at least one $R^{G3a}$ is substituted phenyl. In certain embodiments, at least one $R^{G3a}$ is unsubstituted phenyl. In certain embodiments, at least one $R^{G3a}$ is substituted heteroaryl. In certain embodiments, at least one $R^{G3a}$ is unsubstituted heteroaryl. In certain embodiments, at least one $R^{G3a}$ is substituted pyridyl. In certain embodiments, at least one $R^{G3a}$ is unsubstituted pyridyl. In certain embodiments, at least one $R^{G3a}$ is a nitrogen protecting group when attached to a nitrogen atom. In certain embodiments, at least one $R^{G3a}$ is Bn, BOC, Cbz, Fmoc, trifluoroacetyl, triphenylmethyl, or Ts when attached to a nitrogen atom. In certain embodiments, $R^{G3a}$ is an oxygen protecting group when attached to an oxygen atom. In certain embodiments, $R^{G3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{G3a}$ is a sulfur protecting group when attached to a sulfur atom. In certain embodiments, $R^{G3a}$ is acetamidomethyl, t-Bu, 3-nitro-2-pyridine sulfenyl, 2-pyridine-sulfenyl, or triphenylmethyl when attached to a sulfur atom. In certain embodiments, two $R^{G3a}$ groups are joined to form a substituted heterocyclic ring. In certain embodiments, two $R^{G3a}$ groups are joined to form an unsubstituted heterocyclic ring. In compounds of Formula (II), $R^G$ may include a substituent $R^{G4}$. In certain embodiments, $R^{G4}$ is a leaving group. In certain embodiments, $R^{G4}$ is halogen. In certain embodiments, $R^{G4}$ is F. In certain embodiments, $R^{G4}$ is Cl. In certain embodiments, $R^{G4}$ is Br. In certain embodiments, $R^{G4}$ is I (iodine). In certain embodiments, $R^{G4}$ is —$OS(=O)_wR^{G4a}$. In certain embodiments, w is 1. In certain embodiments, w is 2. In certain embodiments, $R^{G4}$ is —OMs. In certain embodiments, $R^{G4}$ is —OTf. In certain embodiments, $R^{G4}$ is —OTs. In certain embodiments, $R^{G4}$ is —OBs. In certain embodiments, $R^{G4}$ is 2-nitrobenzenesulfonyloxy. In certain embodiments, $R^{G4}$ is —$OR^{G4a}$. In certain embodiments, $R^{G4}$ is —OMe. In certain embodiments, $R^{G4}$ is —$OCF_3$. In certain embodiments, $R^{G4}$ is —OPh. In certain embodiments, $R^{G4}$ is —$OC(=O)R^{G4a}$. In certain embodiments, $R^{G4}$ is —OC(=O)Me. In certain embodiments, $R^{G4}$ is —$OC(=O)CF_3$. In certain embodiments, $R^{G4}$ is —OC(=O)Ph. In certain embodiments, $R^{G4}$ is —OC(=O)Cl. In certain embodiments, $R^{G4}$ is —$OC(=O)OR^{G4a}$. In certain embodiments, $R^{G4}$ is —OC(=O)OMe. In certain embodiments, $R^{G4}$ is —OC(=O)O(t-Bu).

In certain embodiments, $R^{G4a}$ is substituted alkyl. In certain embodiments, $R^{G4a}$ is unsubstituted alkyl. In certain embodiments, $R^{G4a}$ is $C_{1-6}$ alkyl. In certain embodiments, $R^{G4a}$ is methyl. In certain embodiments, $R^{G4a}$ is ethyl. In certain embodiments, $R^{G4a}$ is propyl. In certain embodiments, $R^{G4a}$ is butyl. In certain embodiments, $R^{G4a}$ is substituted alkenyl. In certain embodiments, $R^{G4a}$ is unsubstituted alkenyl. In certain embodiments, $R^{G4a}$ is vinyl. In certain embodiments, $R^{G4a}$ is substituted alkynyl. In certain embodiments, $R^{G4a}$ is unsubstituted alkynyl. In certain embodiments, $R^{G4a}$ is ethynyl. In certain embodiments, $R^{G4a}$ is substituted carbocyclyl. In certain embodiments, $R^{G4a}$ is unsubstituted carbocyclyl. In certain embodiments, $R^{G4a}$ is substituted heterocyclyl. In certain embodiments, $R^{G4a}$ is unsubstituted heterocyclyl. In certain embodiments, $R^{G4a}$ is substituted aryl. In certain embodiments, $R^{G4a}$ is unsubstituted aryl. In certain embodiments, $R^{G4a}$ is substituted phenyl. In certain embodiments, $R^{G4a}$ is unsubstituted phenyl. In certain embodiments, $R^{G4a}$ is substituted heteroaryl. In certain embodiments, $R^{G4a}$ is unsubstituted heteroaryl. In certain embodiments, $R^{G4a}$ is substituted pyridyl. In certain embodiments, $R^{G4a}$ is unsubstituted pyridyl.

In compounds of Formula (II), $R^G$ may include a substituent $R^{G5}$. In certain embodiments, $R^{G5}$ is H. In certain embodiments, $R^{G5}$ is substituted alkyl. In certain embodiments, $R^{G5}$ is unsubstituted alkyl. In certain embodiments, $R^{G5}$ is $C_{1-6}$ alkyl. In certain embodiments, $R^{G5}$ is methyl. In certain embodiments, $R^{G5}$ is ethyl. In certain embodiments, $R^{G5}$ is propyl. In certain embodiments, $R^{G5}$ is butyl. In certain embodiments, $R^{G5}$ is a nitrogen protecting group. In certain embodiments, $R^{G5}$ is Bn, BOC, Cbz, Fmoc, trifluoroacetyl, triphenylmethyl, or Ts.

In certain embodiments, $R^{G1}$ and $R^{G2}$ are each hydrogen. In certain embodiments, $R^{G1}$ and $R^{G3}$ are each hydrogen. In certain embodiments, $R^{G2}$ and $R^{G3}$ are each hydrogen. In certain embodiments, $R^{G1}$, $R^{G2}$, and $R^{G3}$ are each hydrogen. In certain embodiments, $R^{G1}$, $R^{G2}$, and $R^{G3}$, and $R^{G5}$ are each hydrogen.

In certain embodiments, b is 1. In certain embodiments, b is 2.

In certain embodiments, t is 0. In certain embodiments, t is 1. In certain embodiments, t is 2. In certain embodiments, t is 3. In certain embodiments, t is 4. In certain embodiments, t is 5. In certain embodiments, t is 6.

In certain embodiments, U is —O—. In certain embodiments, U is =O. In certain embodiments, U is —S—. In certain embodiments, U is =S. In certain embodiments, U is —$NR^{G6}$—, wherein $R^{G6}$ is hydrogen, $C_{1-6}$ alkyl, or a nitrogen protecting group. In certain embodiments, U is —NH—. In certain embodiments, U is —$NCH_3$—. In certain embodiments, U is —N(BOC)—. In certain embodiments, U is —N(Fmoc)-. In certain embodiments, U is —N(Cbz)-. In certain embodiments, U is —N(Bn)—. In certain embodiments, U is =$NR^{G6}$, wherein $R^{G6}$ is hydrogen, $C_{1-6}$ alkyl, or a nitrogen protecting group. In certain embodiments, U is =NH. In certain embodiments, U is =$NCH_3$. In certain embodiments, U is =NTs. In certain embodiments, U is =NBn. In certain embodiments, U is =$NCH(Ph)_2$.

In certain embodiments, $R^G$ is of the formula:

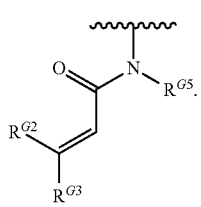

In certain embodiments, $R^G$ is of the formula:

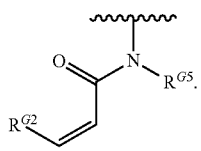

In certain embodiments, $R^G$ is of the formula:

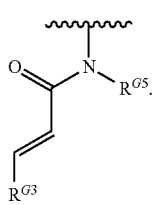

In certain embodiments, $R^G$ is of the formula:

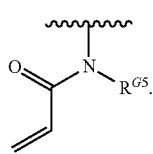

In certain embodiments, $R^G$ is of the formula:

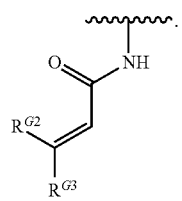

In certain embodiments $R^G$ is of the formula:

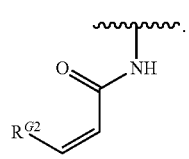

In certain embodiments, $R^G$ is of the formula:

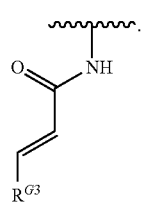

In certain embodiments, $R^G$ is of the formula:

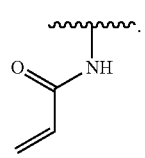 [SMILES: *NC(=O)C=C]

In certain embodiments, $R^G$ is of the formula:

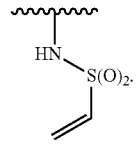

In certain embodiments, $R^G$ is Of the formula:

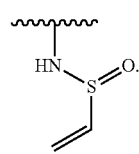

In certain embodiments, $R^G$ is of the formula:

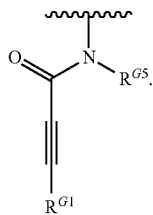

In certain embodiments, $R^G$ is of the formula:

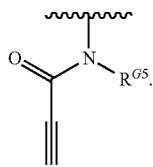

In certain embodiments, $R^G$ is of the formula:

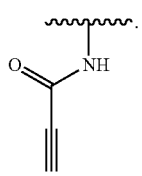

In certain embodiments, $R^G$ is of the formula:

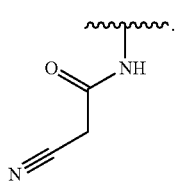

In certain embodiments, $R^G$ is of the formula:

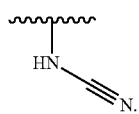

In certain embodiments, $R^G$ is of the formula:

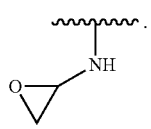

In certain embodiments, $R^G$ is of the formula:

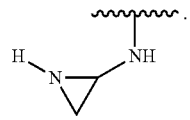 [SMILES: *NC1CN1]

In certain embodiments, $R^G$ is Of the formula:

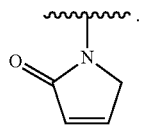

In certain embodiments, $R^G$ is of the formula:

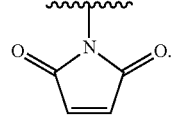

In certain embodiments, $R^G$ is Of the formula:

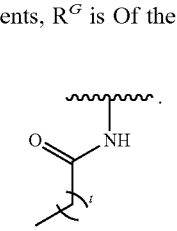

In certain embodiments, $R^G$ is of the formula:

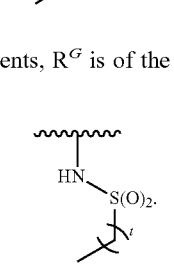

In certain embodiments, $R^G$ is of the formula:

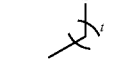

In certain embodiments, $R^G$ is Of the formula:

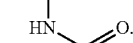

In certain embodiments, R$^G$ is of the formula:

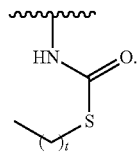

In certain embodiments, R$^G$ is of the formula:

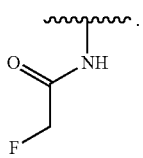

In certain embodiments, R$^G$ is of the formula:

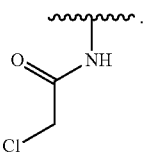 [SMILES: *NC(=O)CCl]

In certain embodiments, the compound of Formula (II) is of Formula (II-1):

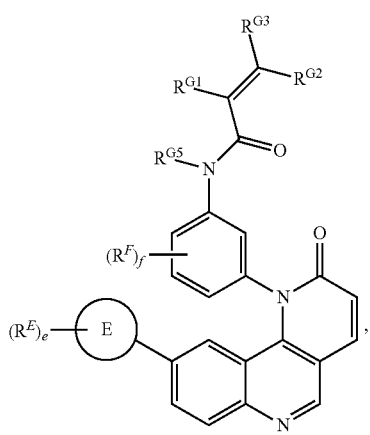

(II-1)

or a pharmaceutically acceptable salt, solvate, hydrate, polymorph, co-crystal, tautomer, stereoisomer, isotopically labeled derivative, and prodrug thereof.

In certain embodiments, the compound of Formula (II) is of the formula:

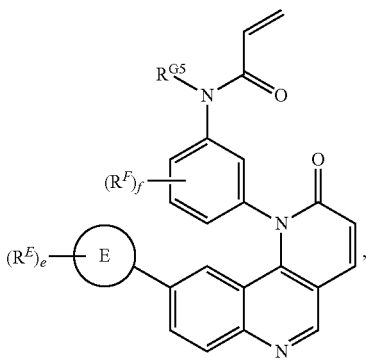

or a pharmaceutically acceptable salt, solvate, hydrate, polymorph, co-crystal, tautomer, stereoisomer, isotopically labeled derivative, and prodrug thereof.

In certain embodiments, the compound of Formula (II) is of Formula (II-2):

(II-2)

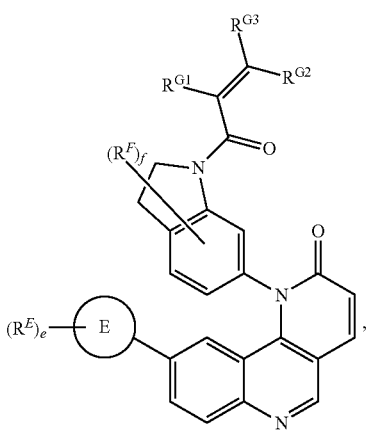

or a pharmaceutically acceptable salt, solvate, hydrate, polymorph, co-crystal, tautomer, stereoisomer, isotopically labeled derivative, and prodrug thereof.

In certain embodiments, the compound of Formula (II) is of the formula:

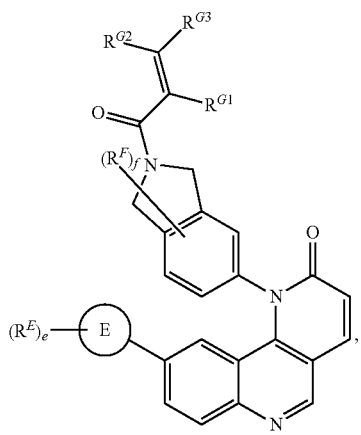

or a pharmaceutically acceptable salt, solvate, hydrate, polymorph, co-crystal, tautomer, stereoisomer, isotopically labeled derivative, and prodrug thereof.

In certain embodiments, the compound of Formula (II) is of the formula:

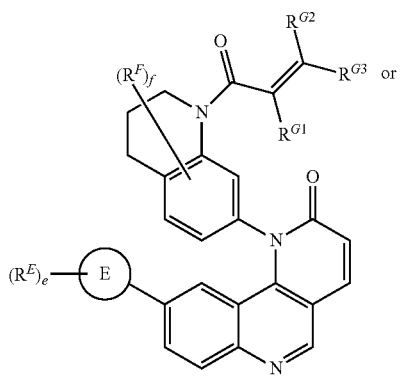 or

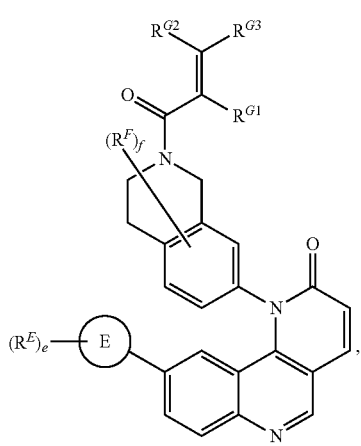

or a pharmaceutically acceptable salt, solvate, hydrate, polymorph, co-crystal, tautomer, stereoisomer, isotopically labeled derivative, and prodrug thereof.

In certain embodiments, the compound of Formula (II) is of the formula:

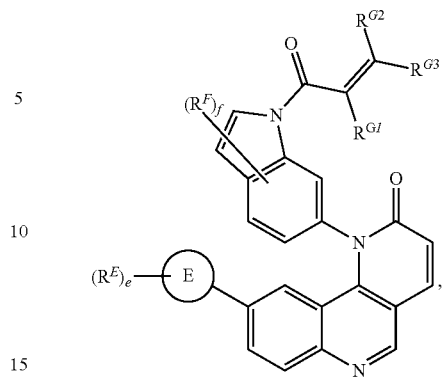

or a pharmaceutically acceptable salt, solvate, hydrate, polymorph, co-crystal, tautomer, stereoisomer, isotopically labeled derivative, and prodrug thereof.

In certain embodiments, the compound of Formula (II) is of the formula:

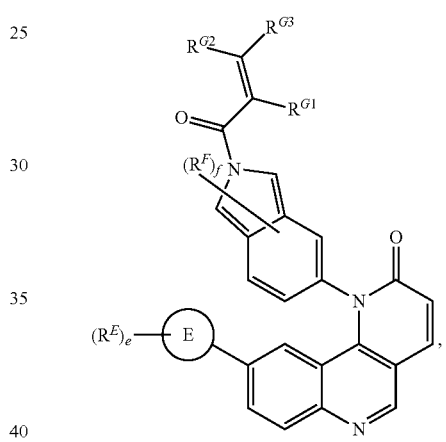

or a pharmaceutically acceptable salt, solvate, hydrate, polymorph, co-crystal, tautomer, stereoisomer, isotopically labeled derivative, and prodrug thereof.

In certain embodiments, the compound of Formula (II) is of the formula:

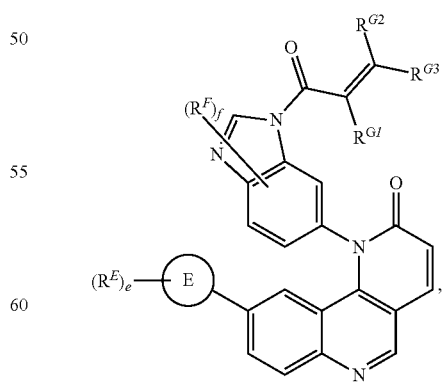

or a pharmaceutically acceptable salt, solvate, hydrate, polymorph, co-crystal, tautomer, stereoisomer, isotopically labeled derivative, and prodrug thereof.

In certain embodiments, the compound of Formula (II) is selected from the group consisting of:
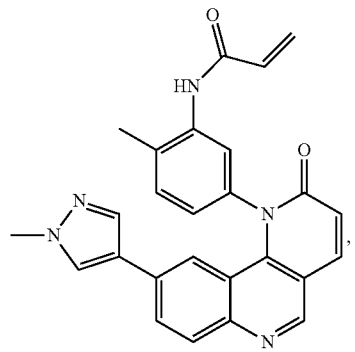
(II-3)
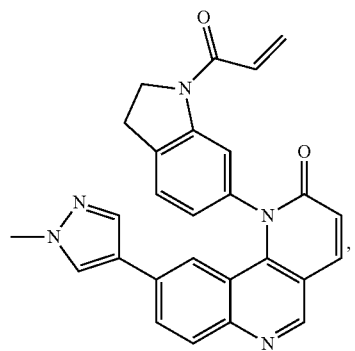
(II-4)
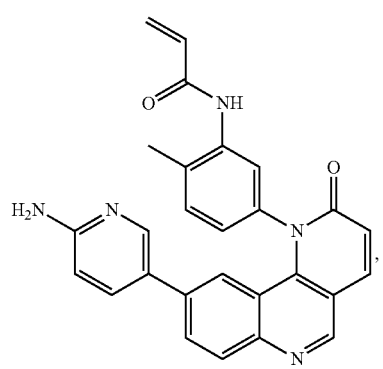
(II-5)
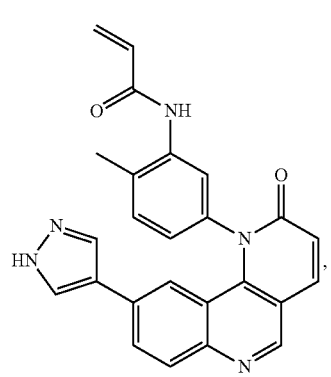
(II-6)
-continued
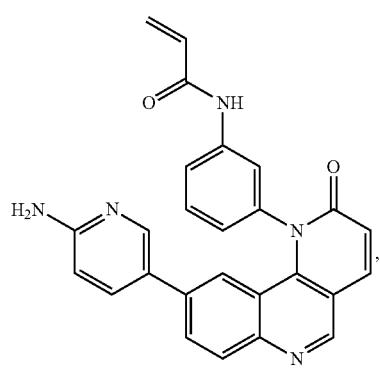
(II-7)
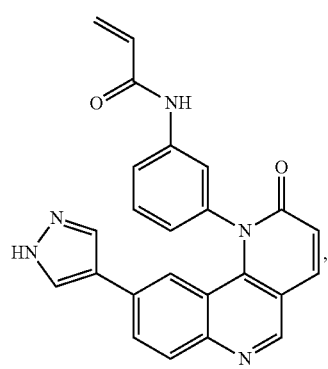
(II-8)
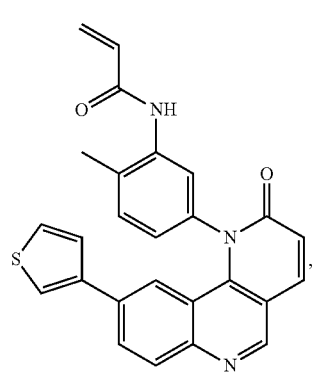
(II-9)
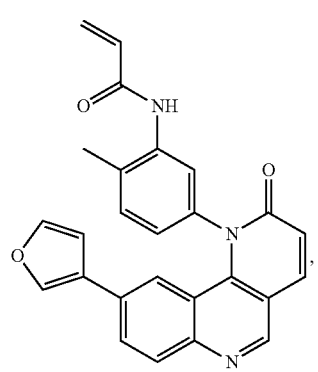
(II-10)

(II-11) 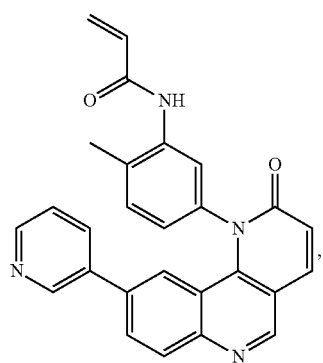
(II-15) 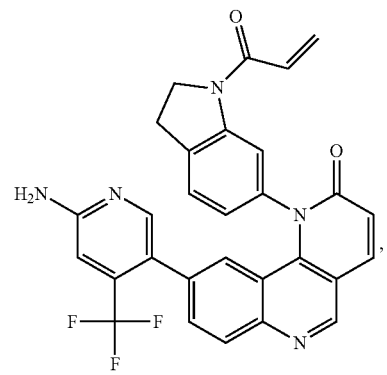
(II-12) 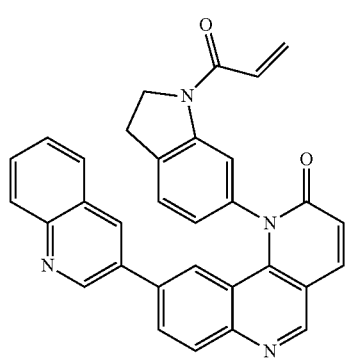
(II-16) 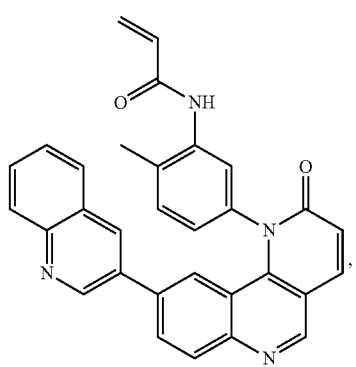
(II-13) 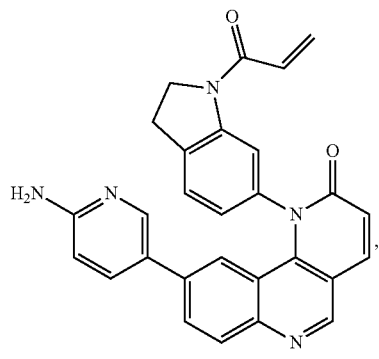
(II-17) 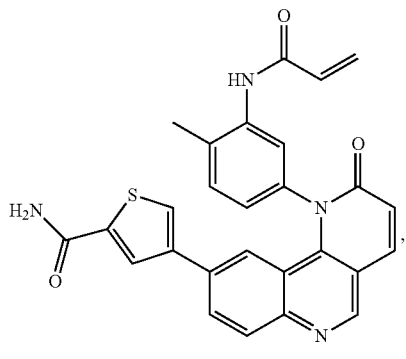
(II-14) 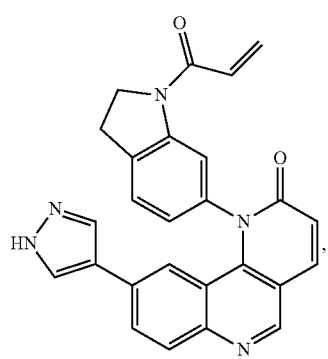
(II-18) 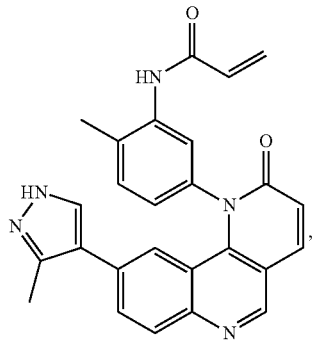

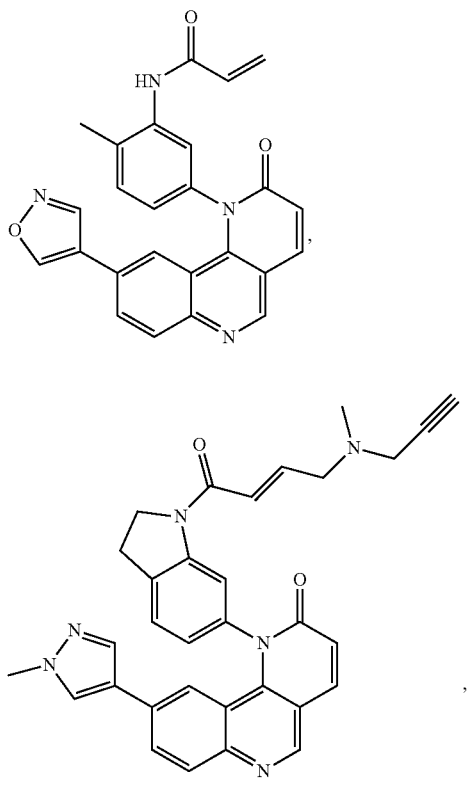

(II-19)
(II-20)
(II-21)
(II-22)

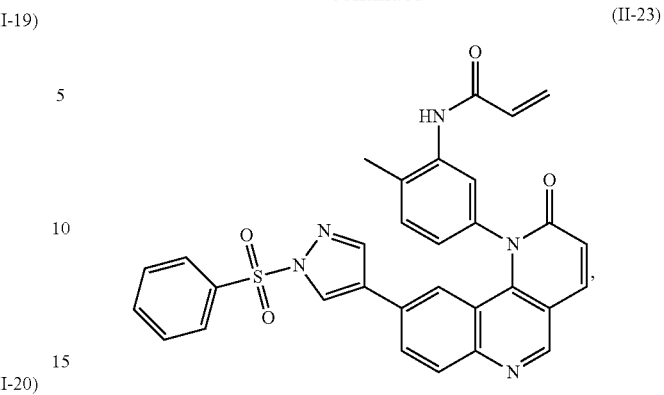

(II-23)

and pharmaceutically acceptable salts, solvates, hydrates, polymorphs, co-crystals, tautomers, stereoisomers, isotopically labeled derivatives, and prodrugs thereof.

The compounds of Formula (II) may bear multiple binding motifs for binding to a kinase, such as a tyrosine kinase (e.g., BMX). Ring E of the compounds of Formula (II) may be accommodated by a hydrophobic pocket in the ATP-binding site of BMX. Functionalities on Ring E and/or $R^G$ may bind to residues of BMX, such as hinge residues Tyr491, Ile492, Leu543, and Val403. Functional groups of $R^G$ may form one or more hydrogen bonds with BMX. Moreover, the Michael acceptor moiety of $R^G$ may react with a cysteine residue (e.g., Cys496) of BMX to allow covalent attachment of the compound to BMX.

In certain embodiments, the compound of Formula (I) or (II), or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount. In certain embodiments, the therapeutically and/or propylactically effective amounts are amounts useful for the treatment and/or prevention of diseases associated with the overexpression and/or aberrant activity of the kinase (e.g., a tyrosine kinase (e.g., BMX)). In certain embodiments, the disease is a proliferative disease, including, but are not limited to, cancer, benign neoplasm, angiogenesis, inflammatory diseases, and autoimmune diseases. In certain embodiments, the disease is a metabolic disease. In certain embodiments, the disease is diabetes (e.g., type 2 diabetes and gestational diabetes). An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical compositions described herein can be prepared by any method known in the art of pharmacology. In general, such preparatory methods include the steps of bringing the compound of Formula (I) or (II) (the "active ingredient") into association with a carrier or excipient, and/or one or more other accessory ingredients, and then, if necessary and/or desirable, shaping, and/or packaging the product into a desired single- or multi-dose unit.

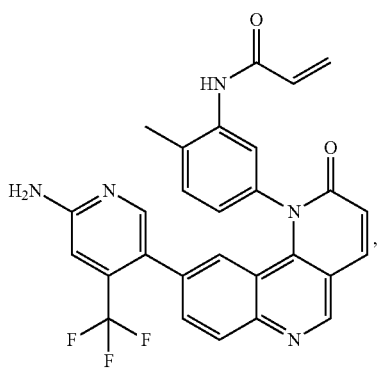

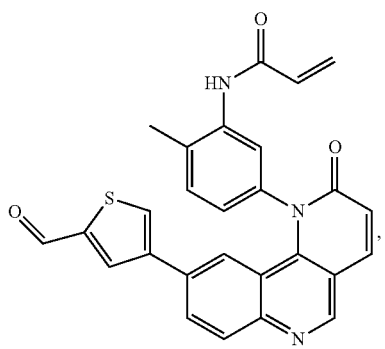

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration.

Formulations suitable for topical administration include, but are not limited to, liquid and/or semi-liquid preparations such as liniments, lotions, oil in water and/or water in oil emulsions such as creams, ointments and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) or (II) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents.

The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, anti-proliferative agents, anti-cancer agents, anti-diabetic agents, anti-inflammatory agents, immunosuppressant agents, and pain-relieving agents. Therapeutically active agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form.

Thus, in one aspect, provided are kits including a first container comprising a compound of Formula (I) or (II), or a pharmaceutically acceptable salt, solvate, hydrate, polymorph, co-crystal, tautomer, stereoisomer, isotopically labeled derivative, and prodrug thereof, or a pharmaceutical composition thereof. In certain embodiments, the kits described herein are useful in preventing and/or treating a proliferative disease in a subject. In certain embodiments, the kits further include instructions for administering the compound, or a pharmaceutically acceptable salt, solvate, hydrate, polymorph, co-crystal, tautomer, stereoisomer, isotopically labeled derivative, and prodrug thereof, or a pharmaceutical composition thereof, to a subject to prevent and/or treat a proliferative disease. In certain embodiments, the kits and instructions provide for treating a proliferative disease.

In certain embodiments, the subject administered the inventive compound, or composition as described hererin, is an animal. The animal may be of either sex and may be of any stage of development. In certain embodiments, the animal is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Methods of Treatment and Uses

Aspects of the invention encompass methods for treating a variety of kinase-associated diseases in a subject. A kinase-associated disease is any disease or disorder that is directly or indirectly linked to the expression or activity of a kinase, including overexpression, increased activity, and/or aberrant activity of the kinase. The methods comprise administering to a subject in need thereof a kinase inhibitor in an amount effective to treat the disease.

In certain embodiments, the kinase is a tyrosine kinase, and the inhibitor is a tyrosine kinase inhibitor. In certain embodiments, the kinase is a non-receptor tyrosine kinase. In certain embodiments, the kinase is a Tec kinase, including but not limited to TEC, BTK, ITK, RLK/TXK and/or BMX. In certain embodiments, the kinase is EGFR, HER2, HER4, mTOR, Blk, Lkbl, TAK1, CLK1/2, JAK3, PIK3CG, DYRKIA, MKNK2, MEK5, PIK3CA(I800L), DYRK2, IRAK3, CSNK2A2, FLT3(D835Y), YSK4, FLT3(N841I), DYRKIB, JNK3, JNK1, PIK4CB, FLT3(ITD), and/or PIP5K2C. In some embodiments, the kinase is BMX, and the inhibitor is a BMX inhibitor. In some embodiments, the BMX inhibitor is a compound of Formula (I) or (II). In some embodiments, the BMX inhibitor is a compound of Formula (I). In other embodiments, the BMX inhibitor is a compound of Formula (II).

In some embodiments, the disease is characterized by overexpression, increased activity, and/or aberrant activity of BMX. The methods comprise administering to a subject in need thereof an inhibitor of BMX in an amount effective to treat the disease.

Overexpression, increased activity, and/or aberrant activity is understood to mean increased production of BMX protein and/or increased kinase activity of BMX protein by a cell as compared to a wild type cell. This can be triggered by a variety of causes, including, but not limited to, mutations, gene amplification of the BMX gene, increased stability or half-life of mRNA, increased translation of mRNA into protein, increased activity of the BMX protein, increased stability of the BMX protein, or a combination of any of these factors. Overexpression, increased activity, and/or aberrant activity of BMX can be determined by comparing the expression and/or activity levels of BMX in normal, healthy tissue or cells with expression and/or activity levels in diseased tissue or cells.

Examples of diseases characterized by overexpression, increased activity, and/or aberrant activity of BMX include, but are not limited to, proliferative diseases such as cancers (i.e., "malignant neoplasms"), benign neoplasms, angiogenesis, inflammatory diseases, and autoimmune diseases, and diseases associated with insulin resistance.

Exemplary cancers that can be treated by the methods of the invention include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In certain embodiments, the cancer is selected from the group consisting of prostate cancer, basal cell carcinoma, biliary tract cancer, bladder cancer, bone cancer, brain cancer, CNS cancer, breast cancer, cervical cancer, choriocarcinoma, colon cancer, rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, liver cancer, lung cancer, lymphoma, melanoma, myeloma, neuroblastoma, oral cavity cancer, ovarian cancer, pancreatic cancer, retinoblastoma, rhabdomyosarcoma, rectal cancer, renal cancer, cancer of the respiratory system, sarcoma, skin cancer, stomach cancer, testicular cancer, thyroid cancer, uterine cancer, and cancers of the urinary system. In certain embodiments, the cancer is prostate cancer.

Exemplary benign neoplasms include, but are not limited to, lipoma, chondroma, adenomas, acrochordon, senile angiomas, seborrheic keratoses, lentigos, and sebaceous hyperplasias.

In one embodiment, the disease to be treated with the compounds herein is Waldenström's macroglobulinemia (WM). WM is a distinct clinicopathological entity resulting from the accumulation, predominantly in the bone marrow, of clonally related lymphocytes, lymphoplasmacytic cells and plasma cells, which secrete a monoclonal IgM protein. This condition is considered to correspond to the lymphoplasmacytic lymphoma (LPL) as defined by the World Health Organization lymphoma classification system. A highly recurrent somatic mutation (myeloid differentiation factor 88 [MYD88]L265P) in WM patients has been described using whole genome sequencing (WGS), and its presence subsequently confirmed by Sanger's DNA sequencing and allele-specific PCR. In total, 91% of WM/LPL patients expressed MYD88 L265P. By Sanger or allele-specific PCR, MYD88 L265P is detected in up to half of patients with IgM monoclonal gammopathy of undetermined significance, and its presence, as well as expression level are associated with malignant progression. In addition, MYD88 L265P has also been reported in ABC type DLBCL (14-29%), primary central nervous system lymphoma (33%), MALT lymphoma (9%), and chronic lymphocytic leukemia (2.9%) by either whole-genome, whole-exome or Sanger DNA sequencing. MYD88 is an adaptor molecule for Toll-like receptors (TLRs) with the exception of TLR-3 and interleukin-1 receptor (IL-1R) signaling. Following TLR or IL-1R stimulation, MYD88 is recruited to the activated receptor complex as a homodimer which then complexes with IRAK4 and activates IRAK1 and IRAK2. Tumor necrosis factor receptor associated factor 6 (TRAF6) is then activated by IRAK1 leading to NFκB activation via IκBα phosphorylation. Studies have demonstrated that survival of ABC DLBCL cells was sustained by presence of the MYD88 L265P, but not wild-type MYD88. Additionally, the studies showed that MYD88 L265P stimulated IRAK1 phosphorylation and NFKB signaling. It has also been reported that MYD88 L265P signals through IRAK1 and Bruton's Tyrosine Kinase (BTK) to mediate the activation of NF-kB independently. Moreover, it has been shown that MYD88 L265P promotes survival of WM through the activation of NF-kB thereby providing a framework for the therapeutic targeting of the MYD88 signaling pathway in WM.

An inflammatory disease can be either an acute or chronic inflammatory condition and can result from infections or non-infectious causes. Inflammatory diseases that can be prevented and/or treated by the methods of the invention include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyosifis, pemphigus, pemphigoid, diabetes (e.g., Type I), myasthenia gravis, Hashimoto's thyroditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomylitis, optic neuritis, temporal arteritis, transverse myelitis, necrotizing fasciilitis, and necrotizing enterocolitis.

Exemplary autoimmune diseases that can be prevented and/or treated by the methods of the invention include, but are not limited to, glomerulonephritis, Goodspature's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis, Sjogren's syndrome, Crohn's disease, Reiter's syndrome, ankylosing spondylitis, Lyme arthritis, GuillainBarre syndrome, Hashimoto's thyroiditis, and cardiomyopathy.

Some aspects of the invention involve a method to prevent and/or treat insulin resistance in a subject. The method comprises administering to a subject in need thereof an inhibitor of BMX in an amount effective to treat the disease. Insulin resistance or glucose intolerance is a condition characterized by the body's inability to properly use insulin or blood sugar. In this condition normal amounts of insulin are inadequate to produce a normal insulin response from fat muscle or liver cells. Insulin resistance in fat cells results in hydrolysis of stored triglycerides which elevates free fatty acids in the blood plasma. Insulin resistance in muscle reduces glucose uptake whereas insulin resistance in liver reduces glucose storage with both effects serving to elevate blood glucose. High plasma levels of insulin and glucose due to insulin resistance often lead to diabetes, hyperglycemia, hyperinsulinemia, dyslipidemia, obesity, polycystic ovarian disease, hypertension, and cardiovascular disease. Accordingly, some embodiments of the invention involve treating diseases associated with insulin resistance such as diabetes, hyperglycemia, hyperinsulinemia, dyslipidemia, obesity, polycystic ovarian disease, hypertension, and cardiovascular disease.

A subject in need of treatment is a subject identified as having a kinase-associated disease, i.e., the subject has been diagnosed by a physician (e.g., using methods well known in the art) as having a kinase-associated disease. In some embodiments, the subject in need of treatment is a subject suspected of having or developing a kinase-associated disease, such as a subject presenting one or more symptoms indicative of a kinase-associated disease. For example, a subject suspected of having a kinase-associated disease, such as an autoimmune disease, may display abnormal titres of autoantibodies. The subject having abnormal titres of autoantibodies may have at least one other symptom of autoimmune disease or may be without other symptoms associated with autoimmune disease. The term "subject in need of treatment" further includes people who once had a kinase-associated disease but whose symptoms have ameliorated.

One or more additional pharmaceutical agents, such as anti-cancer agents (e.g., chemotherapeutics), anti-inflammatory agents, steroids, immunosuppressants, radiation therapy, or other agents, can be used in combination with the compounds of Formula (I) or (II) for treatment of kinase-associated diseases. The one or more additional pharmaceutical agents can be administered to the subject simultaneously or sequentially. Inhibition of one or more additional kinases may be useful in potentiating the antiproliferative activities of one or more of the compounds described herein. Additional kinase inhibitors that may be useful as additional pharmaceutical agents include kinase inhibitors such as inhibitors of mTOR (AZD8055, Torin1, Torin2, and WYE125132), PI3K (GDC0941), EGFR and Her2 (erlotinib, gefitinib, and lapatinib), and the allosteric Akt inhibitor (MK2206). In one embodiment, the additional pharmaceutical agent is MK2206. Other exemplary agents that may be useful in combination with the compounds described herein include bortezomib, ixazomib, carfilzomib, oprozomib, bendamustine, cyclophosphamide, rituximab, ofatumumab, chlorambucil, everolimus, ibrutinib, idelalisib, plerixafor, and/or BMS-936564 CXCR4 antibody.

Exemplary chemotherapeutic agents include alkylating agents such as nitrogen mustards, ethylenimines, methylmelamines, alkyl sulfonates, nitrosuoureas, and triazenes; antimetabolites such as folic acid analogs, pyrimidine analogs, in particular fluorouracil and cytosine arabinoside, and purine analogs; natural products such as vinca alkaloids epi-podophyllotoxins, antibiotics, enzymes, and biological response modifiers; and miscellaneous products such as platinum coordination complexes, anthracenedione, substituted urea such as hydroxyurea, methyl hydrazine derivatives, and adrenocorticoid suppressant.

Exemplary chemotherapeutic agents also include anthracycline antibiotics, actinomycin D, plicamycin, puromycin, gramicidin D, paclitaxel, colchicine, cytochalasin B, emetine, maytansine, amsacrine, cisplatin, carboplatin, mitomycin, altretamine, cyclophosphamide, lomustine, and carmustine.

An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In some embodiments, the inhibitor of BMX is chronically administered to the subject in need of treatment for a disease associated with insulin resistance. "Chronic" as used herein refers to continuous, regular, long-term therapeutic administration, i.e., periodic administration without substantial interruption, such as, for example, daily for a time period of at least several days, weeks or to several years for the purpose of treating a disease associated with insulin resistance. In some embodiments, chronic administration of an inhibitor of BMX comprises maintaining the BMX inhibitor in the subject at chronic steady state plasma levels between about 1 ng/ml and about 10 mg/ml. In some embodiments, chronic administration of an inhibitor of BMX comprises maintaining the BMX inhibitor in the subject at chronic steady state plasma levels between about 5 ng/ml and about 5 tg/ml.

In some embodiments, the chronic administration is for a period of at least 2 weeks, at least 4 weeks, at least 3 months, at least 6 months, at least 12 months, at least 18 months, or at least 24 months.

Another aspect of the invention relates to methods of screening a library of compounds to identify one or more compounds that are useful in the treatment of a disease. In certain embodiments, the library of compounds is a library of compounds of Formula (I) or (II). The methods of screening a library include providing at least two different compounds of Formula (I) or (II), or pharmaceutically acceptable salts, solvates, hydrates, polymorphs, co-crystals, tautomers, stereoisomers, isotopically labeled derivatives, or prodrugs thereof, or pharmaceutical compositions thereof; and performing at least one assay using the different compounds of Formula (I) or (II), or pharmaceutically acceptable salts, solvates, hydrates, polymorphs, co-crystals, tautomers, stereoisomers, isotopically labeled derivatives, or prodrugs thereof, or pharmaceutical compositions thereof, to detect one or more characteristics associated with the disease. In certain embodiments, the methods of screening a library include providing at least two different compounds of Formula (I) or (II), or pharmaceutically acceptable salts thereof, or pharmaceutical compositions thereof; and performing at least one assay using the different compounds of Formula (I) or (II), or pharmaceutically acceptable salts thereof, or pharmaceutical compositions thereof, to detect one or more characteristics associated with the disease. The characteristic to be detected may be a desired characteristic associated with the disease. In certain embodiments, the characteristic is anti-proliferation. In certain embodiments, the characteristic is anti-cancer. In certain embodiments, the characteristic is anti-diabetic. In certain embodiments, the characteristic is enhancing insulin sensitivity. In certain embodiments, the characteristic is reducing insulin resistance. In certain embodiments, the characteristic is inhibition of a kinase. In certain embodiments, the characteristic is inhibition of a tyrosine kinase. In certain embodiments, the characteristic is inhibition of BMX. In certain embodiments, the characteristic is down-regulation of a kinase such as a tyrosine kinase (e.g., BMX). In certain embodiments, the characteristic is suppressing kinase signaling. In certain embodiments, the characteristic is enhancing downstream kinase signaling. The characteristic to be detected may also be an undesired characteristic associated with the disease.

The different compounds of Formula (I) or (II) may be provided from natural sources (see, e.g., Sternberg et al., Proc. Nat. Acad. Sci. USA, (1995) 92:1609-1613) or generated by synthetic methods such as combinatorial chemistry (see, e.g., Ecker et al., Bio/Technology, (1995) 13:351-360 and U.S. Pat. No. 5,571,902). In certain embodiments, the different compounds are provided by liquid-phase or solution synthesis. In certain embodiments, the different compounds are provided by solid-phase synthesis. In certain embodiments, the different compounds are provided by a high-throughput, parallel, or combinatorial synthesis. In certain embodiments, the different compounds are provided by a low-throughput synthesis. In certain embodiments, the different compounds are provided by a one-pot synthesis. The different compounds may be provided robotically or manually. In certain embodiments, the step of providing at least two different compounds of the present invention include arraying into at least two vessels at least two different compounds of the present invention wherein the compounds are bound to solid supports, cleaving the compounds from the solid supports, and dissolving the cleaved compounds in a solvent. The solid supports include, but do not limit to, beads (e.g., resin beads and magnetic beads), hollow fibers, solid fibers, plates, dishes, flasks, meshes, screens, and membranes. In certain embodiments, the solid supports are beads. In certain embodiments, one solid support is capable of supporting at least 50 nmol of a compound. In certain embodiments, one solid support is capable of supporting at least 100 nmol of a compound. In certain embodiments, one solid support is capable of supporting at least 200 nmol of a compound. Each vessel may contain one or more support-bound compounds of the present invention. In certain embodiments, each vessel contains one support-bound compounds of the present invention. The solid supports and/or the compounds may be labeled with one or more labeling agents for the identification or detection of the compounds. The vessels may be wells of a microtiter plate. The solvent may be an inorganic solvent, organic solvent, or a mixture thereof. The steps of arraying, cleaving, and dissolving may be performed robotically or manually.

Typically, the methods of screening a library of compounds involve at least one assay. In certain embodiments, the assay is performed to detect one or more characteristics associated with the disease described herein. The assay may be an immunoassay, such as a sandwich-type assay, competitive binding assay, one-step direct test, two-step test, or blot assay. The step of performing at least one assay may be performed robotically or manually. In certain embodiments, the activity of a kinase is inhibited. In certain embodiments, the activity of a tyrosine kinase is inhibited. In certain embodiments, the activity of BMX is inhibited. In certain embodiments, the expression of a kinase such as a tyrosine kinase (e.g., BMX) is down-regulated. In certain embodiments, kinase signaling is suppressed. In certain embodiments, downstream kinase signaling is enhanced.

In yet another aspect, the present invention provides the compounds of Formula (I) or (II), and pharmaceutically acceptable salts, solvates, hydrates, polymorphs, co-crystals, tautomers, stereoisomers, isotopically labeled derivatives, prodrugs, and compositions thereof, for use in the treatment of a disease in a subject. In certain embodiments, provided in the invention are the compounds of Formula (I) or (II), and pharmaceutically acceptable salts and compositions thereof, for use in the treatment of a disease in a subject.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1

Preparation of the Compounds

Preparation of Compound 3

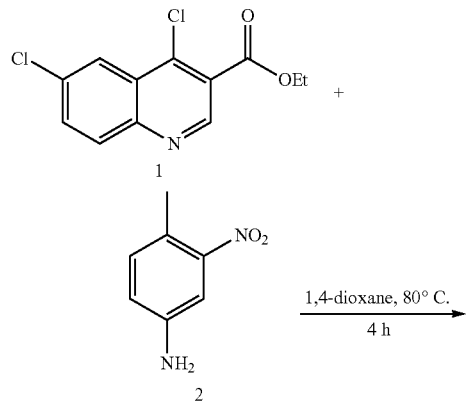

To a solution of 1 (540 mg, 2 mmol, 1 equiv.) in 1,4-dioxane (5 mL) at room temperature in a sealed tube was added 2 (354 mg, 2 mmol, 1 equiv.). The resultant mixture was heated to 80° C. for 4 h, cooled down to room temperature, quenched with NaOH (1N, 10 mL), and extracted with EtOAc (50 mL×3). The combined organic layers were washed with brine (50 mL×3) and dried over $Na_2SO_4$. Volitiles were removed, and the residue was purified with silica gel flash chromatography (hexane: EtOAc=1:3) to give compound 3 (530 mg, 75% yield). LC-MS m/z (M+H): 385.10.

Preparation of Compound 4

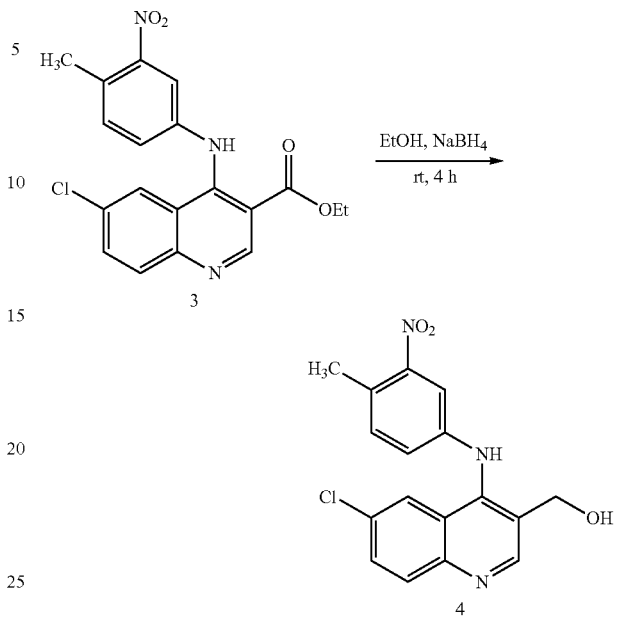

To a solution of 3 (530 mg, 1.5 mmol, 1 equiv.) in EtOH (50 mL) at room temperature was added $NaBH_4$ (285 mg, 5 equiv.). The resultant suspension was stirred at room temperature for 4 h and quenched with $NaHCO_3$ (saturated, 50 mL) carefully. Volitiles were removed, and the residue was diluted with water, extracted with $CH_2Cl_2$ (100 mL×2), and dried over $Na_2SO_4$. After removal of volitiles, the resultant residue was purified with silica gel flash chromatography ($CH_2Cl_2$:MeOH=20:1) to give 4 (257 mg, 50% yield). LC-MS m/z (M+H): 343.22.

Preparation of Compound 5

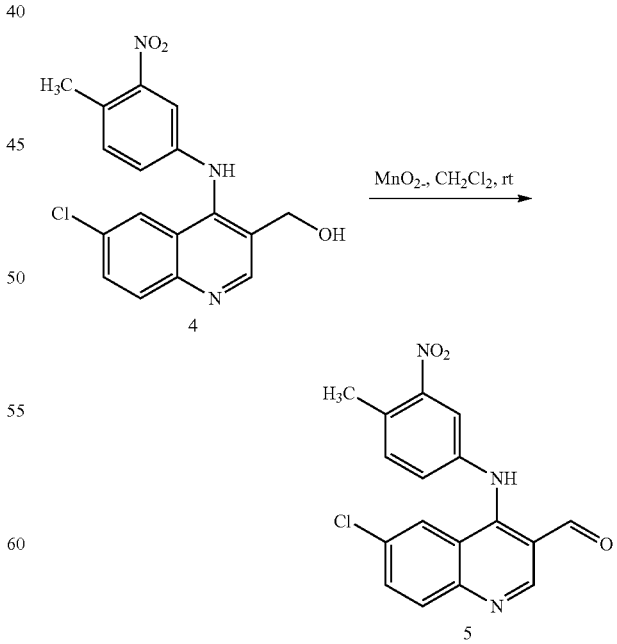

To a solution of 4 (257 mg, 0.75 mmol, 1 equiv.) in $CH_2Cl_2$ (20 mL) at room temperature was added $MnO_2$ (1.28 g, 5 equiv. (weight)). The reaction mixture was stirred at room temperature for 1 h and filtered through Celite®. Volitiles were removed, and the resultant crude product 5 was taken to next step without further purification. LC-MS m/z (M+H): 341.10.

Preparation of compound 6

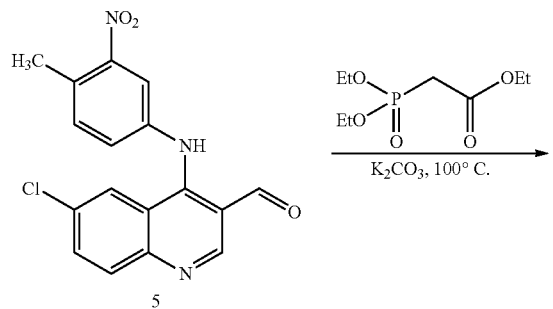

To a solution of 5 in EtOH (10 mL) at room temperature in a sealed tube was added triethylphosphonoacetate (450 µL, 2.25 mmol, 3 equiv.) and K₂CO₃ (518 mg, 3.75 mmol, 5 equiv.). The resultant mixture was heated to 100° C. for 12 h, cooled down to room temperature, diluted with water, and extracted with EtOAc. The combined organic layers were dried over Na₂SO₄. After removal of volitiles, the residue was purified by silica gel flash chromatography (CH₂Cl₂: MeOH=20:1) to give 6 (146 mg, 53% yield). LC-MS m/z (M+H): 365.28.

Preparation of compound 7

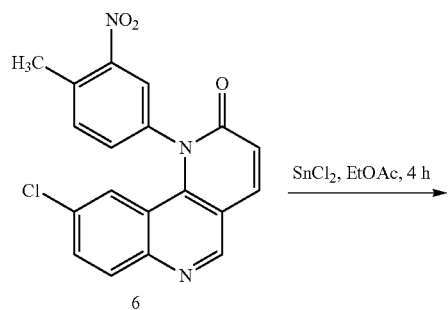

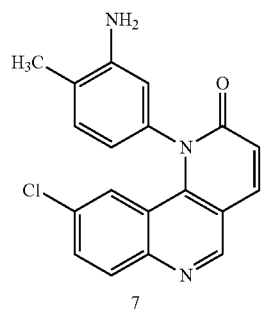

To a solution of 6 (146 mg, 0.4 mmol, 1 equiv.) in EtOAc (10 mL) at room temperature was added SnCl₂.2H₂O (450 mg, 2 mmol, 5 equiv.). The reaction mixture was heated to 70° C. for 4 h and cooled down to room temperature. NaHCO₃ (saturated) solution was added, and the resultant slurry was filtered through Celite® and washed with EtOAc. The filtrate was dried over Na₂SO₄ and concentrated under reduced pressure. Silica gel flash chromatography (CH₂Cl₂: MeOH=9:1) afforded 7 (67 mg, 50% yield). LC-MS m/z (M+H): 335.11.

Preparation of Compound 8

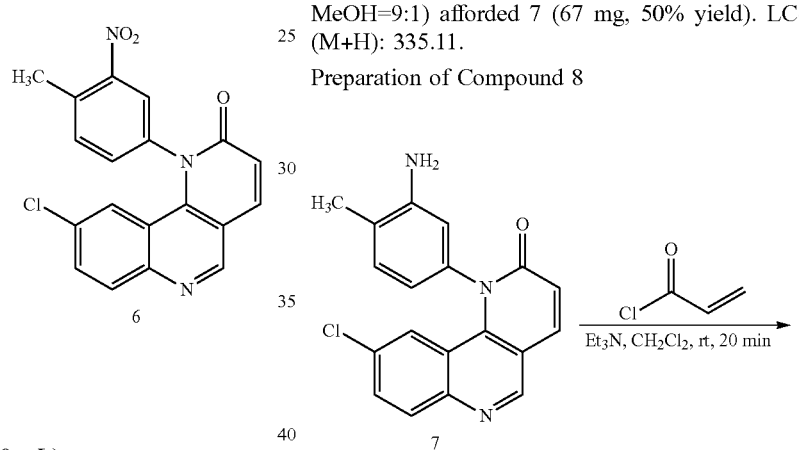

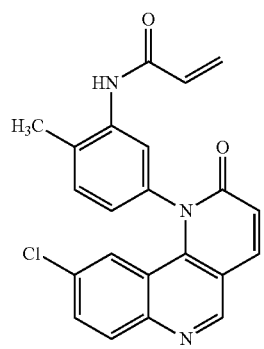

To a solution of 7 (67 mg, 0.2 mmol, 1 equiv.) in CH₂Cl₂ (10 mL) at room temperature was added Et₃N (55 µL, 0.4 mmol, 2 equiv.) and acryloyl chloride (16tL, 0.2 mmol, 1 equiv.). The resultant solution was stirred at room temperature for 10 min, quenched with NaHCO₃ (saturated), and extreacted with CH₂Cl₂. The organic layer was dried with Na₂SO₄ and concentrated under reduced pressure. The resultant residue was purified by silica gel flash chromatography (CH₂Cl₂: MeOH=9:1) to give 8 (62 mg, 80% yield). LC-MS m/z (M+H): 389.11.

Preparation of compound I-14

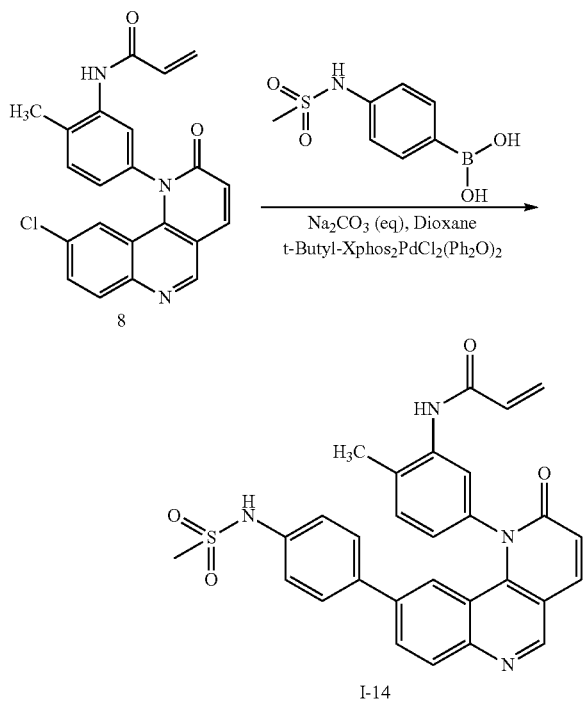

To a solution of 8 (62 mg, 0.16 mmol, 1 equiv.) in dioxane/H₂O (3:1, 4 mL) at room temperature was added (4-(methylsulfonamido)phenyl)boronic acid (68 mg, 0.32 mmol, 2 equiv.), Na$_2$CO$_3$ (1N, 0.48 mL, 0.48 mmol, 3 equiv.), t-butyl-XPhos (7 mg, 0.016 mmol, 0.1 equiv.), and PdCl$_2$(Ph$_3$P)$_3$ (11 mg, 0.016 mmol, 0.1 equiv.). The resultant mixture was heated at 80° C. for 4 h, cooled down to room temperature, and extracted with CH$_2$Cl$_2$. The organic layer was washed with brine and dried over Na$_2$SO$_4$. After removal of volitiles, the residue was purified by silica gel flash chromatography to give 1-14 (33 mg, 40% yield). LC-MS m/z (M+H): 524.20.

Example 2

Biological Assays of the Compounds

Materials

Anti-pFAK (Y576/577), anti-pIGF-1R (Y1165/1166)/Insulin Receptor (Y1189/1190), anti-pMET (Y1234/1235), anti-pACK1 (Y857/858), anti-pFGFR1 (Y653/654), anti-pGSK(S9), anti-pS6 (S235/236), antipAKT(S473), anti-pAKT (T308), anti-ppl30Cas (Y410), anti-Myc tag, anti-MET and anti-IR were obtained from Cell Signaling Technology (Danvers, Mass.). Anti-Flag M2, anti-FAK, anti-pFAK (pY576), anti-pFAK (pY577), anti-PHLPP were obtained from Abcam (Cambridge, Mass.). Anti-BMX and anti-β-actin were obtained from Santa Cruz Biotechnology (Santa Cruz, Calif.). Anti-pTyr (4G10) and anti-tubulin were obtained from Millipore (Billerica, Mass.). Bmxtides were obtained from GenScript Corporation (Piscataway, N.J.). BMX and control siRNA were obtained from Dharmacon (Lafayette, Colo.). 3xFlag-FAK was produced by inserting FAK (pCMV-SPORT6-FAK, Open Biosystems (Lafayette, Colo.)) into p3XFlag-CMV (Sigma-Aldrich, St. Louis, Mo.) between HindIII and BamH1 sites, and mutants were generated using QuikChange Site-Directed Mutagenesis Kit (Stratagene, Santa Clara, Calif.). Myc-ACK1 plasmid was a generous gift from Dr. Wannian Yang (Geisinger System Services, Danville, Pa.). FGFR1 expression vector was a generous gift from Dr. Michal K. Stachowiak (State University of New York at Buffalo). Purified FAK, phosphorylated in vitro by SRC, was obtained from Invitrogen (Carlsbad, Calif.). Bmx-mice were obtained from Dr. K. Alitaro (University of Helsinki, Finland).

Cell Culture and Transfection

HEK293 and COS7 cells were cultured in DMEM/10% FBS (Hyclone, Logan, Utah). LNCaP and VCS2 cells were cultured in RPMI-1640/10% FBS. Primary MEFs were isolated from E13.5 embryos from a Bmx$^{+/-}$ female and a Bmx$^-$ male pair. The cells were trypsinized and cultured in DMEM/10% FBS. The first generation was genotyped, and cells under 5$^{th}$ generation were used. Transfections were performed using Lipofectamine 2000 (Invitrogen, Carlsbad, Calif.). For wound healing assays, cells were grown to confluence, and pipette tips were used to injure the cell surface. Fresh media was then added, and the injured areas were photographed at time points indicated.

Immunological Methods

Cells were lysed with RIPA buffer (50 mM Tris-HCl, pH 8.0, 150 mM NaCl, 1% NP-40, 0.5% deoxycholate, 0.1% SDS, 1 mM EDTA, 1 mM EGTA, 1 mM β-glycerophosphate, 1 mM pyrophosphate, 100 mM sodium fluoride, 1 mM Na$_3$VO$_4$, and protease inhibitors). Lysates were sonicated for 10 s and centrifuged at 13,000 rpm at 4° C. for 15 min. For anti-3xFlag immunoprecipitation, equal amounts of protein (1-5 mg) were mixed with 20-50 μl of anti-3xFlag-conjugated (M2) agarose beads and incubated at 4° C. overnight with continuous agitation. The beads were washed extensively with RIPA buffer followed by TBS buffer, and beads were eluted with 2× Laemmli sample buffer. Samples were boiled for 5 min, and resolved on 4-12% NuPAGE gels (Invitrogen, Carlsbad, Calif.) followed by membrane transfer. Membranes were blocked with 5% milk (or 5% BSA for phosphospecific antibodies) in TBS/0.1% Tween 20 (TBS/T) at room temperature for 1 h and incubated with primary antibodies overnight at 4° C. Membranes were then incubated with secondary antibodies at room temperature for 1 h and developed by ECL. All blots are representative of at least three experiments.

For immunofluorescence, cells grown on glass coverslips were fixed with formaldehyde, incubated with primary antibodies followed by secondary antibodies conjugated with Alexa (Invitrogen, Carlsbad, Calif.) and Hoechst. All micrographs were taken at the same confocal microscope setting. To assess effects of BMX on insulin receptor (IR) in vivo, mice were fasted overnight, injected intraperitoneally with 2 g/kg glucose, and sacrificed after 15 min. Tissues were rapidly removed, frozen in liquid nitrogen, and homogenates were immunoblotted.

In vitro Activity Assays

The in vitro activity of compounds of Formula (I) and (II) in inhibiting BMX and other kinases were obtained using an Invitrogen Select Screening assay as known in the art. The IC$_{50}$ values determined from this assay are shown below.

In vitro Kinase Assays

Purified BMX was mixed with substrate (FAK or Bmx-tides), kinase buffer (final 20 mM HEPES, pH 7.5, 10 mM MgCl$_2$, 20 mM β-glycerophosphate, 1 mM dithiothreitol, 20 μM ATP, 5 mM Na$_3$VO$_4$) and 1 μCi of [γ-$^{32}$P]ATP (omitted for cold in vitro kinase assays analyzed by mass spectroscopy) for 30 min at 30° C. Reactions were stopped with 10 mM EDTA and Laemmli sample buffer. Samples were resolved by 4-12% NuPAGE gel, and visualized by autoradiography. The positional scanning peptide library assay was performed according to published methods (Hutti et al., *Nat. Methods* 1, 27 (2004); Turk et al., *Nat. Protoc.* 1, 375 (2006)). Labelled peptide libraries were spotted onto avidin-coated filter sheets (SAM2 Biotin Capture Membrane, Promega, Madison, Wis.), which were washed, dried, and exposed to a phosphoimager screen.

Tandem Mass Spectrometry (LC/MS/MS)

For all mass spectrometry (MS) experiments, FAK protein was separated using SDS-PAGE, stained with Coomassie blue, and the FAK band was excised. Samples were subjected to reduction with dithiothreitol, alkylation with iodoacetamide, and in-gel digestion with trypsin or chymotrypsin overnight at pH 8.3, followed by reversed-phase microcapillary/tandem mass spectrometry (LC/MS/MS). LC/MS/MS was performed using an Easy-nLC nanoflow HPLC (Proxeon Biosystems, West Palm Beach, Fla.) with a self-packed 75 μm i.d.×15 cm $C_{18}$ column coupled to a LTQ-Orbitrap XL mass spectrometer (Thermo Scientific, Waltham, Mass.) in the data-dependent acquisition and positive ion mode at 300 nL/min. Peptide ions from BMX predicted phosphorylation sites were also targeted in MS/MS mode for quantitative analyses. MS/MS spectra collected via collision induced dissociation in the ion trap were searched against the concatenated target and decoy (reversed) single entry FAK and full Swiss-Prot protein databases using Sequest (Proteomics Browser Software, Thermo Scientific, Waltham, Mass.) with differential modifications for Ser/Thr/Tyr phosphorylation (+79.97) and the sample processing artifacts Met oxidation (+15.99), deamidation of Asn and Gln (+0.984), and Cys alkylation (+57.02). Phosphorylated and unphosphorylated peptide sequences were identified if they initially passed the following Sequest scoring thresholds against the target database: 1+ ions, Xcorr≥2.0 Sf≥0.4, P≥5; 2+ ions, Xcorr≥2.0, Sf≥0.4, P≥5; 3+ ions, Xcorr≥2.60, Sf≥0.4, P≥5, against the target protein database. Passing MS/MS spectra were manually inspected to be sure that all b- and y-fragment ions aligned with the assigned sequence and modification sites. Determination of the exact sites of phosphorylation was aided using FuzzyIons and GraphMod and phosphorylation site maps were created using ProteinReport software (Proteomics Browser Software suite, Thermo Scientific, Waltham, Mass.). False discovery rates (FDR) of peptide hits (phosphorylated and unphosphorylated) were estimated below 1.5% based on reversed database hits (Breitkopf et al., *Current Protocols in Molecular Biology* 98:18.19.1-18.19.27 (2012); Egan et al., *Science* 331, 456 (2011); Dibble et al., *Mol. Cell Biol.* 29, 5657 (2009); Zheng et al., *Mol. Cell* 33, 237 (2009)).

Relative Quantification of Phosphorylation Sites

For relative quantification of phosphorylated peptide signal levels, an isotope-free (label-free) method was used by first integrating the total ion counts (TIC) for each MS/MS sequencing event during a targeted ion MS/MS (TIMM) experiment or a data-dependent acquisition. For each targeted phosphorylation site, a ratio of phosphorylated peptide signal (TIC of phosphorylated form ($TIC_{PO4}$)) to the total peptide signal (TIC of phosphorylated form+TIC of non-phosphorylated form ($TIC_{nonPO4}$)) for each sample was calculated according to the following equation:

$$TIC_{PO4}/(TIC_{PO4}+TIC_{nonPO4})=\text{Ratio of phosphopeptide signal } (R_{PO4})$$

For samples where $TIC_{PO4}$ was not above background, the background value was used. These ratios of phosphopeptide signal were then compared to the same phosphopeptide ratios from the BmxWT (stimulated) and bmxKD (unstimulated) samples according to the following equation:

$$[(R_{PO4}\text{ Unstimulated}/R_{PO4}\text{ Stimulated})-1]\times100=\%\text{ change in phosphorylation}$$

While a direct comparison of phosphopeptide signals between different experimental conditions is not accurate due to differences in sample content, a comparison of the relative ratios of the phosphorylated to nonphosphorylated peptide forms between samples is an accurate measure of signal-level change since the total peptide signal (modified and unmodified) is measured. The above calculations were performed manually using Microsoft Excel and with automated in-house developed software named Protein Modification Quantifier v1.0 (Beth Israel Deaconess Medical Center, Boston, Mass.) (Yuan et al., *Structure* 19, 1084 (2011); Yang et al., *Cancer Res.* 71, 5965 (2011); Jiang et al., *J. Biol. Chem.* 285, 14980 (2010); Asara et al., *Proteomics* 8, 994 (2008)).

Metabolic Assays 8-10-month old mice were used for metabolic assays. For glucose tolerance test (GTT), mice were fasted for 16 h, blood was drawn, and the mice were injected intraperitoneally with 2 g/kg dextrose. Blood glucose and insulin measurement were obtained from tail vein using OneTouch Ultra (Life Scan, Milpitas, Calif.) and Ultra Sensitive Mouse Insulin ELISA Kits (Crystal Chem, Downers Grove, Ill.) Tissues were collected 15 min after injection and frozen in liquid nitrogen until analysis. For insulin tolerance tests, mice were fasted 4 h and were given 0.75 units/kg body weight human recombinant insulin (Invitrogen, Carlsbad, Calif.) intraperitoneally. Blood glucose levels were monitored at indicated time.

Statistical Analysis

Results are expressed as mean±SE. Statistical significance was determined by a two-sided Student's t-test, with $p<0.05$ considered statistically significant.

Molecular Modeling

Molecular modeling was performed on a complex of the BMX (published X-ray crystal structure (Protein Database: 3SXR)) with a compound of Formula (I) or (II) (e.g., I-14). The total free engery of the complex was minimized. An exemplary energy-minimized structure, shown in FIG. 13, indicates that compounds of Formula (I) or (II) (e.g., 1-14) may bind to various residues of BMX, such as hinge residues Tyr491, Ile492, Leu543, and Val403. The modeling results also suggest that the Michael acceptor moiety of compounds of Formula (I) or (II) is in close proximity to and may react with a cysteine residue (e.g., Cys496) of BMX.

DiscoverX Binding Assays

DiscoverX binding assays were performed according to published methods (Fabian et al., *Nat. Biotechnol.* 23, 329-36 (2005); Davis et al., *Nat. Biotechnol.* 29, 1046-51 (2011)). Compounds that bind an active site of a protein (e.g., a kinase, such as BMX, BLK, BTK, JAK3, EGFR (T790M), ITK, TEC, mTOR, or mTORC1) and directly (sterically) or indirectly (allosterically) prevent protein binding to the immobilized ligand, will reduce the amount of protein captured on a solid support. Conversely, compounds that do not bind the protein have no effect on the amount of protein captured on the solid support. Screening hits are identified by measuring the amount of protein captured in test versus control samples by using a quantitative, precise, and ultra-sensitive qPCR method that detects the associated DNA label. In a similar manner, dissociation constants ($K_d$'s) for compound-protein interactions are calculated by measuring the amount of protein captured on the solid support as a function of the test compound concentration.

General Procedure for Anti-Proliferation Assay for Prostate Cancer Cells

Cell proliferation was determined after treatment of I-14 or I-14R for either 48 hours or 5 days using CellTiter-Glo luminescent assay from Promega (USA) and measured using Envision plate reader (PerkinElmer). Data were normalized to control group (DMSO) and represented by the mean of at least two independent measurement with standard error <20%. GI50 were calculated using Prism 5.0 (GraphPad Software, San Diego, Calif.).

Prostate Cancer Cell Apoptosis Studies with Inhibitor Compound

RV1 cells were cultured in 1% FBS/RPMI with different doses of I-14 for 3 days, and then immunostained for cleaved caspase-3 (Cell signaling Technology, green color) and Hoechst 33342 (blue color). Caspase-3 positive cells were counted and normalized to total cell number (N=5).

Cell Proliferation Analysis for Waldenstrom's Macroglobulinemia (WM) Cell Lines

CellTiter-Glo® Luminescent cell viability assay (Promega) was used to assess cell survival following treatment with an inhibitor compound of Formula (I) or (II) (e.g., 1-14). Various cell lines were used including Waldenström's macroglobulinemia (WM) cell lines (BCWM.1, MWCL-1, RPCI-WM1) and B-cell lymphoma cell lines (OCI-Ly3, Ramos, OCI-Ly19). Cells were seeded into 384 well plates with the EL406 Combination Washer Dispenser (BioTek Instruments, Inc.) and inhibitor compounds were injected into the cells culture media with the JANUS Automated Workstation (PerkinElmer Inc.). Cells were treated with a series diluted inhibitor compounds (20~0.04 µM) for 72 hours at 37° C. Luminescent measurement is performed using the 2104 Envision® Multilabel Reader (PerkinElmer Inc.).

Apoptosis Analysis for Primary Patient Bone Marrow Tumor Cells

Primary patient WM cells genotyped for MYD88 L265P, as well as MYD88 WT healthy donor CD19-selected peripheral blood mononuclear cells (PBMCs) were treated with and without inhibitor compounds. Cells were incubated at 37° C. with 0.01~4 µM of an inhibitor compound of Formula (I) or (II) (e.g., 11-4). Apoptosis analysis was performed using Annexin V-FITC/Propidium iodide staining with the Apoptosis Detection Kit I (BD Pharmingen). $1 \times 10^6$/well cells were treated in 24 well plates for~24 hours with inhibitor compounds or corresponding controls. A minimum of 10,000 events were acquired using a BD™ FACSCanto II flow cytometer and analyzed with BD FACS DIVA Software.

Results

Figure 5:
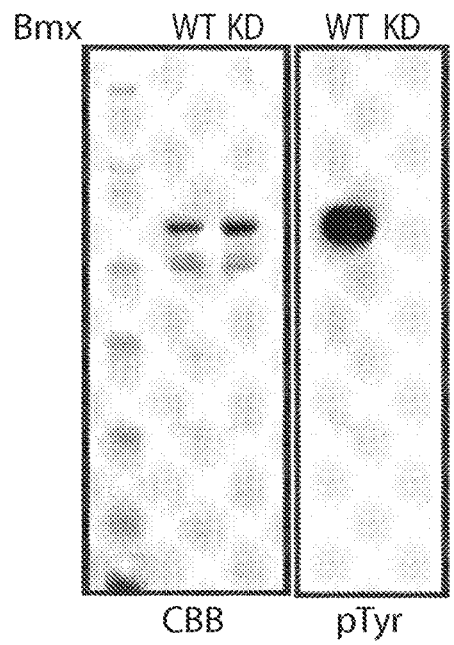
FIG. 5 shows in vitro kinase reactions on purified 3XFlag-BmxWT and 3XFlag-BmxKD proteins. Left panel: Coomassie Briliant Blue staining. Right panel: anti-pTyr blot after in vitro kinase assay showing autophosphorylation by BmxWT.

To gain insight into BMX targets, a modified positional scanning peptide library approach was used to determine whether it has an optimal substrate phosphorylation motif (Hutti et al., Nat. Methods 1, 27 (2004)). As a source of enzymes used stably transfected LNCaP prostate cancer cells and purified 3xFlag-BMX wild-type (BmxWT) and 3xFlag-BMX kinase-dead harboring a K445M mutation (BmxKD) (Jiang et al., J. Biol. Chem. 282, 32689 (2007)) (FIG. 5). The assay employed 198 biotinylated peptide libraries, each containing a tyrosine fixed at the central position and one additional position fixed to one of the 20 naturally occurring amino acids (FIG. 1B). All other positions contained a degenerate mixture of amino acids (excluding serine, threonine, and cysteine). Phosphothreonine and phosphotyrosine (pY) residues were included at the fixed positions to facilitate identification of kinases requiring priming phosphorylation events. To avoid effects due to enzyme recruitment through SH2 or SH3 domains on a solid surface, kinase assays were performed in solution using $\gamma$-$^{32}$P-ATP with the active and kinase-dead BMX. Biotinylated peptides then were captured with a streptavidin-coated membrane, and the preference for each amino acid at each position was determined by the relative level of radio-label incorporation.

Figure 6:
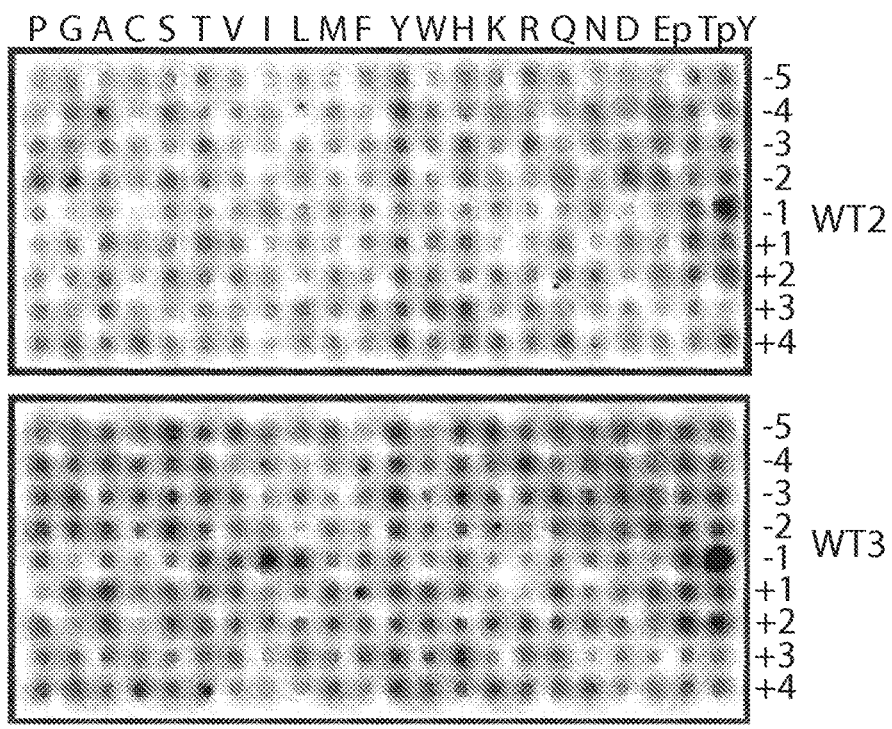
FIG. 6 includes peptide array images on the BmxWT group obtained from two additional independent assays (WT2 and WT3).
Figure 7:
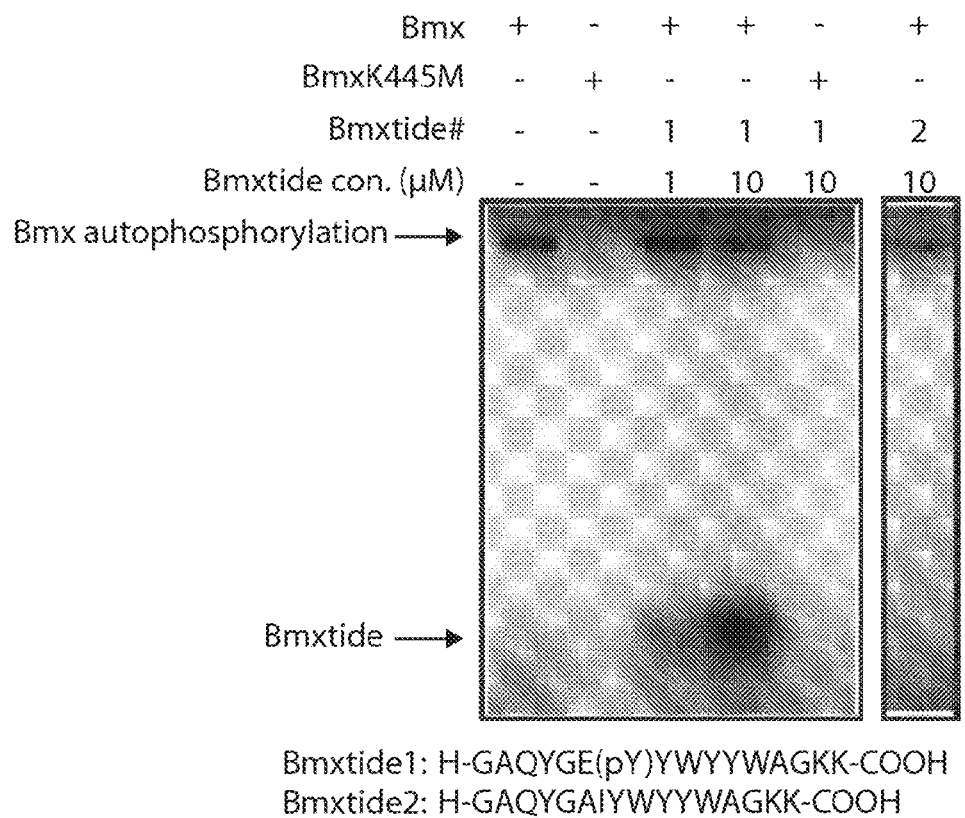
FIG. 7 shows the results of an in vitro kinase assay using Bmxtide 1 or 2 and BmxWT or BmxKD.
Figure 8:
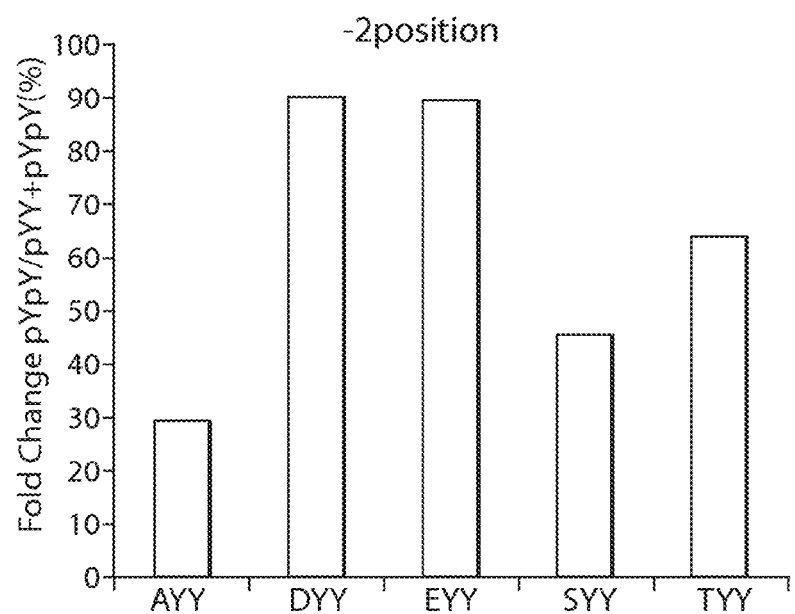
FIG. 8 is a bar graph showing the Bmx substrate motif preference at the −2 position. Bmx substrate motif peptide pool with A/D/E/S/T at the −2 position (and other positions fixed as in Bmxtide 1) were phosphorylated using BmxWT and subjected to mass spectrometry. The preference toward each amino acid at the −2 position was quantified as the level of peptide with the amino acid at the −2 position that was dually phosphorylated divided by the level of peptide with the amino acid at the −2 position that was mono- or dual-phosphorylated.

BMX exhibited strong sequence selectivity at positions surrounding the phosphorylation site (FIG. 1B, WT), whereas BmxKD exhibited minimal activity (FIG. 1B, KD), confirming that peptides were not being phosphorylated by a contaminating kinase. BMX showed a dramatic preference for a priming pY at position −1, with a less marked preference for isoleucine at the −1 position. The kinase also preferred substrates with acidic residues at position −2, and showed a less marked preference for additional tyrosine residues at −4, +2, and +3, and for tryptophan at the +1 position. Data from three independent library screens (FIG. 1B and FIG. 6) were quantified to yield consensus optimal substrates with either pY (matrix shown in Table 1) or isoleucine at the −1 position (peptides 1 and 2, respectively, FIG. 1C). In vitro kinase assays confirmed Bmx phosphorylation of the pY peptide (peptide 1), but a signal with the IY peptide (peptide 2, FIG. 7) was not detected. As peptide 1 contained four tyrosines that were potential phosphorylation sites, in vitro phosphorylated peptide 1 was analyzed using mass spectrometry. Importantly, in addition to non-phosphorylated peptide and peptide phosphorylated at the priming −1 tyrosine, the only peptide detected was tyrosine phosphorylated at both the central and −1 positions (data not shown). Finally, using mass spectrometry to assess the effects of varying the −2 position in peptide 1, a preference for acidic residues was confirmed, with a less marked preference for threonine or serine (FIG. 8). Together these results indicated that pYY was a core substrate motif for BMX.

TABLE 1

BMX matrix for pTyr at −1 position [a]

| | | | | | | | | | | | | | | |
|---|---|---|---|---|---|---|---|---|---|---|---|---|---|---|
| A | 1 | 1 | 0.7 | 1 | 0.7 | 0.8 | 0.3 | 0 | 1.4 | 0.7 | 0.5 | 0.6 | 1 | 1 | 1 |
| R | 1.2 | 1.2 | 1.2 | 1.7 | 0.7 | 0.4 | 0.5 | 0 | 0.3 | 1.1 | 1.3 | 1.4 | 1.2 | 1.2 | 1.2 |
| N | 1.2 | 1.2 | 1.4 | 1.7 | 0.9 | 1.8 | 0.8 | 0 | 0.6 | 0.8 | 0.6 | 0.8 | 1.2 | 1.2 | 1.2 |
| D | 1.2 | 1.2 | 1.2 | 1.4 | 1 | 1.4 | 0.5 | 0 | 1 | 0.7 | 0.2 | 1 | 1.2 | 1.2 | 1.2 |
| C | 1 | 1 | 0.6 | 1.1 | 0.6 | 0.7 | 0.2 | 0 | 0.7 | 0.4 | 0.6 | 1.6 | 1 | 1 | 1 |
| E | 1.2 | 1.2 | 1 | 2.4 | 1.3 | 2.3 | 1.3 | 0 | 1.6 | 0.8 | 0.3 | 0.9 | 1.2 | 1.2 | 1.2 |
| Q | 1.2 | 1.2 | 1.6 | 1.6 | 0.8 | 1.3 | 0.9 | 0 | 1.7 | 1 | 1 | 0.8 | 1.2 | 1.2 | 1.2 |
| G | 1.2 | 1.2 | 1.1 | 1.9 | 1.5 | 1.6 | 0.5 | 0 | 1.3 | 0.7 | 1.5 | 1.6 | 1.2 | 1.2 | 1.2 |
| H | 1.2 | 1.2 | 1 | 1 | 0.4 | 0.6 | 0.8 | 0 | 0.8 | 0.8 | 1.8 | 1.3 | 1 | 1 | 1 |
| I | 1 | 1 | 1.4 | 1 | 0.5 | 0.8 | 2.7 | 0 | 1 | 1 | 1.1 | 0.9 | 1 | 1 | 1 |
| L | 1 | 1 | 0.7 | 1 | 0.6 | 0.8 | 1.6 | 0 | 0.8 | 0.8 | 1.2 | 1 | 1 | 1 | 1 |

TABLE 1-continued

BMX matrix for pTyr at −1 position [a]

| | | | | | | | | | | | | | | | |
|---|---|---|---|---|---|---|---|---|---|---|---|---|---|---|---|
| K | 1 | 1 | 0.8 | 1.1 | 0.5 | 0.4 | 0.4 | 0 | 0.6 | 0.8 | 0.6 | 1 | 1 | 1 | 1 |
| M | 1 | 1 | 1.2 | 1.3 | 1 | 0.7 | 1 | 0 | 1.7 | 0.8 | 1.7 | 1.2 | 1 | 1 | 1 |
| F | 1 | 1 | 0.5 | 1 | 1 | 0.5 | 0.8 | 0 | 0.8 | 1.1 | 1.8 | 1 | 1 | 1 | 1 |
| P | 1.2 | 1.2 | 0.8 | 1.5 | 0.9 | 1.7 | 0.5 | 0 | 0.4 | 0.9 | 0.7 | 1 | 1.2 | 1.2 | 1.2 |
| S | 1.2 | 1.2 | 0.9 | 1.3 | 1 | 1.4 | 0.4 | 0 | 1.7 | 1 | 0.8 | 1 | 1.2 | 1.2 | 1.2 |
| T | 1.2 | 1.2 | 1 | 1.7 | 1.2 | 1.4 | 1.2 | 0 | 1.8 | 1.3 | 1.1 | 1.2 | 1.2 | 1.2 | 1.2 |
| W | 1 | 1 | 1 | 1.2 | 0.8 | 0.3 | 0.5 | 0 | 1.9 | 0.8 | 1.7 | 2 | 1 | 1 | 1 |
| Y | 1.2 | 1.2 | 1.2 | 2.8 | 1.3 | 0.8 | 7.6 | 21 | 1.5 | 1.6 | 2.7 | 1.3 | 1.2 | 1.2 | 1.2 |
| V | 1 | 1 | 0.7 | 0.9 | 0.8 | 0.9 | 1.3 | 0 | 1.4 | 1.2 | 1.3 | 1.4 | 1 | 1 | 1 |
| * | 0.1 | 0.1 | 0.1 | 0.1 | 0.1 | 0.1 | 0.1 | 0 | 0.1 | 0.1 | 0.1 | 0.1 | 1 | 1 | 1 |
| | | | −5 | −4 | −3 | −2 | −1 | | +1 | +2 | +3 | +4 | | | |

[a] The images from the positional peptide library assays were quantified. Each score represents the preference of BMX toward the fixed peptide in each well.

Using the PhosphoSite Plus database from Cell Signaling Technology (www.phosphosite.org), proteins containing pYpY were screened as potential BMX substrates. Surprisingly, many receptor and nonreceptor tyrosine kinases met the BMX substrate motif requirement (Table 2). These sites are highly conserved and, in the receptor tyrosine kinases, are located in kinase domains where they can undergo autophosphorylation in response to hormone/growth factor binding and are required for full kinase activity (Calalb et al., *Mol. Cell Biol.* 15, 954 (1995); Ciccimaro et al., *Rapid Commun. Mass Spectrom.* 20, 3681 (2006); avelyukis et al., *Nat. Struct. Biol.* 8, 1058 (2001); Hubbard, *Embo. J.* 16, 5572 (1997); Bae et al., *Cell* 138, 514 (2009)). To validate the predicted substrate motif on intact proteins, commercially available antibodies recognizing pYpY were used in several tyrosine kinases. Immunoblotting with an antibody recognizing the pYpY in MET revealed increased reactivity when cells were cotransfected with MET and BmxWT plasmids versus a BmxKD plasmid (FIG. 1D, left panel). Cotransfection with BmxWT similarly increased reactivity when the cells in serum free medium (SFM) were stimulated with hepatocyte growth factor (HGF) (FIG. 1D, right panel). Cotransfection of BMX with FAK markedly increased pYpY levels (pY576/577) in the FAK kinase domain (FIG. 1E, left panel). In contrast, the SRC-mediated phosphorylation of Y576 was not markedly increased, and there was no detectable Y577 monophosphorylation, consistent with BMX phosphorylation of Y577 only after a priming phosphorylation of Y576. Transfected BMX also markedly increased pY576/577 on endogenous FAK, without increasing pY576 (FIG. 1E, right panel). Finally, it was found that BMX increased pYpY in FGFR1 (FIG. 1F) and in the non-receptor tyrosine kinase ACK1 (FIG. 1G). JAK2 was also examined, as BMX was reported recently to be required for STAT3 activation in glioblastoma stem cells (Guryanova et al., *Cancer Cell* 19, 498 (2011)), but a clear effect of transfected BmxWT on the pYpY site in the JAK2 kinase domain was not seen.

TABLE 2

List of proteins with dual tyrosine (pYpY) phosphorylation[a]

| | Name | Site | Domain | Sequence |
|---|---|---|---|---|
| InsR Family | InsR_Human | 1189, 1190 | Kinase domain | FGMTRDIYETDYYRKGGKGL |
| | IGF1R_Human | 1165, 1166 | Kinase domain | FGMTRDIYETDYYRKGGKGL |
| FGFR Family | FGFR1_Human | 653, 654 | Kinase domain | RDIHHIDYYKKTTNG |
| | FGFR2_Human | 656, 657 | Kinase domain | RDINNIDYYKKTTNGR |
| | FGFR3_Human | 647, 648 | Kinase domain | RDVHNLDYYKKTTNGR |
| | FGFR4_Human | 642, 643 | Kinase domain | RGVHHIDYYKKTSNGR |
| Met Family or related | Met_Human | 1234, 1235 | Kinase domain | FGLARDMYDKEYYSVHNKTG |
| | RON_Human | 1238, 1239 | Kinase domain | RDILDREYYSVQQHRH |
| | MER_Human | 753, 754 | Kinase domain | FGLSKKIYSGDYYRQGRIAK |
| | Axl_Human | 695, 696 | Kinase domain | FGLSKKIYNGDYYRQGRIAK |
| | Tyro3/SKY_Human | 685, 686 | Kinase domain | FGLSRKIYSGDYYRQGCASK |
| Trk Family or related | TrkA_Human | 680, 681 | Kinase domain | FGMSRDIYSTDYYRVGGRT |
| | TrkB_Human | 706, 707 | Kinase domain | FGMSRDVYSTDYYRVGGHT |
| | TrkC_Human | 709, 710 | Kinase domain | FGMSRDVYSTDYYRLFNPS |
| | MuSK_Human | 755, 756 | Kinase domain | FGLSRNIYSADYYKANEND |
| | DDR2_Human | 740, 741 | Kinase domain | FGMSRNLYSGDYYRIQGRA |
| | DDR1_Human | 796, 797 | Kinase domain | FGMSRNLYAGDYYRVQGRAV |
| FAK, Syk Family | FAK_Human | 576, 577 | Kinase domain | RYMEDSTYYKASKGK |
| | Pyk2_Human | 579, 580 | Kinase domain | RYIEDEDYYKASVTRL |
| | Syk_Human | 525, 526 | Kinase domain | ALRADENYYKAQTHGK |
| | ZAP70_Human | 429, 493 | Kinase domain | ALGADDSYYTARSAGK |
| Jak Family or related | Jak1_Human | 1034, 1035 | Kinase domain | AIETDKEYYTVKDDR |
| | Jak2_Human | 1007, 1008 | Kinase domain | VLPQDKEYYKVKEPG |
| | Jak3_Human | 980, 981 | Kinase domain | LLPLDKDYYVVREPG |
| | Tyk2_Human | 1054, 1055 | Kinase domain | AVPEGHEYYRVREDG |

TABLE 2-continued

List of proteins with dual tyrosine (pYpY) phosphorylation[a]

| | Name | Site | Domain | Sequence |
|---|---|---|---|---|
| Src Family | Fgr_Human | 208, 209 | SH2 domain | RKLDMGGYYITTRVQ |
| | Fyn_Human | 213, 214 | SH2 domain | RKLDNGGYYITTRAQF |
| | Yes_Human | 221, 222 | SH2 domain | RKLDNGGYYITTRAQF |
| | Lyn_Human | 192, 193 | SH2 domain | RSLDNGGYYISPRITF |
| | Blk_Human | 187, 188 | SH2 domain | RCLDEGGYYISPRITF |
| ACK | Ack_Human | 859, 860 | | KKVSSTHYYLLPERP |

[a]Data are based on mass spectrometry data in the PhosphoSite Plus database from Cell Signaling Technology (www.phosphosite.org).

Figure 9A:
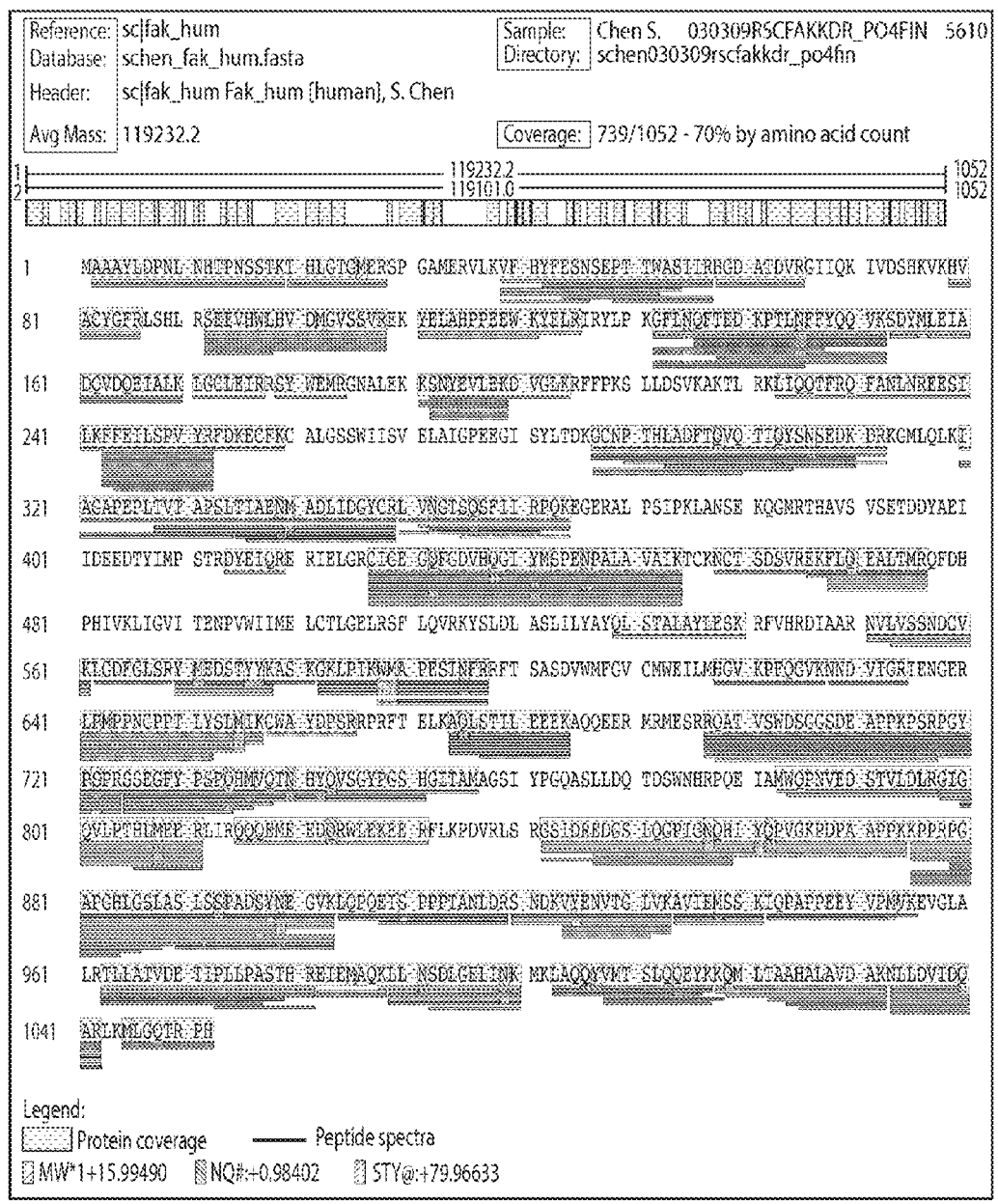
FIG. 9 depicts the mass spectrometry results for FAK tyrosine phosphorylation. Shown are phosphopeptide maps for SRC phosphoryated FAK after in vitro kinase reactions with BmxWT (FIG. 9A) or BmxKD (FIG. 9B).
Figure 9B:
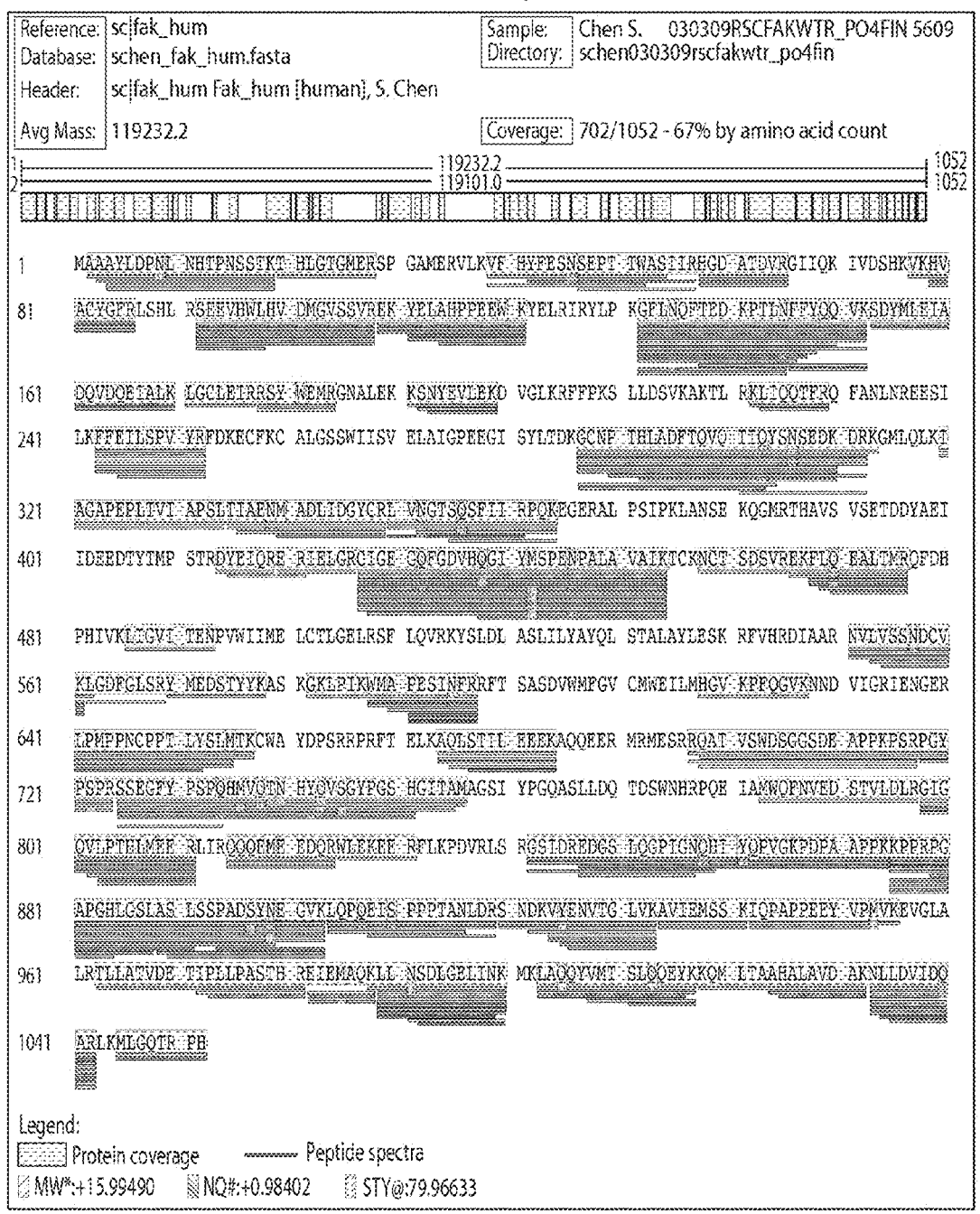

The BMX PH domain can interact with the FERM domain of FAK, with subsequent membrane recruitment and activation of BMX by FAK associated SRC (Chen et al., Nat. Cell Biol. 3, 439 (2001)). Therefore, what was next focused on was to determine whether FAK was a physiological BMX substrate. To confirm FAK Y576/577 phosphorylation, mass spectrometric analysis of FAK was performed after in vitro kinase reactions with wild-type or kinase-dead BMX. The substrate used was a commercial recombinant FAK that was initially phosphorylated in vitro by SRC. Tyrosine phosphorylated peptides identified in the BmxWT sample are shown in FIG. 2A, although the analysis was not comprehensive due to limited peptide coverage (complete phosphorylation maps of FAK with BmxWT and BmxKD are shown in FIGS. 9A-B). As expected, tyrosine phosphorylation at Y576 alone was found, reflecting the in vitro phosphorylation by SRC. Dual phosphorylation at Y576/Y577 was observed only with wild-type BMX, and phosphorylation at Y577 alone was did not detected, consistent with previous data showing Y576 is phosphorylated prior to Y577 (Ciccimaro et al., Rapid Commun. Mass Spectrom. 20, 3681 (2006)).

Figure 2B:
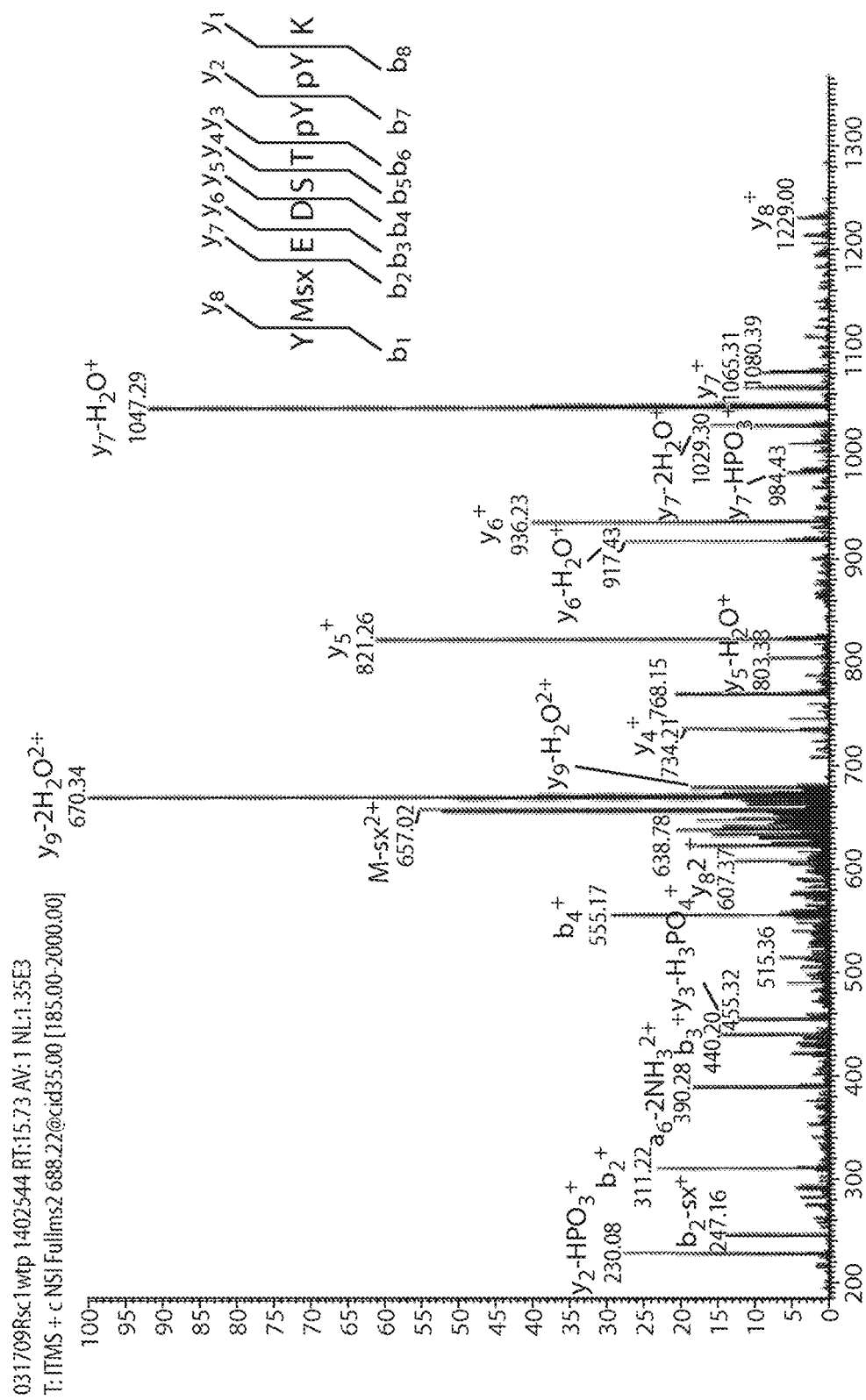
FIG. 2B is a mass spectrometry spectrum for pY576/Y577 dual phosphorylated peptide.
Figure 2C:
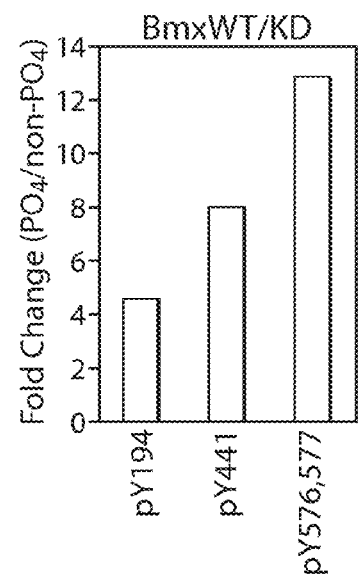
FIG. 2C is a bar graph showing the relative phosphorylated peptide signal levels in the BmxWT vs. BmxKD samples quantified using isotope-free LC/MS/MS method. Shown in FIG. 2D are immunoblotting results where 293 cells were cotransfected with BmxKD or BmxWT plasmids and wildtype or indicated mutant FAK vectors, and whole cell lysates were immunoblotted with pY576/577 antibody (weak reactivity with Y576A and Y577A mutants may reflect endogenous FAK). The results of FIG. 2D establish the specificity of the pFAK Y576/577 antibody.
Figure 2D:
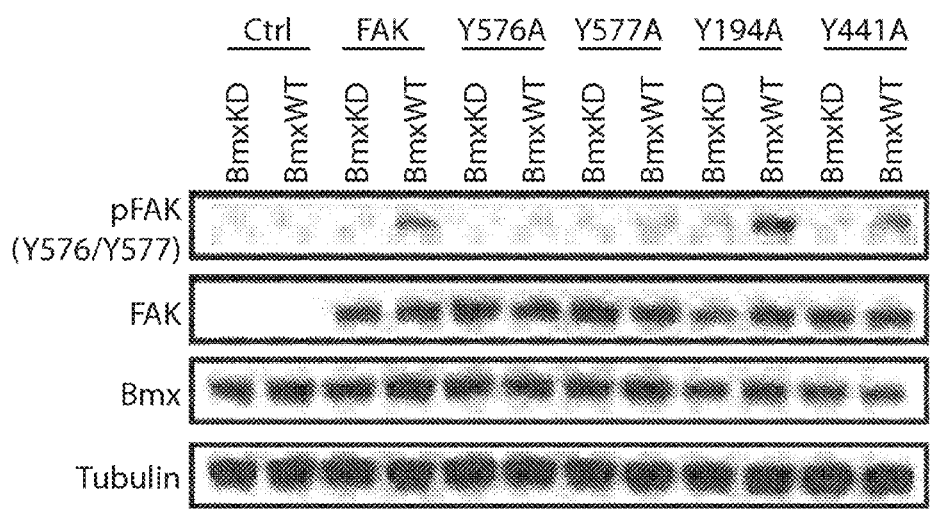
FIG. 2 shows that FAK is phosphorylated by BMX at Y577. Recombinant SRC-phosphorylated FAK was phosphorylated in vitro with recombinant BmxWT or BmxKD and analyzed by mass spectrometry. Phosphopeptides detected in the BmxWT sample are shown in FIG. 2A.

To generate more quantitative data, an isotope-free targeted mass spectrometric approach was used to quantify relative ratios of peptides phosphorylated at Y576, Y577, or at both sites. Among all detected peptides containing Y576/577 in the BmxWT treated sample, 81% were phosphorylated only at Y576, and 8.4% were dually phosphorylated at Y576 and Y577 (spectra for dual phosphopeptide is shown in FIG. 2B). In contrast, while 86% of Y576/577 containing peptides in the BmxKD treated sample were phosphorylated at Y576, there were no peaks above background (0.66%) detected for the pY576/577 peptide, indicating an increase of at least 12-fold by wild-type BMX (FIG. 2C). Less marked increases in phosphorylation also were found at two other sites targeted for analysis, Y194 and Y441 (the latter being an IY site) (FIG. 2C). Finally, cells cotransfected with BmxWT or BmxKD and a series of mutant FAKs were examined. Reactivity of wild-type FAK with the pY576/577 antibody again was increased by BmxWT, and this increase was abrogated by the Y576A and Y577A mutations (but not Y194A or Y441A mutations), supporting the specificity of the antibody and further establishing that BMX can phosphorylate FAK Y577 in vivo subsequent to priming by phosphorylation at Y576 (FIG. 2D).

Figure 3A:
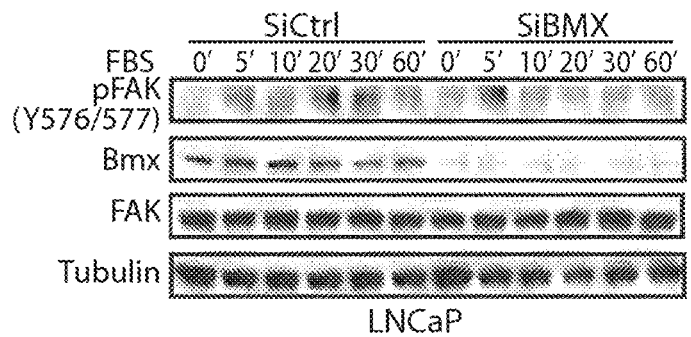
FIGS. 3A-B show the immunoblotting results where BMX (SiBMX) or control siRNA (SiCtrl) transfected LNCaP cells (FIG. 3A) or VCS2 cells (FIG. 3B) were serum starved for 72 h, serum was stimulated for the indicated times, and the whole cell lysates were immunoblotted.
Figure 3B:
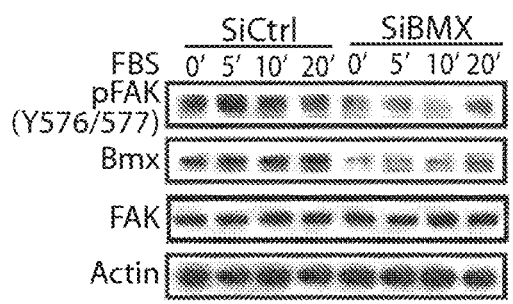
Figure 3C:
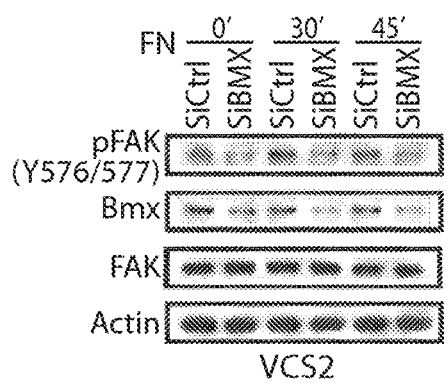
FIG. 3C shows the immunoblotting results where BMX (SiBMX) or control siRNA (SiCtrl) transfected VCS2 cells were serum starved for 72 h, trypsinized, and kept in suspension for 1 h followed by plating onto fibronectin (FN)-coated dishes for the indicated times.

BMX expression is increased in prostate cancer, and transgenic BMX overexpression in mouse prostate induces intraepithelial neoplasia (Dai et al., Cancer Res. 66, 8058 (2006)). Therefore, to analyze FAK phosphorylation by endogenous BMX, siRNA was used to decrease BMX in two human prostate cancer cell lines (VCS2 and LNCaP) expressing relatively high levels of endogenous BMX. LNCaP cells, which are PTEN deficient and subsequently have PI-3K pathway activation, were transfected with BMX or control siRNA and then serum starved for 72 hours, followed by serum stimulation and immunoblotting for FAK pY576/577. BMX knockdown did not prevent an increase at 5 minutes, but it markedly decreased the duration of the response (FIG. 3A). In VCS2 cells (derived from a VCaP xenograft that relapsed after castration) (Cai et al., Cancer Cell 20, 457 (2011)), BMX siRNA decreased pY576/Y577 under serum starved conditions and also impaired the response to serum stimulation (FIG. 3B). As FAK links both growth factor and matrix/integrin stimulation to intracellular signals that promote cell migration, matrix stimulated FAK phosphorylation was also analyzed. BMX siRNA reduced FAK pY576/577 under basal and fibronectin stimulated conditions (FIG. 3C).

Figure 3D:
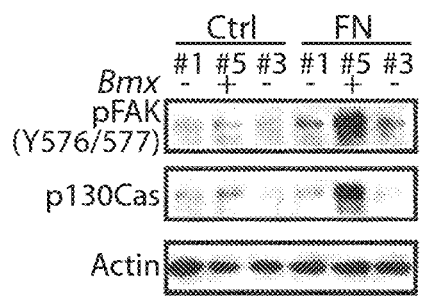
FIG. 3D shows the immunoblotting results where widetype for Bmx (Bmx$^+$) or BMX negative (Bmx$^-$) MEFs were suspended for 1 h (Ctrl) or then plated onto fibronectin-coated dishes for 30 min (FN).
Figure 10:
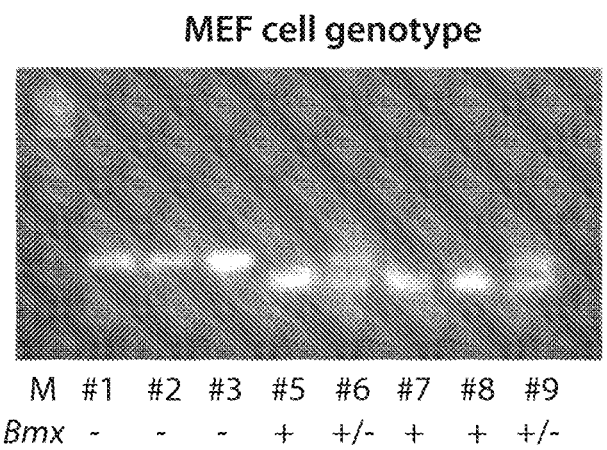
FIG. 10 shows the results of the genotyping of MEFs from embryos derived from Bmx− and Bmx+/− breeding. MEFs #5, #7, and #8 were wildtype, MEFs #1, #2, and #3 were Bmx−/−, and MEFs #6 and #9 were Bmx+/−.

Bmx$^-$ mice appear normal, but have a defect in ischemia induced angiogenesis that could reflect decreased FAK activity and migration of endothelial cells (He et al., J. Clin. Invest. 116, 2344 (2006)). Therefore, mouse embryonic fibroblasts (MEFs) from Bmx$^-$ mice were examined. Male littermates that were wildtype for Bmx (Bmx$^+$) or Bmx negative (Bmx$^-$), or females that were heterozygous for Bmx (Bmx$^{+/-}$) were identified by genotyping and used to generate shortterm MEF lines (FIG. 10). Lower basal FAK pY576/Y577 in Bmx compared to Bmx$^+$ MEFs was detected, and pY576/Y577 in Bmx$^-$ MEFs after fibronectin stimulation was marked decreased (FIG. 3D). Phosphorylation of p130Cas, a direct downstream substrate of FAK, also was markedly impaired, consistent with the requirement for Y576/577 phosphorylation to fully activate FAK.

Figure 3E:
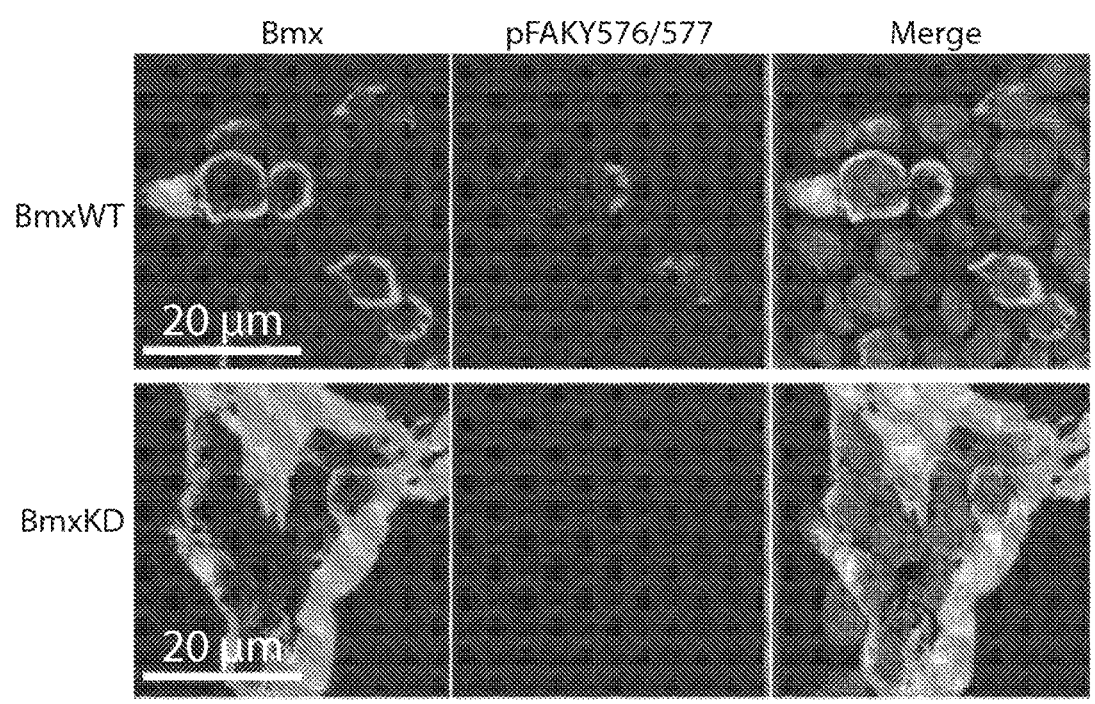
FIG. 3E shows the immunostaining results where BmxWT or BmxKD vectors were transfected into 293 cells and immunostained for BMX and FAK pY576/Y577.
Figure 3F:
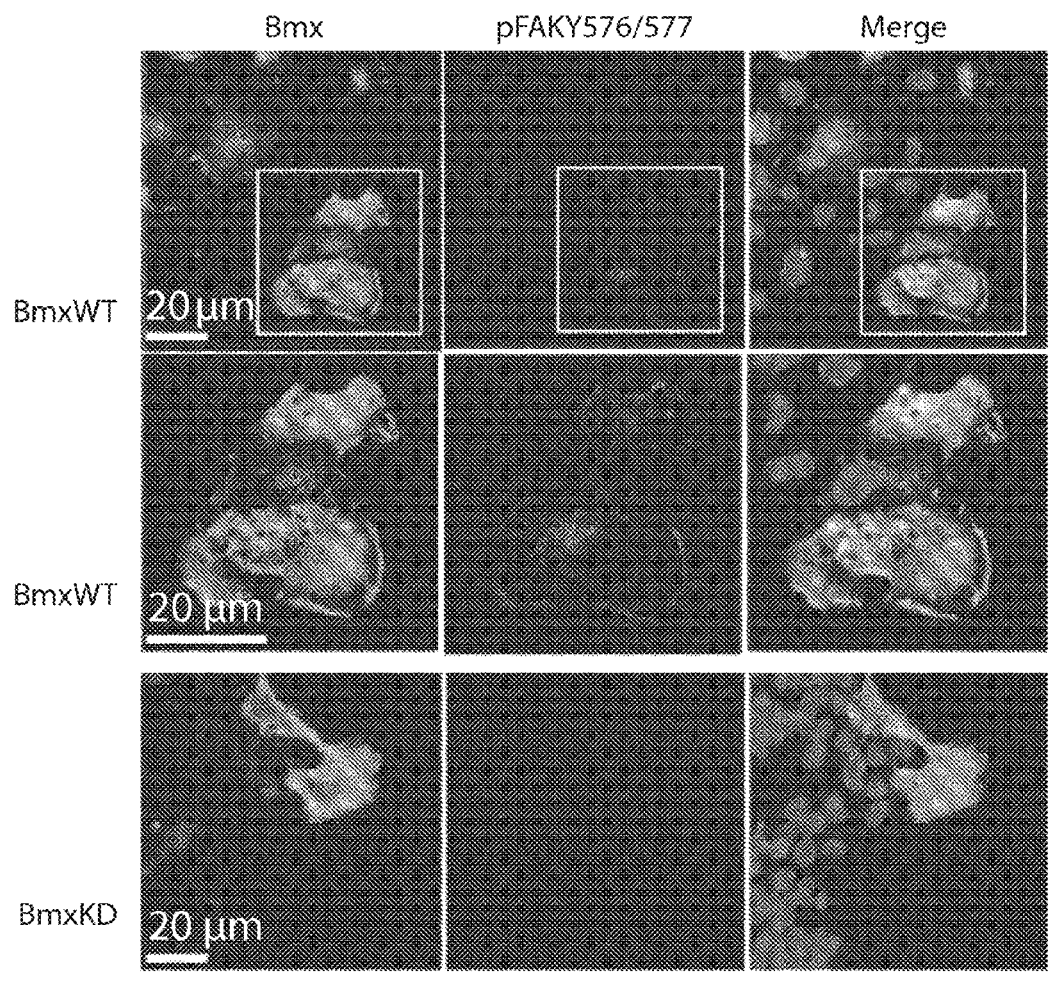
FIG. 3F shows the immunostaining results where scratch wounds were introduced into BmxWT or BmxKD transfected COS7 cells, and pictures of the leading edge were taken after 3 h.
Figure 3G:
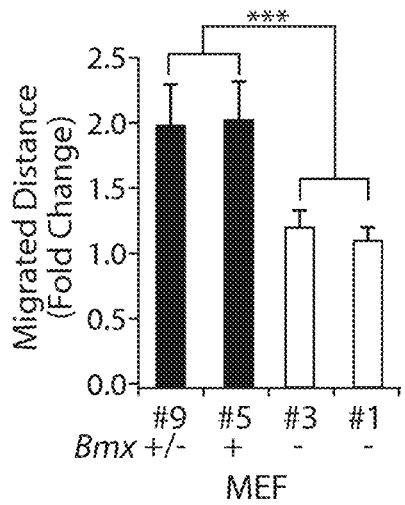
FIG. 3G is a bar graph showing the migrated distances where scratch wounds were introduced into confluent heterozygous for Bmx (Bmx$^{+/-}$), Bmx$^+$, or Bmx$^-$ MEFs, and the leading edges were photographed at 0 and 9 h. The migrated distance was measured and normalized to #1 Bmx-group. Error bars depict standard error (SE) for three experiments (***: $p<0.001$).
Figure 11:
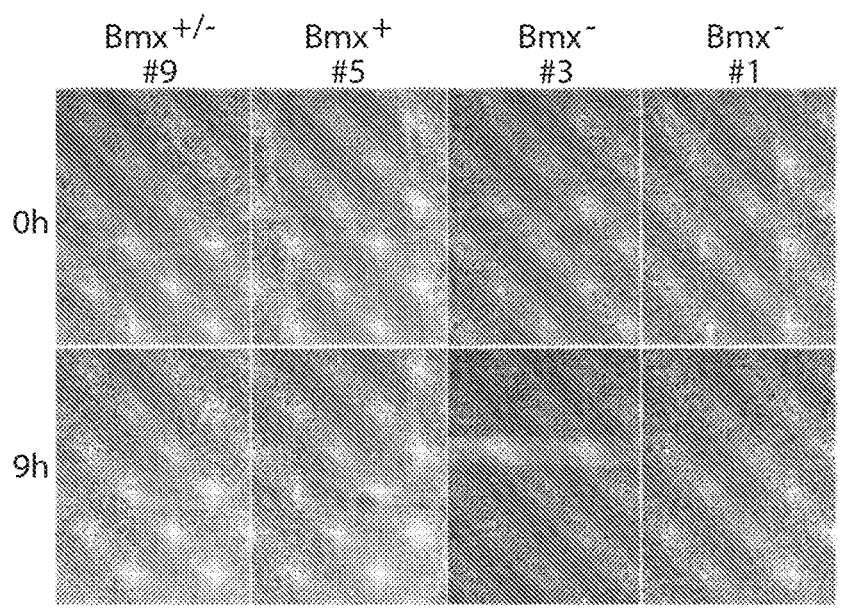
FIG. 11 illustrates that Bmx− MEFs display decreased wound healing. Bmx+/− or Bmx− MEFs were grown to confluence, scratch wounds were introduced with pipette tips, and pictures were taken over 0 to 9 h.

BMX stimulated FAK pY576/Y577 was most evident at lower cell density, consistent with a requirement for a priming Y576 phosphorylation by SRC at the plasma membrane. To test this hypothesis, immunofluorescence was used to assess the cellular localization of transfected BMX and endogenous FAK pY576/Y577. Cells transfected with BmxWT, but not BmxKD, showed strong FAK pY576/577 staining that colocalized with BMX at the plasma membrane (FIG. 3E). To further assess the localization of BMX and pY576/Y577 FAK in response to a physiological FAK stimulus, scratch wounds were introduced into COS7 cells transfected with BmxWT or BmxKD. Immunostaining done at about 3 hours showed co-localization of pY576/577 FAK with BmxWT, but not BmxKD, in lamellipodia of migrating cells at the leading edge (FIG. 3F). Wound healing assays were next performed to determine the influence of endogenous BMX on cell migration. Scratch wounds were introduced on MEFs grown to confluency, and pictures of the leading edge were taken at time points 0 and 9 hours (FIG. 11). Bmx$^-$ MEFs showed impaired wound healing compared to Bmx$^+$ MEFs and Bmx$^{+/-}$-MEFs from female mice (FIG.

Figure 3H:
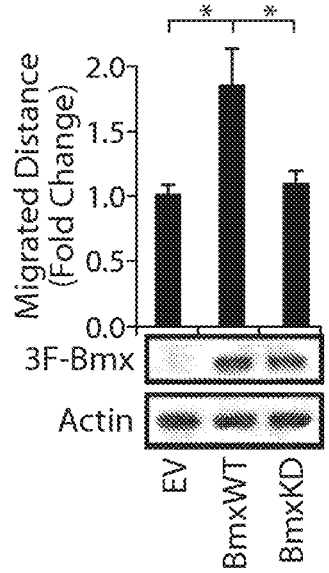
FIG. 3H is a bar graph showing the migrated distances where scratch wounds were introduced into confluent Bmx$^-$ MEFs stably overexpressing BmxWT, BmxKD, or empty vector (EV), and the leading edges were photographed at 0 and 9 h. The migrated distance was measured and normalized to EV group. Error bar depict standard error (SE) for three independent experiments (*: $p<0.05$).
Figure 3I:
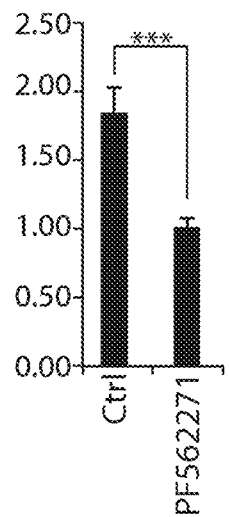
FIG. 3I is a bar graph showing the migrated distances where Bmx$^-$ MEF cells stably overexpressing BmxWT were preincubated with FAK inhibitor (PF562271) for 4 h. Scratch wounds were introduced into the cells, and the leading edges were photographed at 0 and 9 h. The migrated distance was measured and normalized to control group (Ctrl). Error bars depict standard error (SE) for three experiments (***: $p<0.001$).

3G). BMX downregulation by siRNA similarly impaired wound healing in LNCaP cells (FIG. 12). This defect in the Bmx⁻ MEFs could be corrected by transfection with BmxWT, but not BmxKD (FIG. 3H), and the stimulatory effect of BmxWT could be blocked by a FAK antagonist (PF562271) (FIG. 3I). Together these findings show that BMX activates FAK by phosphorylating Y577 subsequent to a priming phosphorylation at Y576.

Figure 4A:
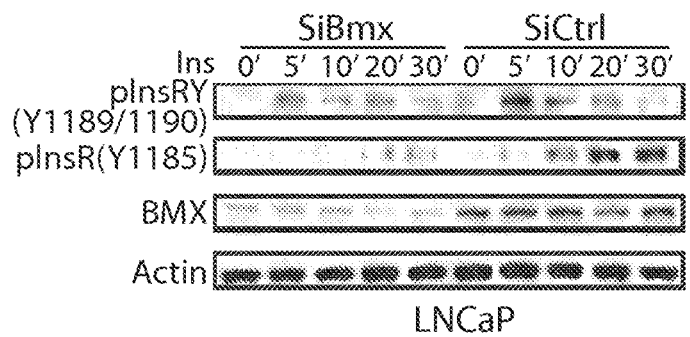
FIG. 4A shows the immunoblotting results where LNCaP cells transfected with BMX (SiBmx) or nontargeting control siRNA (SiCtrl) were serum starved for 12 h, stimulated with insulin (100 nM) (Ins) for 0-30 minutes, and immunoblotted with IR pY1189/Y1190 or pY1185 antibody.
Figure 4B:
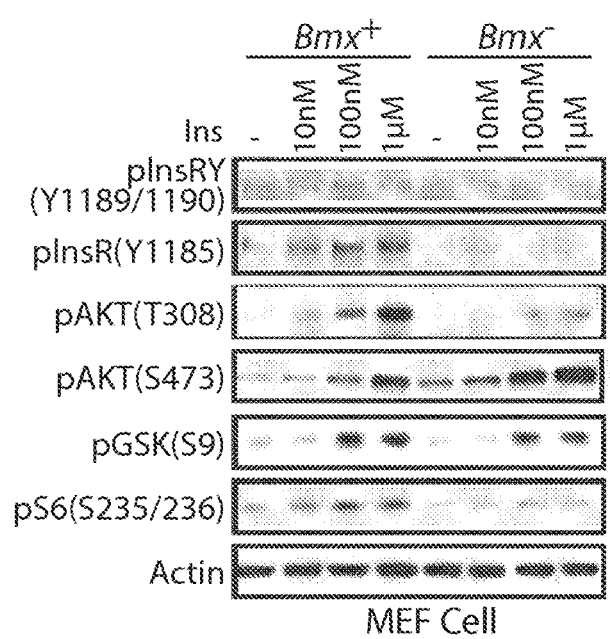
FIG. 4B shows the immunoblotting results where Bmx$^+$ and Bmx$^-$ MEFs were serum starved for 48 h and stimulated with insulin for 10 min, and whole cell lysates were immunoblotted.
Figure 4C:
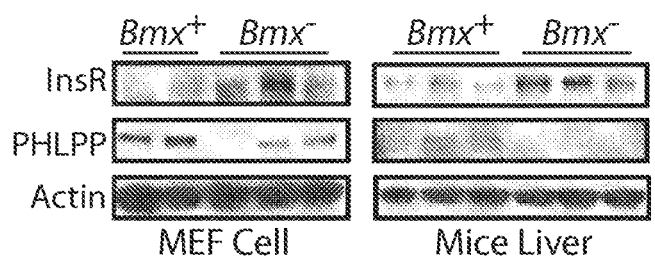
FIG. 4C shows the immunoblotting results where whole cell lysates from independent Bmx$^+$ and Bmx$^-$ MEF cell lines or livers were blotted.

An additional candidate BMX substrate is insulin receptor (IR), which in addition to pY1189/1190 in its kinase domain undergoes phosphorylation at Y1185 to achieve full activation (Table 2) (Hubbard, *Embo. J.* 16, 5572 (1997); White et al., *J. Biol. Chem.* 263, 2969 (1988); zynski et al., *Biochem. Biophys. Res. Commun.* 279, 955 (2000); Baserga, *Exp. Cell Res.* 253, 1 (1999)). Immunoblotting with pY1189/1190 and pY1185 IR antibodies showed that BMX downregulation by siRNA in LNCaP cells impaired insulin stimulated IR activation (FIG. 4A). Interestingly, Y1185 is preceded by an isoleucine, suggesting that it may be an IY motif for BMX. Insulin stimulated IR phosphorylation similarly was impaired in Bmx⁻ MEFs (FIG. 4B), despite higher levels of total IR expression in Bmx⁻ versus Bmx⁺ MEFs (FIG. 4C). Insulin stimulated phosphorylation of AKT at T308, which is mediated by PDK1 immediately downstream of PI-3K, also was decreased in Bmx⁻ MEFs, as was phosphorylation of AKT substrate GSK3β and downstream S6 (FIG. 4B). In contrast, AKT phosphorylation at S473, which is mediated by TORC2 and generally correlates with T308 phosphorylation, was not decreased (FIG. 4B). Consistent with this result, expression of the phosphatase PHLPP, which dephosphorylates AKT pS473 (Gao et al., *Mol. Cell* 18, 13 (2005)), was decreased in the Bmx⁻ MEFs (FIG. 4C). Moreover, increased levels of total IR and decreased PHLPP in vivo in liver from Bmx⁻ mice were also observed (FIG. 4C), indicating that cells were adapting to decreased IR signaling and PI-3K/AKT pathway activity.

Figure 4D:
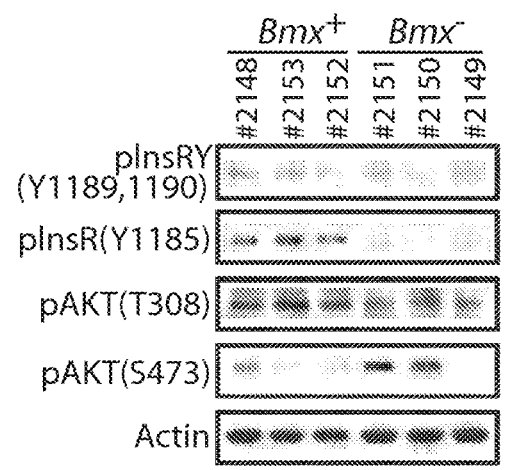
FIGS. 4D-G: following an overnight fast, 8-10 months old Bmx$^+$ and Bmx$^-$ mice were injected intraperitoneally with 2 g/kg glucose. Liver was harvested after 15 min, and lysates were immunoblotted (FIG. 4D). GSK pS9 and S6 pSer235, 236 signals were quantified and normalized to actin (FIG. 4E). Blood glucose (FIG. 4F) and insulin levels (FIG. 4G) were measured at indicated times.
Figure 4E:
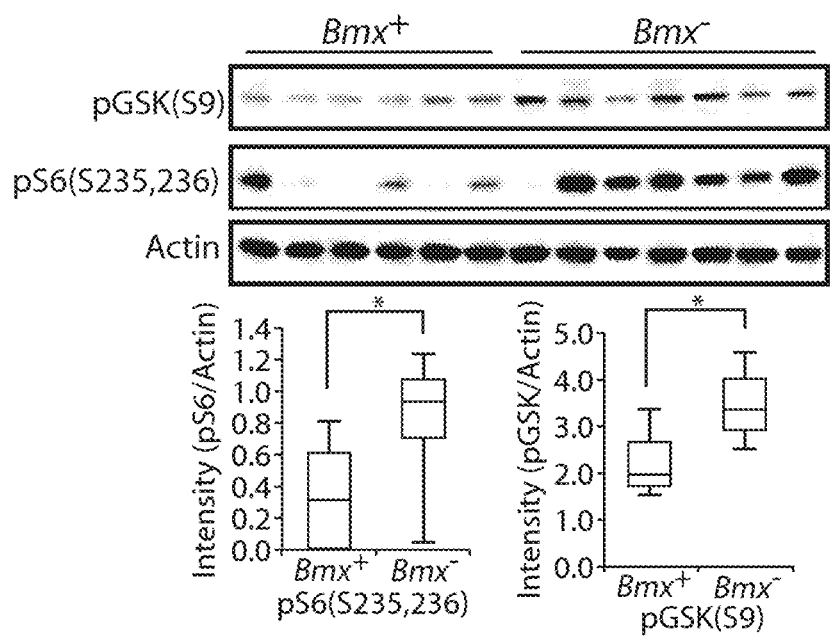
Figure 4F:
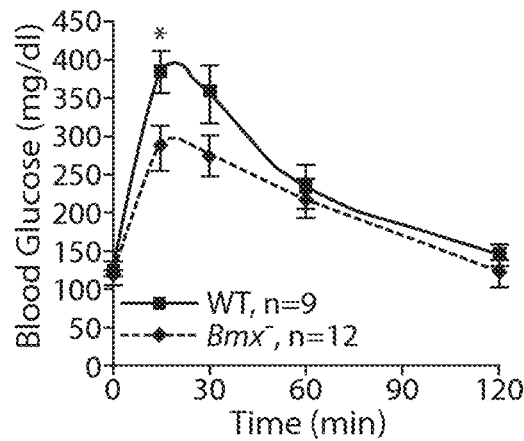
Figure 4G:
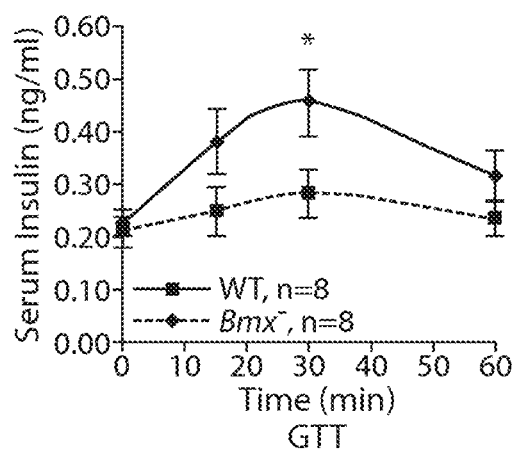
Figure 4H:
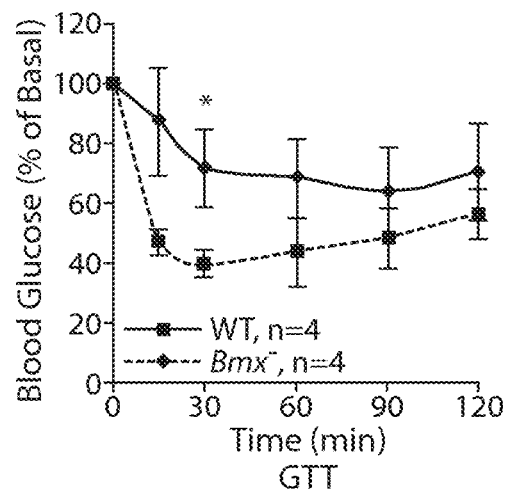
FIG. 4H: following 4 h fast, 8-10-month old Bmx$^+$ and Bmx$^-$ mice were injected with insulin (0.75 U/kg), and blood glucose was measure at indicated times.

To assess effects on insulin signaling in vivo, liver from mice was examined that were sacrificed 15 minutes after injection with glucose to stimulate insulin secretion. As observed in the Bmx⁻ MEFs, phosphorylation of IR and of AKT at T308 were reduced, while pAKT473 was increased (FIG. 4D). Moreover, analysis of GSK33 and S6 phosphorylation in liver from a series of Bmx⁺ versus Bmx⁻ mice showed that signaling downstream of AKT was actually enhanced in the Bmx⁻ mice (FIG. 4E). Consistent with the increased AKT signaling in liver, glucose tolerance testing showed lower peak serum glucose (FIG. 4F) and insulin levels (FIG. 4G) in Bmx-mice. Insulin tolerance testing confirmed that Bmx mice had an increased response to insulin (FIG. 4H). These findings demonstrate that chronic loss of BMX leads to adaptations including downregulation of PHLPP (which also dephosphorylates S6 kinase), which may enhance responses to some stimuli.

Compounds of Formula (I) or (II) show inhibitory activity against BMX. Shown in Table 3 are exemplary in vitro $IC_{50}$ data of these compounds.

TABLE 3

In vitro $IC_{50}$ values of exemplary compounds of Formula (I) or (II) in inhibiting BMX

| Compound | $IC_{50}$ (nM) |
| --- | --- |
| I-7 | 15.9 |
| I-8 | 40.6 |
| I-10 | >10,000 |
| I-11 | 18.1 |
| I-12 | 173 |
| I-13 | 18.1 |
| I-14 | 7.99 |
| I-15 | >1,000 |
| I-16 | 27.8 |
| I-17 | 399 |
| I-18 | 13.3 |
| II-3 | 8.16 |
| II-4 | 6.73 |
| II-5 | 12.9 |
| II-6 | 7.36 |
| II-7 | 15.7 |
| II-8 | 10.5 |
| II-9 | 19.7 |
| II-10 | 12.1 |
| II-11 | 66.1 |
| II-12 | 5.62 |
| II-13 | 13.3 |
| II-14 | 8.75 |
| II-16 | 18.5 |
| II-20 | 479 |

Compounds of Formula (I) or (II) may covalently attach to BMX by reacting with a cysteine residue (e.g., Cys496) of BMX. The compounds of Formula (I) or (II) may also form covalent bonds to equivalently positioned cysteine residues in other kinases, such as EGFR, Jak3, BLK, BTK, TEC, Txk, and ITK. Shown in FIG. 14 are the sequences of fragments of exemplary kinases that include cysteine residues to which the compounds of Formula (I) or (II) may attach. An X-ray co-crystal structure of compound II-6 on EGFR (T790M) is shown in U.S. povisional patent application, U.S. Ser. No. 61/622,828.

Figure 15A:
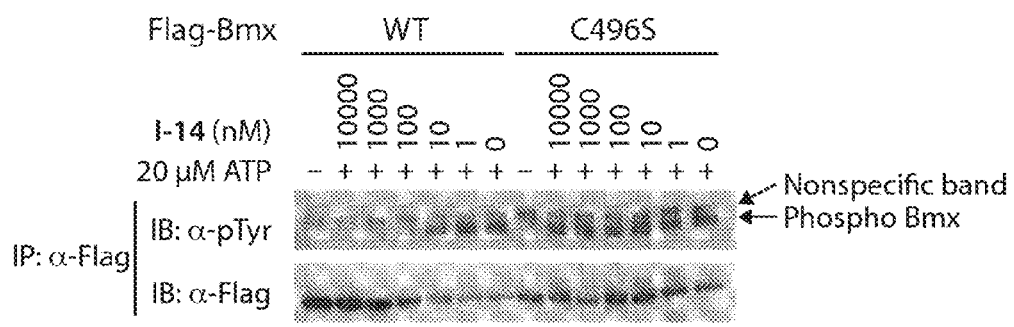
FIG. 15A shows that compound I-14 inhibits autophosphorylation of wild-type (WT) BMX at 10-100 nM, but does not inhibit the cysteine to serine mutant BMX (C496S) at up to 10,000 nM.
Figure 15B:
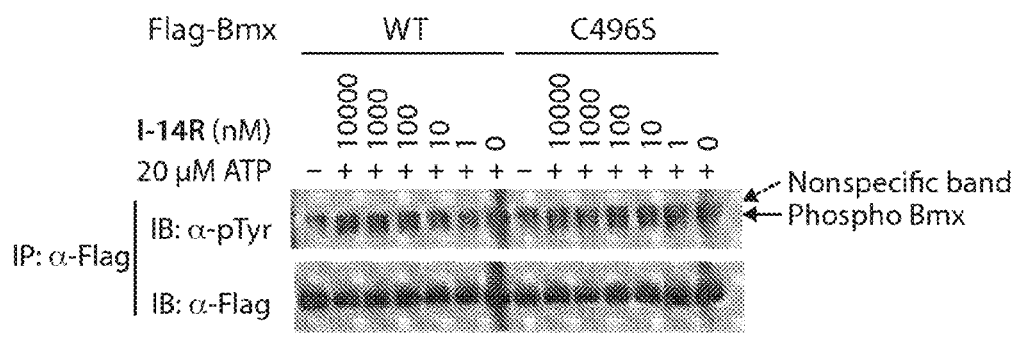
FIG. 15B shows that the reversible analog (compound I-14R) does not inhibit BMX autophosphorylation at up to 10,000 nM.
Figure 16A:
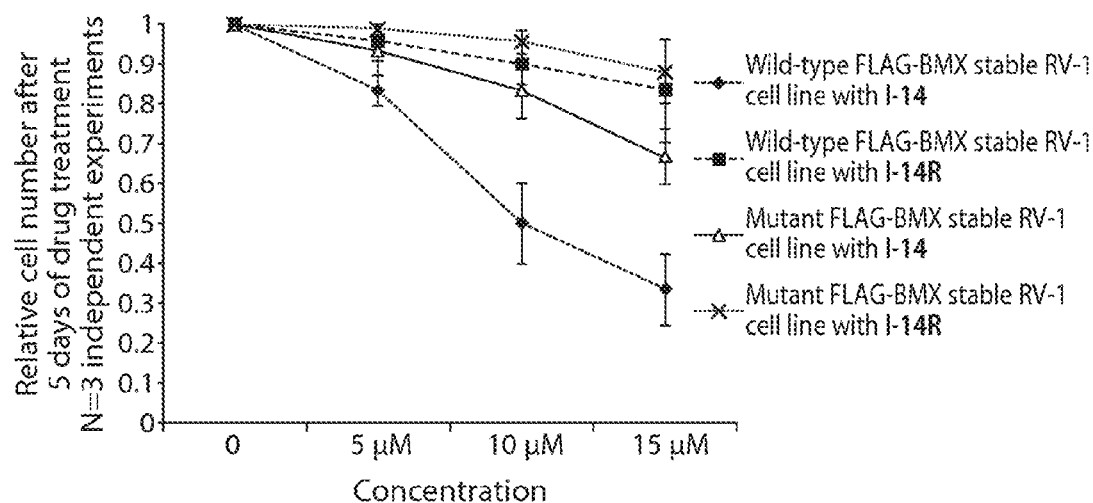
FIG. 16A shows that treatment of BMX wildype cells (versus C496S mutant BMX) with compound I-14 (versus compound I-14R) most potently reduces cell recovery.
Figure 16B:
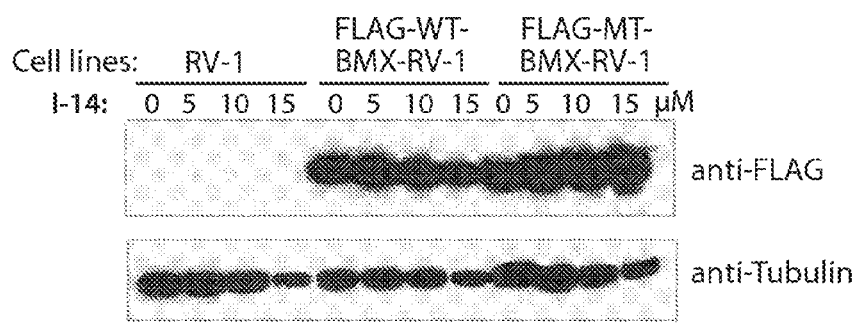
FIG. 16B shows that the wild-type and mutant BMX are expressed at comparable levels.
Figure 17B:
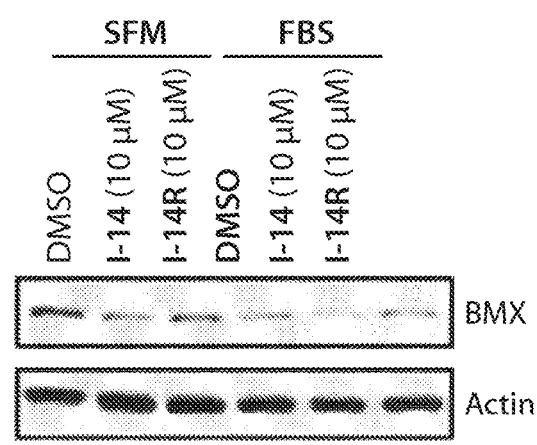
FIG. 17B shows that the irreversible drug (compound I-14) is more potent at decreased BMX.

The Michael receptor moiety (e.g., the group of any one of Formulae (i-1)-(i-17) and (ii-1)-(ii-17)) of a compound of Formula (I) or (II) may be responsible for the covalent attachment of the compound to a kinase. The Michael receptor moiety is typically electrophilic and capable of reacting with a nucleophile such as a cysteine residue of the kinase (e.g., Cys496 of BMX). In contrast, a compound (e.g., compound I-14R, shown below) that does not include a Michael receptor moiety and is not be able to form covalent attachment to a kinase is expected not to show inhibitory activity against the kinase. Illustrated in FIGS. 15A-B is the result of an IP kinase assay of both wide type BMX and BMXC496S with compound I-14 or I-14R. Shown in FIG. 16A is the assaying result of compounds I-14 and I-14R in stably transfected wide type BMX and BMXC496S in RV-1 cancer cell line.

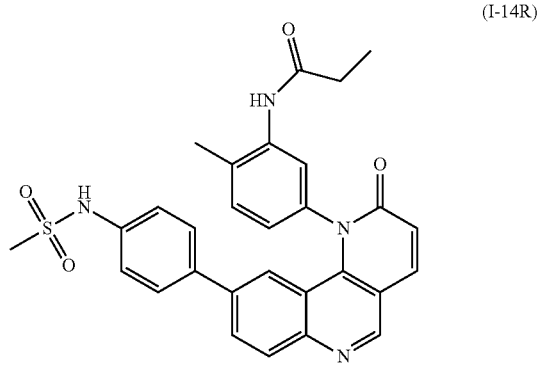 [SMILES: CCC(=O)Nc1cc(-n2c(=O)ccc3cnc4ccc(-c5ccc(NS(C)(=O)=O)cc5)cc4c32)ccc1C]

(I-14R)

Compounds of Formula (I) or (II) (e.g., 1-14 and II-6) may be active in inhibiting a variety of kinases, such as BMX, BLK, BTK, JAK3, EGFR(T790M), ITK, TEC, mTOR, and mTORC1 (Table 4). Also shown in Table 4 are percent control values of these compounds obtained from a DiscoverX binding assay.

TABLE 4

$IC_{50}$ and percent-control values of compounds I-14 and II-6

| | I-14 | | II-6 | |
|---|---|---|---|---|
| Kinase | $IC_{50}$ (nM) | Percent Control (%) | $IC_{50}$ (nM) | Percent Control (%) |
| BMX | 7.99 | 29 | 7.36 | 4.6 |
| BLK | 377 | 40 | 30.2 | 2.4 |
| BTK | 10.4 | 0.95 | 5.34 | 0.2 |
| JAK3 | 175 | 20 | 38.1 | 0 |
| EGFR(T790M) | 4280 | 2.1 | 98.8 | 1.8 |
| ITK | 5250 | 52 | | 29 |
| TEC | 653 | 27 | | 6 |
| mTOR | 325 | | 21.9 | 0 |
| mTORC1 | 7400 | | | |
| CLK1/2 | | | 384/50 | 0.4/1.0 |

Compounds of Formula (I) or (II) (e.g., I-14) may also be active in inhibiting the proliferation of a range of cell lines, such as a panel of murine Ba/F3 cells that were transformed with TEL fusion proteins (e.g., TEL-BMX, TEL-JAK1, TEL-JAK2, TEL-JAK3, TEL-JAK3 (+IL-3), TYK2E957D, TEL-Abl, and TEL-BLK). Shown in Table 5 are $GI_{50}$ (i.e., concentration required to inhibit cell growth by 50%) values of compound I-14 in inhibiting the growth of those exemplary cell lines.

TABLE 5

$GI_{50}$ values of compound I-14 in inhibiting the growth of exemplary cell lines

| | Cell line | | | | | | | |
|---|---|---|---|---|---|---|---|---|
| | WT-Ba/F3 | TEL-BMX | TEL-JAK1 | TEL-JAK2 | TEL-JAK3 | TEL-JAK3 (+IL-3) | TYK2E957D | TEL-Abl | TEL-BLK |
| $GI_{50}$ (µM) | >10 | 0.025 | 4.92 | 5.83 | 7.98 | 7.77 | 6.09 | >10 | 3.64 |

The present study has revealed a unique substrate motif for BMX and shown that BMX functions to amplify tyrosine kinase signaling by phosphorylation of kinase domain pYY sites. It is proposed that the initial priming tyrosine phosphorylation is mediated by autophosphorylation in response to hormone binding or by other kinases (such as SRC for FAK), and that BMX may be recruited through its SH2 domain and mediate transphosphorylation to achieve full activation. While acute downregulation of BMX may suppress multiple signal transduction pathways, chronic loss of BMX activity as occurs in Bmx⁻ mice leads to adaptations, including decreased PHLPP, which may actually enhance downstream signaling in response to some stimuli. The central role of BMX in modulating tyrosine kinase signal transduction pathways indicates that BMX inhibitors may be efficacious in many proliferative diseases (e.g., cancers, benign neoplasms, angiogenesis, inflammatory diseases, and autoimmune diseases) that are characterized by increased tyrosine kinase signaling. Conversely, chronic exposure to BMX inhibitors may enhance signaling downstream of some receptor tyrosine kinases and could be efficacious in some diseases including type 2 diabetes characterized by insulin resistance.

Antiproliferative Activity of I-14 Against Prostate Cancer Cell Lines

The ability of I-14 to inhibit the proliferation of a small panel of prostate cancer cell lines, including RV-1, DU-145, PC-3, VACP, and C4-2 was studied. Shown in Table 6 are GI50 values of compound I-14 in inhibiting the growth of those exemplary prostate cancer cell lines.

TABLE 6

$GI_{50}$ values of compound I-14 in inhibiting the growth of exemplary cell lines

| Cell line | RV-1 | DU-145 | PC-3 | VACP | C4-2 |
|---|---|---|---|---|---|
| $GI_{50}$ (µM) | 2.54 | 4.38 | 5.37 | 2.46 | >10 |

Figure 18A:
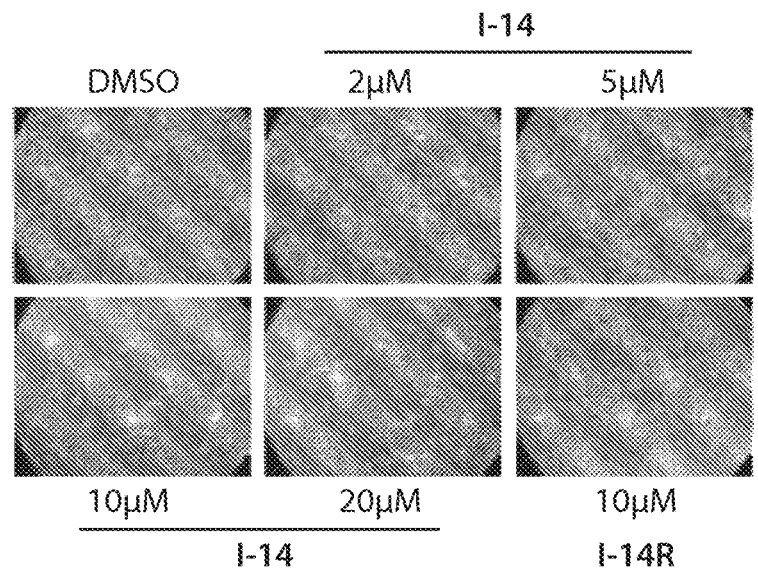
FIGS. 18A-18B show the effects of compound I-14 versus I-14R (at 10 μM) on RV1 cell recovery.
Figure 18B:
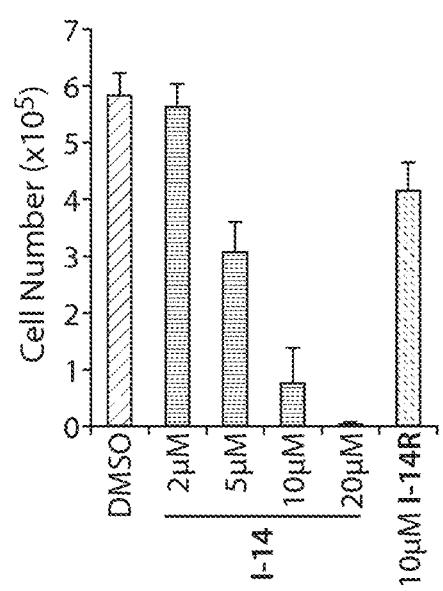
Figure 18C:
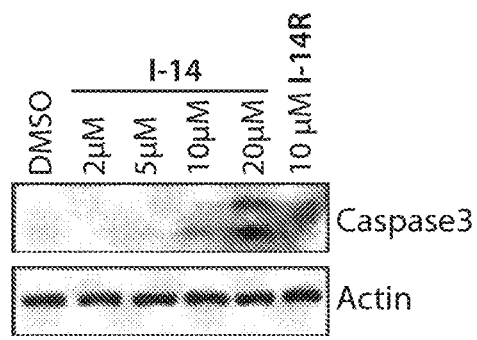
FIG. 18C shows that compound I-14 at 10-20 μM causes apoptosis based on increase cleaved caspase 3.
Figure 18D:
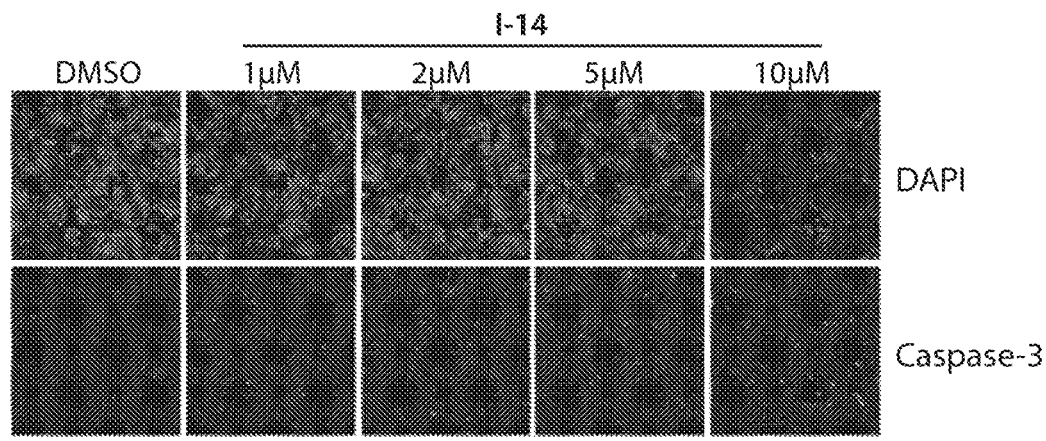
FIGS. 18D-18E show that compound I-14 causes an increase in the number of apoptotic cells based on cleaved caspase 3 staining.
Figure 18E:
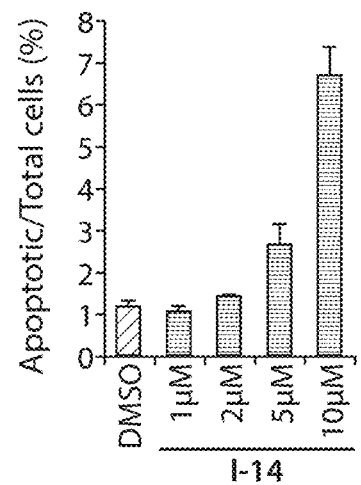
Figure 19:
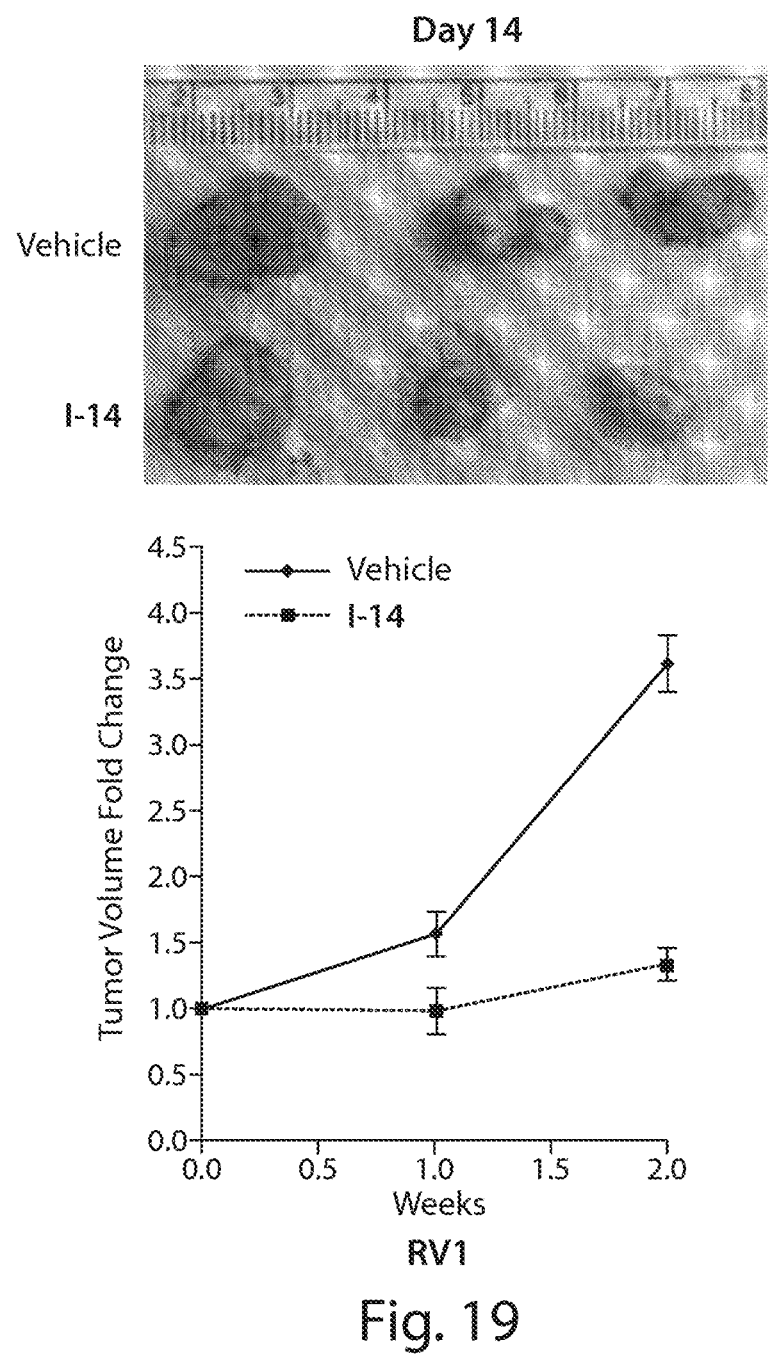
FIG. 19 shows that RV1 xenograft growth over 2 weeks is decreased by in vivo treatment with an BMX inhibitor (e.g., compound I-14).

The effects of I-14 on RV-1 cells was further studied. The proliferation of RV-1 cells following a 5 day incubation with I-14 was inhibited with an IC50 of 2.53 µM. Treatment of RV-1 cells with a 1 uM concentration of I-14 was sufficient to inhibit BMX autophosphorylation. Treatment of RV-1 cells with a 5 pM concentration of 1-14 resulted in reduced cell numbers and induced apoptosis as assessed by Caspase 3 staining. In contrast, the non-covalent analogue, I-14R, did not possess antiproliferative effects against RV-1 cells at concentrations below 10 µM. FIG. 18D shows the foregoing results.

Further, treatment of RV-1 cells with I-14 affected BMX protein levels using RV-1 cells stably transfected with both wild-type and C496S mutant BMX. BMX protein levels in RV-1 cells were significantly reduced by a 72 h treatment of 1-14 (5 µM) but not with I-14R. With blockage of nascent protein synthesis using cyclohexamide, the level of ectopically expressed BMX protein in RV-1 cells was observed to decrease upon treatment with I-14 as compared to the control and treatment with I-14R. Moreover, the depletion could be rescued upon stable overexpression of the C496S mutant BMX. The results suggest that, in addition to inhibiting BMX catalytic activity, I-14 can also decrease BMX protein levels.

Combination Studies of I-14 with MK2206 in Prostate Cancer Cell Line

Figure 20A:
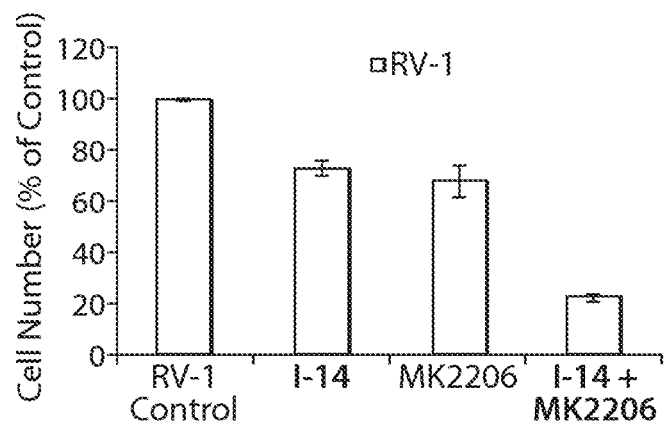
FIG. 20 shows the synergistic combination study of I-14 (2.5 PM) with the Akt inhibitor MK2206 (200 nM) (FIG. 20A) and the flow cytometry analysis of the drug combination effect on apoptosis (FIG. 20B).
Figure 20B:
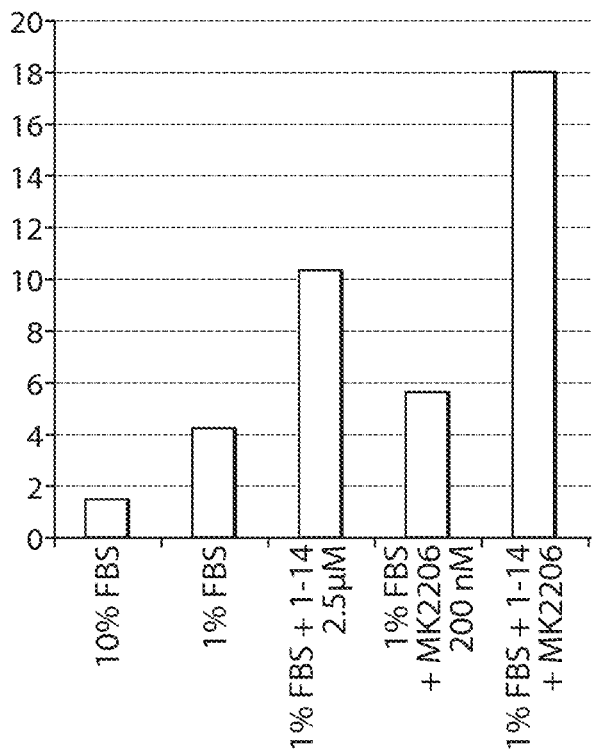
Figure 21:
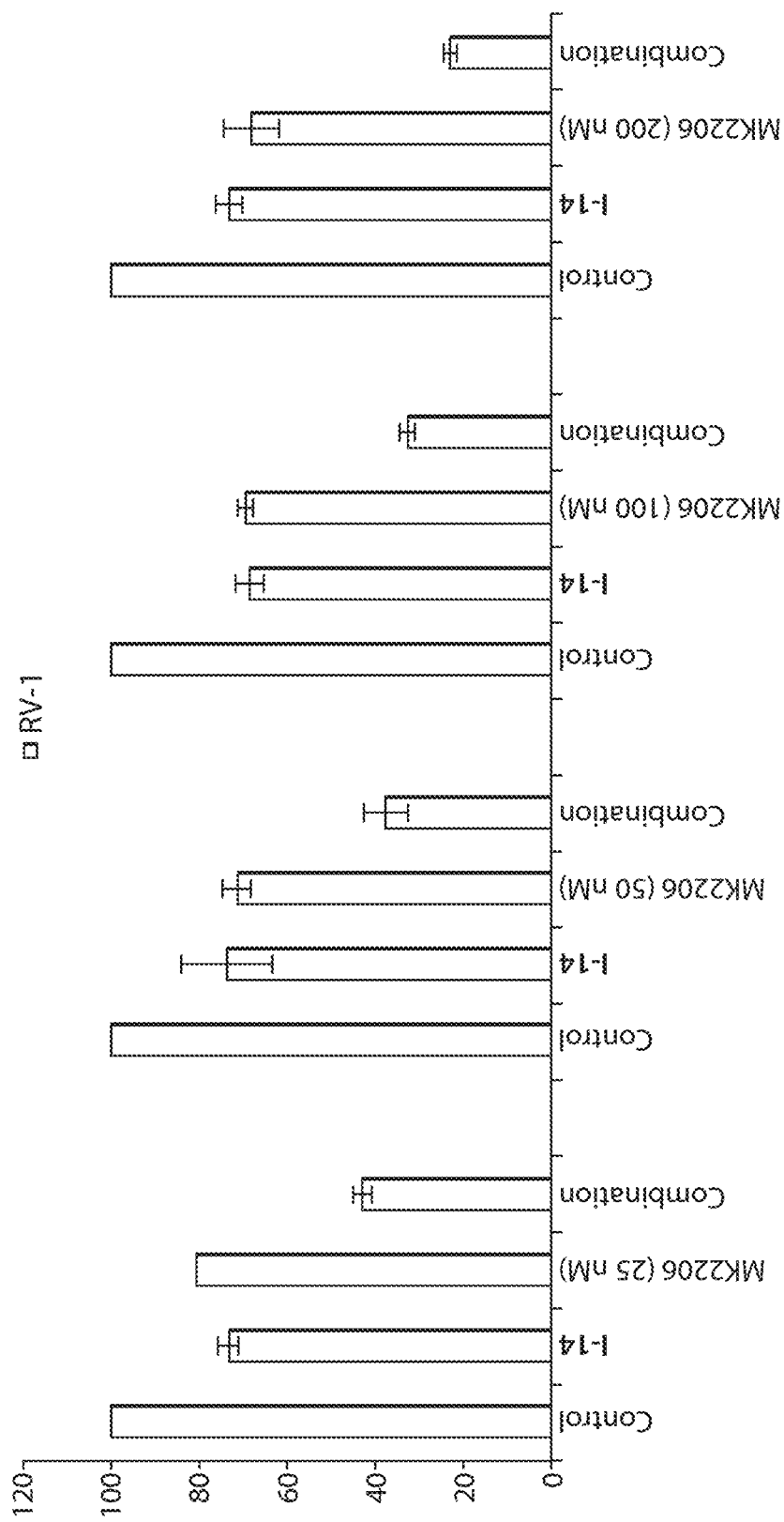
FIG. 21 shows the dose-response experiments at various MK2206 concentrations with I-14 in RV-1 cells after approximately 5-days of inhibitor treatment of RV-1 cells. The cells were cultured in DMEM+1% FBS. 2500 nM of 1-14 was used with and without 25, 50, 100, 200 nM of MK2206.

Dose-response experiments demonstrated with concentrations as low as 25 nM of MK2206 could potentiate the antiproliferative activity of I-14 against RV-1 cells. Fluorescence activated cell sorting (FACS) using propidiumiodide (PI) staining demonstrated that the inhibitor combination increased apoptosis as assessed by the percentage of sub-G1 cells without exerting major effects on the cell cycledistribution. FIGS. 20A, 20B, and 21 show results of the I-14 and MK2206 combination studies.

Apoptosis Analysis of B-Cells by II-4

Figure 22:
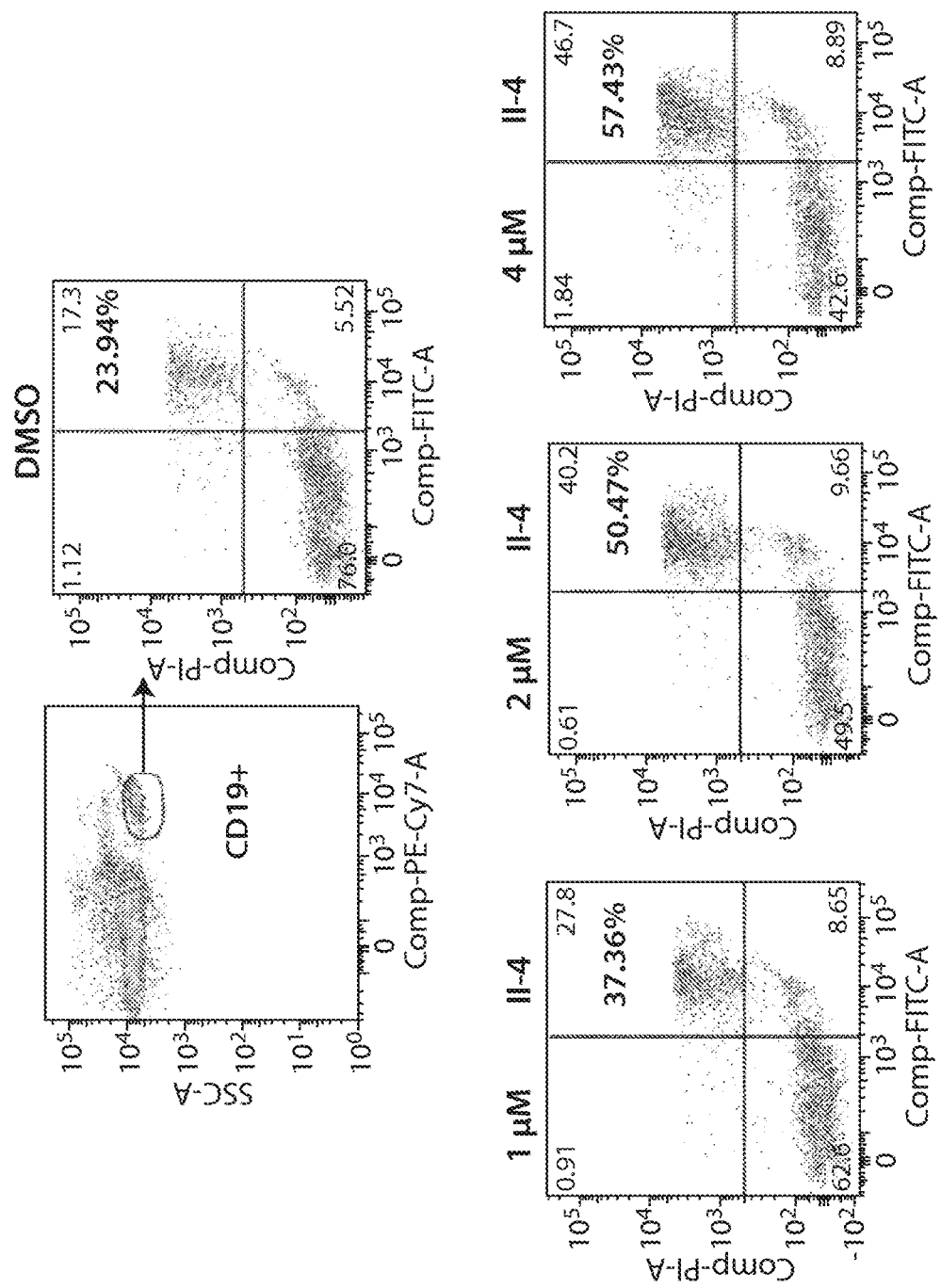
FIG. 22 show survival assessment by annexin V/propidium iodide staining for CD19+B-cells isolated from a patient and treated with II-4.
Figure 23:
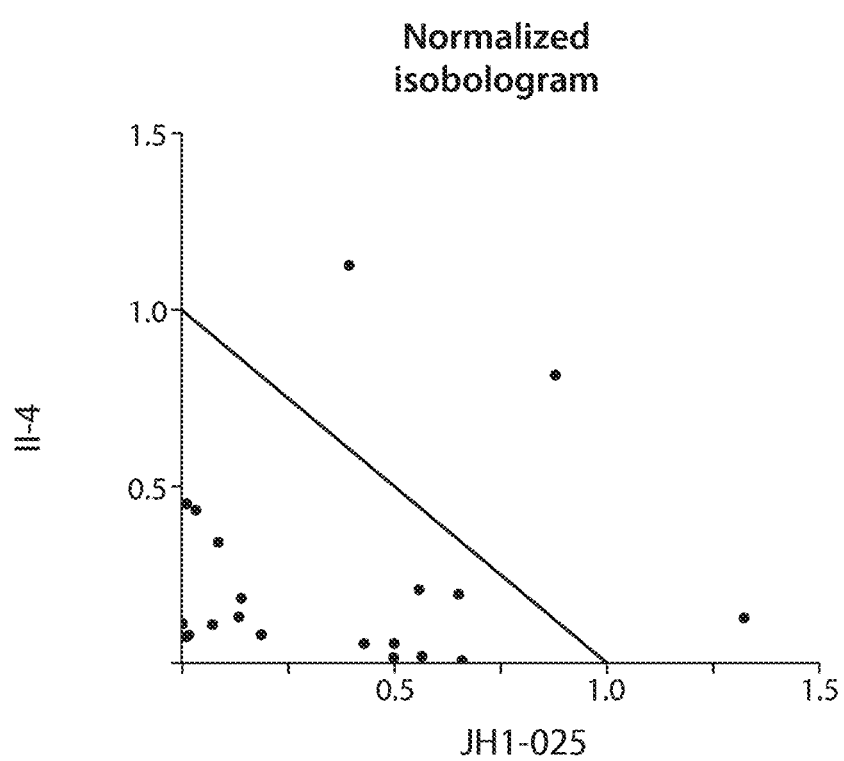
FIG. 23 shows a normalized isobologram for II-4 synergy with JH1-025 (an IRAK1/4 inhibitor).

In CD 19+B-cells isolated from a waldenstrom's macroglobulinemia patient following six months of ibrutinib treatment, II-4 effectively killed ex vivo cells (see FIG. 22). Similar results have been obtained for two other patients.

TABLE 7

IC$_{50}$ values for various compounds with exemplary kinases.

| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| I-7 | 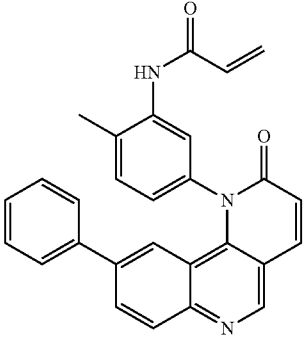 [SMILES: C=CC(=O)Nc1cc(-n2c(=O)ccc3cnc4ccc(-c5ccccc5)cc4c32)ccc1C] | 25 | 16 | 210 | 250 | — | — | — | — |
| I-8 | 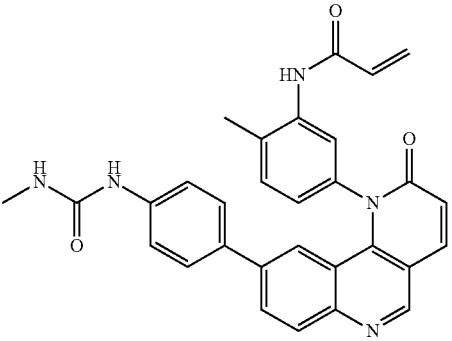 [SMILES: C=CC(=O)Nc1cc(-n2c(=O)ccc3cnc4ccc(-c5ccc(NC(=O)NC)cc5)cc4c32)ccc1C] | 66 | — | — | — | — | — | — | 4170 |
| I-9 | 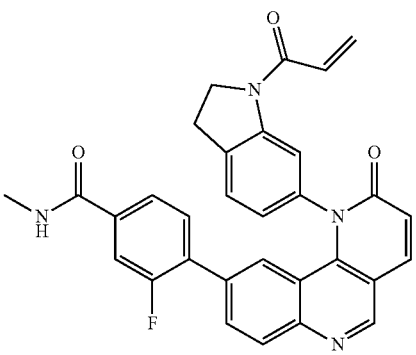 [SMILES: C=CC(=O)N1CCc2ccc(-n3c(=O)ccc4cnc5ccc(-c6ccc(C(=O)NC)cc6F)cc5c43)cc21] | 54 | — | — | — | — | — | — | — |

TABLE 7-continued

IC₅₀ values for various compounds with exemplary kinases.

| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| I-10 | 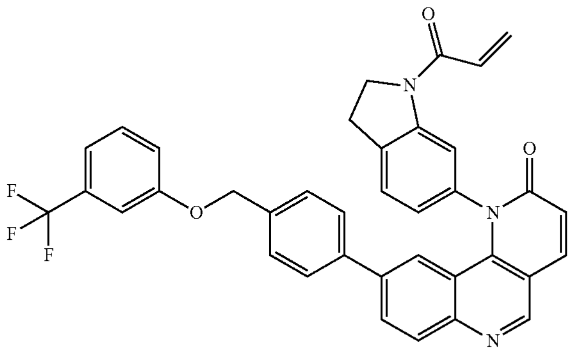 [SMILES: C=CC(=O)N1CCc2ccc(-n3c(=O)ccc4cnc5ccc(-c6ccc(COc7cccc(C(F)(F)F)c7)cc6)cc5c43)cc21] | 1060 | >10,000 | — | — | — | — | — | — |
| I-11 | 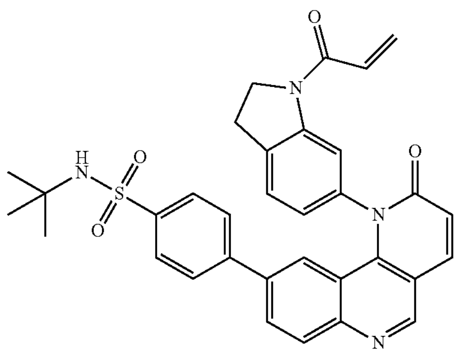 [SMILES: C=CC(=O)N1CCc2ccc(-n3c(=O)ccc4cnc5ccc(-c6ccc(S(=O)(=O)NC(C)(C)C)cc6)cc5c43)cc21] | 11 | 18 | 536 | — | — | — | — | — |
| I-12 | 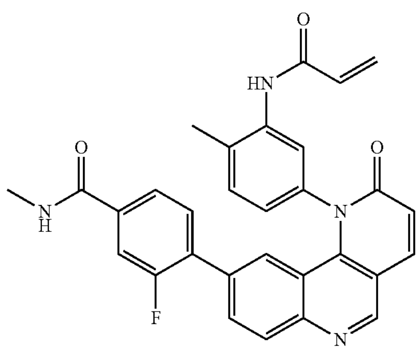 [SMILES: C=CC(=O)Nc1cc(-n2c(=O)ccc3cnc4ccc(-c5ccc(C(=O)NC)cc5F)cc4c32)ccc1C] | — | 173 | — | — | — | — | — | — |
| I-13 | 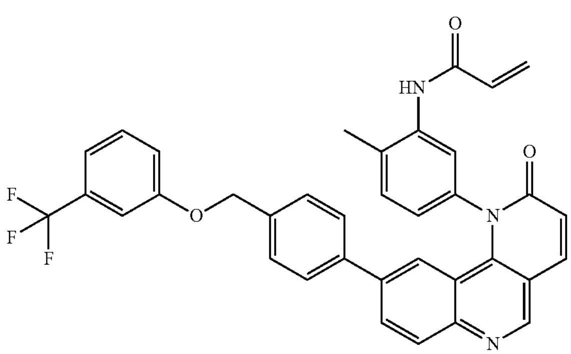 [SMILES: C=CC(=O)Nc1cc(-n2c(=O)ccc3cnc4ccc(-c5ccc(COc6cccc(C(F)(F)F)c6)cc5)cc4c32)ccc1C] | 37 | 28 | — | — | — | — | — | — |

TABLE 7-continued
IC$_{50}$ values for various compounds with exemplary kinases.
| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| I-14 | 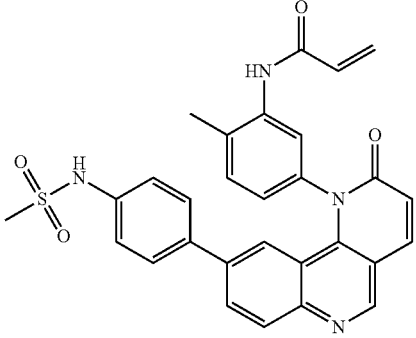 [SMILES: C=CC(=O)Nc1cc(-n2c(=O)ccc3cnc4ccc(-c5ccc(NS(C)(=O)=O)cc5)cc4c32)ccc1C] | 49 | 8 | 325 | 377 | 653 | >3300 | — | 175 |
| I-15 | 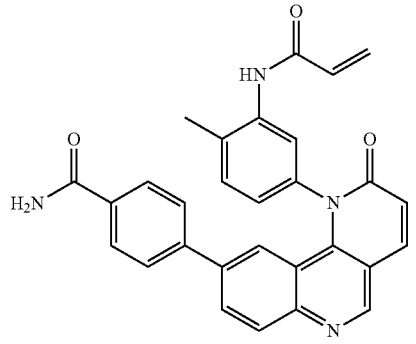 [SMILES: C=CC(=O)Nc1cc(-n2c(=O)ccc3cnc4ccc(-c5ccc(C(N)=O)cc5)cc4c32)ccc1C] | 79 | 41 | — | — | — | — | — | — |
| I-16 | 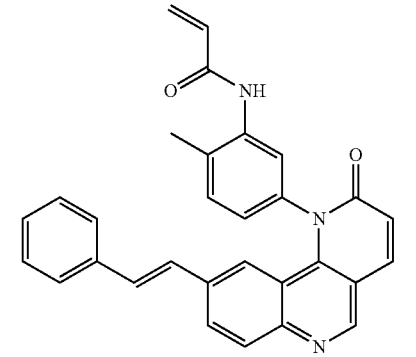 [SMILES: C=CC(=O)Nc1cc(-n2c(=O)ccc3cnc4ccc(/C=C/c5ccccc5)cc4c32)ccc1C] | 105 | 28 | — | — | — | — | — | — |
| I-17 | 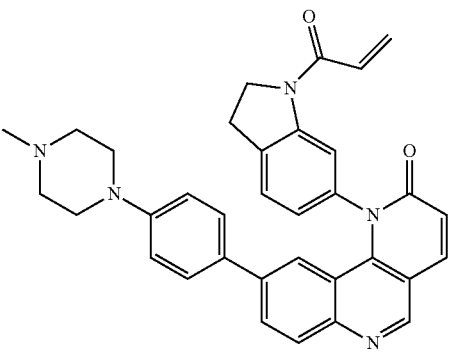 [SMILES: C=CC(=O)N1CCc2ccc(-n3c(=O)ccc4cnc5ccc(-c6ccc(N7CCN(C)CC7)cc6)cc5c43)cc21] | 155 | 399 | 516 | — | — | — | — | 5580 |

TABLE 7-continued

IC₅₀ values for various compounds with exemplary kinases.

| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| I-18 | 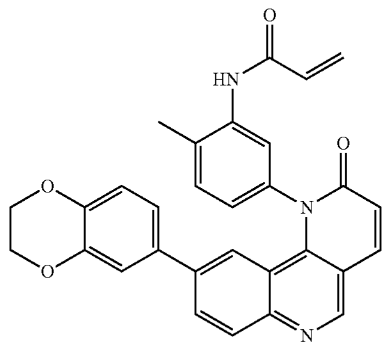 [SMILES: C=CC(=O)Nc1cc(-n2c(=O)ccc3cnc4ccc(-c5ccc6c(c5)OCCO6)cc4c32)ccc1C] | 16 | 13 | 642 | — | — | — | — | — |
| I-19 | 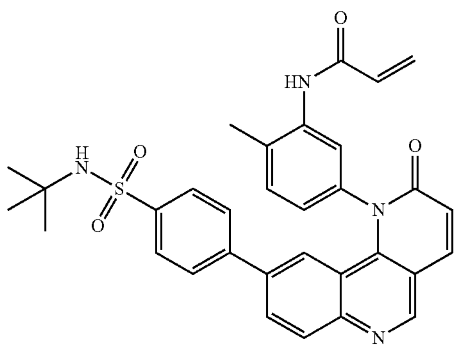 [SMILES: C=CC(=O)Nc1cc(-n2c(=O)ccc3cnc4ccc(-c5ccc(S(=O)(=O)NC(C)(C)C)cc5)cc4c32)ccc1C] | — | — | — | — | — | — | — | — |
| I-20 | 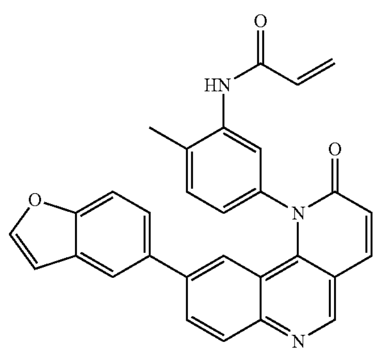 [SMILES: C=CC(=O)Nc1cc(-n2c(=O)ccc3cnc4ccc(-c5ccc6occc6c5)cc4c32)ccc1C] | — | — | — | — | — | — | — | — |
| I-21 | 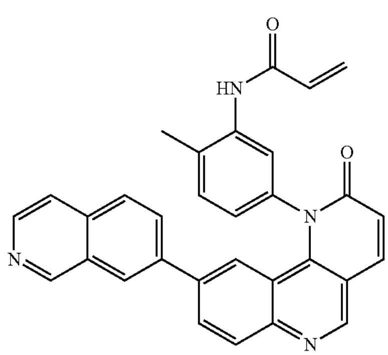 [SMILES: C=CC(=O)Nc1cc(-n2c(=O)ccc3cnc4ccc(-c5ccc6ccncc6c5)cc4c32)ccc1C] | — | — | — | — | — | — | — | — |

TABLE 7-continued

IC₅₀ values for various compounds with exemplary kinases.

| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| I-22 | 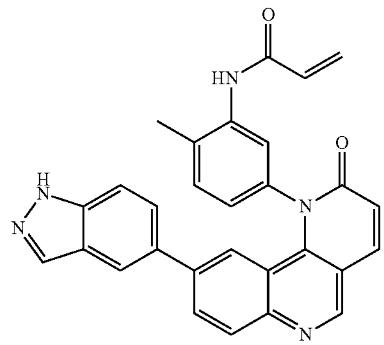 [SMILES: C=CC(=O)Nc1cc(-n2c(=O)ccc3cnc4ccc(-c5ccc6[nH]ncc6c5)cc4c32)ccc1C] | — | — | — | — | — | — | — | — |
| I-23 | 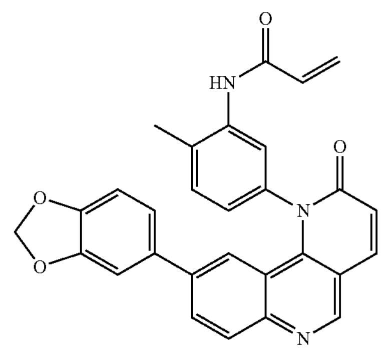 [SMILES: C=CC(=O)Nc1cc(-n2c(=O)ccc3cnc4ccc(-c5ccc6c(c5)OCO6)cc4c32)ccc1C] | — | — | — | — | — | — | — | — |
| I-24 | 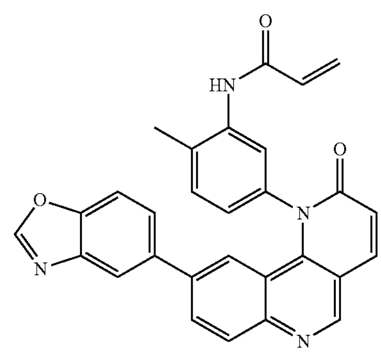 [SMILES: C=CC(=O)Nc1cc(-n2c(=O)ccc3cnc4ccc(-c5ccc6ocnc6c5)cc4c32)ccc1C] | — | — | — | — | — | — | — | — |
| I-25 | 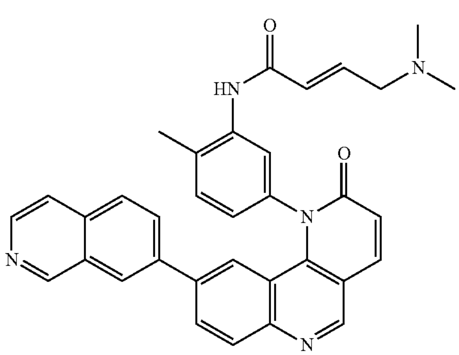 [SMILES: Cc1ccc(-n2c(=O)ccc3cnc4ccc(-c5ccc6ccncc6c5)cc4c32)cc1NC(=O)/C=C/CN(C)C] | — | — | — | — | — | — | — | — |

TABLE 7-continued

IC$_{50}$ values for various compounds with exemplary kinases.

| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| I-26 | 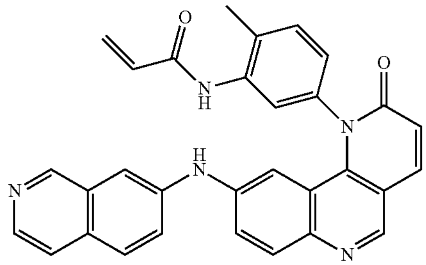 [SMILES: C=CC(=O)Nc1cc(-n2c(=O)ccc3cnc4ccc(Nc5ccc6ccncc6c5)cc4c32)ccc1C] | — | — | — | — | — | — | — | — |
| I-27 | 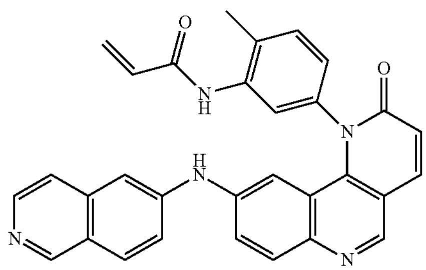 [SMILES: C=CC(=O)Nc1cc(-n2c(=O)ccc3cnc4ccc(Nc5ccc6cnccc6c5)cc4c32)ccc1C] | — | — | — | — | — | — | — | — |
| I-28 | 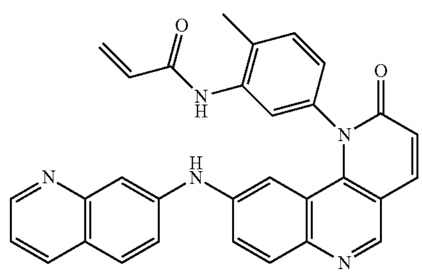 [SMILES: C=CC(=O)Nc1cc(-n2c(=O)ccc3cnc4ccc(Nc5ccc6cccnc6c5)cc4c32)ccc1C] | — | — | — | — | — | — | — | — |
| I-29 | 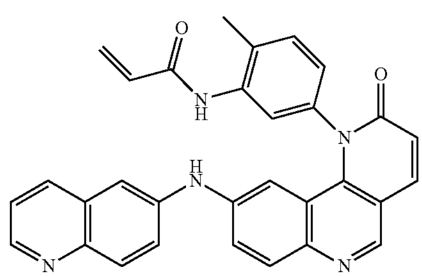 [SMILES: C=CC(=O)Nc1cc(-n2c(=O)ccc3cnc4ccc(Nc5ccc6ncccc6c5)cc4c32)ccc1C] | — | — | — | — | — | — | — | — |
| II-3 | 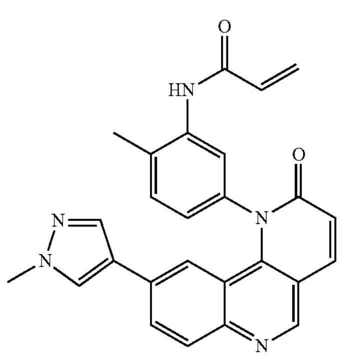 [SMILES: C=CC(=O)Nc1cc(-n2c(=O)ccc3cnc4ccc(-c5cnn(C)c5)cc4c32)ccc1C] | 14 | 8 | 173 | — | — | — | — | — |

TABLE 7-continued

IC$_{50}$ values for various compounds with exemplary kinases.

| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| II-4 | 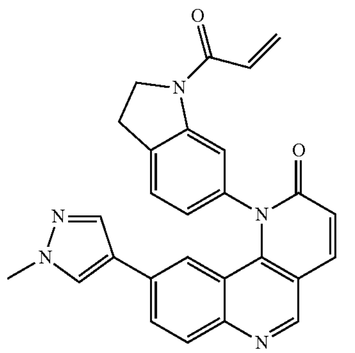 [SMILES: C=CC(=O)N1CCc2ccc(-n3c(=O)ccc4cnc5ccc(-c6cnn(C)c6)cc5c43)cc21] | 7 | 7 | 1200 | 366 | 195 | >3300 | — | 5180 |
| II-5 | 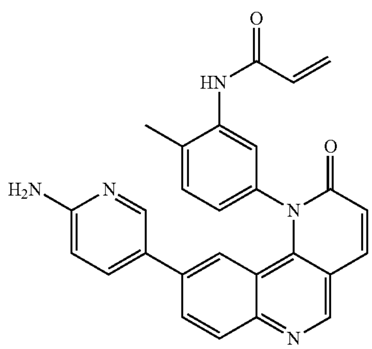 [SMILES: C=CC(=O)Nc1cc(-n2c(=O)ccc3cnc4ccc(-c5ccc(N)nc5)cc4c32)ccc1C] | 16 | 13 | 17 | — | — | — | — | — |
| II-6 | 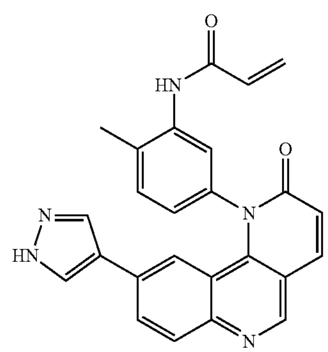 [SMILES: C=CC(=O)Nc1cc(-n2c(=O)ccc3cnc4ccc(-c5cn[nH]c5)cc4c32)ccc1C] | 5 | 7 | 22 | 30 | — | 717 | 384/50 | 38 |
| II-7 | 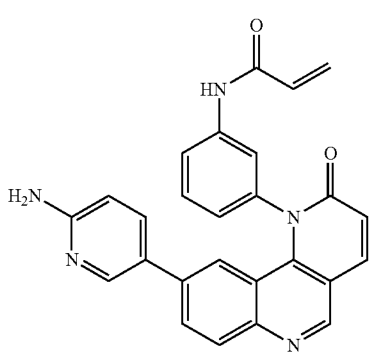 [SMILES: C=CC(=O)Nc1cccc(-n2c(=O)ccc3cnc4ccc(-c5ccc(N)nc5)cc4c32)c1] | 19 | 16 | 19 | — | — | — | — | — |

TABLE 7-continued

IC$_{50}$ values for various compounds with exemplary kinases.

| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| II-8 | 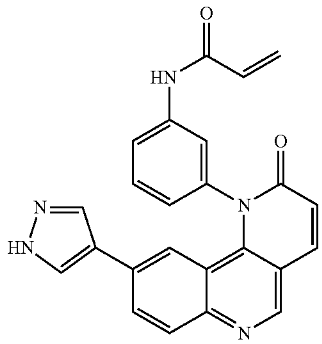 [SMILES: C=CC(=O)Nc1cccc(-n2c(=O)ccc3cnc4ccc(-c5cn[nH]c5)cc4c32)c1] | 18 | 11 | 41 | — | — | — | — | — |
| II-9 | 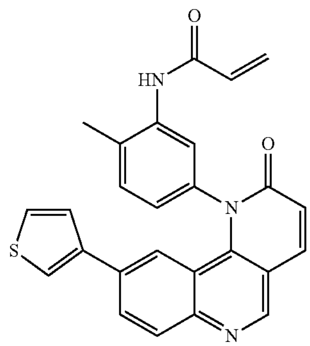 [SMILES: C=CC(=O)Nc1cc(-n2c(=O)ccc3cnc4ccc(-c5ccsc5)cc4c32)ccc1C] | 39 | 20 | 369 | — | — | — | — | — |
| II-10 | 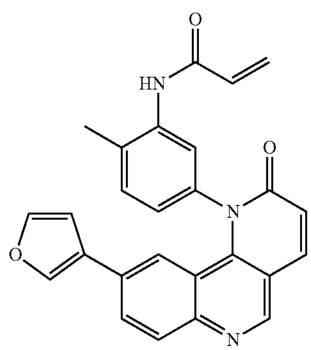 [SMILES: C=CC(=O)Nc1cc(-n2c(=O)ccc3cnc4ccc(-c5ccoc5)cc4c32)ccc1C] | 17 | 12 | 4790 | — | — | — | — | 492 |
| II-11 | 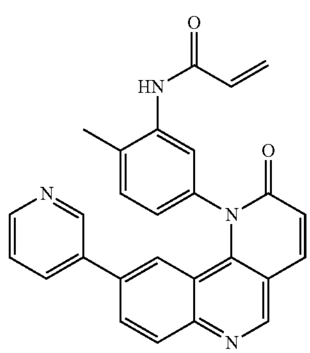 [SMILES: C=CC(=O)Nc1cc(-n2c(=O)ccc3cnc4ccc(-c5cccnc5)cc4c32)ccc1C] | 115 | 66 | 1 | 1950 | — | — | — | 1520 |

TABLE 7-continued

IC$_{50}$ values for various compounds with exemplary kinases.

| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| II-12 | 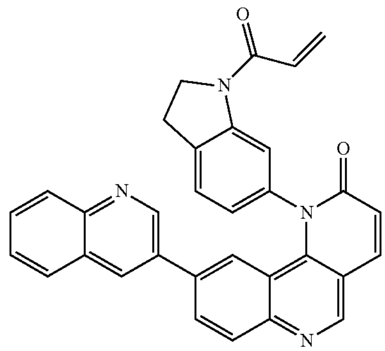 [SMILES: C=CC(=O)N1CCc2ccc(-n3c(=O)ccc4cnc5ccc(-c6cnc7ccccc7c6)cc5c43)cc21] | 7 | 6 | 59 | — | — | — | — | — |
| II-13 | 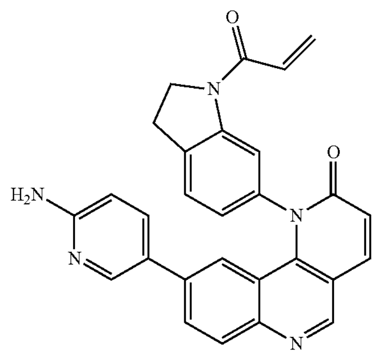 [SMILES: C=CC(=O)N1CCc2ccc(-n3c(=O)ccc4cnc5ccc(-c6ccc(N)nc6)cc5c43)cc21] | 6 | 13 | 98 | 300 | 27 | — | — | 5640 |
| II-14 | 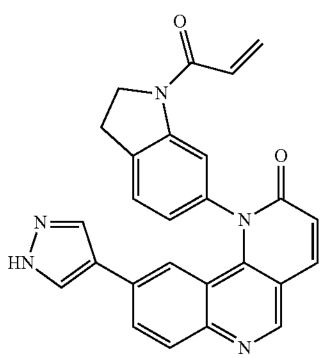 [SMILES: C=CC(=O)N1CCc2ccc(-n3c(=O)ccc4cnc5ccc(-c6cn[nH]c6)cc5c43)cc21] | 12 | 9 | 209 | 247 | 57 | — | — | 2150 |
| II-15 | 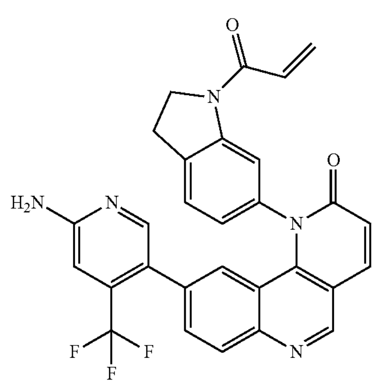 [SMILES: C=CC(=O)N1CCc2ccc(-n3c(=O)ccc4cnc5ccc(-c6cnc(N)cc6C(F)(F)F)cc5c43)cc21] | 337 | — | — | — | — | — | — | — |

TABLE 7-continued

IC$_{50}$ values for various compounds with exemplary kinases.

| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| II-16 | 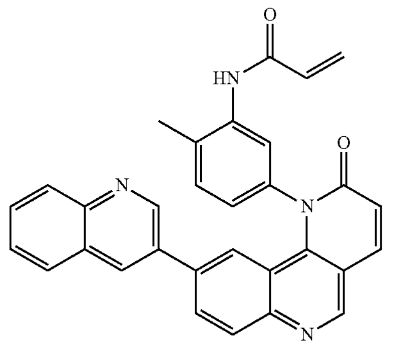 [SMILES: C=CC(=O)Nc1cc(-n2c(=O)ccc3cnc4ccc(-c5cnc6ccccc6c5)cc4c32)ccc1C] | 25 | 19 | 32 | — | — | — | — | — |
| II-17 | 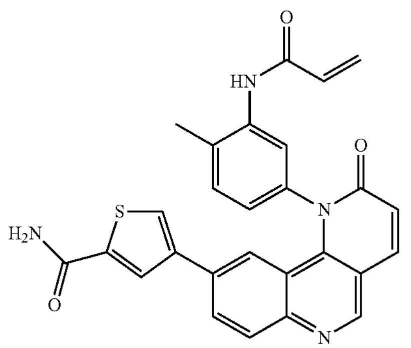 [SMILES: C=CC(=O)Nc1cc(-n2c(=O)ccc3cnc4ccc(-c5csc(C(N)=O)c5)cc4c32)ccc1C] | — | — | — | — | — | — | — | — |
| II-18 | 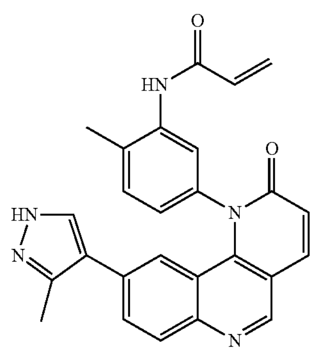 [SMILES: C=CC(=O)Nc1cc(-n2c(=O)ccc3cnc4ccc(-c5c[nH]nc5C)cc4c32)ccc1C] | — | — | — | — | — | — | — | — |
| II-19 | 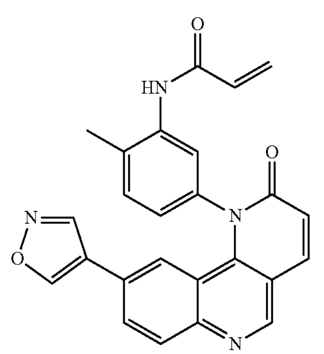 | — | — | — | — | — | — | — | — |

TABLE 7-continued

IC$_{50}$ values for various compounds with exemplary kinases.

| Compound No. | Structure | BTK IC$_{50}$ (nM) | BMX IC$_{50}$ (nM) | mTOR IC$_{50}$ (nM) | BLK IC$_{50}$ (nM) | Tec IC$_{50}$ (nM) | TAK1 IC$_{50}$ (nM) | CLK1/2 IC$_{50}$ (nM) | JAK3 IC$_{50}$ (nM) |
|---|---|---|---|---|---|---|---|---|---|
| II-20 | 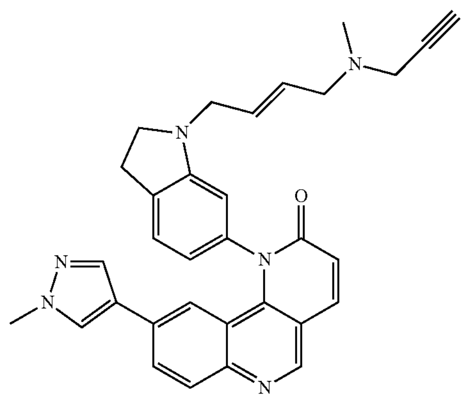 [SMILES: C#CCN(C)C/C=C/CN1CCc2ccc(-n3c(=O)ccc4cnc5ccc(-c6cnn(C)c6)cc5c43)cc21] | 641 | 479 | — | — | — | — | — | — |
| II-21 | 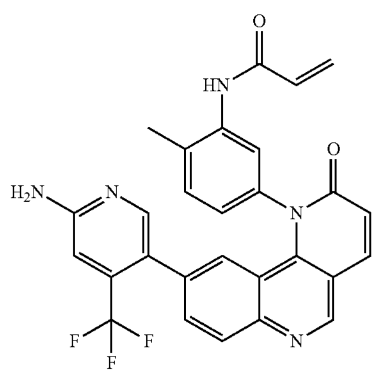 [SMILES: C=CC(=O)Nc1cc(-n2c(=O)ccc3cnc4ccc(-c5cnc(N)cc5C(F)(F)F)cc4c32)ccc1C] | — | — | — | — | — | — | — | — |
| II-22 | 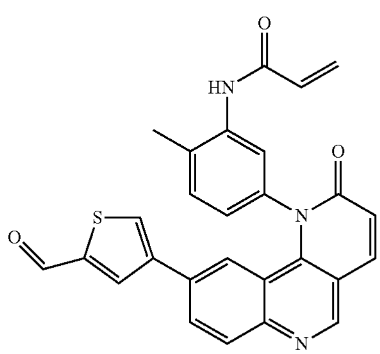 [SMILES: C=CC(=O)Nc1cc(-n2c(=O)ccc3cnc4ccc(-c5csc(C=O)c5)cc4c32)ccc1C] | — | — | — | — | — | — | — | — |
| II-23 | 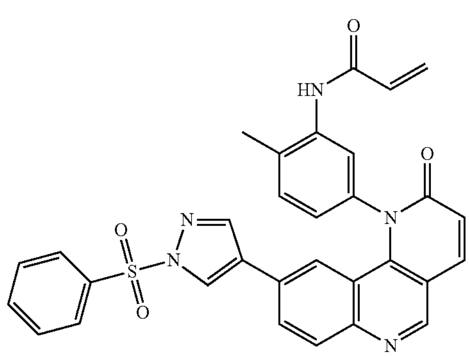 [SMILES: C=CC(=O)Nc1cc(-n2c(=O)ccc3cnc4ccc(-c5cnn(S(=O)(=O)c6ccccc6)c5)cc4c32)ccc1C] | — | — | — | — | — | — | — | — |

TABLE 8

EC50 values for various compounds in exemplary WM and lymphoma cell lines.

| Internal Molecule Name | Compound No. | Structure | BCWM.1 $EC_{50}$ (nM) | MWCL-1 $EC_{50}$ (nM) | PRCIWM-1 $EC_{50}$ (nM) | OCI-Ly3 $EC_{50}$ (nM) | Ramos $EC_{50}$ (nM) | OCI-Ly19 $EC_{50}$ (nM) |
|---|---|---|---|---|---|---|---|---|
| QL-XI-77 | I-7 | 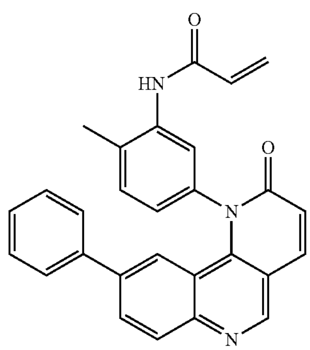 [SMILES: C=CC(=O)Nc1cc(-n2c(=O)ccc3cnc4ccc(-c5ccccc5)cc4c32)ccc1C] | 180 | 950 | — | 380 | 310 | 10 |
| QL-XII-37 | I-8 | 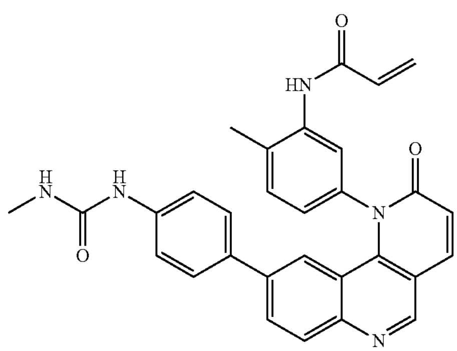 [SMILES: C=CC(=O)Nc1cc(-n2c(=O)ccc3cnc4ccc(-c5ccc(NC(=O)NC)cc5)cc4c32)ccc1C] | — | — | — | — | — | — |
| QL-XII-48 | I-9 | 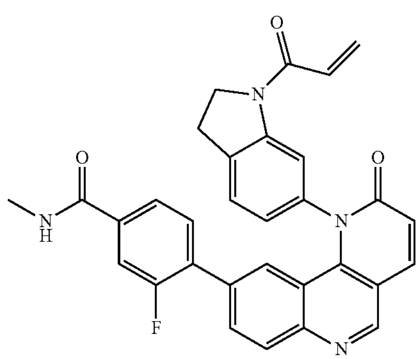 [SMILES: C=CC(=O)N1CCc2ccc(-n3c(=O)ccc4cnc5ccc(-c6ccc(C(=O)NC)cc6F)cc5c43)cc21] | — | — | — | — | — | — |
| QL-XII-50 | I-10 | 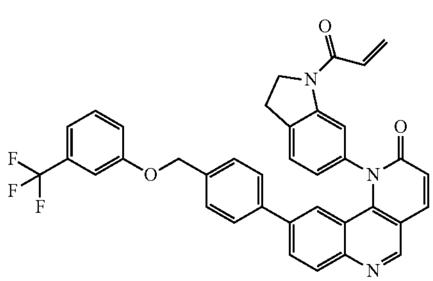 [SMILES: C=CC(=O)N1CCc2ccc(-n3c(=O)ccc4cnc5ccc(-c6ccc(COc7cccc(C(F)(F)F)c7)cc6)cc5c43)cc21] | 2120 | 5750 | — | 3660 | 3770 | 290 |

TABLE 8-continued

EC50 values for various compounds in exemplary WM and lymphoma cell lines.

| Internal Molecule Name | Compound No. | Structure | BCWM.1 EC$_{50}$ (nM) | MWCL-1 EC$_{50}$ (nM) | PRCIWM-1 EC$_{50}$ (nM) | OCI-Ly3 EC$_{50}$ (nM) | Ramos EC$_{50}$ (nM) | OCI-Ly19 EC$_{50}$ (nM) |
|---|---|---|---|---|---|---|---|---|
| QL-XII-51 | I-11 | [structure] | — | — | — | — | — | — |
| QL-XII-57 | I-12 | [structure] | — | — | — | — | — | — |
| QL-XII-58 | I-13 | [structure] | — | — | — | — | — | — |
| QL-XII-61 | I-14 | [structure] | 1100 | 1390 | — | >20,000 | >20,000 | 900 |

TABLE 8-continued

EC50 values for various compounds in exemplary WM and lymphoma cell lines.

| Internal Molecule Name | Compound No. | Structure | BCWM.1 EC$_{50}$ (nM) | MWCL-1 EC$_{50}$ (nM) | PRCIWM-1 EC$_{50}$ (nM) | OCI-Ly3 EC$_{50}$ (nM) | Ramos EC$_{50}$ (nM) | OCI-Ly19 EC$_{50}$ (nM) |
|---|---|---|---|---|---|---|---|---|
| QL-XII-63 | I-15 | 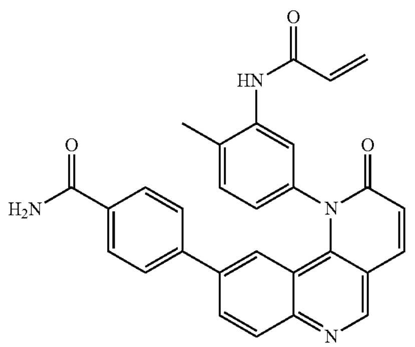 [SMILES: C=CC(=O)Nc1cc(-n2c(=O)ccc3cnc4ccc(-c5ccc(C(N)=O)cc5)cc4c32)ccc1C] | — | — | — | — | — | — |
| QL-XII-66 | I-16 | 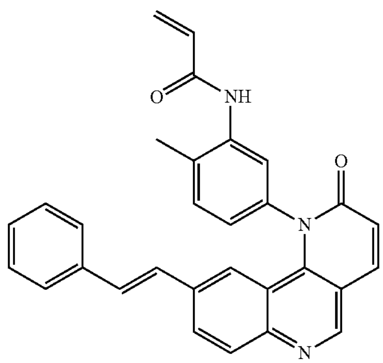 [SMILES: C=CC(=O)Nc1cc(-n2c(=O)ccc3cnc4ccc(/C=C/c5ccccc5)cc4c32)ccc1C] | 490 | 1780 | — | 1120 | 420 | 80 |
| QL-XII-91 | I-17 | 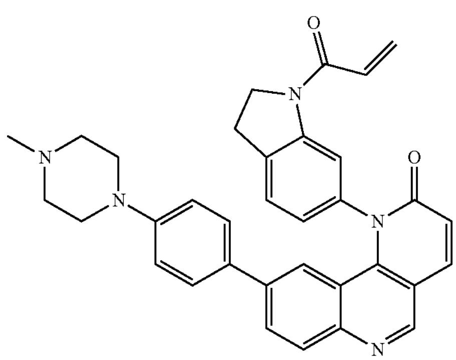 [SMILES: C=CC(=O)N1CCc2ccc(-n3c(=O)ccc4cnc5ccc(-c6ccc(N7CCN(C)CC7)cc6)cc5c43)cc21] | 490 | 1780 | — | 1120 | 420 | 80 |
| QL-XII-115 | I-18 | 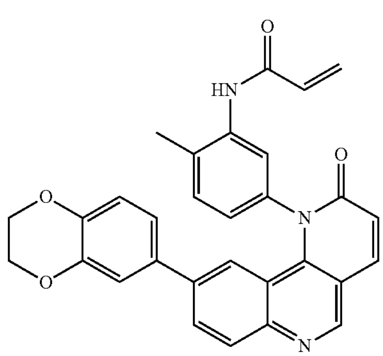 [SMILES: C=CC(=O)Nc1cc(-n2c(=O)ccc3cnc4ccc(-c5ccc6c(c5)OCCO6)cc4c32)ccc1C] | — | — | — | — | — | — |

TABLE 8-continued

EC50 values for various compounds in exemplary WM and lymphoma cell lines.

| Internal Molecule Name | Compound No. | Structure | BCWM.1 EC$_{50}$ (nM) | MWCL-1 EC$_{50}$ (nM) | PRCIWM-1 EC$_{50}$ (nM) | OCI-Ly3 EC$_{50}$ (nM) | Ramos EC$_{50}$ (nM) | OCI-Ly19 EC$_{50}$ (nM) |
|---|---|---|---|---|---|---|---|---|
| QL-XII-59 | I-19 | 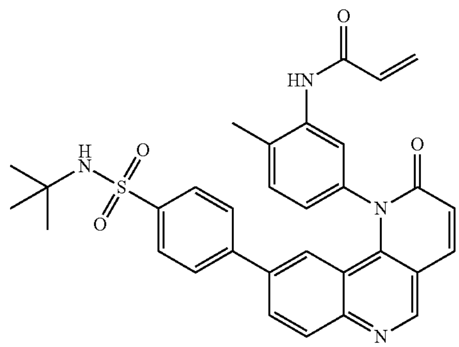 [SMILES: C=CC(=O)Nc1cc(-n2c(=O)ccc3cnc4ccc(-c5ccc(S(=O)(=O)NC(C)(C)C)cc5)cc4c32)ccc1C] | — | — | — | — | — | — |
| YKL-02-030 | I-20 | 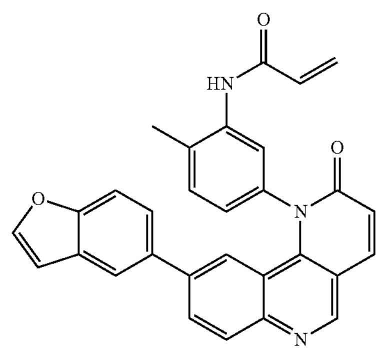 [SMILES: C=CC(=O)Nc1cc(-n2c(=O)ccc3cnc4ccc(-c5ccc6occc6c5)cc4c32)ccc1C] | 1020 | 798 | — | 1100 | 602 | >20000 |
| YKL-02-039 | I-21 | 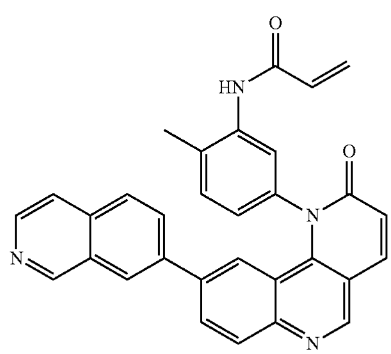 [SMILES: C=CC(=O)Nc1cc(-n2c(=O)ccc3cnc4ccc(-c5ccc6ccncc6c5)cc4c32)ccc1C] | 93 | 56 | — | 109 | 57 | 90 |
| YKL-02-041 | I-22 | 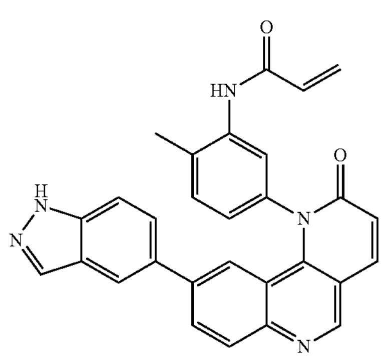 [SMILES: C=CC(=O)Nc1cc(-n2c(=O)ccc3cnc4ccc(-c5ccc6[nH]ncc6c5)cc4c32)ccc1C] | 203 | 117 | — | 180 | 91 | 51 |

TABLE 8-continued

EC50 values for various compounds in exemplary WM and lymphoma cell lines.

| Internal Molecule Name | Compound No. | Structure | BCWM.1 $EC_{50}$ (nM) | MWCL-1 $EC_{50}$ (nM) | PRCIWM-1 $EC_{50}$ (nM) | OCI-Ly3 $EC_{50}$ (nM) | Ramos $EC_{50}$ (nM) | OCI-Ly19 $EC_{50}$ (nM) |
|---|---|---|---|---|---|---|---|---|
| YKL-02-057 | I-23 | 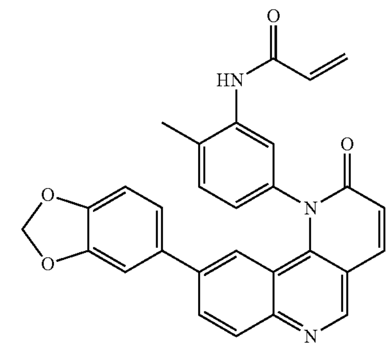 [SMILES: C=CC(=O)Nc1cc(-n2c(=O)ccc3cnc4ccc(-c5ccc6c(c5)OCO6)cc4c32)ccc1C] | 849 | 610 | | 1170 | 653 | 19 |
| YKL-02-070 | I-24 | 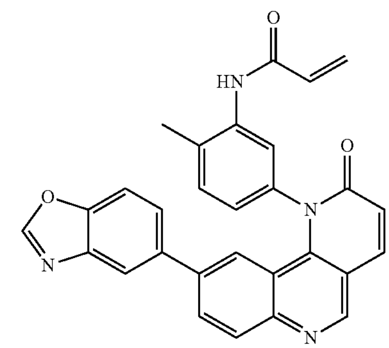 [SMILES: C=CC(=O)Nc1cc(-n2c(=O)ccc3cnc4ccc(-c5ccc6ocnc6c5)cc4c32)ccc1C] | 345 | 284 | — | 516 | 355 | 24 |
| YKL-02-157 | I-25 | 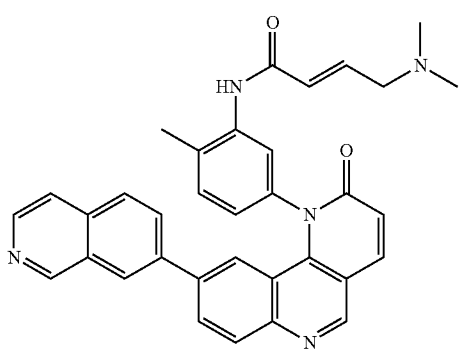 [SMILES: Cc1ccc(-n2c(=O)ccc3cnc4ccc(-c5ccc6ccncc6c5)cc4c32)cc1NC(=O)/C=C/CN(C)C] | — | — | — | — | — | — |
| YKL-02-146 | I-26 | 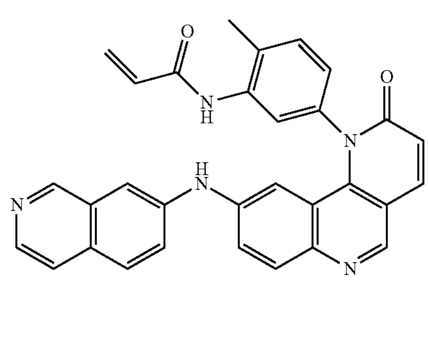 [SMILES: C=CC(=O)Nc1cc(-n2c(=O)ccc3cnc4ccc(Nc5ccc6ccncc6c5)cc4c32)ccc1C] | 3580 | 6820 | 663 | 3340 | 3830 | 659 |

TABLE 8-continued

EC50 values for various compounds in exemplary WM and lymphoma cell lines.

| Internal Molecule Name | Compound No. | Structure | BCWM.1 EC$_{50}$ (nM) | MWCL-1 EC$_{50}$ (nM) | PRCIWM-1 EC$_{50}$ (nM) | OCI-Ly3 EC$_{50}$ (nM) | Ramos EC$_{50}$ (nM) | OCI-Ly19 EC$_{50}$ (nM) |
|---|---|---|---|---|---|---|---|---|
| YKL-02-147 | I-27 | 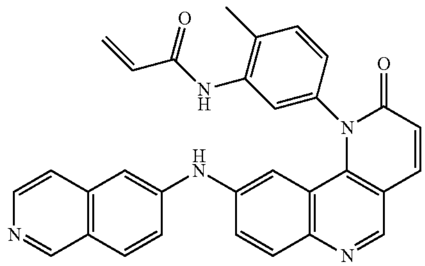 [SMILES: C=CC(=O)Nc1cc(-n2c(=O)ccc3cnc4ccc(Nc5ccc6cnccc6c5)cc4c32)ccc1C] | 1350 | 9150 | 345 | 2590 | 6280 | 374 |
| YKL-02-148 | I-28 | 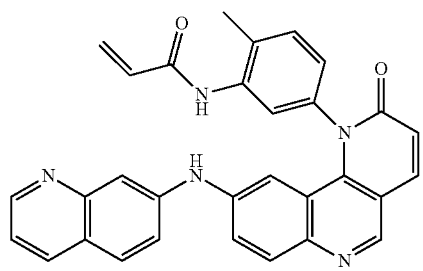 [SMILES: C=CC(=O)Nc1cc(-n2c(=O)ccc3cnc4ccc(Nc5ccc6cccnc6c5)cc4c32)ccc1C] | 4440 | 7490 | 691 | 3590 | 3430 | 1050 |
| YKL-02-149 | I-29 | 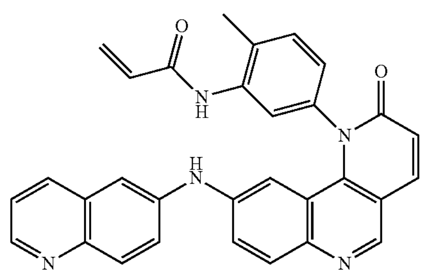 [SMILES: C=CC(=O)Nc1cc(-n2c(=O)ccc3cnc4ccc(Nc5ccc6ncccc6c5)cc4c32)ccc1C] | 2200 | 7290 | 528 | 3080 | 2570 | 390 |
| QL-XII-56 | II-3 | 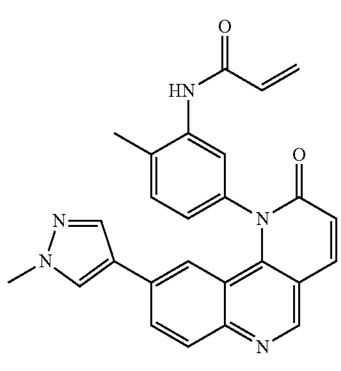 [SMILES: C=CC(=O)Nc1cc(-n2c(=O)ccc3cnc4ccc(-c5cnn(C)c5)cc4c32)ccc1C] | — | — | — | — | — | — |

TABLE 8-continued

EC50 values for various compounds in exemplary WM and lymphoma cell lines.

| Internal Molecule Name | Compound No. | Structure | BCWM.1 EC$_{50}$ (nM) | MWCL-1 EC$_{50}$ (nM) | PRCIWM-1 EC$_{50}$ (nM) | OCI-Ly3 EC$_{50}$ (nM) | Ramos EC$_{50}$ (nM) | OCI-Ly19 EC$_{50}$ (nM) |
|---|---|---|---|---|---|---|---|---|
| QL-XII-47 | II-4 | | 120 | 190 | — | 190 | — | 30 |
| QL-X-134 | II-5 | | 643 | 1550 | 86 | 408 | 872 | 454 |
| QL-X-138 | II-6 | | 50 | 180 | — | 80 | 40 | 40 |
| QL-X-132 | II-7 | | — | — | — | — | — | — |

TABLE 8-continued

EC50 values for various compounds in exemplary WM and lymphoma cell lines.

| Internal Molecule Name | Compound No. | Structure | BCWM.1 EC$_{50}$ (nM) | MWCL-1 EC$_{50}$ (nM) | PRCIWM-1 EC$_{50}$ (nM) | OCI-Ly3 EC$_{50}$ (nM) | Ramos EC$_{50}$ (nM) | OCI-Ly19 EC$_{50}$ (nM) |
|---|---|---|---|---|---|---|---|---|
| QL-XI-13 | II-8 | 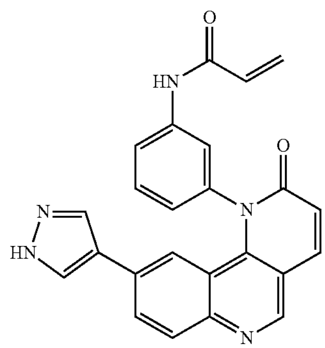 [SMILES: C=CC(=O)Nc1cccc(-n2c(=O)ccc3cnc4ccc(-c5cn[nH]c5)cc4c32)c1] | — | — | — | — | — | — |
| QL-XI-75 | II-9 | 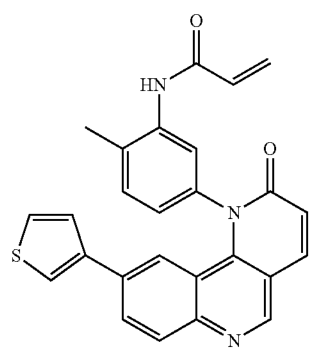 [SMILES: C=CC(=O)Nc1cc(-n2c(=O)ccc3cnc4ccc(-c5ccsc5)cc4c32)ccc1C] | — | — | — | — | — | — |
| QL-XI-76 | II-10 | 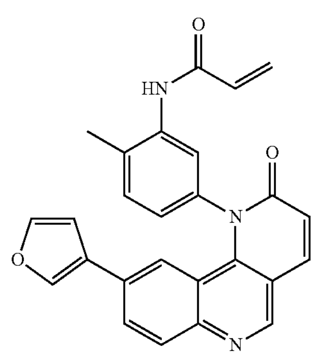 [SMILES: C=CC(=O)Nc1cc(-n2c(=O)ccc3cnc4ccc(-c5ccoc5)cc4c32)ccc1C] | 410 | 2160 | — | 480 | 280 | 70 |
| QL-XII-03 | II-11 | 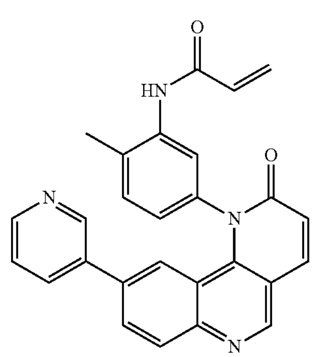 [SMILES: C=CC(=O)Nc1cc(-n2c(=O)ccc3cnc4ccc(-c5cccnc5)cc4c32)ccc1C] | 190 | 670 | — | 240 | 200 | 90 |

TABLE 8-continued

EC50 values for various compounds in exemplary WM and lymphoma cell lines.

| Internal Molecule Name | Compound No. | Structure | BCWM.1 EC$_{50}$ (nM) | MWCL-1 EC$_{50}$ (nM) | PRCIWM-1 EC$_{50}$ (nM) | OCI-Ly3 EC$_{50}$ (nM) | Ramos EC$_{50}$ (nM) | OCI-Ly19 EC$_{50}$ (nM) |
|---|---|---|---|---|---|---|---|---|
| QL-XII-44 | II-12 | 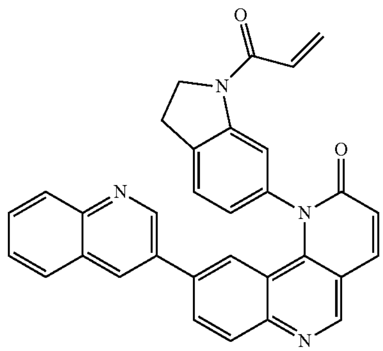 [SMILES: C=CC(=O)N1CCc2ccc(-n3c(=O)ccc4cnc5ccc(-c6cnc7ccccc7c6)cc5c43)cc21] | — | — | — | — | — | — |
| QL-XII-45 | II-13 | 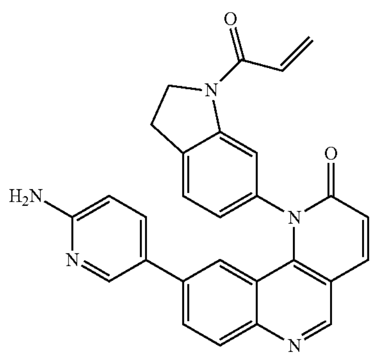 [SMILES: C=CC(=O)N1CCc2ccc(-n3c(=O)ccc4cnc5ccc(-c6ccc(N)nc6)cc5c43)cc21] | 770 | 2470 | — | 1670 | 1350 | 100 |
| QL-XII-46 | II-14 | 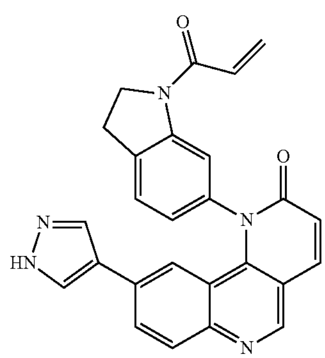 [SMILES: C=CC(=O)N1CCc2ccc(-n3c(=O)ccc4cnc5ccc(-c6cn[nH]c6)cc5c43)cc21] | 320 | 650 | — | 500 | 360 | 160 |
| QL-XII-49 | II-15 | 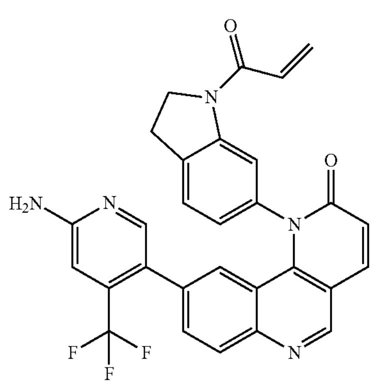 [SMILES: C=CC(=O)N1CCc2ccc(-n3c(=O)ccc4cnc5ccc(-c6cnc(N)cc6C(F)(F)F)cc5c43)cc21] | — | — | — | — | — | — |

TABLE 8-continued

EC50 values for various compounds in exemplary WM and lymphoma cell lines.

| Internal Molecule Name | Compound No. | Structure | BCWM.1 EC$_{50}$ (nM) | MWCL-1 EC$_{50}$ (nM) | PRCIWM-1 EC$_{50}$ (nM) | OCI-Ly3 EC$_{50}$ (nM) | Ramos EC$_{50}$ (nM) | OCI-Ly19 EC$_{50}$ (nM) |
|---|---|---|---|---|---|---|---|---|
| QL-XII-54 | II-16 | 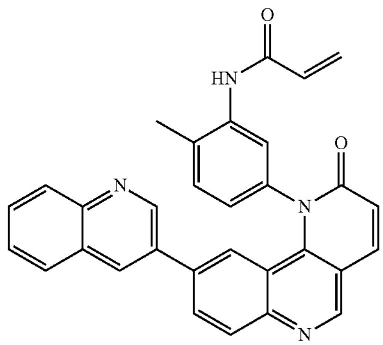 [SMILES: C=CC(=O)Nc1cc(-n2c(=O)ccc3cnc4ccc(-c5cnc6ccccc6c5)cc4c32)ccc1C] | — | — | — | — | — | — |
| QL-XII-01 | II-17 | 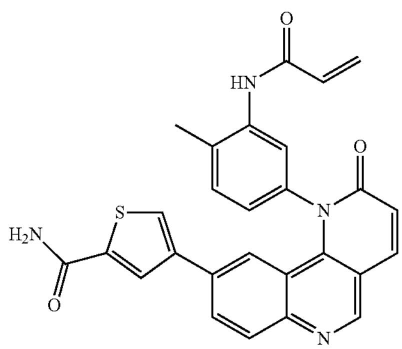 [SMILES: C=CC(=O)Nc1cc(-n2c(=O)ccc3cnc4ccc(-c5csc(C(N)=O)c5)cc4c32)ccc1C] | — | — | — | — | — | — |
| QL-XII-04 | II-18 | 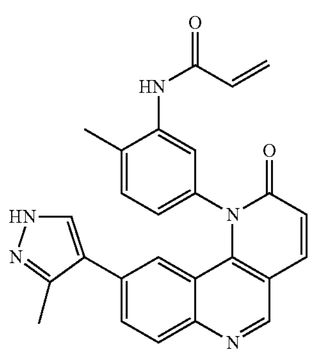 [SMILES: C=CC(=O)Nc1cc(-n2c(=O)ccc3cnc4ccc(-c5c[nH]nc5C)cc4c32)ccc1C] | — | — | — | — | — | — |
| QL-XII-36 | II-19 | 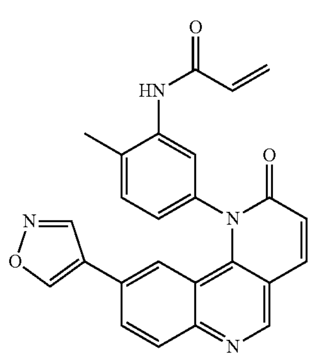 | — | — | — | — | — | — |

TABLE 8-continued

EC50 values for various compounds in exemplary WM and lymphoma cell lines.

| Internal Molecule Name | Compound No. | Structure | BCWM.1 EC$_{50}$ (nM) | MWCL-1 EC$_{50}$ (nM) | PRCIWM-1 EC$_{50}$ (nM) | OCI-Ly3 EC$_{50}$ (nM) | Ramos EC$_{50}$ (nM) | OCI-Ly19 EC$_{50}$ (nM) |
|---|---|---|---|---|---|---|---|---|
| QL-XII-47-AL | II-20 | 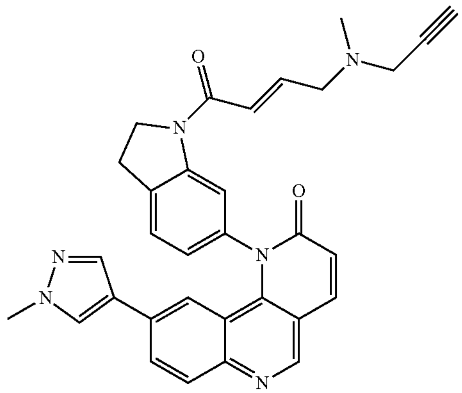 [SMILES: C#CCN(C)C/C=C/C(=O)N1CCc2ccc(-n3c(=O)ccc4cnc5ccc(-c6cnn(C)c6)cc5c43)cc21] | 60 | 134 | 49 | 70 | 107 | 87 |
| QL-XII-55 | II-21 | 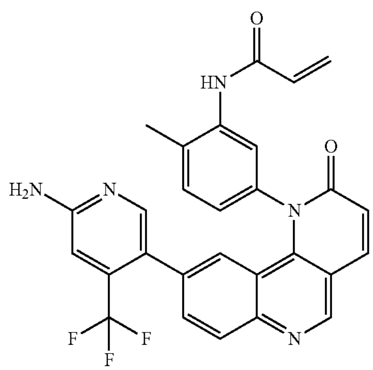 [SMILES: C=CC(=O)Nc1cc(-n2c(=O)ccc3cnc4ccc(-c5cnc(N)cc5C(F)(F)F)cc4c32)ccc1C] | — | — | — | — | — | — |
| QL-XII-60 | II-22 | 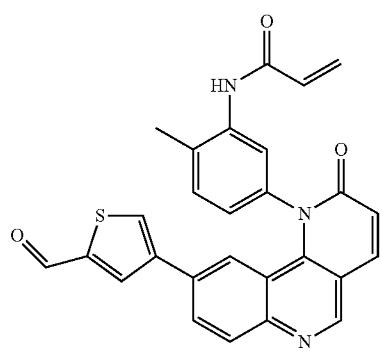 [SMILES: C=CC(=O)Nc1cc(-n2c(=O)ccc3cnc4ccc(-c5csc(C=O)c5)cc4c32)ccc1C] | — | — | — | — | — | — |
| YKL-02-134 | II-23 | 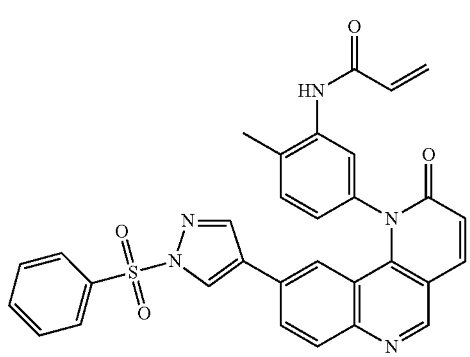 [SMILES: C=CC(=O)Nc1cc(-n2c(=O)ccc3cnc4ccc(-c5cnn(S(=O)(=O)c6ccccc6)c5)cc4c32)ccc1C] | 643 | 1550 | 86 | 408 | 872 | 454 |

TABLE 9

Percent inhibition for I-14 and II-6 for various exemplary kinases.

| Kinase Target | I-14 (% inhibition at 1 uM) | II-6 (% inhibition at 1 uM) |
| --- | --- | --- |
| BTK | 0.95 | 0.2 |
| PIK3CG | 2.8 | 4.2 |
| JAK3(JH1domain-catalytic) | 6.6 | 0 |
| MTOR | 45 | 0 |
| DYRK1A | 100 | 0.1 |
| MKNK2 | 100 | 0.15 |
| MEK5 | 100 | 0.3 |
| TAK1 | 83 | 0.35 |
| CLK1 | 95 | 0.4 |
| PIK3CA(I800L) | 46 | 0.45 |
| DYRK2 | 100 | 0.6 |
| IRAK3 | 73 | 0.7 |
| CSNK2A2 | 100 | 1.2 |
| FLT3(D835Y) | 100 | 1.2 |
| YSK4 | 100 | 1.2 |
| EGFR(T790M) | 11 | 1.4 |
| CLK2 | 100 | 1.6 |
| FLT3(N841I) | 85 | 1.6 |
| DYRK1B | 100 | 1.8 |
| JNK3 | 100 | 1.8 |
| JNK1 | 93 | 1.9 |
| PIK4CB | 79 | 2.3 |
| BLK | 40 | 2.4 |
| FLT3(ITD) | 99 | 2.4 |
| PIP5K2C | 5.6 | 2.7 |

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

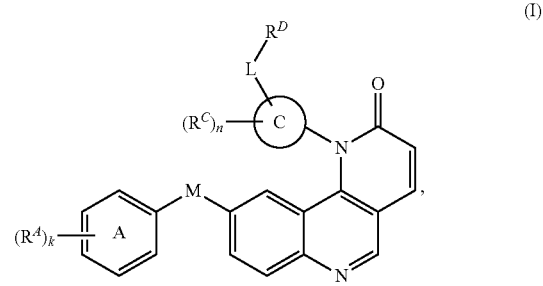

(I)

or a pharmaceutically acceptable salt thereof;
wherein:

is Ring A, wherein Ring A is a phenyl ring optionally substituted with k instances of $R^4$;

each instance of $R^4$ is independently hydrogen, halogen, optionally substituted $C_{1-6}$ alkyl, optionally substituted $C_{2-6}$ alkenyl, optionally substituted $C_{2-6}$ alkynyl, optionally substituted, monocyclic, 5- or 6-membered heterocyclyl, —$OR^{41}$, —$N(R^{41})_2$, —$SR^{41}$, —CN, —$C(=O)R^{41}$, —$C(=O)OR^{41}$, —$C(=O)N(R^{41})_2$, —$NO_2$, —$N_3$, —$NR^{41}C(=O)R^{41}$, —$NR^{41}C(=O)OR^{41}$, —$NR^{41}C(=O)N(R^{41})_2$, —$NR^{41}S(=O)_2R^{41}$, —$NR^{41}S(=O)_2OR^{41}$, —$NR^{41}S(=O)_2N(R^{41})_2$, —$NR^{41}S(=O)R^{41}$, —$NR^{41}S(=O)OR^{41}$, —$NR^{41}S(=O)N(R^{41})_2$, —OC(=O)R$^{A1}$, —OC(=O)OR$^{A1}$, —OC(=O)N(R$^{A1}$)$_2$, —OS(=O)R$^{A1}$, —OS(=O)OR$^{A1}$, —OS(=O)N(R$^{A1}$)$_2$, —OS(=O)$_2$R$^{A1}$, —OS(=O)$_2$OR$^{A1}$, —OS(=O)$_2$N(R$^{A1}$)$_2$, —S(=O)R$^{A1}$, —S(=O)OR$^{A1}$, —S(=O)N(R$^{A1}$)$_2$, —S(=O)$_2$R$^{A1}$, —S(=O)$_2$OR$^{A1}$, or —S(=O)$_2$N(R$^{A1}$); wherein each occurrence of R$^{A1}$ is independently hydrogen, optionally substituted acyl, optionally substituted C$_{1-6}$ alkyl, optionally substituted C$_{2-6}$ alkenyl, optionally substituted C$_{2-6}$ alkynyl, a nitrogen protecting group when attached to a nitrogen atom, an oxygen protecting group when attached to an oxygen atom, or a sulfur protecting group when attached to a sulfur atom;

k is 0, 1, 2, or 3;

M is a bond or an unsubstituted C$_{1-3}$ hydrocarbon chain;

is Ring C, wherein Ring C is a phenyl ring optionally fused with a monocyclic, 5- or 6-membered heterocyclic ring and is optionally substituted with n instances of R$^C$;

each instance of R$^c$ is independently hydrogen, halogen, or optionally substituted methyl;

n is 0, 1, or 2;

L is a bond or an optionally substituted C$_{1-3}$ hydrocarbon chain;

R$^D$ is of the formula:

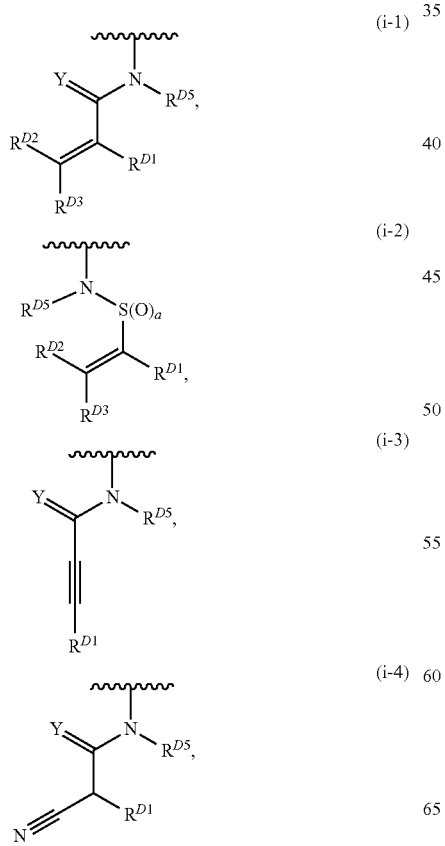

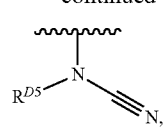

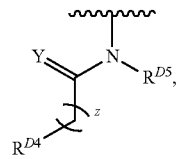

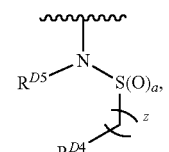

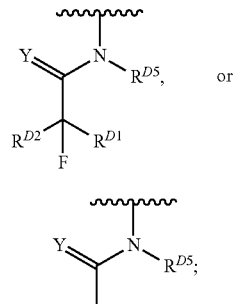

wherein:

R$^{D1}$ is hydrogen, halogen, optionally substituted C$_{1-6}$ alkyl, optionally substituted C$_{2-6}$ alkenyl, optionally substituted C$_{2-6}$ alkynyl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, or —C(=O)N(R$^{D1a}$)$_2$, wherein each occurrence of R$^{D1a}$ is independently hydrogen, optionally substituted C$_{1-6}$ alkyl, optionally substituted C$_{2-6}$ alkenyl, or optionally substituted C$_{2-6}$ alkynyl;

R$^{D2}$ is hydrogen, halogen, optionally substituted C$_{1-6}$ alkyl, optionally substituted C$_{2-6}$ alkenyl, optionally substituted C$_{2-6}$ alkynyl, —CN, —NO$_2$, —OR$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, or —C(=O)N(R$^{D2a}$)$_2$, wherein each occurrence of R$^{D2a}$ is independently hydrogen, optionally substituted C$_{1-6}$ alkyl, optionally substituted C$_{2-6}$ alkenyl, or optionally substituted C$_{2-6}$ alkynyl;

R$^{D3}$ is hydrogen, halogen, optionally substituted C$_{1-6}$ alkyl, optionally substituted C$_{2-6}$ alkenyl, optionally substituted C$_{2-6}$ alkynyl, —CN, —NO$_2$, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, or —C(=O)N(R$^{D3a}$)$_2$, wherein each occurrence of R$^{D3a}$ is independently hydrogen, optionally substituted C$_{1-6}$ alkyl, optionally substituted C$_{2-6}$ alkenyl, or optionally substituted C$_{2-6}$ alkynyl;

$R^{D4}$ is a leaving group, wherein the leaving group is halogen, alkoxycarbonyloxy, aryloxycarbonyloxy, alkanesulfonyloxy, arenesulfonyloxy, alkyl-carbonyloxy, arylcarbonyloxy, aryloxy, alkoxy, N,O-dimethylhydroxylamino, pixyl, haloformate, phosphineoxide, epoxide, cyclic sulfate, or —OS($=$O)$_r$R$^{z1}$, wherein:

$R^{z1}$ is optionally substituted $C_{1-6}$ alkyl, optionally substituted $C_{2-6}$ alkenyl, or optionally substituted $C_{2-6}$ alkynyl; and r is 1 or 2;

$R^{D5}$ is hydrogen, optionally substituted $C_{1-6}$ alkyl, or a nitrogen protecting group;

Y is O;

a is 1 or 2; and z is 0, 1, 2, 3, 4, 5, or 6;

when an optionally substituted moiety referred to above is substituted with one or more substituents at a carbon atom, the one or more substituents at the carbon atom are independently halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C($=$O)R$^{aa}$, —CO$_2$H, —CHO, —C(OR$^{cc}$)$_2$, —CO$_2$R$^{aa}$, —OC($=$O)R$^{aa}$, —OCO$_2$R$^{aa}$, —C($=$O)N(R$^{bb}$)$_2$, —OC($=$O)N(R$^{bb}$)$_2$, —NR$^{bb}$C($=$O)R$^{aa}$, —NR$^{bb}$CO$_2$R$^{aa}$, —NR$^{bb}$C($=$O)N(R$^{bb}$)$_2$, —C($=$NR$^{bb}$)R$^{aa}$, —C($=$NR$^{bb}$)OR$^{aa}$, —OC($=$NR$^{bb}$)R$^{aa}$, —OC($=$NR$^{bb}$)OR$^{aa}$, —C($=$NR$^{bb}$)N(R$^{bb}$)$_2$, —OC($=$NR$^{bb}$)N(R$^{bb}$)$_2$, —NR$^{bb}$C($=$NR$^{bb}$)N(R$^{bb}$)$_2$, —C($=$O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S($=$O)R$^{aa}$, —OS($=$O)R$^{aa}$, —Si(R$^{aa}$)$_3$, —OSi(R$^{aa}$)$_3$ —C($=$S)N(R$^{bb}$)$_2$, —C($=$O)SR$^{aa}$, —C($=$S)SR$^{aa}$, —SC($=$S)SR$^{aa}$, —SC($=$O)SR$^{aa}$, —OC($=$O)SR$^{aa}$, —SC($=$O)OR$^{aa}$, —SC($=$O)R$^{aa}$, —P($=$O)(R$^{aa}$)$_2$, —OP($=$O)(R$^{aa}$)$_2$, —OP($=$O)(OR$^{cc}$)$_2$, —P($=$O)(NR$^{bb}$)$_2$, —OP($=$O)(NR$^{bb}$)$_2$, —NR$^{bb}$P($=$O)(OR$^{cc}$)$_2$, —NR$^{bb}$P($=$O)(NR$^{bb}$)$_2$, —P(R$^{cc}$)$_2$, —OP(R$^{cc}$)$_2$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, or $C_{2-10}$ alkynyl, wherein each of the alkyl, alkenyl, and alkynyl is independently substituted with 0, 1, 2, 3, 4, or 5 R$^{dd}$ groups; or two geminal hydrogen atoms on the carbon atom are replaced with $=$O, $=$S, $=$NN(R$^{bb}$)$_2$, $=$NNR$^{bb}$C($=$O)R$^{aa}$, $=$NNR$^{bb}$C($=$O)OR$^{aa}$, $=$NNR$^{bb}$S($=$O)$_2$R$^{aa}$, $=$NR$^{bb}$, or $=$NOR$^{cc}$;

when an optionally substituted moiety referred to above is substituted with one or more substituents at a nitrogen atom, the one or more substituents at the nitrogen atom are independently a nitrogen protecting group, —OH, —OR$^{aa}$, —N(R$^{cc}$)$_2$, —CN, —C($=$O)R$^{aa}$, —C($=$O)N(R$^{cc}$)$_2$, —CO$_2$R$^{aa}$, —SO$_2$R$^{aa}$, —C($=$NR$^{bb}$)R$^{aa}$, —C($=$NR$^{cc}$)OR$^{aa}$, —C($=$NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C($=$S)N(R$^{cc}$)$_2$, —C($=$O)SR$^{cc}$, —C($=$S)SR$^{cc}$, —P($=$O)(R$^{aa}$)$_2$, —P($=$O)(NR$^{cc}$)$_2$, $C_{1-10}$ alkyl, $C_{1-10}$ perhaloalkyl, $C_{2-10}$ alkenyl, or $C_{2-10}$ alkynyl, wherein each of the alkyl, alkenyl, and alkynyl is independently substituted with 0, 1, 2, 3, 4, or 5 R$^{dd}$ groups;

wherein:

each instance of R$^{aa}$ is, independently, $C_{1-10}$ alkyl, $C_{1-10}$ perhaloalkyl, $C_{2-10}$ alkenyl, $C_{2-10}$ alkynyl, or phenyl, wherein each of the alkyl, alkenyl, alkynyl, and phenyl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C($=$O)R$^{aa}$, —C($=$O)N(R$^{cc}$)$_2$, —CO$_2$R$^{aa}$, —SO$_2$R$^{aa}$, —C($=$NR$^{cc}$)OR$^{aa}$, —C($=$NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C($=$S)N(R$^{cc}$)$_2$, —C($=$O)SR$^{cc}$, —C($=$S)SR$^{cc}$, —P($=$O)(R$^{aa}$)$_2$, —P($=$O)(NR$^{cc}$)$_2$, $C_{1-10}$ alkyl, $C_{1-10}$ perhaloalkyl, $C_{2-10}$ alkenyl, and $C_{2-10}$ alkynyl, wherein each of the alkyl, alkenyl, and alkynyl is independently substituted with 0, 1, 2, 3, 4, or 5 R$^{dd}$ groups;

each instance of R$^{cc}$ is, independently, selected from hydrogen, $C_{1-10}$ alkyl, $C_{1-10}$ perhaloalkyl, $C_{2-10}$ alkenyl, and $C_{2-10}$ alkynyl, wherein each of the alkyl, alkenyl, and alkynyl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C($=$O)R$^{ee}$, —CO$_2$H, —CO$_2$R$^{ee}$, —OC($=$O)R$^{ee}$, —OCO$_2$R$^{ee}$, —C($=$O)N(R$^{ff}$)$_2$, —OC($=$O)N(R$^{ff}$)$_2$, —NR$^{ff}$C($=$O)R$^{ee}$, —NR$^{ff}$CO$_2$R$^{ee}$, —NR$^{ff}$C($=$O)N(R$^{ff}$)$_2$, —C($=$NR$^{ff}$)OR$^{ee}$, —OC($=$NR$^{ff}$)R$^{ee}$, —OC($=$NR$^{ff}$)OR$^{ee}$, —C($=$NR$^{ff}$)N(R$^{ff}$)$_2$, —OC($=$NR$^{ff}$)N(R$^{ff}$)$_2$, —NR$^{ff}$C($=$NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S($=$O)R$^{ee}$, —Si(R$^{ee}$)$_3$, —OSi(R$^{ee}$)$_3$, —C($=$S)N(R$^{ff}$)$_2$, —C($=$O)SR$^{ee}$, —C($=$S)SR$^{ee}$, —SC($=$S)SR$^{ee}$, —P($=$O)(R$^{ee}$)$_2$, —OP($=$O)(R$^{ee}$)$_2$, —OP($=$O)(OR$^{ee}$)$_2$, $C_{1-6}$ alkyl, $C_{1-6}$ perhaloalkyl, $C_{2-6}$ alkenyl, and $C_{2-6}$ alkynyl, wherein each of the alkyl, alkenyl, and alkynyl is independently substituted with 0, 1, 2, 3, 4, or 5 R$^{gg}$ groups, or two geminal R$^{dd}$ substituents can be joined to form $=$O or $=$S;

each instance of R$^{ee}$ is, independently, selected from $C_{1-6}$ alkyl, $C_{1-6}$ perhaloalkyl, $C_{2-6}$ alkenyl, and $C_{2-6}$ alkynyl, wherein each of the alkyl, alkenyl, and alkynyl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ perhaloalkyl, $C_{2-6}$ alkenyl, and $C_{2-6}$ alkynyl, wherein each of the alkyl, alkenyl, and alkynyl is independently substituted with 0, 1, 2, 3, 4, or 5 R$^{gg}$ groups;

each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C($=$O)(C$_{1-6}$ alkyl), —CO$_2$H, —CO$_2$(C$_{1-6}$ alkyl), —OC($=$O)(C$_{1-6}$ alkyl), —OCO$_2$(C$_{1-6}$ alkyl), —C($=$O)NH$_2$, —C($=$O)N(C$_{1-6}$ alkyl)$_2$, —OC($=$O)NH(C$_{1-6}$ alkyl), —NHC($=$O)(C$_{1-6}$ alkyl), —N(C$_{1-6}$ alkyl)C($=$O)(C$_{1-6}$ alkyl), —NHCO$_2$(C$_{1-6}$ alkyl), —NHC($=$O)N(C$_{1-6}$ alkyl)$_2$, —NHC($=$O)NH(C$_{1-6}$ alkyl), —NHC($=$O)NH$_2$, —C($=$NH)O(C$_{1-6}$ alkyl), —OC($=$NH)(C$_{1-6}$ alkyl), —OC($=$NH)OC$_{1-6}$ alkyl, —C($=$NH)N(C$_{1-6}$ alkyl)$_2$, —C($=$NH)NH (C$_{1-6}$ alkyl), —C($=$NH)NH$_2$, —OC($=$NH)N (C$_{1-6}$ alkyl)$_2$, —OC(NH)NH(C$_{1-6}$ alkyl), —OC (NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, or C$_{2-6}$ alkynyl; or two geminal R$^{gg}$ substituents can be joined to form =O or =S; and X$^-$ is a counterion;

when an optionally substituted moiety referred to above is substituted with a substituent at an oxygen atom, the substituent at the oxygen atom is an oxygen protecting group;

when an optionally substituted moiety referred to above is substituted with a substituent at a sulfur atom, the substituent at the sulfur atom is an sulfur protecting group; and each occurrence of the heterocyclyl or heterocyclic ring independently comprises 1 to 4 ring heteroatoms independently selected from the group consisting of nitrogen, oxygen, and sulfur, as valency permits.

2. The compound of claim 1, or a pharmaceutically acceptable salt thereof, wherein R$^D$ is of Formula (i-1):

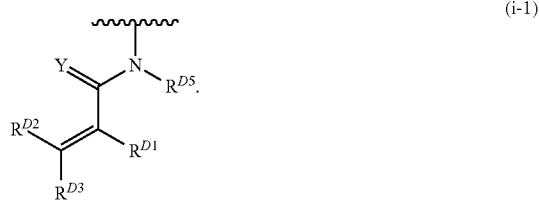

3. The compound of claim 1, or a pharmaceutically acceptable salt thereof, wherein Ring C is a phenyl ring optionally substituted with n instances of R$^c$.

4. The compound of claim 1, or a pharmaceutically acceptable salt thereof, wherein L is a bond or —CH$_2$—.

5. The compound of claim 1, wherein the compound is of Formula (I-1):

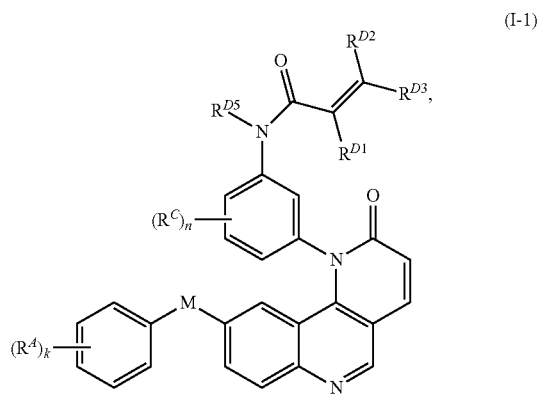

or a pharmaceutically acceptable salt thereof.

6. The compound of claim 1, wherein the compound is of Formula (I-2):

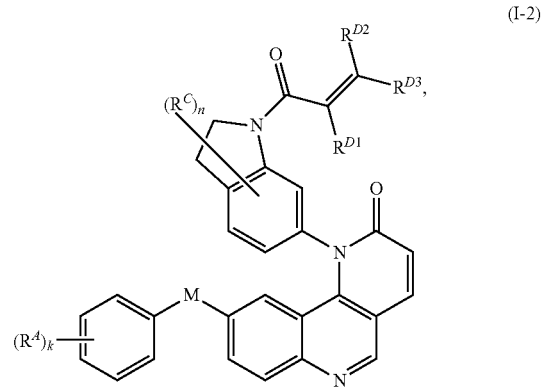

or a pharmaceutically acceptable salt thereof.

7. The compound of claim 1, or a pharmaceutically acceptable salt thereof, wherein M is a bond.

8. The compound of claim 1, or a pharmaceutically acceptable salt thereof, wherein M is trans-CH=CH—.

9. The compound of claim 1, wherein the compound is of Formula (I-3):

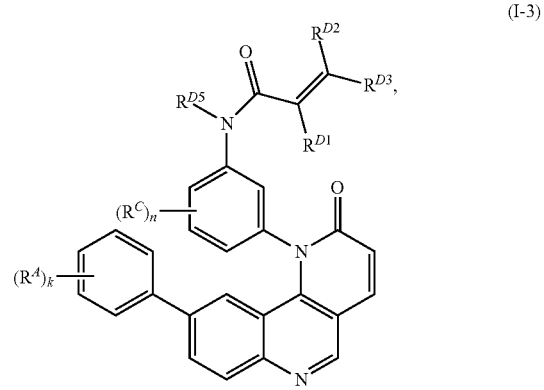

or a pharmaceutically acceptable salt thereof.

10. The compound of claim 1, wherein the compound is of Formula (I-4):

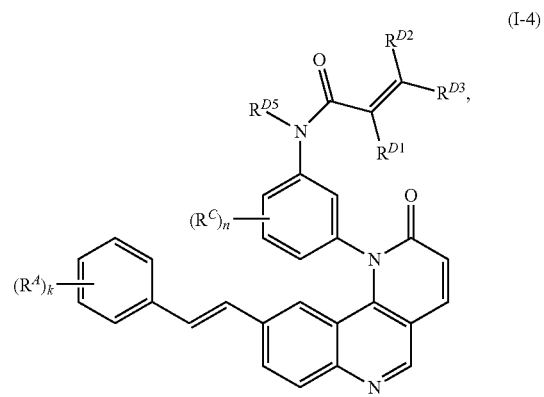

or a pharmaceutically acceptable salt thereof.

11. The compound of claim 1, wherein the compound is of Formula (I-5):

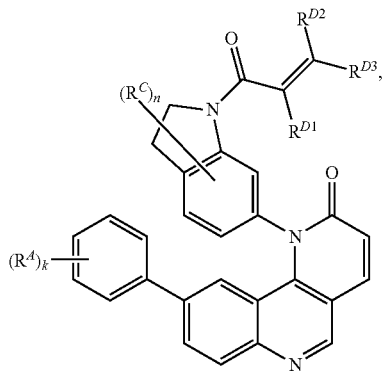
(I-5)

or a pharmaceutically acceptable salt thereof.

12. The compound of claim 1, wherein the compound is of Formula (I-6):

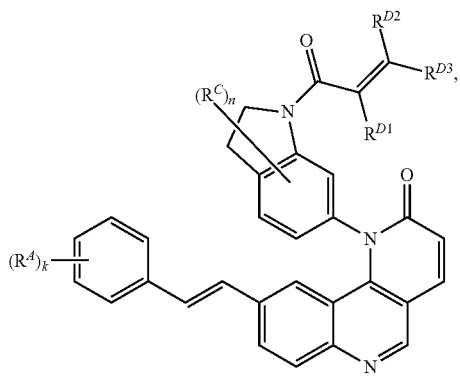
(I-6)

or a pharmaceutically acceptable salt thereof.

13. The compound of claim 1, or a pharmaceutically acceptable salt thereof, wherein:
 $R^c$ is optionally substituted methyl; and
 n is 1.

14. The compound of claim 1, wherein the compound is of the formula:

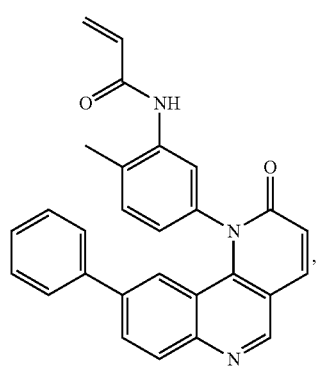
(I-7)

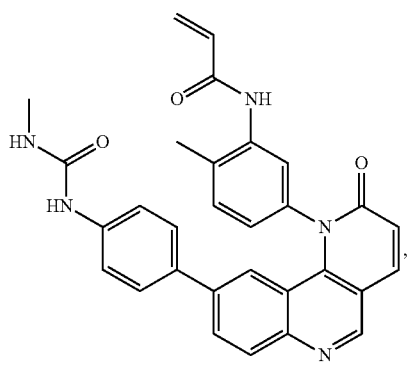
(I-8)

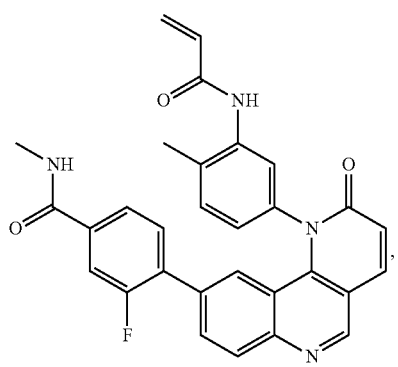
(I-12)

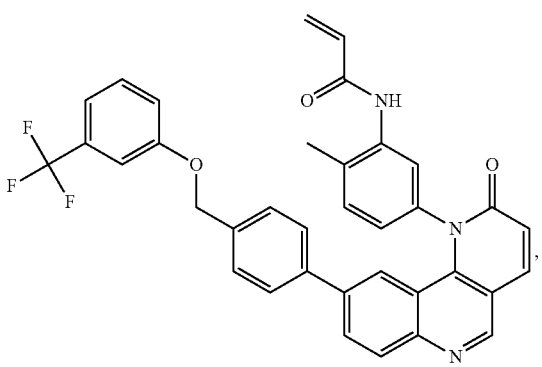
(I-13)

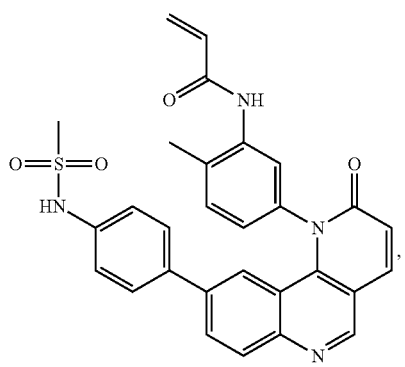
(I-14)

(I-15)

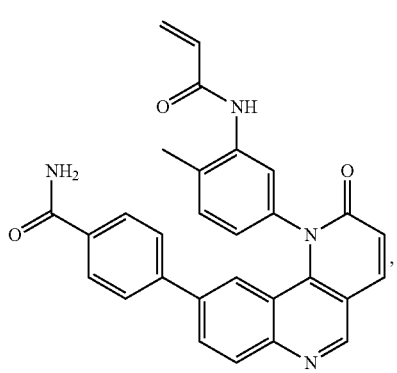

, or (I-16)

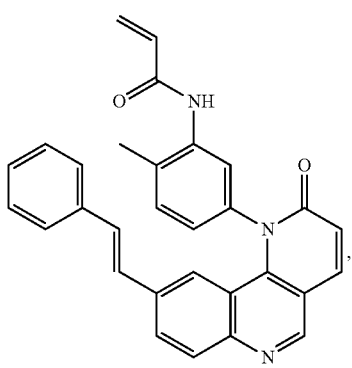

or a pharmaceutically acceptable salt thereof.

15. A pharmaceutical composition comprising a compound of claim 1, or a pharmaceutically acceptable salt thereof, and optionally a pharmaceutically acceptable excipient.

16. A method for treating a disease characterized by overexpression of bone marrow kinase on X chromosome (BMX) or associated with aberrant activity of BMX, the method comprising:
administering to a subject in need thereof a compound of claim 1, or a pharmaceutically acceptable salt thereof, in an amount effective to treat the disease, wherein the disease is prostate cancer or lymphoma.

17. A method of suppressing kinase signaling in a biological sample or subject, the method comprising:
administering to the biological sample or subject a compound of claim 1, or a pharmaceutically acceptable salt thereof, in an amount effective to suppress the kinase signaling.

18. The compound of claim 1, or a pharmaceutically acceptable salt thereof, wherein M is an unsubstituted $C_2$ hydrocarbon chain.

19. The compound of claim 1, or a pharmaceutically acceptable salt thereof, wherein n is 0.

20. The compound of claim 1, or a pharmaceutically acceptable salt thereof, wherein $R^D$ is of the formula:

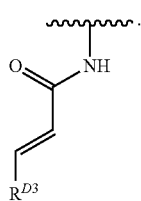

21. The compound of claim 1, or a pharmaceutically acceptable salt thereof, wherein $R^D$ is of the formula:

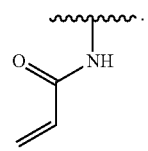

22. The compound of claim 1, wherein the compound is of the formula:

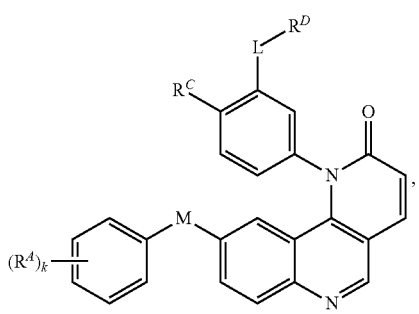

or a pharmaceutically acceptable salt thereof.

23. The compound of claim 1, wherein the compound is of the formula:

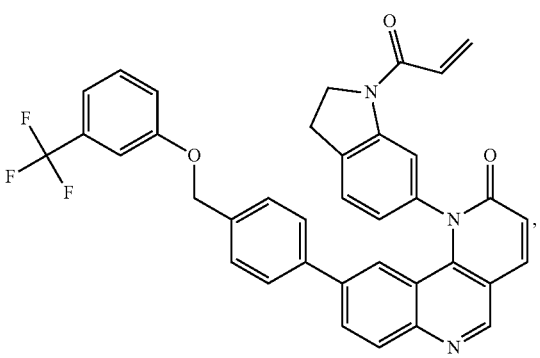

-continued

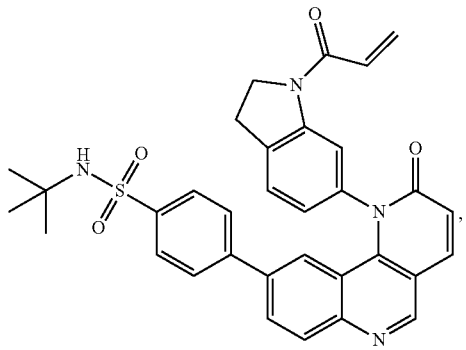
(I-11)

or

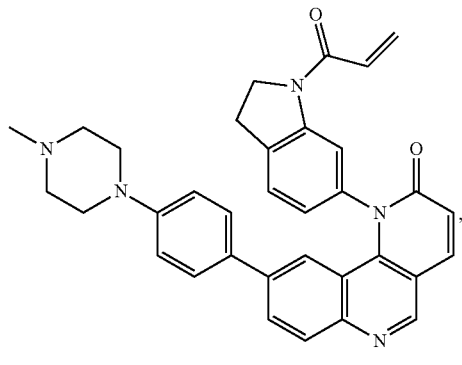
(I-17)

or a pharmaceutically acceptable salt thereof.

24. The compound of claim 1, or a pharmaceutically acceptable salt thereof, wherein Ring C is a phenyl ring fused with a monocyclic, 5- or 6-membered heterocyclic ring and is optionally substituted with n instances of $R^c$.

25. The compound of claim 1, wherein the compound is of the formula:

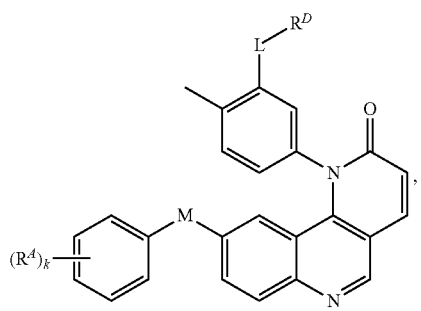

or a pharmaceutically acceptable salt thereof.

26. The compound of claim 1, or a pharmaceutically acceptable salt thereof, wherein at least one instance of $R^A$ is $-NR^{41}S(=O)_2R^{41}$.

27. The compound of claim 1, wherein the compound is of the formula:

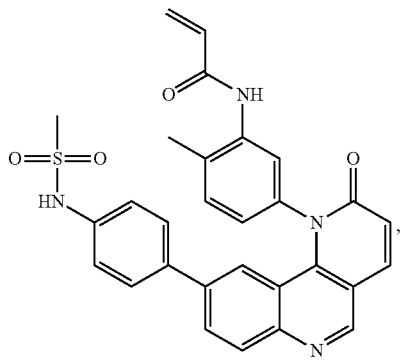
(I-14)

or a pharmaceutically acceptable salt thereof.

28. The pharmaceutical composition of claim 15, wherein the compound is of the formula:

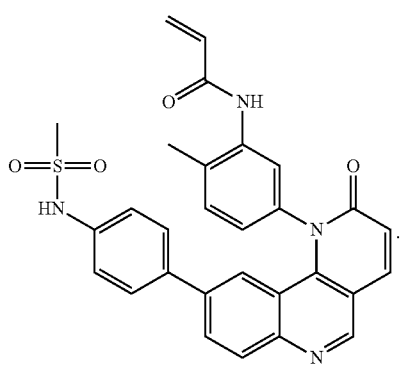
(I-14)

29. The method of claim 16, wherein the compound is of the formula:

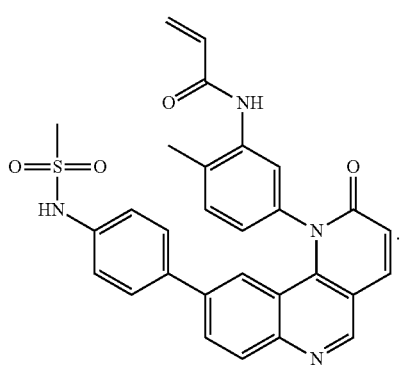
(I-14)

30. The method of claim 17, wherein the compound is of the formula:

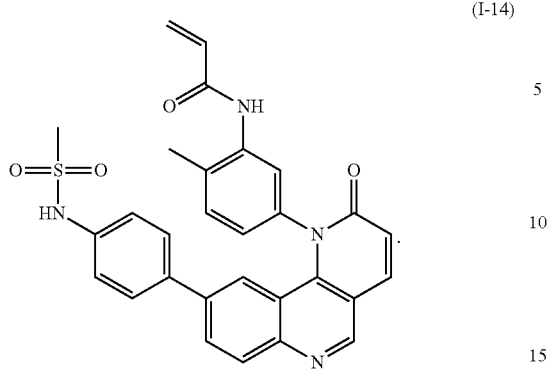

(I-14)

31. The method of claim 16, wherein the disease is prostate cancer.

32. The method of claim 16, wherein the disease is lymphoma.

33. The method of claim 32, wherein the lymphoma is Waldenström's macroglobulinemia.

34. The method of claim 32, wherein the lymphoma is Hodgkin's lymphoma.

35. The method of claim 32, wherein the lymphoma is non-Hodgkin's lymphoma.

36. The method of claim 32, wherein the lymphoma is B-cell lymphoma.

37. The method of claim 32, wherein the lymphoma is T-cell lymphoma.

* * * * *

UNITED STATES PATENT AND TRADEMARK OFFICE
CERTIFICATE OF CORRECTION

PATENT NO. : 10,000,483 B2  
APPLICATION NO. : 14/436387  
DATED : June 19, 2018  
INVENTOR(S) : Nathanael S. Gray et al.

Page 1 of 1

It is certified that error appears in the above-identified patent and that said Letters Patent is hereby corrected as shown below:

In the Claims

Claim 1, Column 213, Line 6, the text: "-S(=O)$_2$N(R$^{A1}$)" should be replaced with the text: -- –S(=O)$_2$N(R$^{A1}$)$_2$--.

Claim 1, Column 215, Lines 34-35, the text: "–OSi(R$^{aa}$)$_3$ –C(=S)N(R$^{bb}$)$_2$" should be replaced with the text: -- –OSi(R$^{aa}$)$_3$, –C(=S)N(R$^{bb}$)$_2$--.

Signed and Sealed this  
Thirty-first Day of December, 2019

Andrei Iancu  
*Director of the United States Patent and Trademark Office*